United States Patent
Di Francesco et al.

(10) Patent No.: US 11,725,008 B2
(45) Date of Patent: Aug. 15, 2023

(54) ETHANEDIAMINE-HETEROCYCLE DERIVATIVES AS INHIBITORS OF PROTEIN ARGININE METHYLTRANSFERASES

(71) Applicant: Board of Regents, The University of Texas System, Austin, TX (US)

(72) Inventors: Maria Emilia Di Francesco, Houston, TX (US); Philip Jones, Houston, TX (US); Timothy Joseph McAfoos, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/307,568

(22) Filed: May 4, 2021

(65) Prior Publication Data

US 2023/0027126 A1    Jan. 26, 2023

Related U.S. Application Data

(63) Continuation of application No. 16/290,675, filed on Mar. 1, 2019, now Pat. No. 11,028,083.

(60) Provisional application No. 62/637,147, filed on Mar. 1, 2018.

(51) Int. Cl.
| | |
|---|---|
| C07D 471/04 | (2006.01) |
| C07D 498/04 | (2006.01) |
| A61P 35/02 | (2006.01) |
| A61P 3/00 | (2006.01) |
| C07D 487/04 | (2006.01) |
| A61K 45/06 | (2006.01) |

(52) U.S. Cl.
CPC .............. *C07D 471/04* (2013.01); *A61P 3/00* (2018.01); *A61P 35/02* (2018.01); *C07D 487/04* (2013.01); *C07D 498/04* (2013.01); *A61K 45/06* (2013.01)

(58) Field of Classification Search
CPC .................................. C07D 471/04; A61P 3/00
See application file for complete search history.

(56) References Cited

U.S. PATENT DOCUMENTS

| | | |
|---|---|---|
| 5,002,941 A | 3/1991 | Adams |
| 11,028,083 B2 | 6/2021 | Di Francesco |
| 2013/0059845 A1 | 3/2013 | Song |
| 2014/0315904 A1 | 10/2014 | Chesworth |
| 2014/0323537 A1 | 10/2014 | Chesworth |
| 2016/0031839 A1 | 2/2016 | Chesworth |

FOREIGN PATENT DOCUMENTS

| | | |
|---|---|---|
| EP | 2221053 | 8/2010 |
| WO | 2014144659 | 9/2014 |
| WO | 2014153090 | 9/2014 |
| WO | 2014153100 | 9/2014 |
| WO | 2014153172 | 9/2014 |
| WO | 2014153208 | 9/2014 |
| WO | 2014153214 | 9/2014 |
| WO | 2014153226 | 9/2014 |
| WO | 2014153235 | 9/2014 |
| WO | 2016022605 | 2/2016 |
| WO | 2016044556 | 3/2016 |
| WO | 2016044576 | 3/2016 |
| WO | 2016044585 | 3/2016 |
| WO | 2016044626 | 3/2016 |
| WO | 2017136699 | 8/2017 |
| WO | 2017145013 | 8/2017 |
| WO | 2019169326 | 9/2019 |

OTHER PUBLICATIONS

Duncan, K. et al., "Structure and Property Guided Design in the Identification of PRMT5 Tool Compound EPZ015666", ACS Med Chem Lett., 7(2):162-6, (2015).
Fedoriw, A. et al., "Anti-tumor Activity of the Type I PRMT Inhibitor, GSK3368715, Synergizes with PRMT5 Inhibition through MTAP Loss", Cancer Cell, 36(1):100-14, (2019).
Ferreira de Freitas, R. et al., "Discovery of a Potent Class I Protein Arginine Methyltransferase Fragment Inhibitor", J Med Chem., 59(3):1176-83, (2016).
International Application No. PCT/US2019/020395; International Preliminary Report on Patentability, dated Sep. 10, 2020; 5 pages.
International Application No. PCT/US2019/020395; International Search Report and Written Opinion of the International Searching Authority, dated May 13, 2019; 6 pages.
Mitchell, L. et al., "Aryl Pyrazoles as Potent Inhibitors of Arginine Methyltransferases: Identification of the First PRMT6 Tool Compound", ACS Med Chem Lett., 6(6):655-9, (2015).
Sack, J. et al., "Structural basis for CARM1 inhibition by indole and pyrazole inhibitors", Biochem J., 436(2):331-9, (2011).
U.S. Appl. No. 16/290,675; Examiner-Initiated Interview Summary, dated Oct. 8, 2020; 1 page.
U.S. Appl. No. 16/290,675; Notice of Allowance, dated Oct. 8, 2020; 20 pages.

*Primary Examiner* — Golam M Shameem
(74) *Attorney, Agent, or Firm* — Cynthia Hathaway; Lauren L. Stevens; Erik M. Larsen

(57) ABSTRACT

The present invention relates to ethanediamine-heterocycle compounds that are able to act as inhibitors of PRMTs (protein arginine methyltransferases) for treating cancer and other diseases mediated by PRMTs.

13 Claims, No Drawings

ETHANEDIAMINE-HETEROCYCLE DERIVATIVES AS INHIBITORS OF PROTEIN ARGININE METHYLTRANSFERASES

This application is a division of U.S. application Ser. No. 16/290,675, filed Mar. 1, 2019, which claims the benefit of priority of U.S. Provisional Application No. 62/637,147, filed Mar. 1, 2018, the disclosures of which are hereby incorporated by reference as if written herein in their entireties.

STATEMENT OF GOVERNMENT INTEREST

This invention was made with government support under W81XWH-11-1-0418 awarded by the Department of Defense. The government has certain rights in the invention.

Disclosed herein are new heterocyclic compounds and compositions and their application as pharmaceuticals for the treatment of disease. Methods of inhibition of protein arginine methyltransferases (PRMTs) activity, in particular type I PRMTs, in a human or animal subject are also provided for the treatment diseases such as cancer.

Eukaryotic cells contain enzymes that are capable of posttranslational modification of amino acid residues in proteins. This modification has been shown to affect the function, localization, and stability of proteins. Introduction of methyl (—$CH_3$) groups in amino acid moieties, a process known as methylation, is a common means employed by organisms for altering the behavior of proteins, particularly those containing arginine residues. Methylation of arginine residues is perhaps the most widespread methylation pathways in mammalian cells. Arginine ("Arg" or "R") contains a side-chain guanidine moiety, having the chemical formula —N=C($NH_2$)$_2$, or a tautomer thereof. Methylation of arginine residues can be expected to modulate significantly the function of a protein, due to disruption of both ion pairs and hydrogen bonds, and introduction of unfavorable steric interactions (Yanzhong Yang et al., *Nature Reviews*, 13, 37-50, 2013; Copeland et al., *Nature Reviews*, 8, 724-732, 2009).

An expanding class of enzymes termed "protein arginine N-methyltransferases" ("PRMTs") performs both mono- and dimethylation of the guanidine functionality of arginine residues in proteins. These enzymes incorporate methyltransferase functionality that utilizes S-adenosyl methionine as a methyl group donor. PRMTs comprises two major types, termed I and II. Both type I and type II enzymes catalyze monomethylating of the guanidine of arginine, forming —N=C($NH_2$)(NH$CH_3$) moiety (and tautomers). Type I enzymes also promote asymmetrical dimethylation of arginine residues, forming the —N=C($NH_2$)(N($CH_3$)$_2$) moieties (and tautomers). In contrast, type II enzymes promote symmetrical dimethylation of arginine residues, forming the —N=C(NH$CH_3$)$_2$ moiety (and tautomers). Also included in the PRMT class of enzymes are type III enzymes, which produces only the monomethylated product, and type IV enzymes, which methylate the non-terminal guanidine nitrogen of arginine residues, forming the —N($CH_3$)—C(=NH)(NH$_2$) moiety (and tautomers).

Nine PRMTs have been identified in humans; each has a methyltransferase domain. Of these, PRMT1, a type I PRMT, is the primary enzyme responsible for the asymmetric dimethylation of arginine residues in yeast, trypanosomes, and humans. The protein is found in both the cytoplasm and the nucleus of yeast and human cells, and performs asymmetric dimethylation on both histones as well as a large number of non-histone protein substrates. Arginine methylation has been involved in several key cellular processes, including signal transduction, regulation of gene transcription, mRNA splicing and DNA repair (Mark T. Bedford et al., *Molecular Cell*, 18, 263-272, 2005), and overexpression of PRMTs has often been associated with various cancers. For example, overexpression of PRMT1 has been observed in numerous cancers, including breast, prostate, lung, colon, bladder cancers and leukemia. Therefore, inhibition of PRMTs, including inhibition of type I PRMTs, can be effective in the treatment of cancer. Similarly, PRMTs have been associated with additional diseases including diabetes, cardiovascular, renal and muscular diseases (Mark T. Bedford et al., *Molecular Cell*, 18, 263-272, 2005). Inhibition of PRMTs, including inhibition of type I PRMTs, can be effective in the treatment of such diseases.

Novel compounds and pharmaceutical compositions, certain of which have been found to inhibit type I PRMTs, in particular PRMT1 have been discovered, together with methods of synthesizing and using the compounds including methods for the treatment of type I PRMT-mediated diseases in a patient by administering the compounds.

DETAILED DESCRIPTION

Provided herein is Embodiment 1: a compound having structural Formula I:

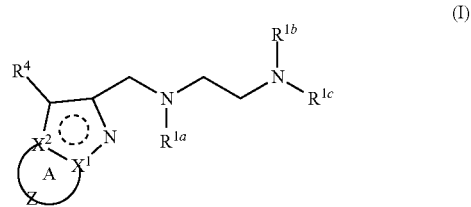

or a salt thereof, wherein:
A is a monocyclic heterocycloalkyl ring comprising 5 to 7 ring members including:
  $X^1$ and $X^2$,
  Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and
  all other ring members Y, which are chosen from —$CH_2$—, —$CHR^2$—, and —$C(R^2)_2$—;
$R^{1a}$, $R^{1b}$, and $R^{1c}$ are independently chosen from H and $CH_3$;
either $X^1$ is C and $X^2$ is N, or $X^1$ is N and $X^2$ is C;
each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or
any two $R^2$ or $R^3$, when directly attached to the same atom, forms a 3-7 membered cycloalkyl or heterocycloalkyl ring;
$R^4$ is chosen from cycloalkyl, heterocycloalkyl, aryl and heteroaryl, any of which is optionally substituted with 1, 2, 3, or 4 $R^6$ groups;
each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when directly attached to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

each R$^6$ is independently chosen from C$_{1-6}$alkyl, cyanoC$_{1-6}$ alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo;

each R$^7$ is independently chosen from C$_{1-6}$alkyl, haloC$_{1-6}$alkyl, aryl, heteroaryl, C$_{3-6}$cycloalkyl, heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each R$^8$ is independently chosen from C$_{1-6}$alkyl, haloC$_{1-6}$alkyl, C$_{3-6}$cycloalkyl, and haloC$_{3-6}$cycloalkyl.

Certain compounds disclosed herein may possess useful type I PRMTs inhibiting activity, and may be used in the treatment or prophylaxis of a disease or condition in which type I PRMTs play an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting type I PRMTs. Other embodiments provide methods for treating a PRMT-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of type I PRMTs.

The disclosure provides the following further embodiments:

Embodiment 2: the compound of Embodiment 1, wherein A comprises 5 ring members.

Embodiment 3: the compound of Embodiment 1, wherein A comprises 6 ring members.

Embodiment 4: the compound of Embodiment 1, wherein A comprises 7 ring members.

Embodiment 5: the compound of any one of Embodiments 1-4, wherein Y is chosen from —CH$_2$— and —CHR$^2$—.

Embodiment 6: the compound of Embodiment 5, wherein each Y is —CH$_2$—.

Provided herein is Embodiment 7: the compound of Embodiment 1 having structural Formula Ia:

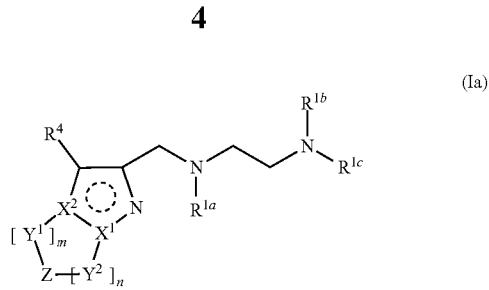

(Ia)

or a salt thereof, wherein:

R$^{1a}$, R$^{1b}$, and R$^{1c}$ are independently chosen from H and CH$_3$;

either X$_1$ is C and X$_2$ is N, or X$_1$ is N and X$_2$ is C;

Y$^1$ and Y$^2$ are independently chosen from —CH$_2$—, —CHR$^2$—, and —C(R$^2$)$_2$—;

Z is chosen from —CH$_2$—, —CHR$^3$—, —C(R$^3$)$_2$—, —N(R$^{5a}$)—, N(COR$^{5a}$)—, —N(CONR$^{5a}$R$^{5b}$)—, —N(SO$_2$R$^{5a}$)—, —O—, and —SO$_2$—;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

R$^4$ is chosen from cycloalkyl, heterocycloalkyl, aryl, and heteroaryl, any of which is optionally substituted with 1, 2, 3, or 4 R$^6$ groups;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when attached directly to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

each R$^6$ is independently chosen from C$_{1-6}$alkyl, cyanoC$_{1-6}$ alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo;

each R$^7$ is independently chosen from C$_{1-6}$alkyl, haloC$_{1-6}$alkyl, aryl, heteroaryl, C$_{3-6}$cycloalkyl, heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each $R^8$ is independently chosen from $C_{1-6}$alkyl, halo$C_{1-6}$alkyl, $C_{3-6}$cycloalkyl, and halo$C_{3-6}$cycloalkyl; and either m is 1 and n is chosen from 1 and 2, or m is 2 and n is chosen from 0 and 1.

The disclosure provides the following further embodiments:

Embodiment 8: the compound of Embodiment 7, wherein m is 1.

Embodiment 9: the compound of Embodiment 8, wherein n is 2.

Embodiment 10: the compound of Embodiment 7, wherein m is 2.

Embodiment 11: the compound of Embodiment 10, wherein n is 0.

Embodiment 12: the compound of either one of Embodiments 8 and 10, wherein n is 1.

Embodiment 13: the compound of any one of Embodiments 7-12, wherein $Y^1$ and $Y^2$ are independently chosen from —$CH_2$— and —$CHR^2$—.

Embodiment 14: the compound of Embodiment 13, wherein $Y^1$ and $Y^2$ are —$CH_2$—.

Embodiment 15: the compound of any one of Embodiments 1-14, wherein $R^4$ is chosen from aryl and heteroaryl, either of which is optionally substituted with 1, 2, 3, or 4 $R^6$ groups.

Embodiment 16: the compound of any one of Embodiments 1-14, wherein $R^4$ is chosen from monocyclic aryl, bicyclic aryl, monocyclic heteroaryl, and bicyclic heteroaryl, any of which is optionally substituted with 1, 2, 3, or 4 $R^6$ groups.

Embodiment 17: the compound of any one of Embodiments 1-14, wherein $R^4$ is chosen from cycloalkyl and heterocycloalkyl, either of which is optionally substituted with 1, 2, 3, or 4 $R^6$ groups.

Embodiment 18: the compound of Embodiment 17, wherein $R^4$ is chosen from 3-7 membered monocyclic cycloalkyl and 3-7 membered monocyclic heterocycloalkyl, either of which is optionally substituted with 1, 2, 3, or 4 $R^6$ groups.

Embodiment 19: the compound of Embodiment 18, wherein $R^4$ is chosen from cyclohexyl, cyclohexen-1-yl, piperidin-4-yl, 3,6-dihydropyridin-1(2H)-4-yl, any one of which is optionally substituted with 1, 2, 3, or 4 $R^6$ groups.

Embodiment 20: the compound of Embodiment 19, wherein $R^4$ is cyclohexyl, and is optionally substituted with 1, 2, 3, or 4 $R^6$ groups.

Embodiment 21: the compound of Embodiment 17, wherein $R^4$ is chosen from bicycloalkyl and heterobicycloalkyl, either of which is optionally substituted with 1, 2, 3, or 4 $R^6$ groups.

Embodiment 22: the compound of Embodiment 21, wherein $R^4$ is chosen from 6-11 membered bicycloalkyl and 6-11 membered heterobicycloalkyl, either of which is optionally substituted with 1, 2, 3, or 4 $R^6$ groups.

Embodiment 23: the compound of Embodiment 22, wherein $R^4$ is bicyclo[3.1.0]hexan-2-yl, and is optionally substituted with 1, 2, 3, or 4 $R^6$ groups.

Embodiment 24: the compound of Embodiment 21, wherein $R^4$ is chosen from spirocycloalkyl and spiroheterocycloalkyl, either of which is optionally substituted with 1, 2, 3, or 4 $R^6$ groups.

Embodiment 25: the compound of Embodiment 21, wherein $R^4$ is chosen from 8-11 membered spirocycloalkyl and 8-11 membered spiroheterocycloalkyl, either of which is optionally substituted with 1, 2, 3, or 4 $R^6$ groups.

Embodiment 26: the compound of Embodiment 25, wherein $R^4$ is chosen from spiro[3.5]nonanyl, spiro[4.5]decanyl, spiro[5.5]undecanyl, oxaspiro[3.5]nonanyl, oxaspiro[4.5]decanyl, azaspiro[4.5]decanyl, and oxaspiro[5.5]undecanyl, any one of which is optionally substituted with 1, 2, 3, or 4 $R^6$ groups.

Embodiment 27: the compound of Embodiment 26, wherein $R^4$ is chosen from spiro[3.5]nonan-7-yl, spiro[4.5]decan-8-yl, spiro[5.5]undecan-3-yl, 2-oxaspiro[3.5]nonan-7-yl, 1-oxaspiro[4.5]decan-8-yl, 2-oxaspiro[4.5]decan-8-yl, 1-azaspiro[4.5]decan-8-yl, 2-azaspiro-[4.5]decan-8-yl, 1-oxaspiro[5.5]undecan-9-yl, 2-oxaspiro[5.5]undecan-9-yl, and 3-oxaspiro[5.5]-undecan-9-yl, any one of which is optionally substituted with 1, 2, 3, or 4 $R^6$ groups.

Embodiment 28: the compound of any one of Embodiments 1-27, wherein $R^4$ is optionally substituted with 1, 2, or 3 $R^6$ groups.

Embodiment 29: the compound of Embodiment 28, wherein $R^4$ is optionally substituted with 1 or 2 $R^6$ groups.

Embodiment 30: the compound of Embodiment 29, wherein $R^4$ is optionally substituted with 1 $R^6$ group.

Embodiment 31: the compound of Embodiment 29, wherein $R^4$ is substituted with 1 or 2 $R^6$ groups.

Embodiment 32: the compound of Embodiment 29, wherein $R^4$ is substituted with 1 $R^6$ group.

Embodiment 33: the compound of Embodiment 30, wherein $R^4$ is unsubstituted with an $R^6$ group.

Provided herein is Embodiment 34: the compound of Embodiment 1 having structural Formula II:

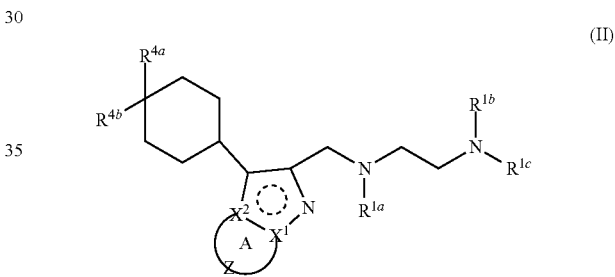

(II)

or a salt thereof, wherein:

A is a monocyclic heterocycloalkyl ring comprising 5 to 7 ring members including:

$X^1$ and $X^2$,

Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and all other ring members Y, which are chosen from —$CH_2$—, —$CHR^2$—, and —$C(R^2)_2$—;

$R^{1a}$, $R^{1b}$, and $R^{1c}$ are independently chosen from H and $CH_3$;

either $X_1$ is C and $X_2$ is N, or $X_1$ is N and $X_2$ is C;

each $R^2$ and $R^3$ is independently chosen from cyano, halo, hydroxy, $C_{1-6}$alkyl, $C_{1-6}$haloalkyl, $C_{1-6}$hydroxyalkyl, $(C_{1-6}$alkoxy$)C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or any two $R^2$ or $R^3$, when directly attached to the same atom, forms a 3-7 membered cycloalkyl or heterocycloalkyl ring;

$R^{4a}$ and $R^{4b}$, together with the atom to which they are attached, form a cycloalkyl or heterocycloalkyl ring, which is optionally substituted with 1, 2, or 3 $R^6$ groups;

each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;

each $R^6$ is independently chosen from $C_{1-6}$alkyl, cyano$C_{1-6}$ alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, (heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

each $R^7$ is independently chosen from $C_{1-6}$alkyl, halo$C_{1-6}$alkyl, aryl, heteroaryl, $C_{3-6}$cycloalkyl, heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

The disclosure provides the following further embodiments:

Embodiment 35: The compound of Embodiment 34, wherein $R^{4a}$ and $R^{4b}$, together with the atom to which they are attached, form a lactone ring, which is optionally substituted with 1, 2, or 3 $R^6$ groups.

Embodiment 36: The compound of Embodiment 34, wherein $R^{4a}$ and $R^{4b}$, together with the atom to which they are attached, form a lactam ring, which is optionally substituted with 1, 2, or 3 $R^6$ groups.

Embodiment 37: the compound of any one of Embodiments 34-36, wherein Y is chosen from —$CH_2$— and —$CHR^2$—.

Embodiment 38: the compound of Embodiment 37, wherein each Y is —$CH_2$—.

Embodiment 39: The compound of any one of Embodiments 34-38, wherein the ring formed by $R^{4a}$ and $R^{4b}$ and the atom to which they are attached is optionally substituted with 1 or 2 $R^6$ groups.

Embodiment 40: The compound of Embodiment 39, wherein the ring formed by $R^{4a}$ and $R^{4b}$ and the atom to which they are attached is substituted with 1 or 2 $R^6$ groups.

Embodiment 41: The compound of Embodiment 39, wherein the ring formed by $R^{4a}$ and $R^{4b}$ and the atom to which they are attached is optionally substituted with 1 $R^6$ group.

Embodiment 42: The compound of Embodiment 41, wherein the ring formed by $R^{4a}$ and $R^{4b}$ and the atom to which they are attached is substituted with 1 $R^6$ group.

Embodiment 43: The compound of Embodiment 39, wherein the ring formed by $R^{4a}$ and $R^{4b}$ and the atom to which they are attached is unsubstituted with an $R^6$ group.

Provided herein is Embodiment 44: the compound of Embodiment 1 having structural Formula IIa:

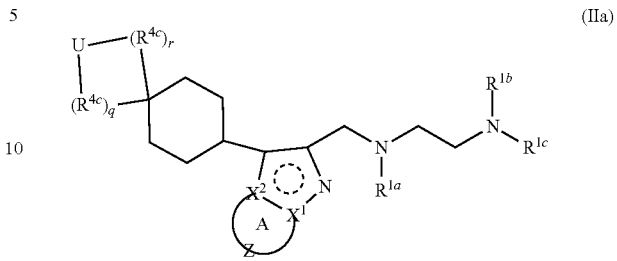

(IIa)

or a salt thereof, wherein:

A is a monocyclic heterocycloalkyl ring comprising 5 to 7 ring members including:
$X^1$ and $X^2$,
Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and
all other ring members Y, which are chosen from —$CH_2$—, —$CHR^2$—, and —$C(R^2)_2$—;

$R^{1a}$, $R^{1b}$, and $R^{1c}$ are independently chosen from H and $CH_3$;

either $X_1$ is C and $X_2$ is N, or $X_1$ is N and $X_2$ is C;

each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or any two $R^2$ or $R^3$, when directly attached to the same atom, forms a 3-7 membered cycloalkyl or heterocycloalkyl ring;

either: q is 0 and r is chosen from 3 and 4,
or: q is 1 and r is chosen from 2 and 3,
or: q is 2 and r is chosen from 1 and 2;

U is chosen from —$CH_2$— and —O—;

each $R^{4c}$ is independently chosen from —$CH_2$—. —CH($R^{6d}$)—, and —$C(R^{6d})_2$—;

each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;

each $R^{6d}$ is independently chosen from $C_{1-6}$alkyl, $C_{1-6}$alkoxy, and ($C_{1-6}$alkoxy)$C_{1-6}$alkyl;

each $R^7$ is independently chosen from $C_{1-6}$alkyl, halo$C_{1-6}$alkyl, aryl, heteroaryl, $C_{3-6}$cycloalkyl, heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

Embodiment 45: the compound of Embodiment 44, wherein U is —O—.

Embodiment 46: the compound of Embodiment 44, wherein U is —CH$_2$—.

Embodiment 47: the compound of any one of Embodiments 44-46, wherein q is 0.

Embodiment 48: the compound of any one of Embodiments 44-46, wherein q is 1.

Embodiment 49: the compound of any one of Embodiments 44-46, wherein q is 2.

Embodiment 50: the compound of Embodiment 47, wherein r is 4.

Embodiment 51: the compound of either one of Embodiments 47 and 48, wherein r is 3.

Embodiment 52: the compound of either one of Embodiments 48 and 49, wherein r is 2.

Embodiment 53: the compound of Embodiment 49, wherein r is 1.

Embodiment 54: the compound of any one of Embodiments 44-53, wherein each $R^{6d}$ is independently chosen from $C_{1-6}$alkyl and $C_{1-6}$alkoxy.

Embodiment 55: the compound of Embodiment 54, wherein $R^{6d}$ is $C_{1-6}$alkyl.

Embodiment 56: the compound of Embodiment 55, wherein each $R^{6d}$ is independently chosen from methyl and ethyl.

Embodiment 57: the compound of Embodiment 56, wherein each $R^{6d}$ is methyl.

Embodiment 58: the compound of any one of Embodiments 44-57, wherein each $R^{4c}$ is independently chosen from —CH$_2$— and —C($R^{6d}$)$_2$—.

Embodiment 59: the compound of Embodiment 58, wherein exactly one $R^{4c}$ is —C($R^{6d}$)$_2$—.

Provided herein is Embodiment 60: the compound of Embodiment 1 having structural Formula IIb:

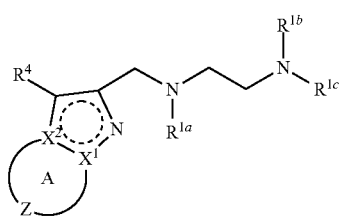

(IIb)

or a salt thereof, wherein:

A is a monocyclic heterocycloalkyl ring comprising 5 to 7 ring members including:
  $X^1$ and $X^2$,
  Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and
  all other ring members Y, which are chosen from —CH$_2$—, —CHR$^2$—, and —C(R$^2$)$_2$—;
$R^{1a}$, $R^{1b}$, and $R^{1c}$ are independently chosen from H and CH$_3$;
each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two $R^2$ or $R^3$, when directly attached to the same atom, forms a 3-7 membered cycloalkyl or heterocycloalkyl ring;

$R^4$ is chosen from:

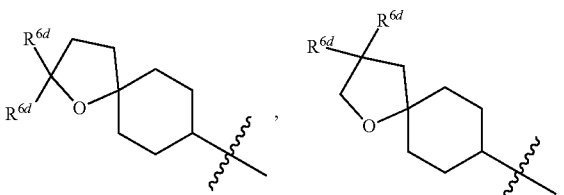

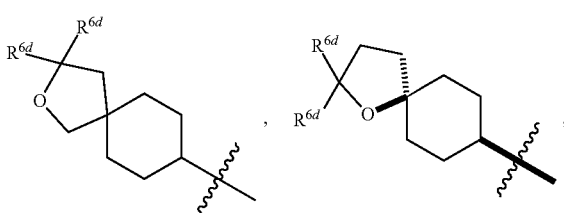

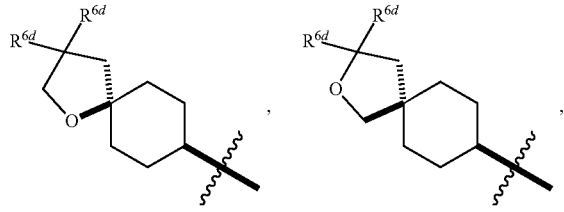

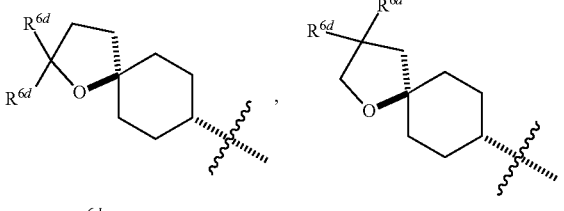

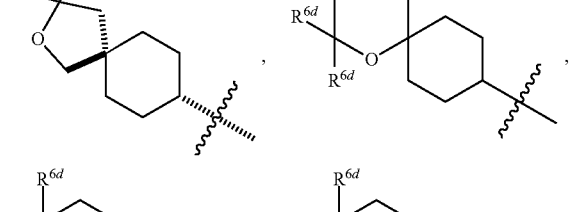

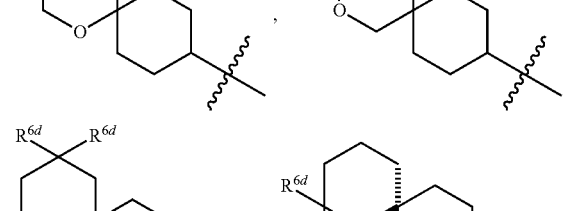

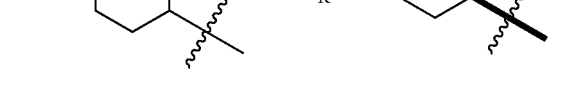

-continued

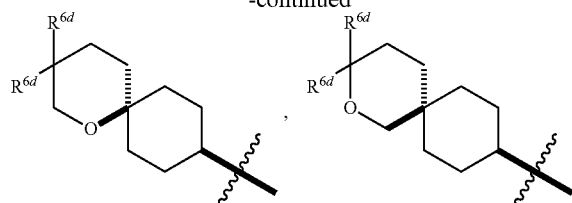

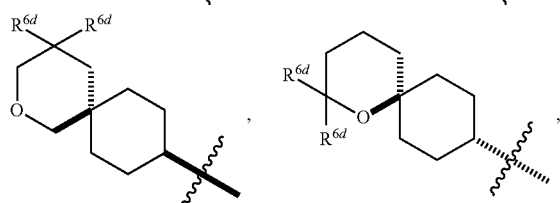

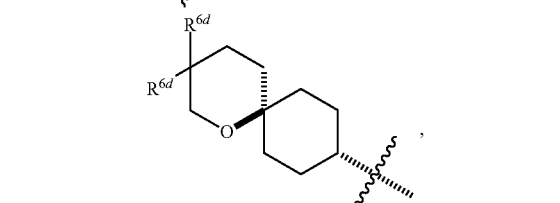

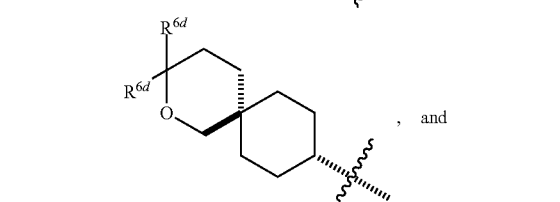

, and

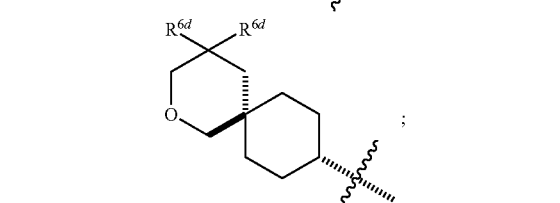

;

each $R^{4c}$ is independently chosen from —CH$_2$—, —CH(R$^{6d}$)—, and —C(R$^{6d}$)$_2$—;

each $R^{5a}$ and $R^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

$R^{6d}$ is chosen from C$_{1-6}$alkyl, C$_{1-6}$alkoxy, and (C$_{1-6}$alkoxy)C$_{1-6}$alkyl;

each $R^7$ is independently chosen from C$_{1-6}$alkyl, haloC$_{1-6}$alkyl, aryl, heteroaryl, C$_{3-6}$cycloalkyl, heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each $R^8$ is independently chosen from C$_{1-6}$alkyl, haloC$_{1-6}$alkyl, C$_{3-6}$cycloalkyl, and haloC$_{3-6}$cycloalkyl.

Embodiment 61: the compound of any one of Embodiments 60, wherein B is chosen from:

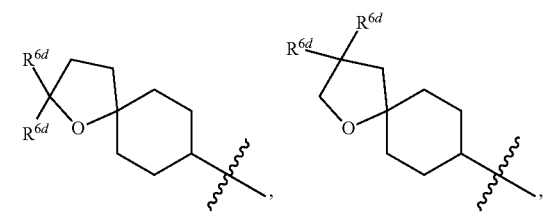

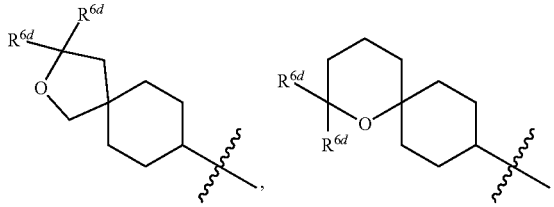

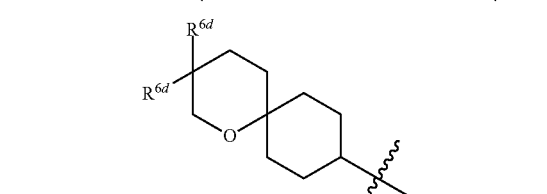

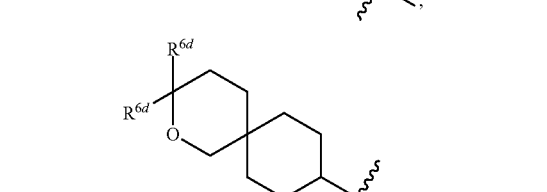

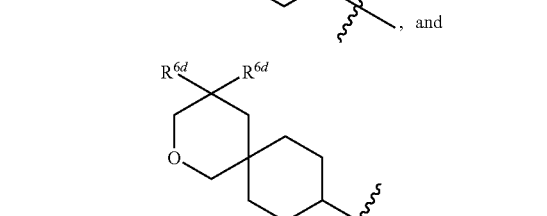

, and

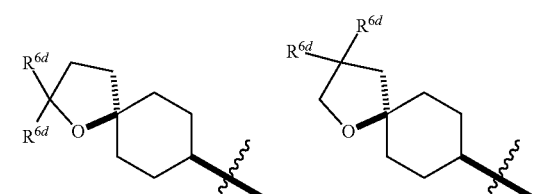

.

Embodiment 62: the compound of Embodiment 60, wherein $R^4$ is chosen from:

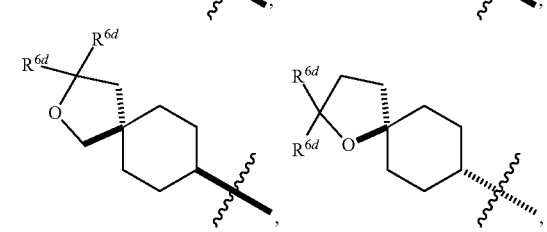

-continued

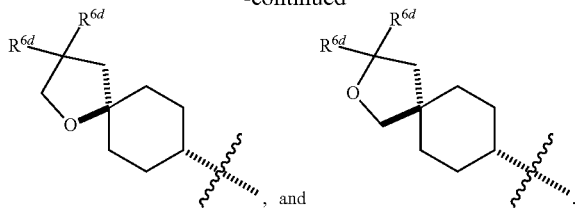

, and

Embodiment 63: the compound of any one of Embodiments 60, wherein B is chosen from:

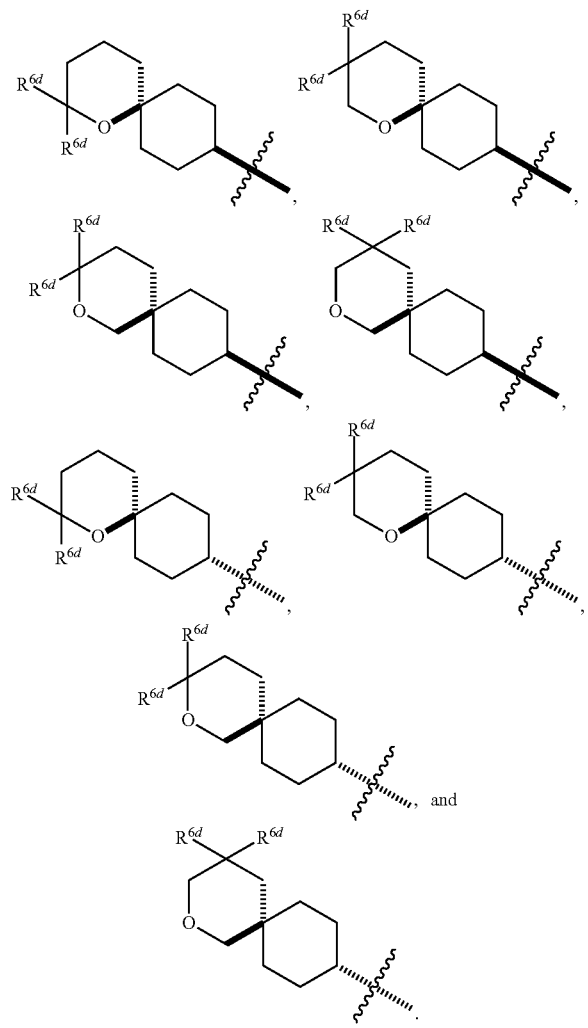

Embodiment 64: the compound of any one of Embodiments 44-63, wherein each $R^{6d}$ is independently chosen from $C_{1-6}$alkyl and $C_{1-6}$alkoxy.

Embodiment 65: the compound of Embodiment 54, wherein $R^{6d}$ is $C_{1-6}$alkyl.

Embodiment 66: the compound of Embodiment 55, wherein each $R^{6d}$ is independently chosen from methyl and ethyl.

Embodiment 67: the compound of Embodiment 56, wherein each $R^{6d}$ is methyl.

Embodiment 68: the compound of any one of Embodiments 44-57, wherein each $R^{4c}$ is independently chosen from —$CH_2$— and —$C(R^{6d})_2$—.

Embodiment 69: the compound of Embodiment 58, wherein exactly one $R^{4c}$ is —$C(R^{6d})_2$—.

Embodiment 70: the compound of any one of Embodiments 1-32, and 34-42, wherein each $R^6$ is independently chosen from $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, ($C_{3-6}$heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo.

Embodiment 71: the compound of any one of Embodiments 1-32, and 34-42, wherein each $R^6$ is independently chosen from $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo.

Embodiment 72: the compound of Embodiment 71, wherein each $R^6$ is independently chosen from $C_{1-6}$alkyl, halo$C_{1-6}$alkyl, ($C_{1-6}$alkoxy)$C_{1-6}$alkyl, (halo$C_{1-6}$alkoxy)$C_{1-6}$alkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, halo, hydroxy, and oxo.

Embodiment 73: the compound of Embodiment 72, wherein each $R^6$ is independently chosen from $C_{1-6}$alkyl, fluoro$C_{1-6}$alkyl, ($C_{1-6}$alkoxy)$C_{1-2}$alkyl, (fluoro$C_{1-6}$alkoxy)$C_{1-2}$alkyl, $COR^7$, COOH, $COOR^7$, $CONH_2$, $CONHR^7$, $CON(R^7)_2$, $NHCOR^7$, $SO_2R^7$, $NHSO_2R^7$, halo, hydroxy, and oxo.

Embodiment 74: the compound of Embodiment 73, wherein each $R^6$ is independently chosen from $C_{1-6}$alkyl, fluoro$C_{1-6}$alkyl, ($C_{1-6}$alkoxy)$C_{1-2}$alkyl, (fluoro$C_{1-6}$alkoxy)$C_{1-2}$alkyl, ($C_{3-6}$cycloalkyl)$C_{1-2}$alkyl, (3-6 membered heterocycloalkyl)$C_{1-2}$alkyl, (phenyl)$C_{1-2}$alkyl, (3-7 membered heteroaryl)$C_{1-2}$alkyl, (($C_{1-6}$alkyl)phenyl)$C_{1-2}$alkyl, (($C_{1-6}$alkyl)3-7 membered heteroaryl)$C_{1-2}$alkyl, $COR^7$, COOH, $COOR^7$, $CONH_2$, $CONHR^7$, $CON(R^7)_2$, $NHCOR^7$, $SO_2R^7$, $NHSO_2R^7$, halo, hydroxy, and oxo.

Embodiment 75: the compound of any one of Embodiments 71-74, wherein each $R^7$ is independently chosen from $C_{1-6}$alkyl, halo$C_{1-6}$alkyl, aryl, heteroaryl, $C_{3-6}$cycloalkyl, $C_{3-6}$heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups.

Embodiment 76: the compound of any one of Embodiments 71-74, wherein each $R^7$ is independently chosen from $C_{1-6}$alkyl, halo$C_{1-6}$alkyl, aryl, heteroaryl, $C_{3-6}$cycloalkyl, 3-6 membered heterocycloalkyl, (aryl)$C_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups.

Embodiment 77: the compound of Embodiment 76, wherein each R$^7$ is independently chosen from C$_{1-6}$alkyl, haloC$_{1-6}$alkyl, C$_{3-6}$cycloalkyl, 3-6 membered heterocycloalkyl, (cycloalkyl)C$_{1-6}$alkyl, and (heterocycloalkyl)C$_{1-6}$alkyl, any of which is optionally substituted with 1 or 2 R$^8$ groups.

Embodiment 78: the compound of Embodiment 77, wherein each R$^7$ is independently chosen from C$_{1-6}$alkyl, fluoroC$_{1-6}$alkyl, C$_{3-6}$cycloalkyl, 3-6 membered heterocycloalkyl, (cycloalkyl)C$_{1-2}$alkyl, and (heteroaryl)C$_{1-2}$alkyl, any of which is optionally substituted with 1 or 2 R$^8$ groups.

Embodiment 79: the compound of Embodiment 77, wherein each R$^7$ is independently chosen from C$_{1-6}$alkyl and haloC$_{1-6}$alkyl.

Embodiment 80: the compound of Embodiment 77, wherein each R$^7$ is independently chosen from C$_{1-6}$alkyl, C$_{3-6}$cycloalkyl, and 3-6 membered heterocycloalkyl, any of which is optionally substituted with 1 or 2 R$^8$ groups.

Embodiment 81: the compound of Embodiment 80, wherein each R$^7$ is C$_{1-6}$alkyl, and is optionally substituted with 1 or 2 R$^8$ groups.

Embodiment 82: the compound of any one of Embodiments 1-32, 34-81, wherein each R$^7$ is optionally substituted with 1 R$^8$ group.

Embodiment 83: the compound of Embodiment 82, wherein each R$^7$ is substituted with one R$^8$ group.

Embodiment 84: the compound of any one of Embodiments 1-32, 34-83, wherein each R$^8$ is independently chosen from C$_{1-6}$alkyl and fluoroC$_{1-6}$alkyl.

Embodiment 85: the compound of Embodiment 84, wherein each R$^8$ is C$_{1-4}$alkyl.

Embodiment 86: the compound of Embodiment 82, wherein each R$^7$ is unsubstituted with an R$^8$ group.

Embodiment 87: the compound of Embodiment 72, wherein each R$^6$ is independently chosen from C$_{1-6}$alkyl, fluoroC$_{1-6}$alkyl, (C$_{1-6}$alkoxy)C$_{1-2}$alkyl, (fluoroC$_{1-6}$alkoxy)C$_{1-2}$alkyl, (C$_{3-6}$cycloalkyl)C$_{1-2}$alkyl, (3-6 membered heterocycloalkyl)C$_{1-2}$alkyl, (phenyl)C$_{1-2}$alkyl, (3-7 membered heteroaryl)C$_{1-2}$alkyl, ((C$_{1-6}$alkyl)phenyl)C$_{1-2}$alkyl, and ((C$_{1-6}$alkyl)3-7 membered heteroaryl)C$_{1-2}$alkyl.

Embodiment 88: the compound of Embodiment 72, wherein each R$^6$ is independently chosen from H, C$_{1-6}$alkyl, C$_{1-6}$alkoxy, (C$_{1-6}$alkoxy)C$_{1-6}$alkyl, and (haloC$_{1-6}$alkoxy)C$_{1-6}$ alkyl.

Embodiment 89: the compound of Embodiment 88, wherein each R$^6$ is independently chosen from H, C$_{1-6}$alkyl, C$_{1-6}$alkoxy, (C$_{1-6}$alkoxy)C$_{1-6}$alkyl, and (fluoroC$_{1-6}$alkoxy)C$_{1-6}$alkyl.

Embodiment 90: the compound of Embodiment 88, wherein each R$^6$ is independently chosen from H, C$_{1-4}$alkyl, C$_{1-4}$alkoxy, C$_{1-4}$alkoxymethyl, and C$_{1-4}$alkoxyethyl.

Embodiment 91: the compound of Embodiment 17, wherein:

R$^4$ is chosen from:

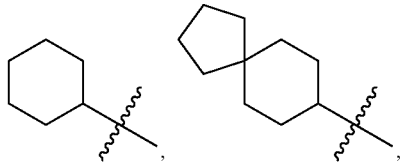

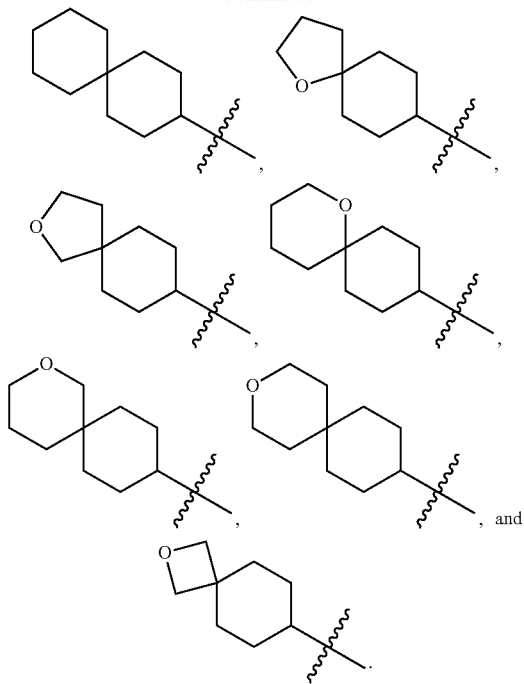

Embodiment 92: the compound of Embodiment 17, wherein:

R$^4$ is chosen from:

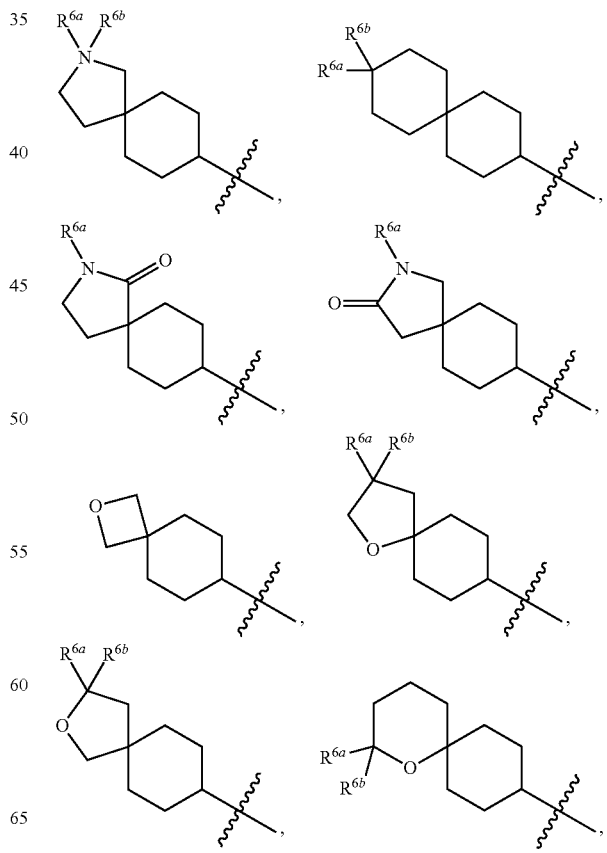

-continued

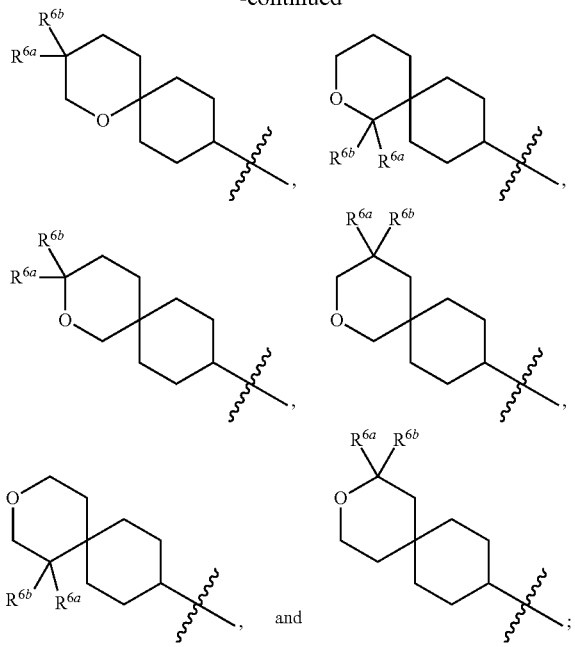

and

R$^{6a}$ and R$^{6b}$ are independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (3-6 membered heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo; and each R$^7$ is independently chosen from C$_{1-6}$alkyl, haloC$_{1-6}$alkyl, aryl, heteroaryl, C$_{3-6}$cycloalkyl, 3-6 membered heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups;

Provided herein is Embodiment 93: the compound of Embodiment 1 having structural Formula III:

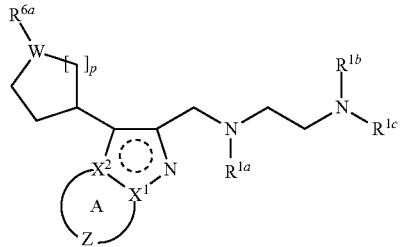

(III)

or a salt thereof, wherein:

A is a monocyclic heterocycloalkyl ring comprising 5 to 7 ring members including:

X$^1$ and X$^2$,

Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$^1$ is C and X$^2$ is N, or X$^1$ is N and X$^2$ is C;

W is chosen from C(R$^{6b}$) and N;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when attached directly to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

R$^{6a}$ and R$^{6b}$ are independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (3-6 membered heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo; and each R$^7$ is independently chosen from C$_{1-6}$alkyl, haloC$_{1-6}$alkyl, aryl, heteroaryl, C$_{3-6}$cycloalkyl, 3-6 membered heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each R$^8$ is independently chosen from C$_{1-6}$alkyl, haloC$_{1-6}$alkyl, C$_{3-6}$cycloalkyl, and haloC$_{3-6}$cycloalkyl; and p is chosen from 1 and 2.

The disclosure provides the following further embodiments:

Embodiment 94: the compound of Embodiment 93, wherein p is 1.

Embodiment 95: the compound of Embodiment 93, wherein p is 2.

Embodiment 96: the compound of any one of Embodiments 93-95, wherein W is C(R$^{6b}$).

Embodiment 97: the compound of any one of Embodiments 93-95, wherein W is N.

Embodiment 98: the compound of any one of Embodiments 93-97, wherein Y is chosen from —CH$_2$— and —CHR$^2$—.

Embodiment 99: the compound of Embodiment 98, wherein each Y is —CH$_2$—.

Provided herein is Embodiment 100: the compound of Embodiment 1 having structural Formula IV:

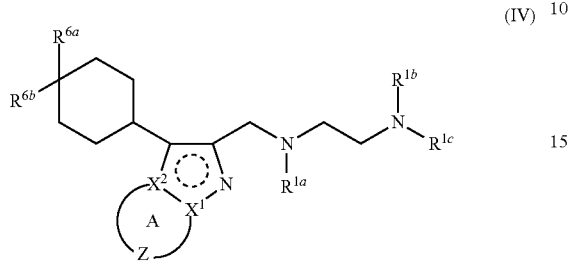

(IV)

or a salt thereof, wherein:

A is a monocyclic heterocycloalkyl ring comprising 5 to 7 ring members including:
X$^1$ and X$^2$,
Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and
all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$_1$ is C and X$_2$ is N, or X$_1$ is N and X$_2$ is C;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when attached directly to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

R$^{6a}$ and R$^{6b}$ are independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)-C$_{3-6}$cycloalkyl, (C$_{3-6}$cycloalkyl)C$_{1-6}$alkyl, (3-6 membered heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)-C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo;

each R$^7$ is independently chosen from C$_{1-6}$alkyl, haloC$_{1-6}$alkyl, aryl, heteroaryl, C$_{3-6}$cycloalkyl, 3-6 membered heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each R$^8$ is independently chosen from C$_{1-6}$alkyl, haloC$_{1-6}$alkyl, C$_{3-6}$cycloalkyl, and haloC$_{3-6}$cycloalkyl.

Provided herein is Embodiment 101: the compound of Embodiment 100 having structural Formula IVa:

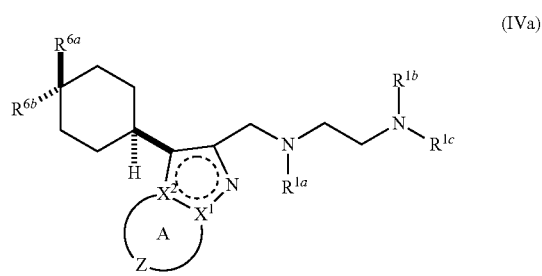

(IVa)

or a salt thereof, wherein:

A is a monocyclic heterocycloalkyl ring comprising 5 to 7 ring members including:
X$^1$ and X$^2$,
Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and
all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$_1$ is C and X$_2$ is N, or X$_1$ is N and X$_2$ is C;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when attached directly to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

R$^{6a}$ is chosen from H, C$_{1-6}$alkyl and haloC$_{1-6}$alkyl;

R$^{6b}$ is chosen from (C$_{1-6}$alkoxy)C$_{1-6}$alkyl, (fluoroC$_{1-6}$alkoxy)C$_{1-6}$alkyl; and each R$^7$ is independently chosen from C$_{1-6}$alkyl, haloC$_{1-6}$alkyl, aryl, heteroaryl, C$_{3-6}$cycloalkyl, 3-6 membered heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

Provided herein is Embodiment 102: the compound of Embodiment 100 having structural Formula IVb:

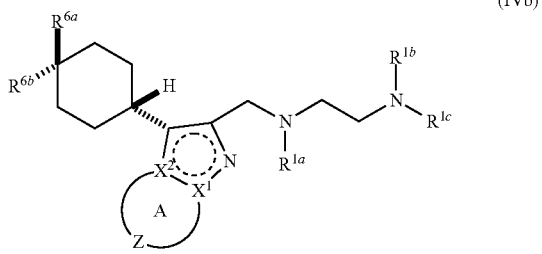

(IVb)

or a salt thereof, wherein:

A is a monocyclic heterocycloalkyl ring comprising 5 to 7 ring members including:
$X^1$ and $X^2$,
Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and
all other ring members Y, which are chosen from —$CH_2$—, —$CHR^2$—, and —$C(R^2)_2$—;
$R^{1a}$, $R^{1b}$, and $R^{1c}$ are independently chosen from H and $CH_3$;
either $X_1$ is C and $X_2$ is N, or $X_1$ is N and $X_2$ is C;
each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or
any two $R^2$ or $R^3$, when directly attached to the same atom, forms a 3-7 membered cycloalkyl or heterocycloalkyl ring;
each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl, or
$R^{5a}$ and $R^{5b}$, when attached directly to the same atom, forms a 3-7 membered cycloalkyl or heterocycloalkyl ring;
$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;
$R^{6a}$ is chosen from H, $C_{1-6}$alkyl and halo$C_{1-6}$alkyl;
$R^{6b}$ is chosen from ($C_{1-6}$alkoxy)$C_{1-6}$alkyl, (fluoro$C_{1-6}$alkoxy)$C_{1-6}$alkyl; and
each $R^7$ is independently chosen from $C_{1-6}$alkyl, halo$C_{1-6}$alkyl, aryl, heteroaryl, $C_{3-6}$cycloalkyl, 3-6 membered heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

The disclosure provides the following further embodiments:

Embodiment 103: the compound of either one of Embodiments 101 and 102, wherein $R^{6a}$ is chosen from methyl, ethyl, 2,2,2-trifluoroethyl, and 3,3,3-trifluoropropyl.

Embodiment 104: the compound of any one of Embodiments 101-103, wherein $R^{6b}$ is chosen from ($C_{1-2}$alkoxy)$C_{1-2}$alkyl, (fluoro$C_{1-2}$alkoxy)$C_{1-2}$alkyl.

Embodiment 105: the compound of any Embodiment 104, wherein $R^{6b}$ is chosen from methoxymethyl, ethoxymethyl, and 2,2,2-trifluoroethoxymethyl.

Embodiment 106: the compound of any one of Embodiments 100-105, wherein Y is chosen from —$CH_2$— and —$CHR^2$—.

Embodiment 107: the compound of Embodiment 106, wherein each Y is —$CH_2$—.

Provided herein is Embodiment 108: the compound of Embodiment 1 having structural Formula V:

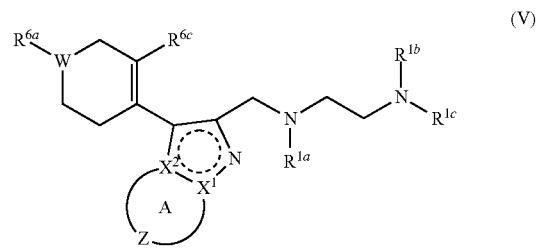

(V)

or a salt thereof, wherein:

A is a monocyclic heterocycloalkyl ring comprising 5 to 7 ring members including:
$X^1$ and $X^2$,
Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and
all other ring members Y, which are chosen from —$CH_2$—, —$CHR^2$—, and —$C(R^2)_2$—;
$R^{1a}$, $R^{1b}$, and $R^{1c}$ are independently chosen from H and $CH_3$;
either $X^1$ is C and $X^2$ is N, or $X^1$ is N and $X^2$ is C;
W is chosen from $C(R^{6b})$ and N;
each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or
any two $R^2$ or $R^3$, when directly attached to the same atom, forms a 3-7 membered cycloalkyl or heterocycloalkyl ring;
each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl, or
$R^{5a}$ and $R^{5b}$, when attached directly to the same atom, forms a 3-7 membered cycloalkyl or heterocycloalkyl ring;
$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl;

$C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;

$R^{6c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, ((($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

$R^{6a}$ and $R^{6b}$ are independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)-$C_{3-6}$cycloalkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo; and each $R^7$ is independently chosen from $C_{1-6}$alkyl, halo$C_{1-6}$alkyl, aryl, heteroaryl, $C_{3-6}$cycloalkyl, 3-6 membered heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

The disclosure provides the following further embodiments:

Embodiment 109: The compound of Embodiment 108, wherein $R^{6c}$ is chosen from H, $C_{1-6}$alkyl, and halo.

Embodiment 110: The compound of Embodiment 109, wherein $R^{6c}$ is H.

Embodiment 111: the compound of any one of Embodiments 108-110, wherein Y is chosen from —$CH_2$— and —$CHR^2$—.

Embodiment 112: the compound of Embodiment 111, wherein each Y is —$CH_2$—.

Embodiment 113: The compound of any one of Embodiments 92-112, wherein:

$R^{6a}$ and $R^{6b}$ are independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)-$C_{3-6}$cycloalkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)-$C_{1-6}$alkyl, $COOR^7$, $CONH_2$, $CONHR^7$, $CON(R^7)_2$, $NHCOR^7$, $NR^7COR^7$, $SO_2R^7$, $SO_2NHR^7$, $SO_2N(R^7)_2$, $NHSO_2R^7$, $NR^7SO_2R^7$, carboxy, cyano, halo, hydroxy, and oxo; and each $R^7$ is independently chosen from $C_{1-6}$alkyl, halo$C_{1-6}$alkyl, aryl, heteroaryl, $C_{3-6}$cycloalkyl, 3-6 membered heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 $R^8$ group; and each $R^8$ is independently chosen from $C_{1-6}$alkyl and halo$C_{1-6}$alkyl.

Embodiment 114: The compound of Embodiment 113, wherein:

$R^{6a}$ and $R^{6b}$ are independently chosen from H, $C_{1-4}$alkyl, halo$C_{1-4}$alkyl, ($C_{1-4}$alkoxy)-$C_{1-2}$alkyl, (halo$C_{1-4}$alkoxy)$C_{1-2}$alkyl, ($C_{3-6}$cycloalkyl)$C_{1-2}$alkyl, (3-6 membered heterocycloalkyl)$C_{1-2}$alkyl, (monocyclic aryl)$C_{1-2}$alkyl, (monocyclic heteroaryl)$C_{1-2}$alkyl, (($C_{1-2}$ alkyl)monocyclic aryl)$C_{1-2}$alkyl, (($C_{1-2}$alkyl) monocyclic heteroaryl)$C_{1-2}$alkyl, $COOR^7$, $CONH_2$, $CONHR^7$, $CON(R^7)_2$, $NHCOR^7$, $NR^7COR^7$, $SO_2R^7$, $SO_2NHR^7$, $SO_2N(R^7)_2$, $NHSO_2R^7$, and $NR^7SO_2R^7$; and each $R^7$ is independently chosen from $C_{1-4}$alkyl, halo$C_{1-4}$alkyl, aryl, heteroaryl, $C_{3-6}$cycloalkyl, 3-6 membered heterocycloalkyl, (aryl)$C_{1-2}$alkyl, (heteroaryl)$C_{1-2}$alkyl, (cycloalkyl)$C_{1-2}$alkyl, and (heterocycloalkyl)$C_{1-2}$alkyl, any of which is optionally substituted with 1 $R^8$ group; and each $R^8$ is independently chosen from $C_{1-4}$alkyl and halo$C_{1-4}$alkyl.

Embodiment 115: The compound of Embodiment 113, wherein:

$R^{6a}$ and $R^{6b}$ are independently chosen from H, $C_{1-4}$alkyl, halo$C_{1-4}$alkyl, ($C_{1-4}$alkoxy)-$C_{1-2}$alkyl, (fluoro$C_{1-4}$alkoxy)$C_{1-2}$alkyl, ($C_{3-6}$cycloalkyl)$C_{1-2}$alkyl, (3-6 membered heterocycloalkyl)$C_{1-2}$alkyl, (phenyl)methyl, (monocyclic heteroaryl)methyl, ((methyl)monocyclic aryl)methyl, ((methyl)monocyclic heteroaryl)methyl, $COOR^7$, $CONH_2$, $CONHR^7$, $CON(R^7)_2$, $NHCOR^7$, $NR^7COR^7$, $5O2R^7$, $SO_2NHR^7$, $SO_2N(R^7)_2$, $NHSO_2R^7$, and $NR^7SO_2R^7$; and each $R^7$ is independently chosen from $C_{1-4}$alkyl, halo$C_{1-4}$alkyl, monocyclic aryl, and monocyclic heteroaryl.

Embodiment 116: The compound of Embodiment 113, wherein $R^{6a}$ and $R^{6b}$ are chosen from H, $C_{1-6}$alkyl, $C_{1-6}$alkoxy, ($C_{1-6}$alkoxy)$C_{1-6}$alkyl, and (fluoro$C_{1-6}$alkoxy)$C_{1-6}$alkyl.

Embodiment 117: The compound of Embodiment 113, wherein $R^{6a}$ and $R^{6b}$ are chosen from H, $C_{1-6}$alkyl, $C_{1-6}$alkoxy, ($C_{1-6}$alkoxy)$C_{1-6}$alkyl, and (fluoro$C_{1-6}$alkoxy)$C_{1-6}$alkyl.

Embodiment 118: The compound of Embodiment 113, wherein $R^{6a}$ and $R^{6b}$ are chosen from H, $C_{1-4}$alkyl, $C_{1-4}$alkoxy, $C_{1-4}$alkoxymethyl, and $C_{1-4}$alkoxyethyl.

Embodiment 119: The compound of Embodiment 113, wherein $R^{6a}$ and $R^{6b}$ are chosen from H, $C_{1-4}$alkyl, $C_{1-4}$alkoxy, (fluoro$C_{1-4}$alkoxy)methyl, and (fluoro$C_{1-4}$alkoxy)ethyl.

Embodiment 120: The compound of Embodiment 113, wherein $R^{6a}$ and $R^{6b}$ are chosen from $C_{1-4}$alkyl and $C_{1-4}$alkoxymethyl, and (fluoro$C_{1-4}$alkoxy)methyl.

Embodiment 121: The compound of Embodiment 113, wherein exactly one of $R^{6a}$ and $R^{6b}$ is $C_{1-4}$alkyl.

Embodiment 122: The compound of Embodiment 121, wherein exactly one of $R^{6a}$ and $R^{6b}$ is ethyl.

Embodiment 123: The compound of Embodiment 121, wherein exactly one of $R^{6a}$ and $R^{6b}$ is methyl.

Embodiment 124: The compound of any one of Embodiments 120-123, wherein $R^{6a}$ is (methoxy)methyl.

Embodiment 125: The compound of any one of Embodiments 120-123, wherein $R^{6b}$ is (methoxy)methyl.

Embodiment 126: The compound of any one of Embodiments 120-123, wherein $R^{6a}$ is (ethoxy)methyl.

Embodiment 127: The compound of any one of Embodiments 120-123, wherein $R^{6b}$ is (ethoxy)methyl.

Embodiment 128: The compound of any one of Embodiments 120-123, wherein $R^{6a}$ is (2,2,2-trifluoroethoxy)methyl.

Embodiment 129: The compound of any one of Embodiments 120-123, wherein $R^{6b}$ is (2,2,2-trifluoroethoxy)methyl.

Embodiment 130: the compound of any one of Embodiments 1-129, wherein Z is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, and —O—.

Embodiment 131: the compound of Embodiment 130, wherein Z is chosen from —CH$_2$—, —CHR$^3$—, and —C(R$^3$)$_2$—.

Embodiment 132: the compound of Embodiment 131, wherein Z is chosen from —CH$_2$—, —CHR$^3$—, and —C(R$^3$)$_2$—.

Embodiment 133: the compound of Embodiment 132, wherein Z is —CHR$^3$—.

Embodiment 134: the compound of Embodiment 132, wherein Z is —C(R$^3$)$_2$—.

Embodiment 135: the compound of any one of Embodiments 1-132, wherein R$^3$ is chosen from cyano, halo, hydroxy, C$_{1-6}$alkyl, C$_{1-6}$haloalkyl, C$_{1-6}$hydroxyalkyl, OR$^{5a}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$.

Embodiment 136: the compound of 135, wherein R$^3$ is chosen from cyano, halo, hydroxy, C$_{1-6}$alkyl, C$_{1-6}$haloalkyl, C$_{1-6}$hydroxyalkyl, and OR$^{5a}$.

Embodiment 137: the compound of 136, wherein R$^3$ is cyano.

Embodiment 138: the compound of 136, wherein R$^3$ is chosen from fluoro, chloro, and bromo.

Embodiment 139: the compound of 138, wherein R$^3$ is chosen from fluoro and chloro.

Embodiment 140: the compound of 139, wherein R$^3$ is fluoro.

Embodiment 141: the compound of 139, wherein R$^3$ is chloro.

Embodiment 142: the compound of 136, wherein R$^3$ is hydroxy.

Embodiment 143: the compound of 136, wherein R$^3$ is C$_{1-6}$alkyl.

Embodiment 144: the compound of 143, wherein R$^3$ is methyl.

Embodiment 145: the compound of 136, wherein R$^3$ is C$_{1-6}$halolkyl.

Embodiment 146: the compound of 145, wherein R$^3$ is C$_{1-6}$fluoroalkyl.

Embodiment 147: the compound of 146, wherein R$^3$ is trifluoromethyl.

Embodiment 148: the compound of 136, wherein R$^3$ is C$_{1-6}$hydroxyakyl.

Embodiment 149: the compound of 148, wherein R$^3$ is hydroxymethyl.

Embodiment 150: the compound of Embodiment 133, wherein R$^3$ is OH.

Embodiment 151: the compound of Embodiment 133, wherein R$^3$ is CH$_3$.

Embodiment 152: the compound of Embodiment 133, wherein R$^3$ is CF$_3$.

Embodiment 153: the compound of Embodiment 133, wherein R$^3$ is CH$_2$OH.

Embodiment 154: the compound of Embodiment 134, wherein Z is —CF$_2$—

Embodiment 155: the compound of Embodiment 134, wherein Z is —C(CH$_3$)$_2$—.

Embodiment 156: the compound of Embodiment 134, wherein: Z is

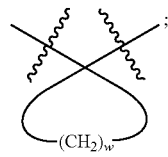

and w is chosen from 2, 3, 4, 5, and 6.

Embodiment 157: the compound of Embodiment 156, wherein w is chosen from 2, 3, 4, and 5.

Embodiment 158: the compound of Embodiment 157, wherein w is chosen from 2, 3, and 4.

Embodiment 159: the compound of Embodiment 158, wherein w is chosen from 2 and 3.

Embodiment 160: the compound of Embodiment 159, wherein w is 2.

Embodiment 161: the compound of Embodiment 156, wherein Z is

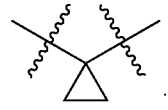 [SMILES: *C1(*)CC1]

Embodiment 162: the compound of Embodiment 131, wherein Z is —CH$_2$—.

Embodiment 163: the compound of any one of Embodiments 1-162, wherein R$^{1a}$ is H.

Embodiment 164: the compound of any one of Embodiments 1-162, wherein R$^{1a}$ is CH$_3$.

Embodiment 165: the compound of any one of Embodiments 1-164, wherein at least one of R$^{1b}$ and R$^{1c}$ is H.

Embodiment 166: the compound of Embodiment 165, wherein exactly one of R$^{1b}$ and R$^{1c}$ is H.

Embodiment 167: the compound of any one of Embodiments 1-166, wherein X$^1$ is C and X$^2$ is N.

Embodiment 168: the compound of any one of Embodiments 1-166, wherein X$^1$ is N and X$^2$ is C.

Embodiment 169: the compound of Embodiment 1, chosen from:

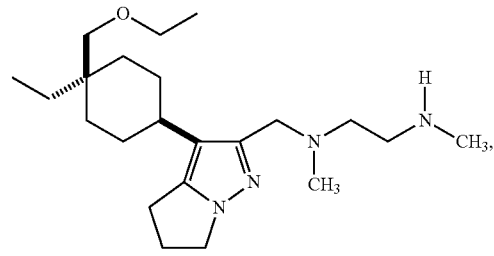

-continued
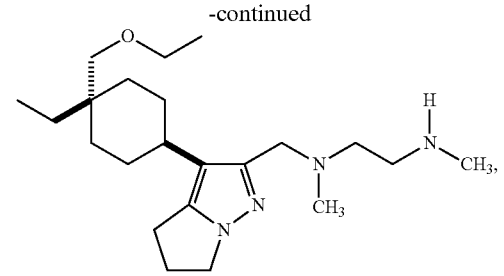
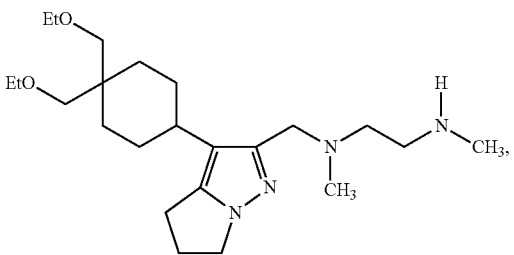
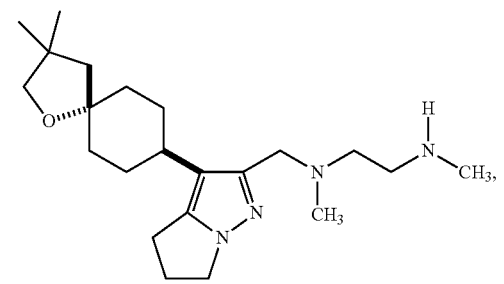
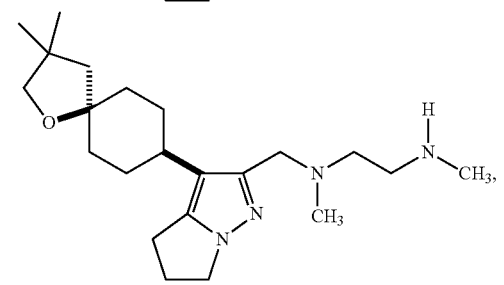
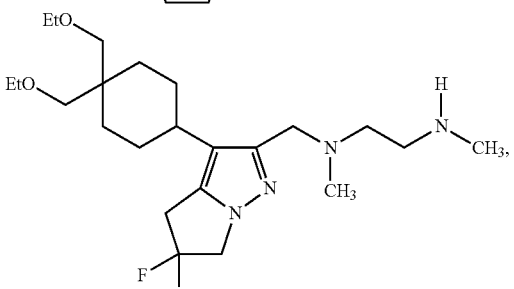
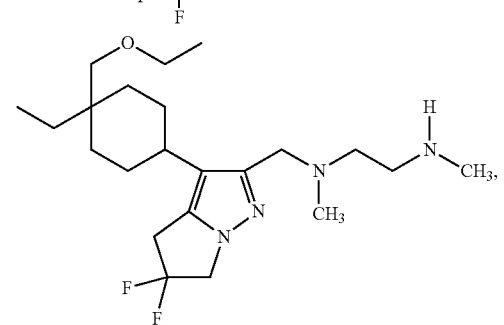
-continued
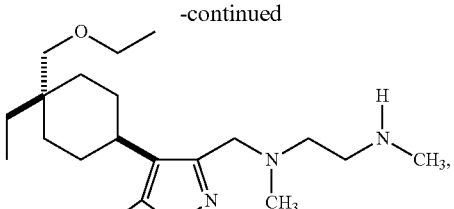
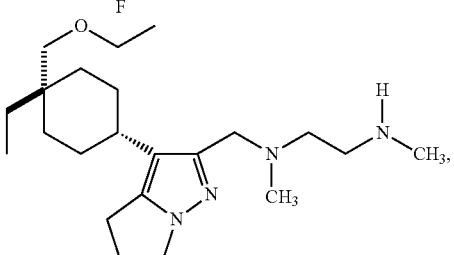
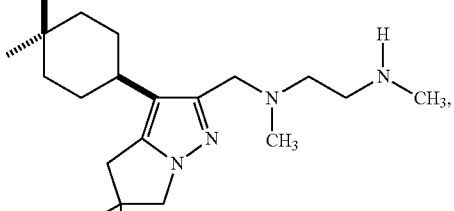
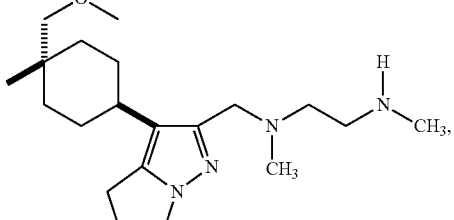
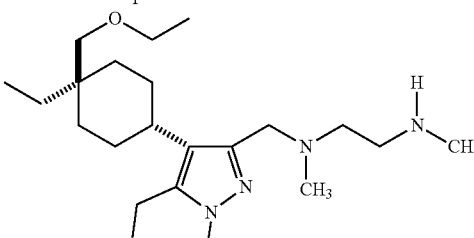
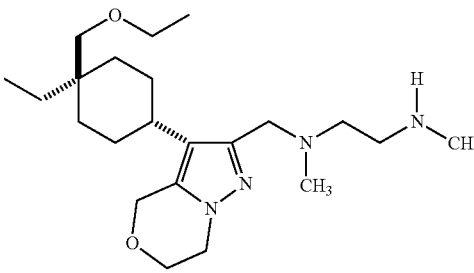

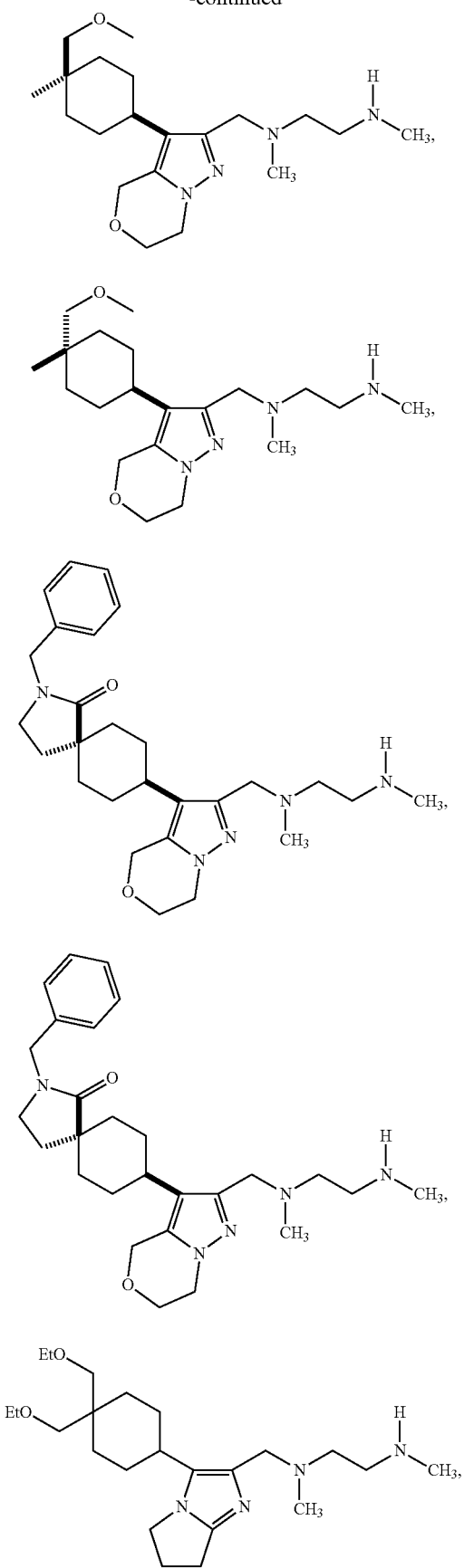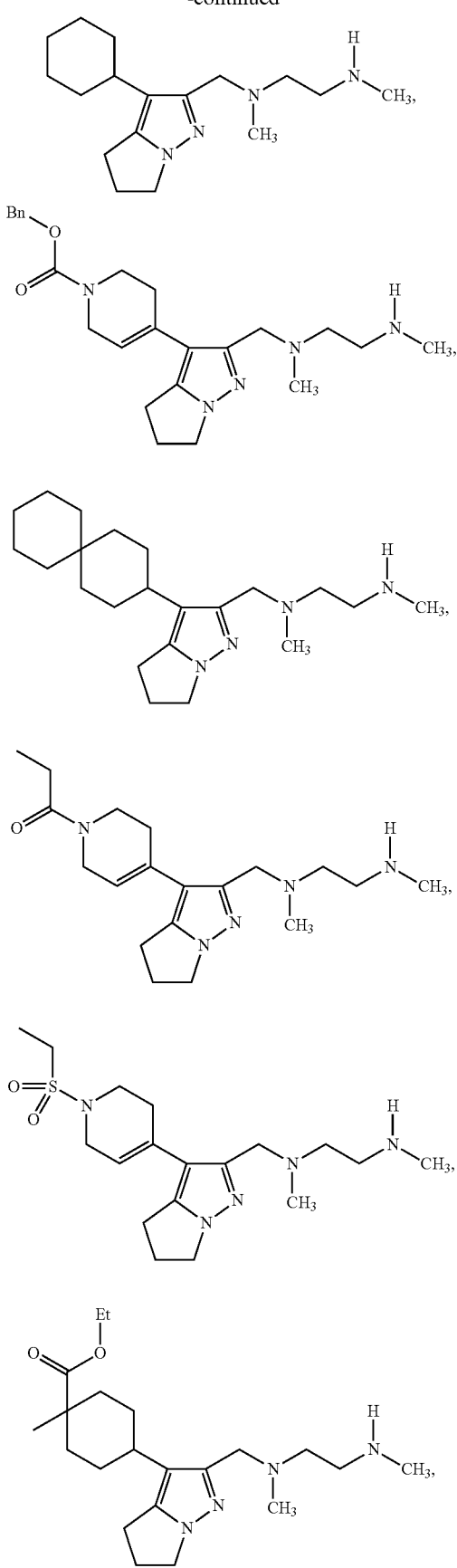

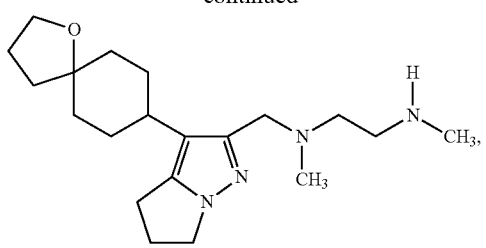
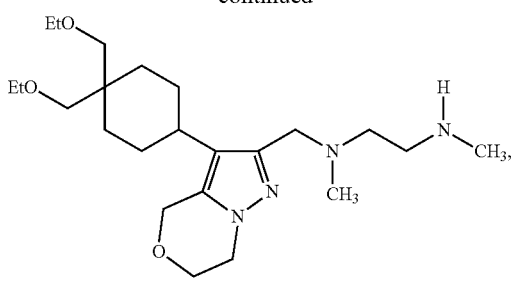
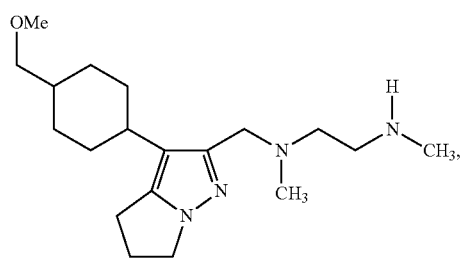
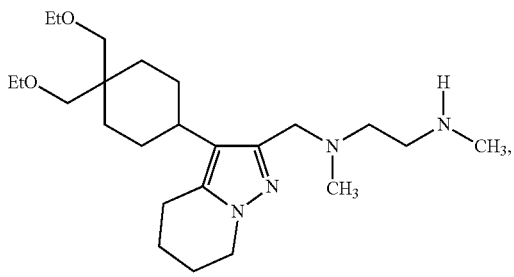
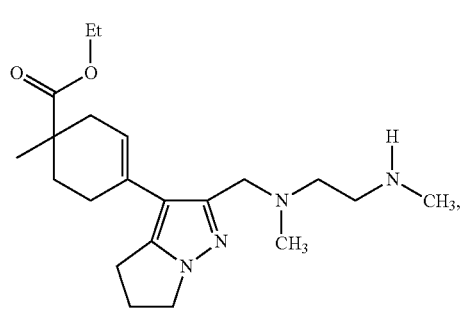
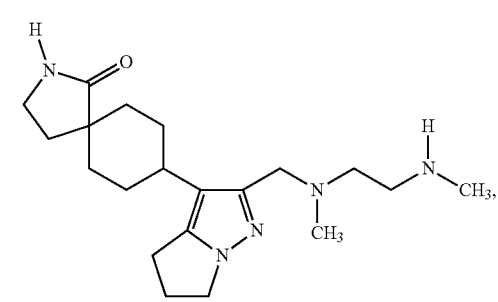
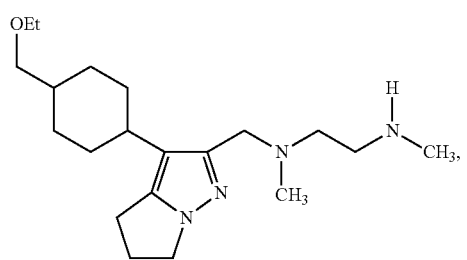
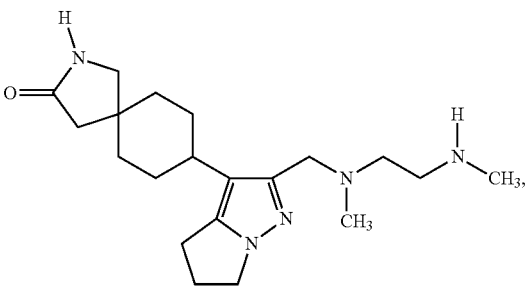
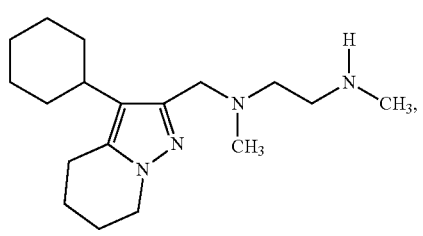
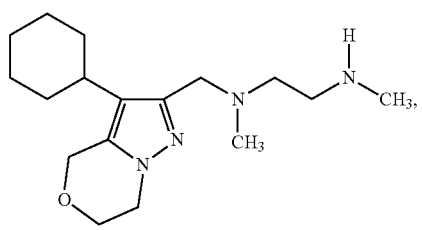
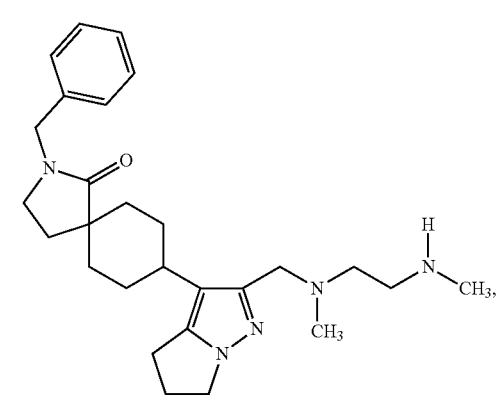

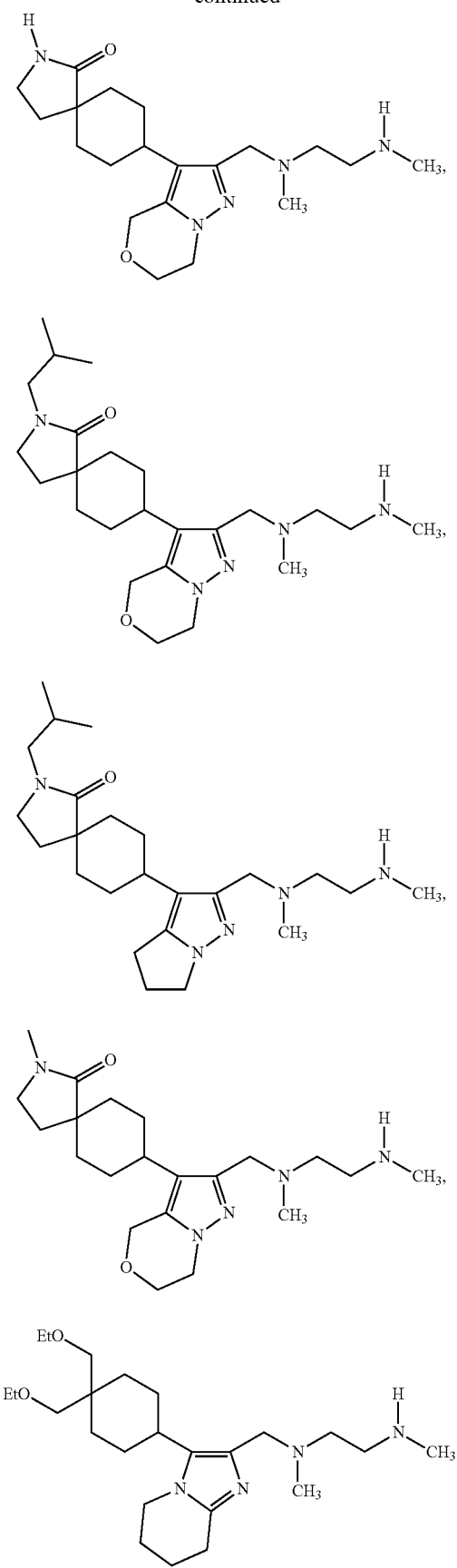
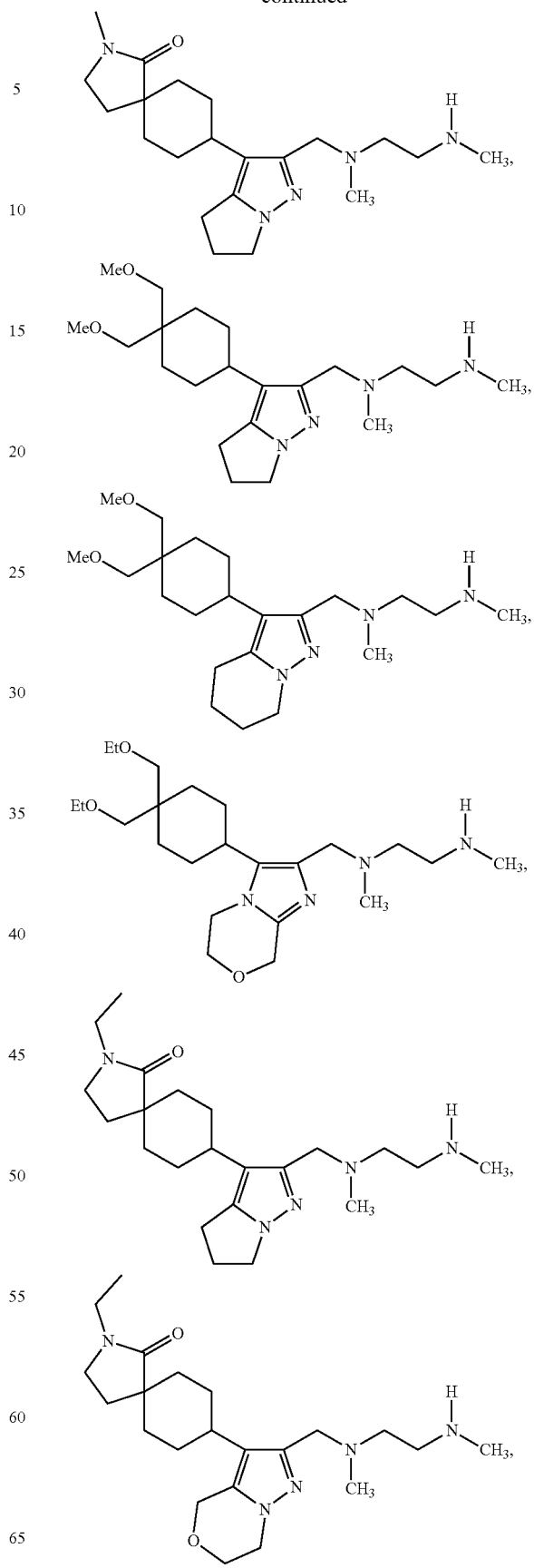

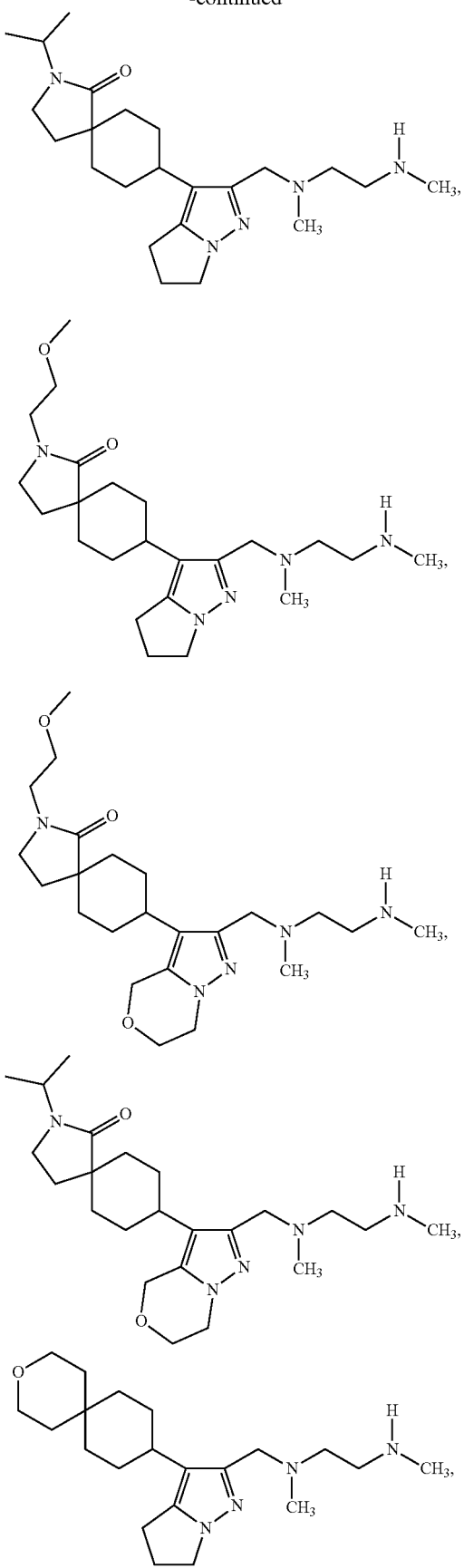
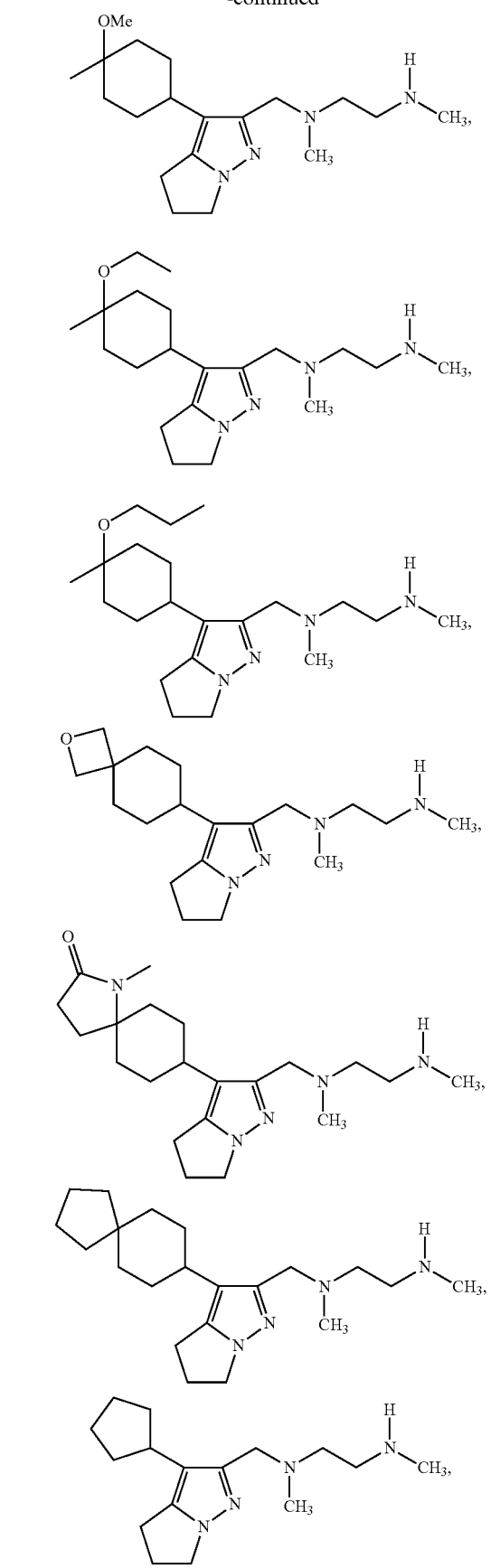

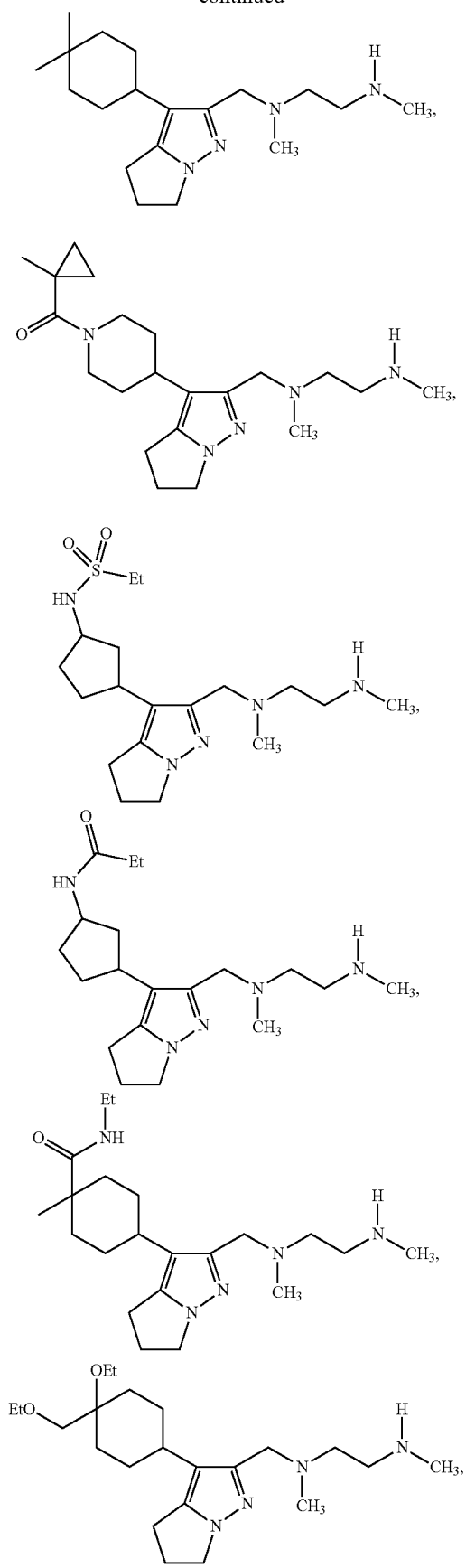
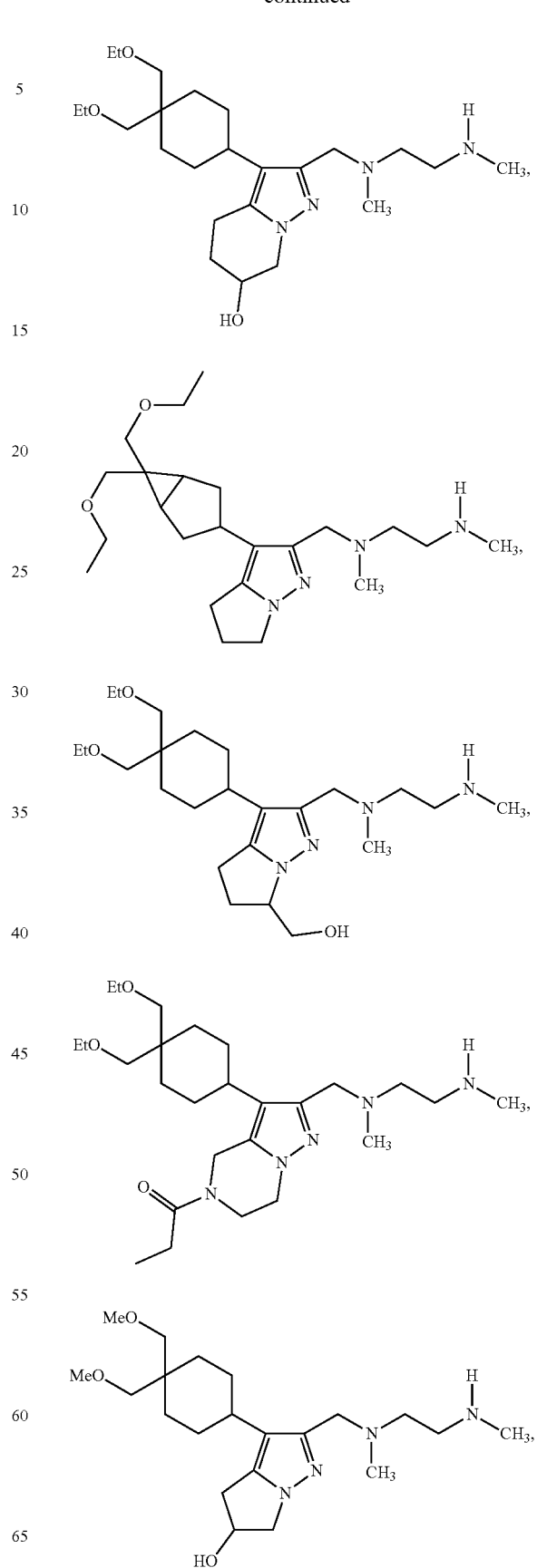

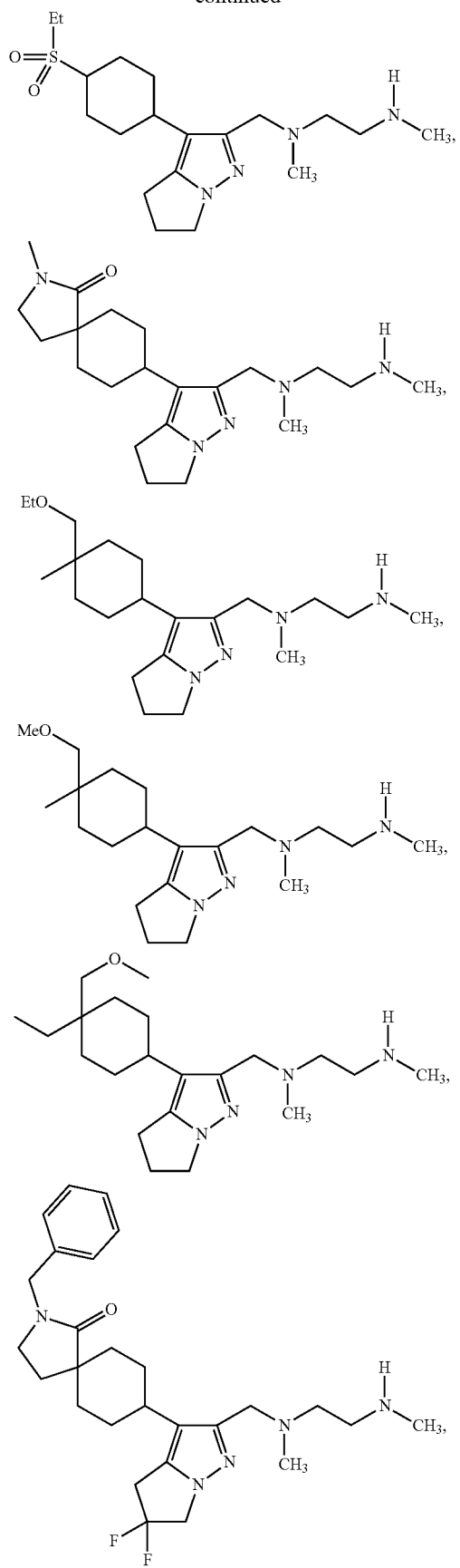
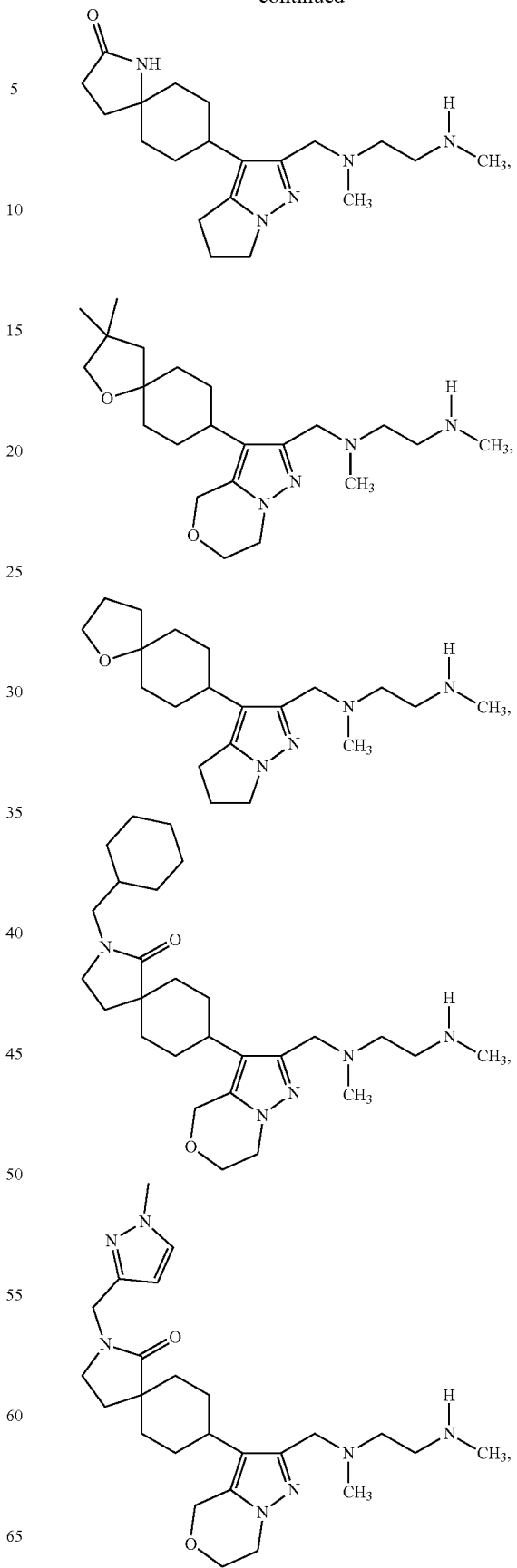

41
-continued
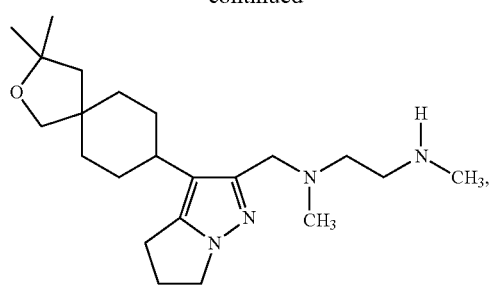
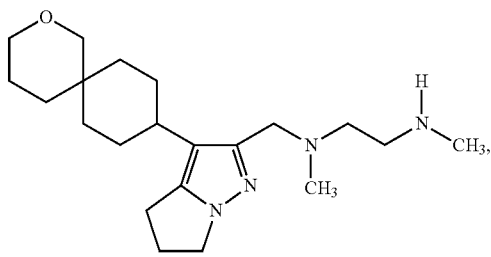
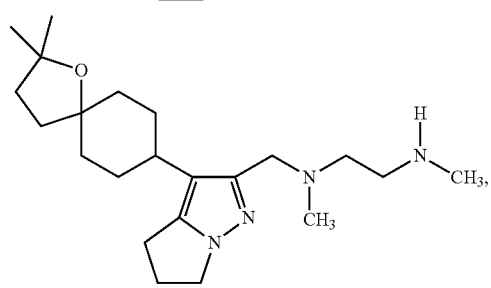
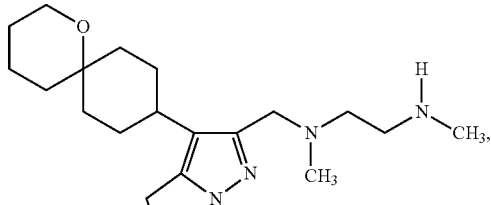
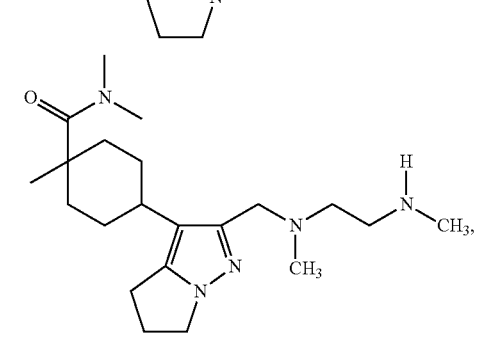
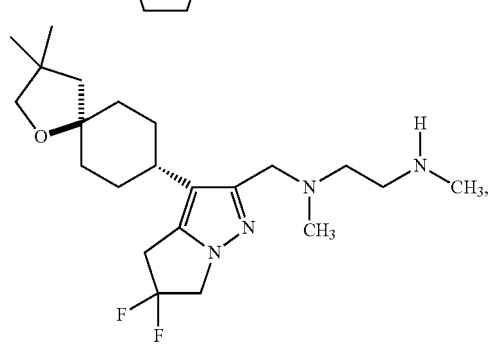
42
-continued
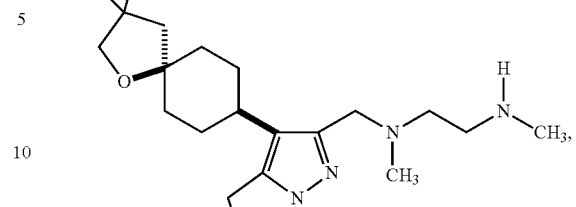
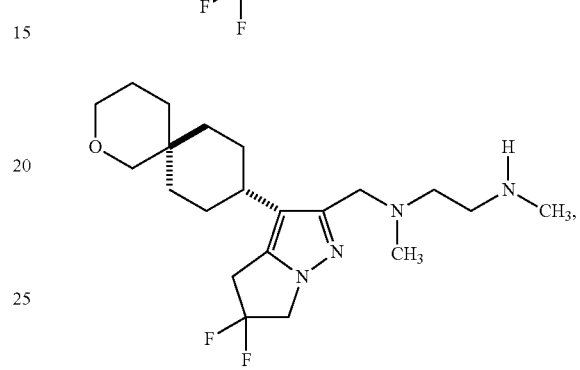
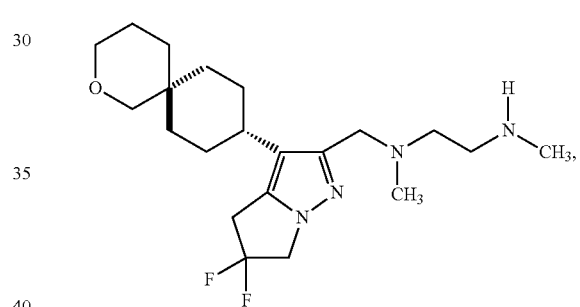
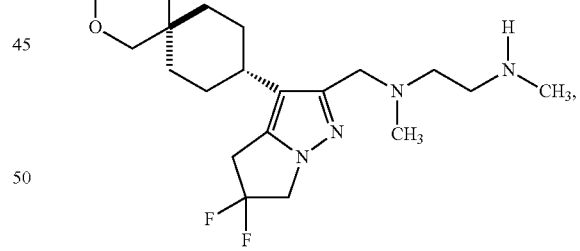
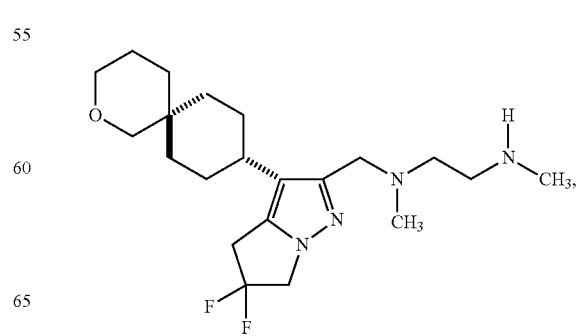

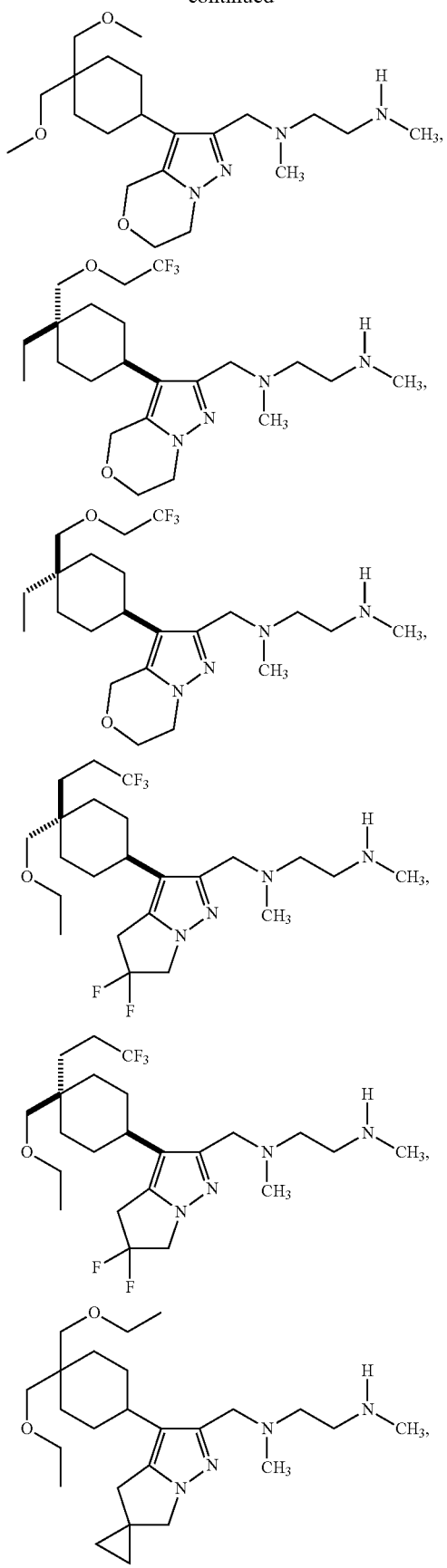
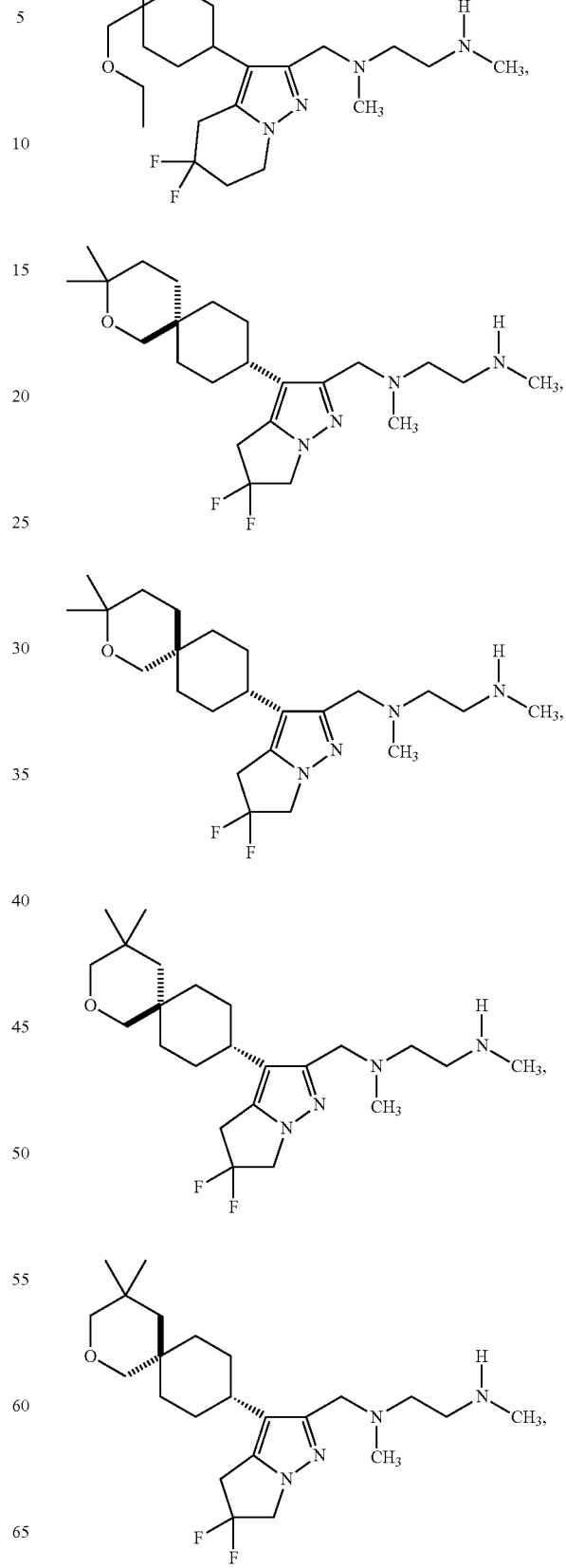

45
-continued
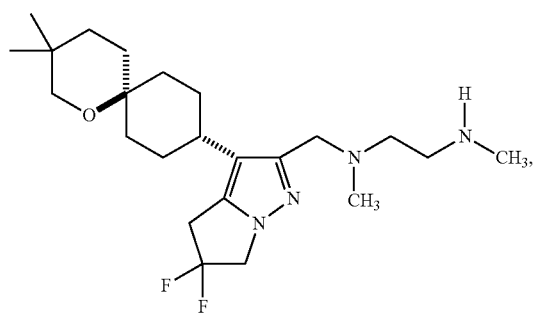
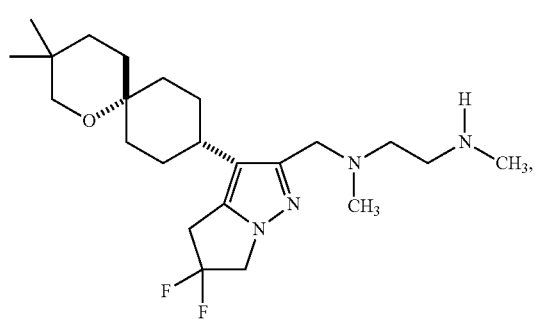
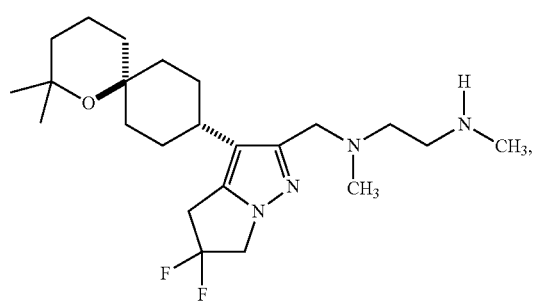
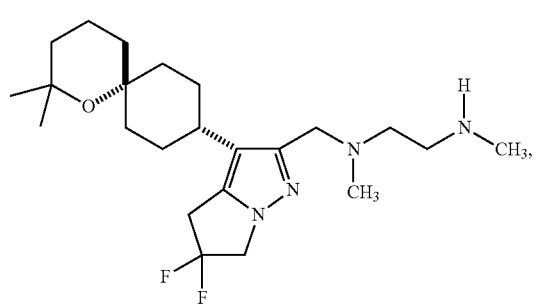
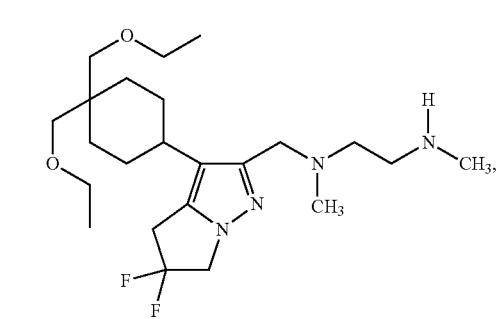
46
-continued
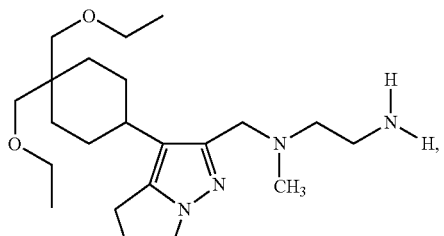
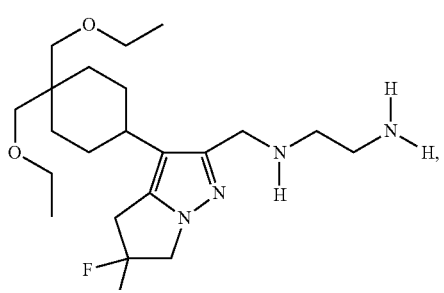
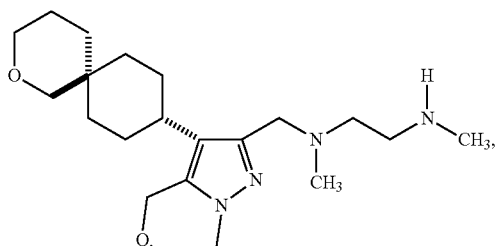
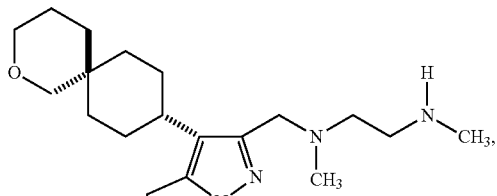
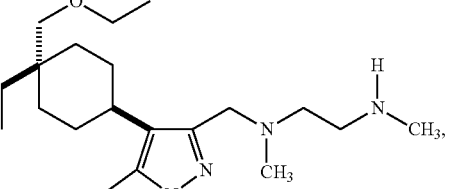
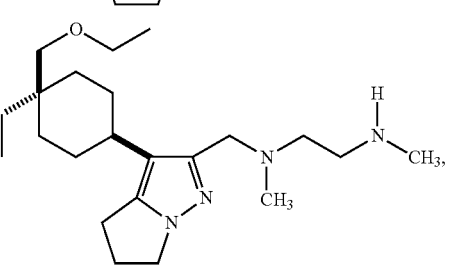

47
-continued
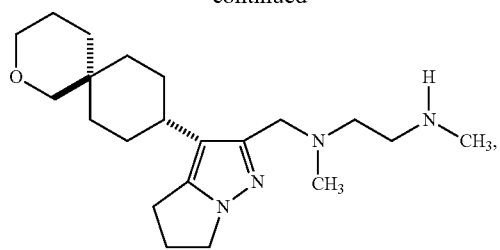
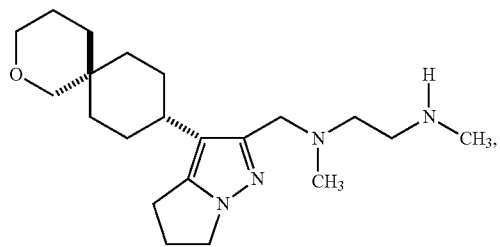
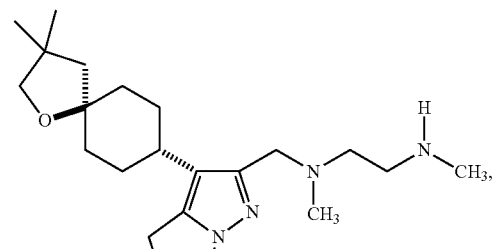
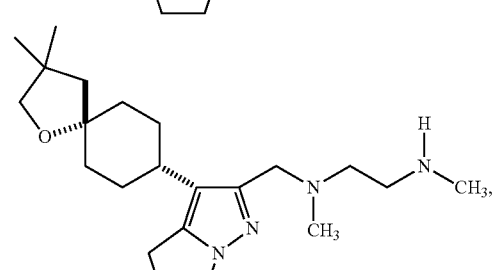
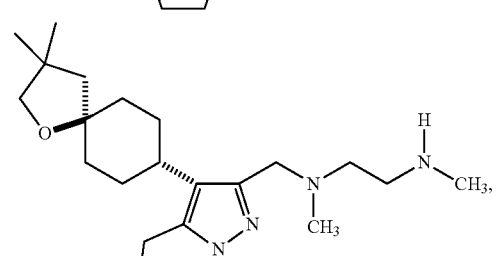
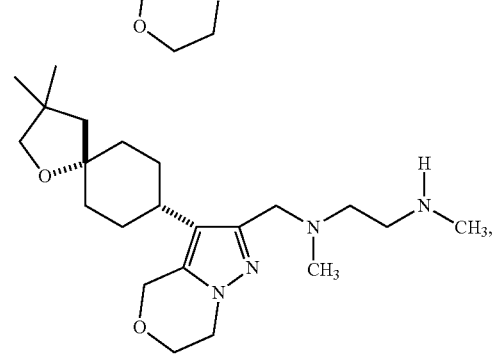
48
-continued
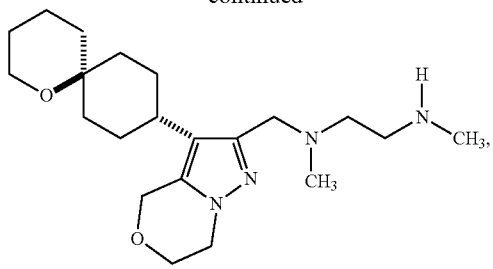
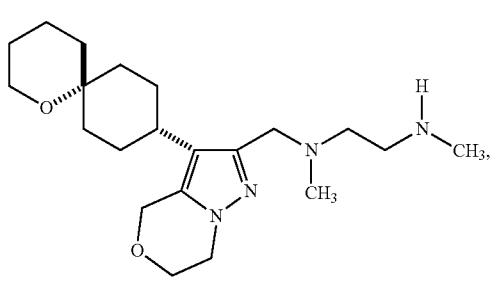
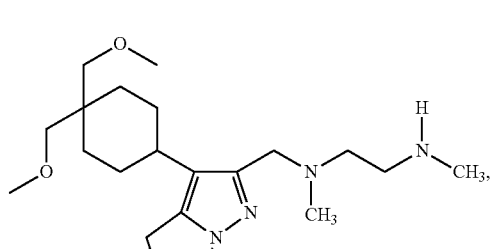
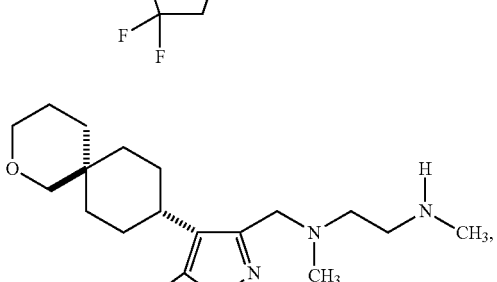
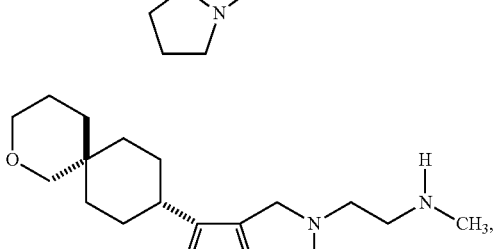
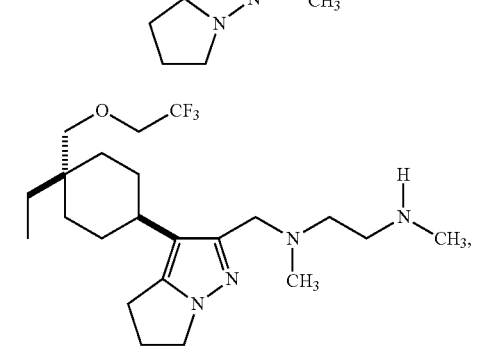

-continued
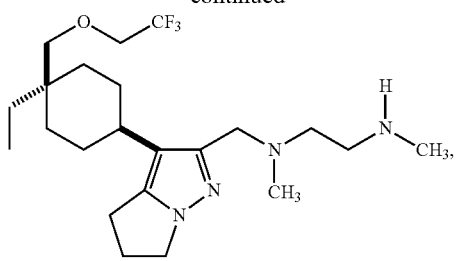
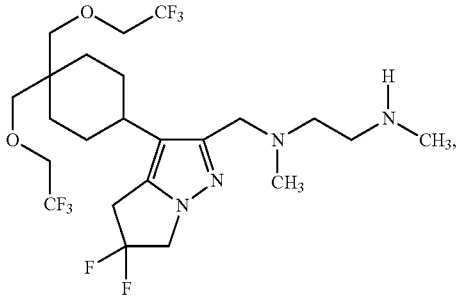
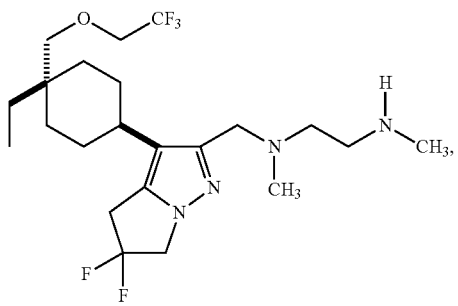
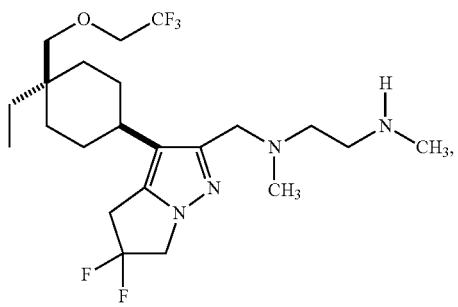
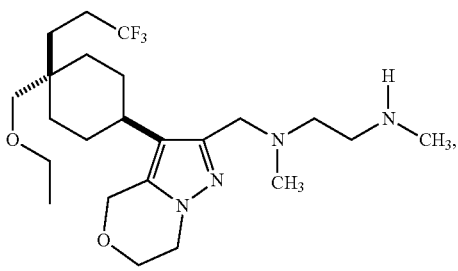
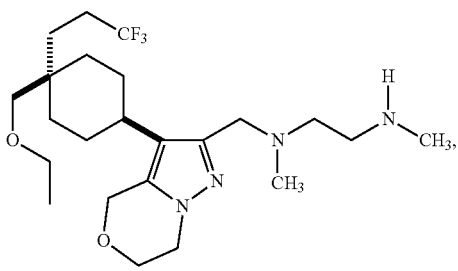
-continued
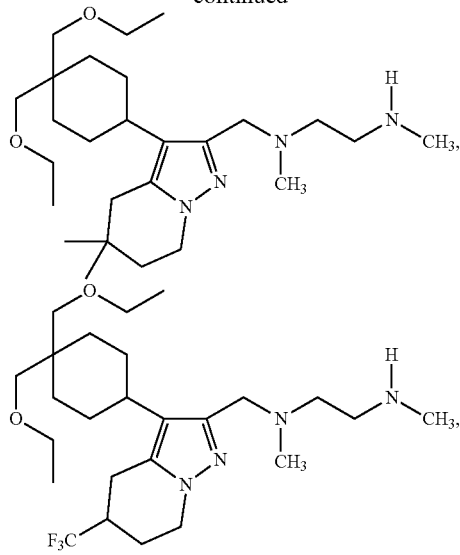
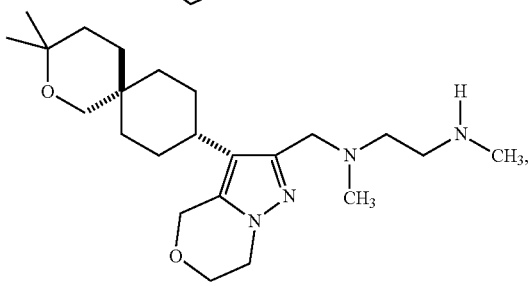
or a salt thereof.
The disclosure provides the following further embodiments:
Embodiment C-1: A compound of structural Formula I
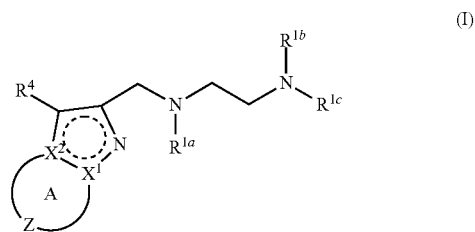
(I)
or a salt thereof, wherein:
A is a monocyclic heterocycloalkyl ring comprising 5 to 7 ring members including:
X$^1$ and X$^2$,
Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$^1$ is C and X$^2$ is N, or X$^1$ is N and X$^2$ is C;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

R$^4$ is chosen from cycloalkyl, heterocycloalkyl, aryl and heteroaryl, any of which is optionally substituted with 1, 2, 3, or 4 R$^6$ groups;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when directly attached to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

each R$^6$ is independently chosen from C$_{1-6}$alkyl, cyanoC$_{1-6}$ alkyl, haloC$_{1-6}$alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (C$_{3-6}$heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo;

each R$^7$ is independently chosen from C$_{1-6}$alkyl, haloC$_{1-6}$alkyl, aryl, heteroaryl, C$_{3-6}$cycloalkyl, C$_{3-6}$heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each R$^8$ is independently chosen from C$_{1-6}$alkyl, haloC$_{1-6}$alkyl, C$_{3-6}$cycloalkyl, and haloC$_{3-6}$cycloalkyl.

Embodiment C-2: The compound as recited in Embodiment C-1, wherein A comprises 5 or 6 ring members.

Embodiment C-3: The compound as recited in Embodiment C-2, wherein each Y is —CH$_2$—.

Embodiment C-4: The compound as recited in Embodiment C-3 wherein Z is chosen from —CH$_2$—, —CHOH—, —CH(CH$_2$OH)—, —CF$_2$—, and —O—.

Embodiment C-5: The compound as recited in Embodiment C-4, wherein R$^4$ is chosen from cycloalkyl and heterocycloalkyl, either of which is optionally substituted with 1, 2, 3, or 4 R$^6$ groups.

Embodiment C-6: The compound as recited in Embodiment C-5, wherein at least one of R$^{1b}$ and R$^{1c}$ is H.

Embodiment C-7: The compound as recited in Embodiment C-6, wherein:

R$^4$ is chosen from cycloalkyl and heterocycloalkyl, either of which is optionally substituted with 1, 2, 3 R$^6$ groups; and each R$^6$ is independently chosen from C$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, and (C$_{3-6}$alkoxy)C$_{3-6}$cycloalkyl.

Embodiment C-8: The compound as recited in Embodiment C-7, wherein

R$^4$ is chosen from cyclopentyl and cyclohexyl, either of which is optionally substituted with 1 or 2 R$^6$ groups; and each R$^6$ is independently chosen from C$_{1-4}$alkyl, (C$_{1-4}$alkoxy)C$_{1-4}$alkyl, and (haloC$_{1-4}$alkoxy)-C$_{1-4}$alkyl.

Embodiment C-9: The compound as recited in Embodiment C-6, wherein X$^1$ is C and X$^2$ is N.

Embodiment C-10: The compound as recited in Embodiment C-6, wherein X$^1$ is N and X$^2$ is C.

Embodiment C-11: The compound as recited in Embodiment C-1, having structural Formula II

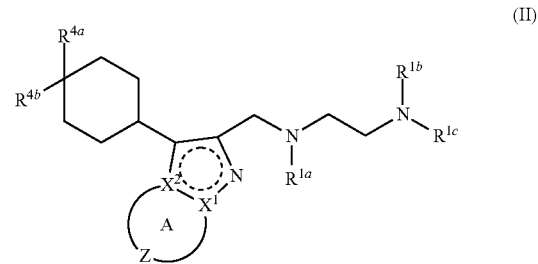

(II)

or a salt thereof, wherein:

A is a monocyclic heterocycloalkyl ring comprising 5 to 7 ring members including:

X$^1$ and X$^2$,

Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$_1$ is C and X$_2$ is N, or X$_1$ is N and X$_2$ is C;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

R$^{4a}$ and R$^{4b}$, together with the atom to which they are attached, form a cycloalkyl or heterocycloalkyl ring, which is optionally substituted with 1, 2, or 3 R$^6$ groups;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;

each $R^6$ is independently chosen from $C_{1-6}$alkyl, cyano$C_{1-6}$ alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, ($C_{3-6}$heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, $COOH$, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

each $R^7$ is independently chosen from $C_{1-6}$alkyl, halo$C_{1-6}$alkyl, aryl, heteroaryl, $C_{3-6}$cycloalkyl, $C_{3-6}$heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups; and each $R^8$ is independently chosen from $C_{1-6}$alkyl, halo$C_{1-6}$alkyl, $C_{3-6}$cycloalkyl, and halo$C_{3-6}$cycloalkyl.

Embodiment C-12: The compound as recited in Embodiment C-11, wherein A comprises 5 or 6 ring members.

Embodiment C-13: The compound as recited in Embodiment C-12, wherein each $R^6$ is independently chosen from $C_{1-6}$alkyl, halo$C_{1-6}$alkyl, ($C_{1-6}$alkoxy)$C_{1-6}$alkyl, (halo$C_{1-6}$ alkoxy)$C_{1-6}$alkyl, ($C_{3-6}$cycloalkyl)$C_{1-6}$alkyl, ($C_{3-6}$heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, and (($C_{1-6}$ alkyl)heteroaryl)$C_{1-6}$alkyl.

Embodiment C-14: The compound as recited in Embodiment C-13, wherein $R^{4a}$ and $R^{4b}$, together with the atom to which they are attached, form a ring chosen from oxetane, tetrahydrofuran, oxane, azetidine, pyrrolidine, and piperidine, any of which is optionally substituted with 1 or 2 $R^6$ groups.

Embodiment C-15: The compound as recited in Embodiment C-14, wherein $R^{4a}$ and $R^{4b}$, together with the atom to which they are attached, form a lactam ring, which is optionally substituted with 1 or 2 $R^6$ groups.

Embodiment C-16: The compound as recited in Embodiment C-15, wherein

A comprises 5 members;

Z is chosen from —$CH_2$— and —$CF_2$—; and each Y is —$CH_2$—.

Embodiment C-17: The compound as recited in Embodiment C-15, wherein

A comprises 6 members;

Z is —O—; and each Y is —$CH_2$—.

Embodiment C-18: The compound as recited in Embodiment C-1, having structural Formula III

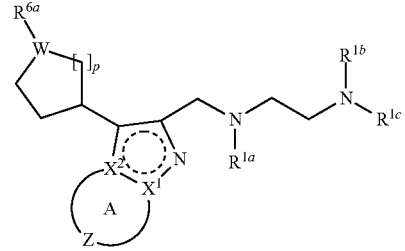

(III)

A is a monocyclic heterocycloalkyl ring comprising 5 to 7 ring members including:

$X^1$ and $X^2$,

Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and all other ring members Y, which are chosen from —$CH_2$—, —$CHR^2$—, and —$C(R^2)_2$—;

$R^{1a}$, $R^{1b}$, and $R^{1c}$ are independently chosen from H and $CH_3$;

either $X^1$ is C and $X^2$ is N, or $X^1$ is N and $X^2$ is C;

W is chosen from $C(R^{6b})$ and N;

each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5c}C(O)OR^{5b}$, $NR^{5c}C(O)NR^{5a}R^{5b}$, and $NR^{5a}SO_2R^{5b}$, or any two $R^2$ or $R^3$, when directly attached to the same atom, forms a 3-7 membered cycloalkyl or heterocycloalkyl ring;

each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and ($C_{3-6}$alkoxy)$C_{3-6}$cycloalkyl;

$R^{6a}$ and $R^{6b}$ are independently chosen from H, $C_{1-6}$alkyl, cyano$C_{1-6}$alkyl, halo$C_{1-6}$alkyl, hydroxy$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, ($C_{3-6}$alkoxy)$C_{3-6}$cycloalkyl, ($C_{3-6}$cycloalkyl)$C_{1-6}$alkyl, ($C_{3-6}$heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, (($C_{1-6}$alkyl)heteroaryl)$C_{1-6}$alkyl, $OR^7$, $CH_2OR^7$, $CH_2CH_2OR^7$, $COR^7$, $COOH$, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

each $R^7$ is independently chosen from $C_{1-6}$alkyl, halo$C_{1-6}$alkyl, aryl, heteroaryl, $C_{3-6}$cycloalkyl, $C_{3-6}$heterocycloalkyl, (aryl)$C_{1-6}$alkyl, (heteroaryl)$C_{1-6}$alkyl, (cycloalkyl)C$_{1-6}$alkyl, and (heterocycloalkyl)C$_{1-6}$alkyl, any of which is optionally substituted with 1 or 2 R$^8$ groups;

each R$^8$ is independently chosen from C$_{1-6}$alkyl, haloC$_{1-6}$ alkyl, C$_{3-6}$cycloalkyl, and haloC$_{3-6}$cycloalkyl; and p is chosen from 1 and 2.

Embodiment C-19: The compound as recited in Embodiment C-18, wherein A comprises 5 or 6 ring members.

Embodiment C-20: The compound as recited in Embodiment C-19, wherein R$^{6a}$ and R$^{6b}$ are independently chosen from H, C$_{1-6}$alkyl, (C$_{1-6}$alkoxy)C$_{1-6}$alkyl, (haloC$_{1-6}$alkoxy) C$_{1-6}$alkyl, C$_{3-6}$cycloalkyl, (C$_{3-6}$alkoxy)C$_{3-6}$cycloalkyl, OR$^7$, COR$^7$, COOH, COOR$^7$, CONH$_2$, CONHR$^7$, CON(R$^7$)$_2$, HCOR$_7$, NHCONHR$^7$, NHCON(R$^7$)$_2$, SO$_2$R$^7$, SO$_2$NHR$^7$, SO$_2$N(R$^7$)$_2$, NHSO$_2$R$^7$, cyano, halo, hydroxy, and oxo.

Embodiment C-21: The compound as recited in Embodiment C-20, wherein

Z is chosen from —CH$_2$—, —CF$_2$—, —C(R$^3$)$_2$—, —N(R$^{5a}$)—, N(COR$^{5a}$)—, and —O—; and each Y is —CH$_2$—.

Embodiment C-22: The compound as recited in Embodiment C-21, wherein:

R$^{6a}$ and R$^{6b}$ are independently chosen from H, C$_{1-6}$alkyl, (C$_{1-6}$alkoxy)C$_{1-6}$alkyl, (fluoroC$_{1-6}$alkoxy)C$_{1-6}$alkyl, C$_{3-6}$cycloalkyl, (C$_{3-6}$alkoxy)C$_{3-6}$cycloalkyl, OR$^7$, COR$^7$, COOH, COOR$^7$, CONH$_2$, CONHR$^7$, CON (R$^7$)$_2$, HCOR$^7$, NHCONHR$^7$, NHCON(R$^7$)$_2$, SO$_2$R$^7$, SO$_2$NHR$^7$, SO$_2$N(R$^7$)$_2$, NHSO$_2$R$^7$, cyano, halo, hydroxy, and oxo; and each R$^7$ is independently chosen from C$_{1-6}$alkyl, fluoroC$_{1-6}$alkyl, C$_{3-6}$cycloalkyl, and C$_{3-6}$heterocycloalkyl.

Embodiment C-23: The compound as recited in Embodiment C-22, wherein:

R$^{6a}$ and R$^{6b}$ are independently chosen from H, C$_{1-6}$alkyl, (C$_{1-6}$alkoxy)C$_{1-6}$alkyl, (fluoroC$_{1-6}$alkoxy)C$_{1-6}$alkyl, C$_{3-6}$cycloalkyl, (C$_{3-6}$alkoxy)C$_{3-6}$cycloalkyl, OR$^7$, COR$^7$, COOH, and COOR$^7$; and each R$^7$ is independently chosen from C$_{1-6}$alkyl and fluoroC$_{1-6}$alkyl.

Embodiment C-24: The compound as recited in Embodiment C-23, wherein R$^{6a}$ and R$^{6b}$ are independently chosen from C$_{1-6}$alkyl, (C$_{1-6}$alkoxy)C$_{1-6}$alkyl, (fluoroC$_{1-6}$alkoxy) C$_{1-6}$alkyl, C$_{3-6}$cycloalkyl, (C$_{3-6}$alkoxy)C$_{3-6}$cycloalkyl, and OR$^7$.

Embodiment C-25: The compound as recited in Embodiment C-24, wherein

W is C(R$^{6b}$);

p is 2; and at least one of R$^{6a}$ and R$^{6b}$ is chosen from C$_{1-6}$alkyl, (C$_{1-6}$alkoxy)C$_{1-6}$alkyl, and (fluoroC$_{1-6}$alkoxy)C$_{1-6}$alkyl.

Embodiment C-26: The compound as recited in Embodiment C-25, wherein at least one of R$^{6a}$ and R$^{6b}$ is chosen from C$_{1-6}$alkoxymethyl, C$_{1-6}$alkoxyethyl, and fluoroC$_{1-6}$alkoxyethyl.

Embodiment C-27: The compound as recited in Embodiment C-1, having structural Formula V (V)

or a salt thereof, wherein:

A is a monocyclic heterocycloalkyl ring comprising 5 to 7 ring members including:

X$^1$ and X$^2$,

Z, which is chosen from —CH$_2$—, —CHR$^3$—, —C(R$^3$)$_2$—, —N(R$^{5a}$)—, N(COR$^{5a}$)—, N(CONR$^{5a}$R$^{5b}$)—, N(SO$_2$R$^{5a}$)—, —O—, and —SO$_2$—, and all other ring members Y, which are chosen from —CH$_2$—, —CHR$^2$—, and —C(R$^2$)$_2$—;

R$^{1a}$, R$^{1b}$, and R$^{1c}$ are independently chosen from H and CH$_3$;

either X$^1$ is C and X$^2$ is N, or X$^1$ is N and X$^2$ is C;

W is chosen from C(R$^{6b}$) and N;

each R$^2$ and R$^3$ is independently chosen from cyano, halo, hydroxy, C$_{1-6}$alkyl, C$_{1-6}$haloalkyl, C$_{1-6}$hydroxyalkyl, (C$_{1-6}$alkoxy)C$_{1-6}$alkyl; OR$^{5a}$, C(O)R$^{5a}$, C(O)OR$^{5a}$, C(O)NR$^{5a}$R$^{5b}$, SO$_2$R$^{5a}$; SO$_2$NR$^{5a}$R$^{5b}$, NR$^{5a}$R$^{5b}$, NR$^{5a}$C(O)R$^{5b}$, NR$^{5c}$C(O)OR$^{5b}$, NR$^{5c}$C(O)NR$^{5a}$R$^{5b}$, and NR$^{5a}$SO$_2$R$^{5b}$, or any two R$^2$ or R$^3$, when directly attached to the same atom, forms a 3-7 membered cycloalkyl or heterocycloalkyl ring;

each R$^{5a}$ and R$^{5b}$ is independently chosen from H, C$_{1-6}$alkyl, cyanoC$_{1-6}$alkyl, haloC$_{1-6}$alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl, or R$^{5a}$ and R$^{5b}$, when attached directly to the same atom, forms a 3-7 membered cycloalkyl or heterocycloalkyl ring;

R$^{5c}$ is chosen from H, C$_{1-6}$alkyl, cyanoC$_{1-6}$alkyl, haloC$_{1-6}$ alkyl, hydroxyC$_{1-6}$alkyl, (C$_{1-6}$alkoxy)C$_{1-6}$alkyl; C$_{3-6}$cycloalkyl, cyanoC$_{3-6}$cycloalkyl, haloC$_{3-6}$cycloalkyl, hydroxyC$_{3-6}$cycloalkyl, and (C$_{3-6}$alkoxy)C$_{3-6}$cycloalkyl;

R$^{6c}$ is chosen from H, C$_{1-6}$alkyl, cyanoC$_{1-6}$alkyl, haloC$_{1-6}$ alkyl, hydroxyC$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$cycloalkyl, (C$_{3-6}$alkoxy)C$_{3-6}$cycloalkyl, (C$_{3-6}$cycloalkyl)C$_{1-6}$alkyl, (C$_{3-6}$heterocycloalkyl)C$_{1-6}$alkyl, (aryl)C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON (R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo;

R$^{6a}$ and R$^{6b}$ are chosen from H, C$_{1-6}$alkyl, cyanoC$_{1-6}$ alkyl, haloC$_{1-6}$alkyl, hydroxyC$_{1-6}$alkyl, (C$_{1-6}$alkoxy) C$_{1-6}$alkyl, (haloC$_{1-6}$alkoxy)C$_{1-6}$alkyl, C$_{3-6}$cycloalkyl, cyanoC$_{3-6}$cycloalkyl, haloC$_{3-6}$cycloalkyl, hydroxyC$_{3-6}$ cycloalkyl, (C$_{3-6}$alkoxy)C$_{3-6}$cycloalkyl, (C$_{3-6}$cycloalkyl)C$_{1-6}$alkyl, (C$_{3-6}$heterocycloalkyl)C$_{1-6}$alkyl, (aryl)

C$_{1-6}$alkyl, (heteroaryl)C$_{1-6}$alkyl, ((C$_{1-6}$alkyl)aryl)C$_{1-6}$alkyl, ((C$_{1-6}$alkyl)heteroaryl)C$_{1-6}$alkyl, OR$^7$, CH$_2$OR$^7$, CH$_2$CH$_2$OR$^7$, COR$^7$, COOH, COOR$^7$, CONH$_2$, CONHR$^7$, CON(R$^7$)$_2$, NHCOR$^7$, NR$^7$COR$^7$, NHCONH$_2$, NHCONHR$^7$, NHCON(R$^7$)$_2$, NR$^7$CONH$_2$, NR$^7$CONHR$^7$, NR$^7$CON(R$^7$)$_2$, SO$_2$R$^7$, SO$_2$NHR$^7$, SO$_2$N(R$^7$)$_2$, NHSO$_2$R$^7$, NR$^7$SO$_2$R$^7$, carboxy, cyano, halo, hydroxy, and oxo, or R$^{6a}$ and R$^{6b}$, when attached directly to the same atom, forms a 3-7 membered cycloalkyl or heterocycloalkyl ring;

each R$^7$ is independently chosen from C$_{1-6}$alkyl, haloC$_{1-6}$alkyl, aryl, heteroaryl, C$_{3-6}$cycloalkyl, C$_{3-6}$heterocycloalkyl, (aryl)C$_{1-6}$alkyl, (heteroaryl)C$_{1-6}$alkyl, (cycloalkyl)C$_{1-6}$alkyl, and (heterocycloalkyl)C$_{1-6}$alkyl, any of which is optionally substituted with 1 or 2 R$^8$ groups; and each R$^8$ is independently chosen from C$_{1-6}$alkyl, haloC$_{1-6}$alkyl, C$_{3-6}$cycloalkyl, and haloC$_{3-6}$cycloalkyl.

Embodiment C-28: The compound as recited in Embodiment C-27, wherein R$^{6c}$ is H.

Embodiment C-29: The compound as recited in Embodiment C-28, wherein A comprises 5 or 6 ring members.

Embodiment C-30: The compound as recited in Embodiment C-29, wherein R$^{6a}$ and R$^{6b}$ are independently chosen from H, C$_{1-6}$alkyl, (C$_{1-6}$alkoxy)C$_{1-6}$alkyl, (haloC$_{1-6}$alkoxy)C$_{1-6}$alkyl, C$_{3-6}$cycloalkyl, (C$_{3-6}$alkoxy)C$_{3-6}$cycloalkyl, OR$^7$, COR$^7$, COOH, COOR$^7$, CONH$_2$, CONHR$^7$, CON(R$^7$)$_2$, HCOR$^7$, NHCONHR$^7$, NHCON(R$^7$)$_2$, SO$_2$R$^7$, SO$_2$NHR$^7$, SO$_2$N(R$^7$)$_2$, NHSO$_2$R$^7$, cyano, halo, hydroxy, and oxo.

Embodiment C-31: A compound chosen from

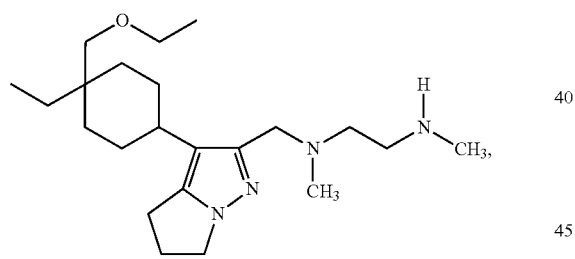

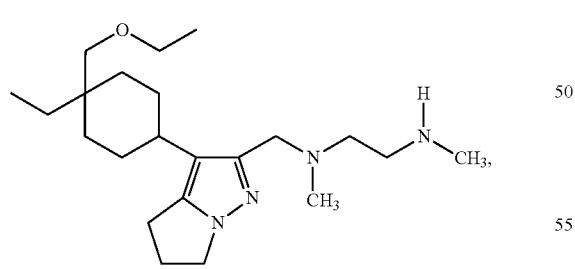

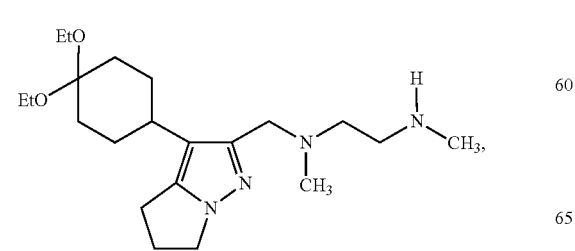

-continued

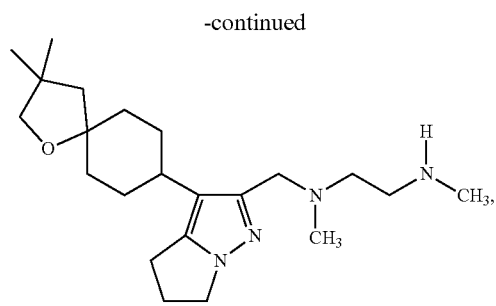

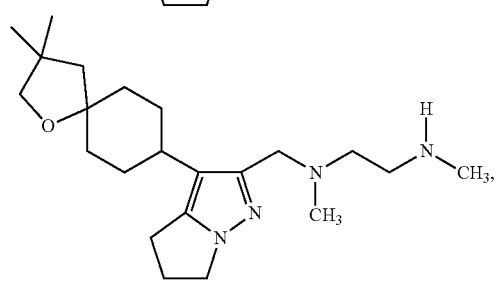

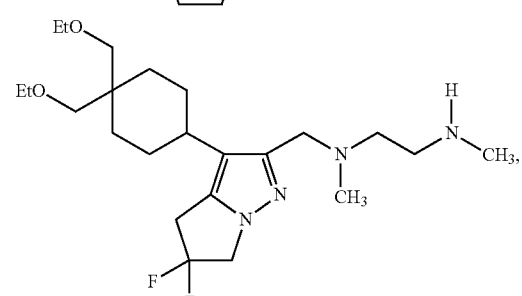

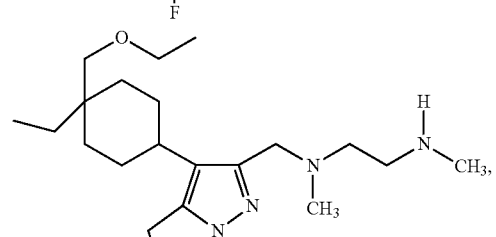

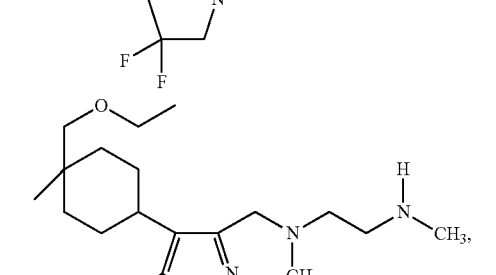

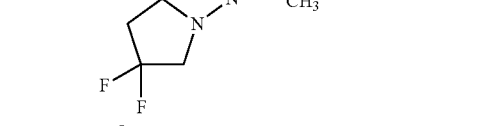

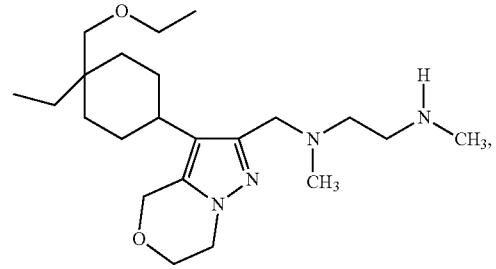

| 59 | 60 |
|---|---|
| -continued | -continued |
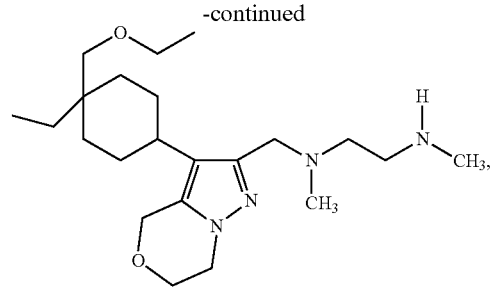
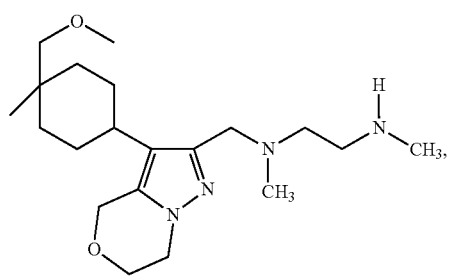
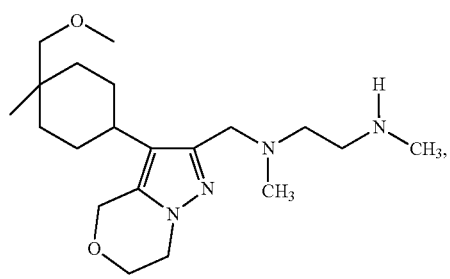
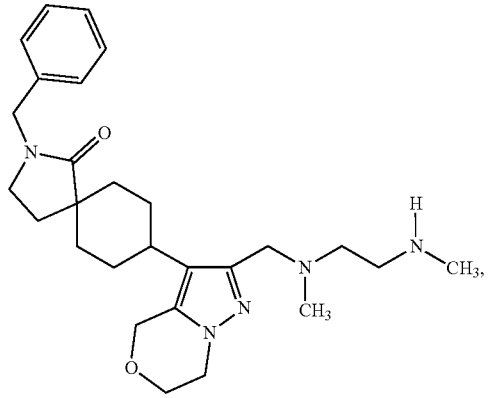
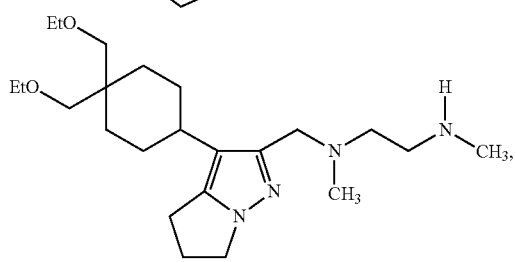
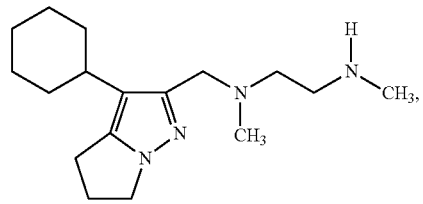
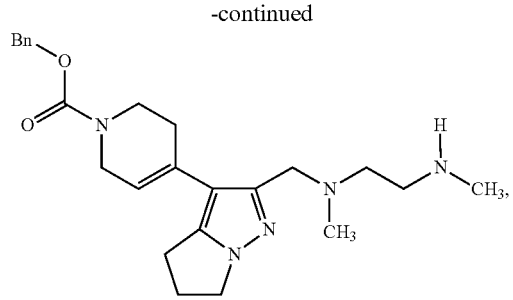
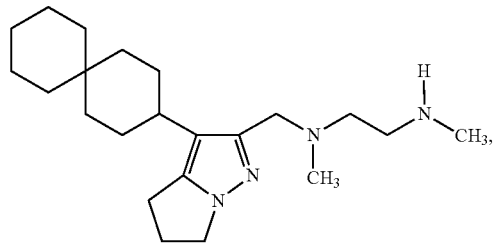
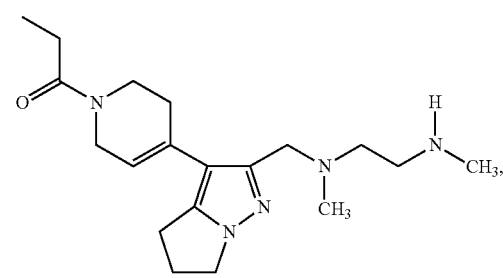
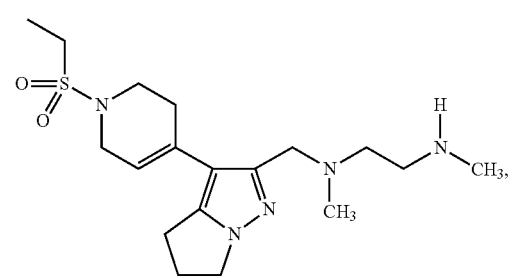
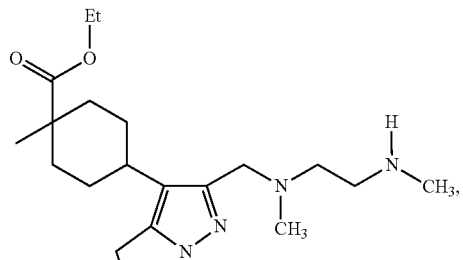
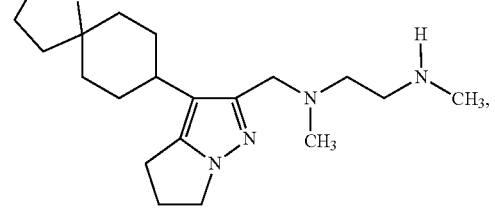

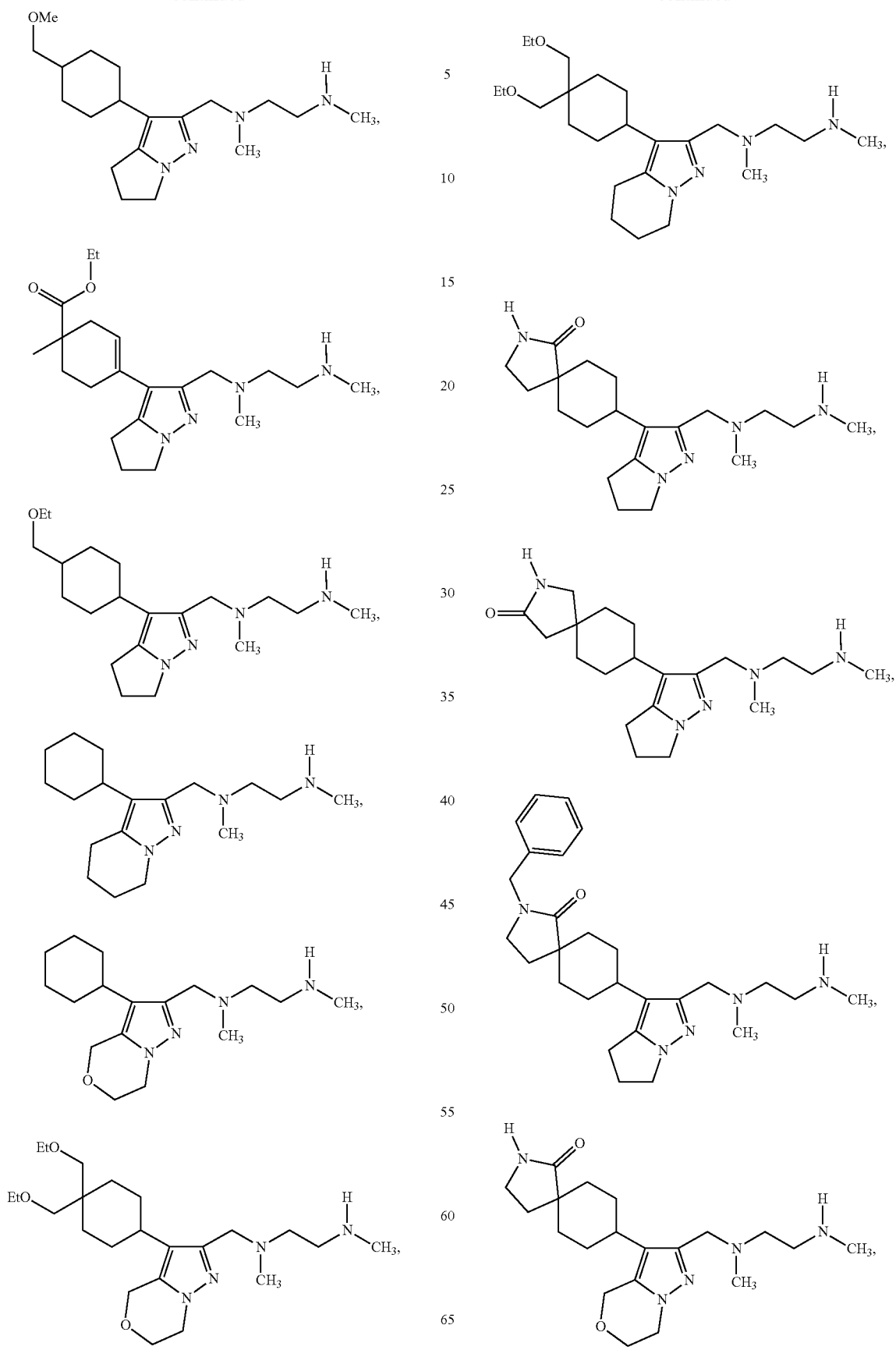

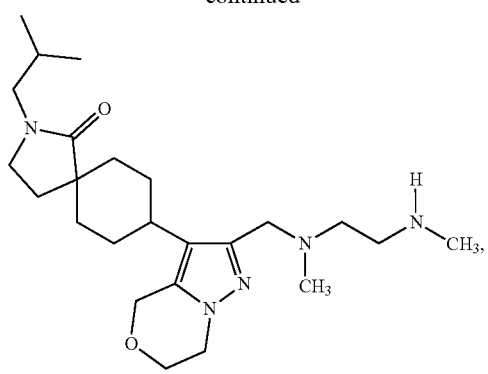
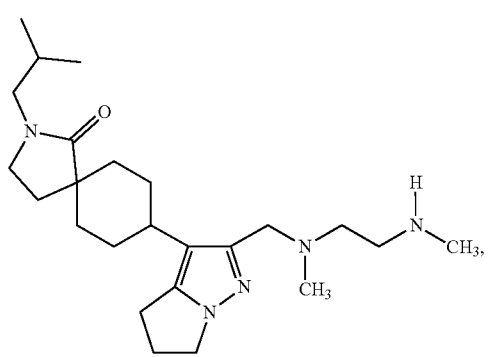
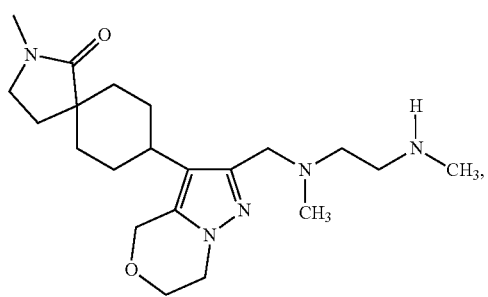
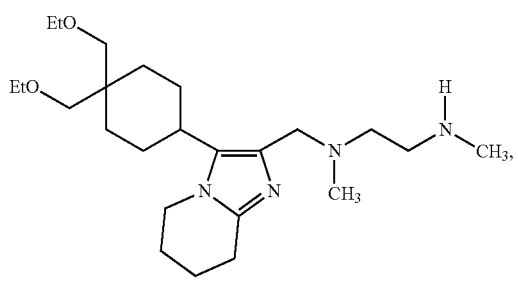
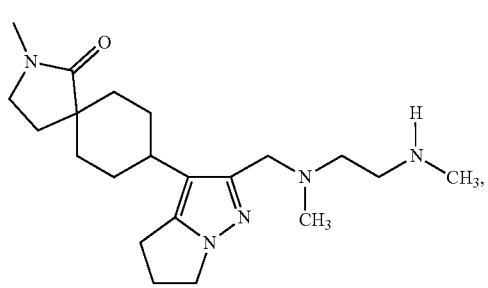
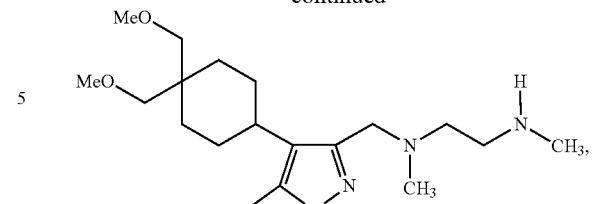
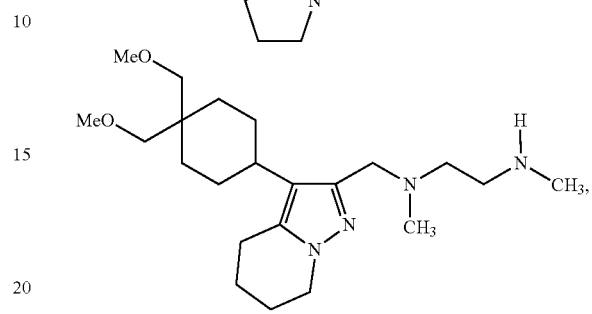
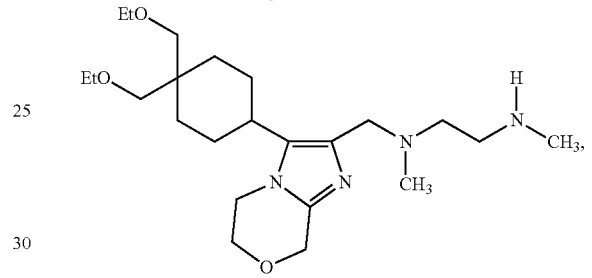
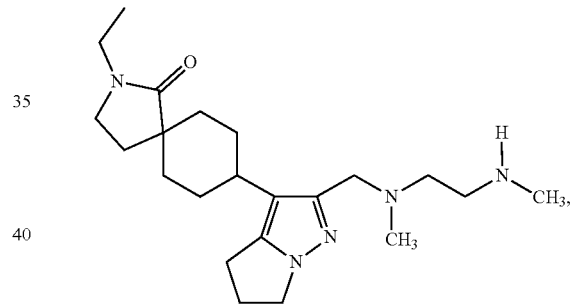
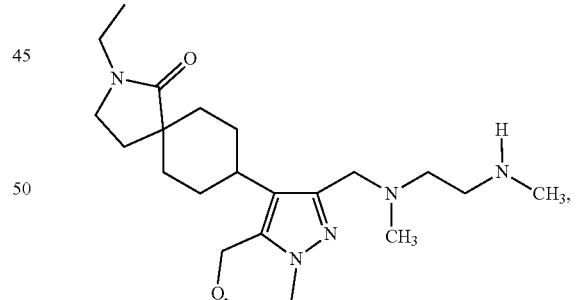
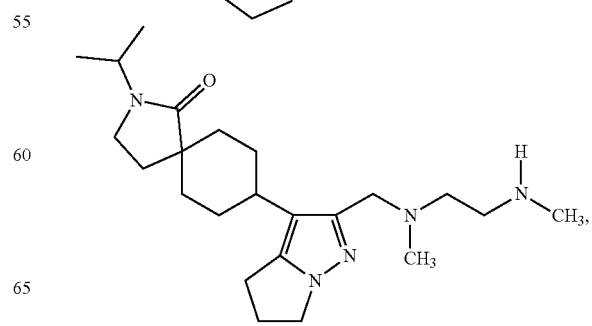

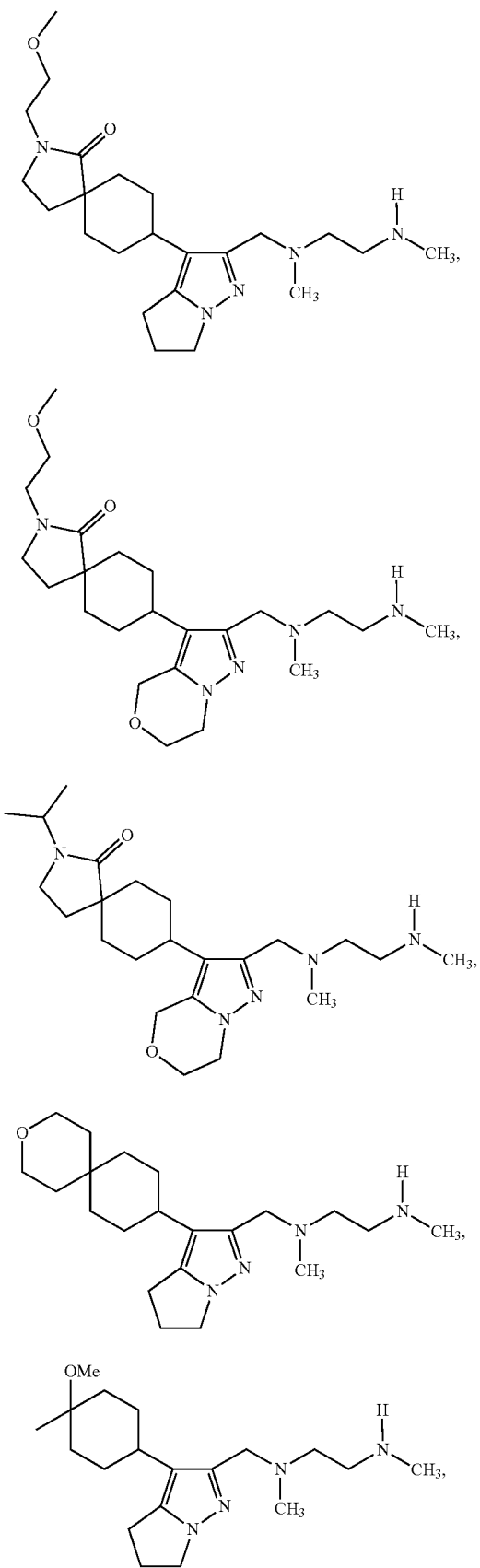
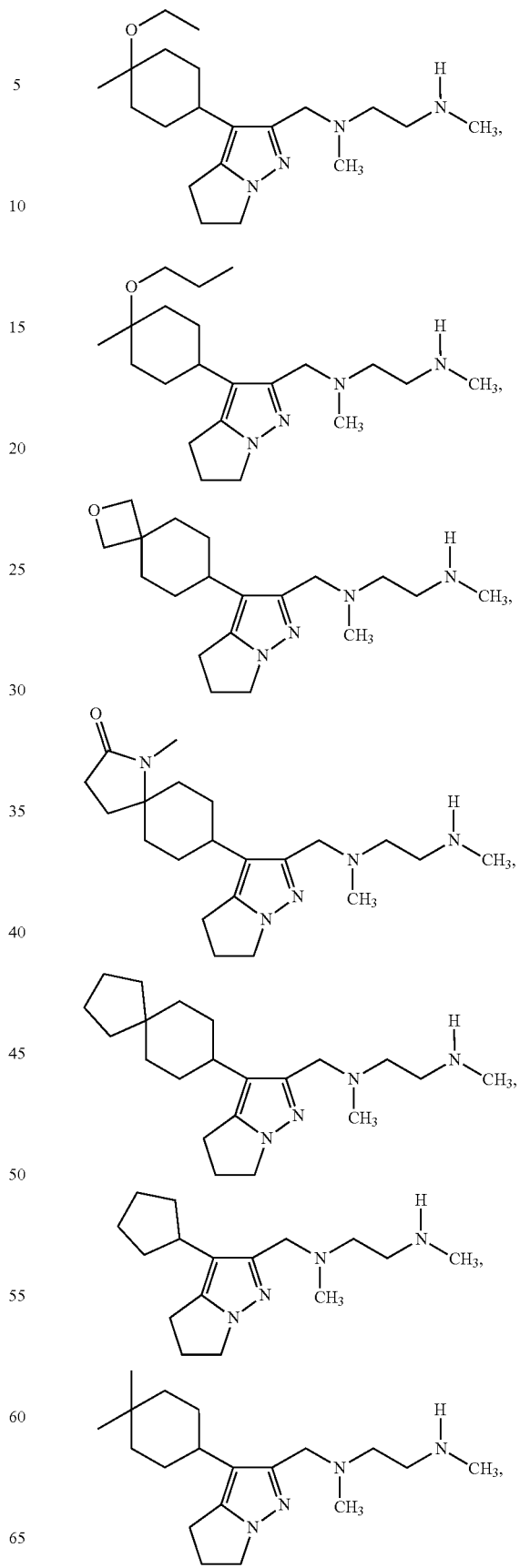

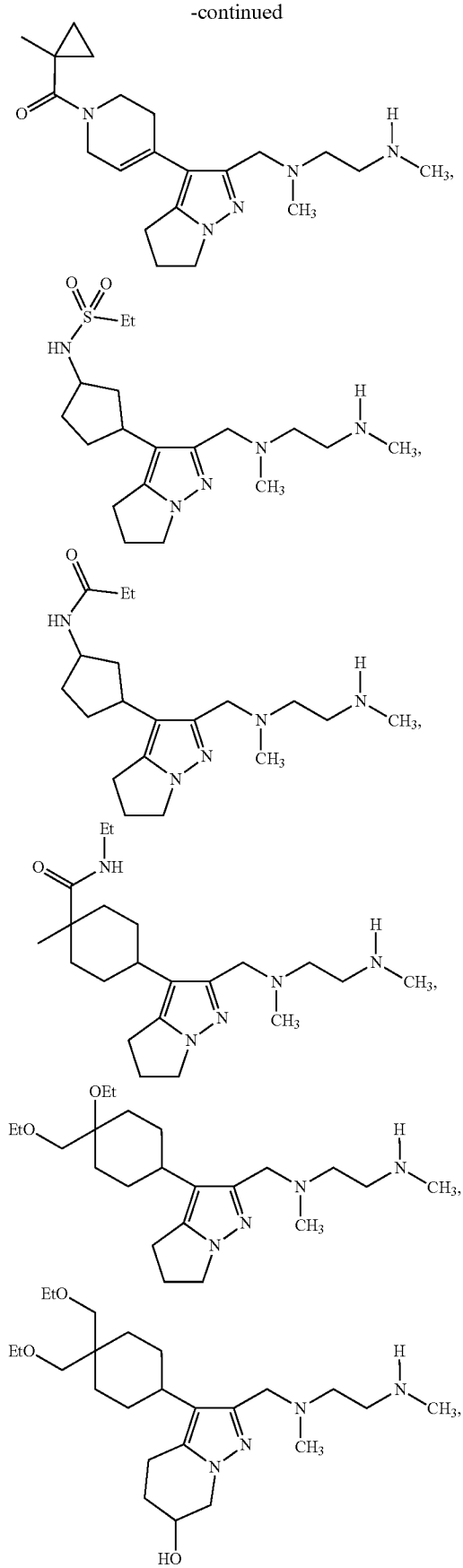
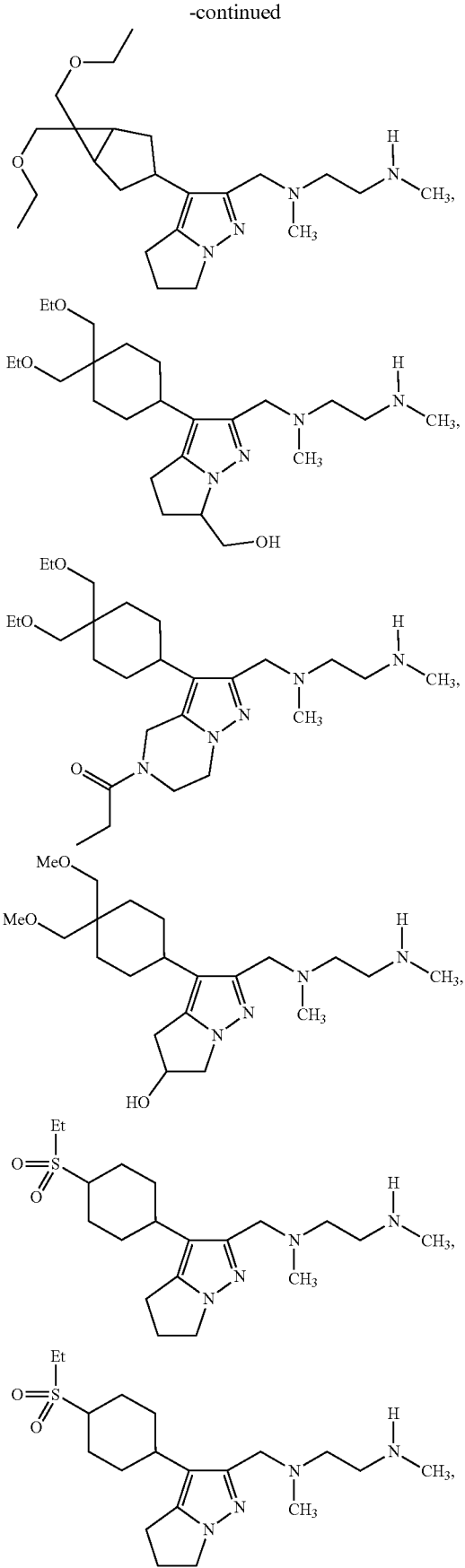

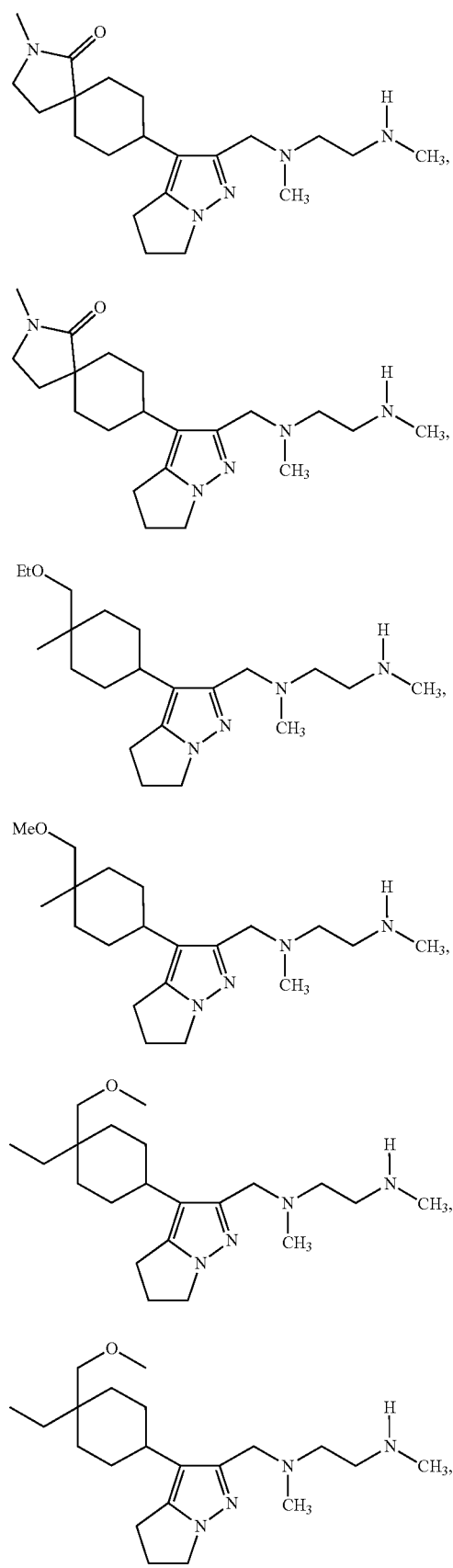
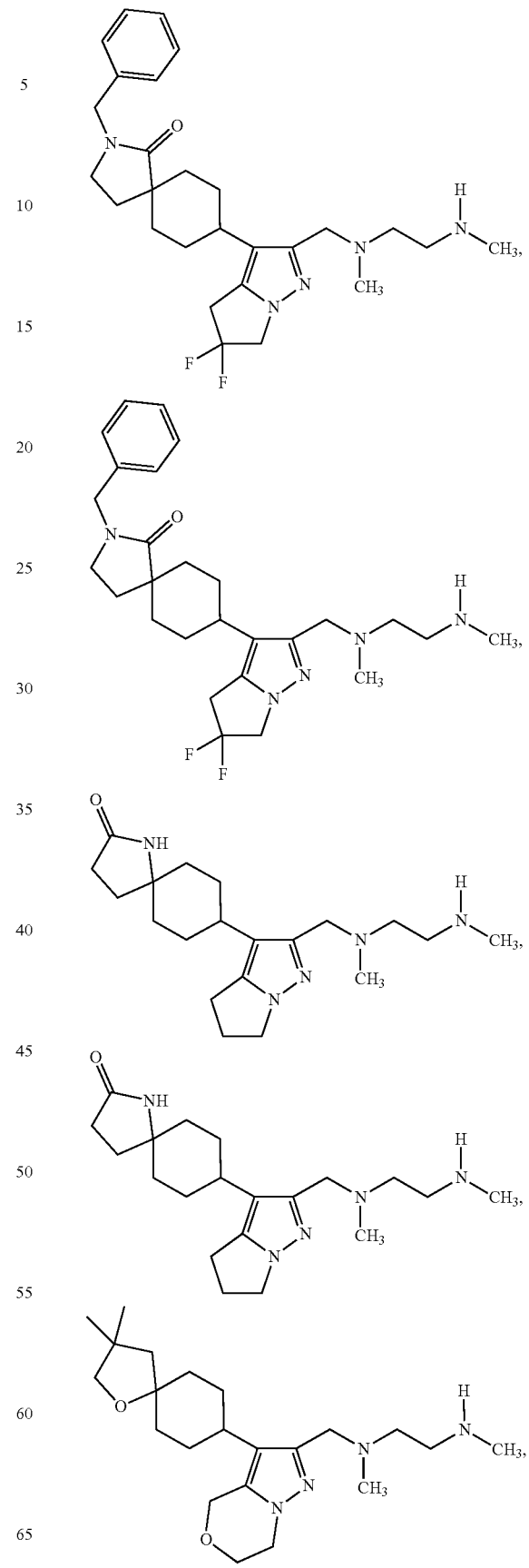

71
-continued
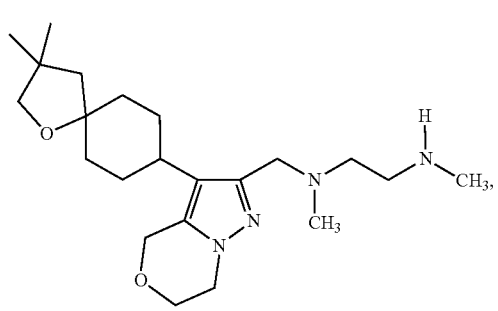
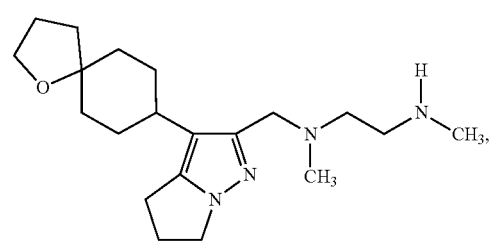
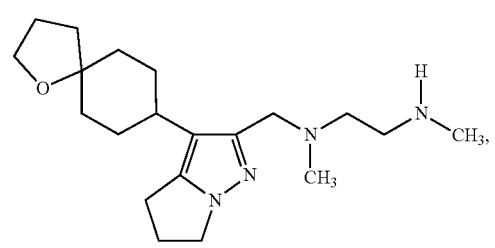
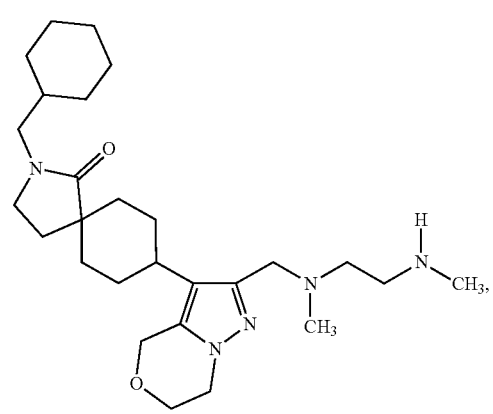
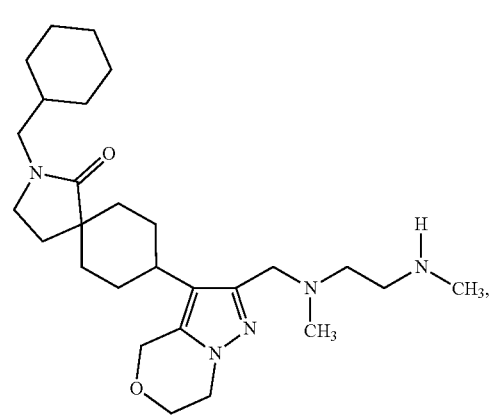
72
-continued
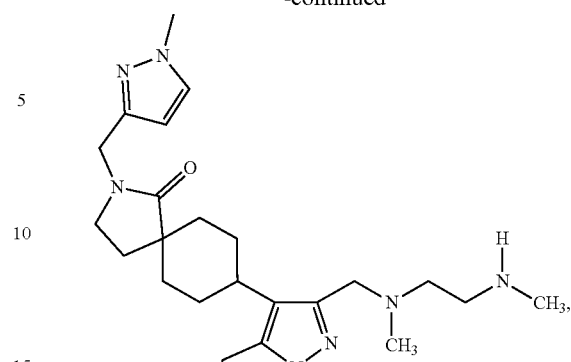
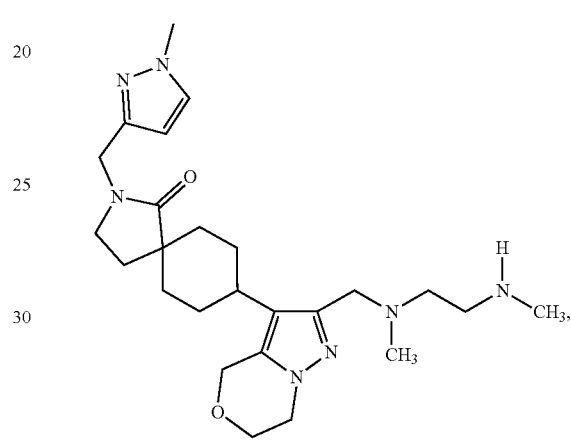
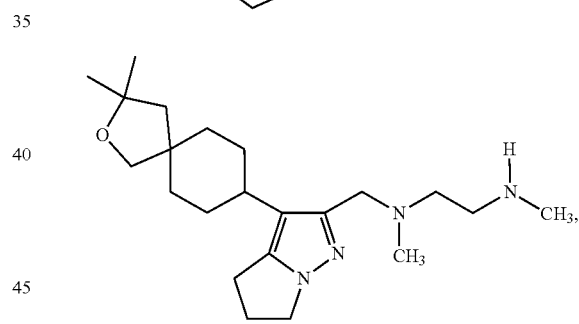
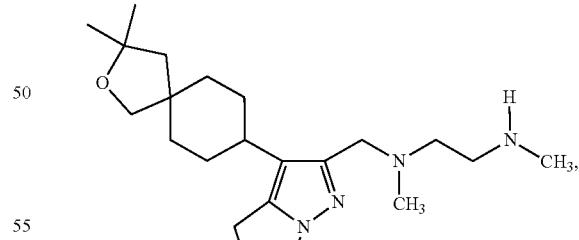
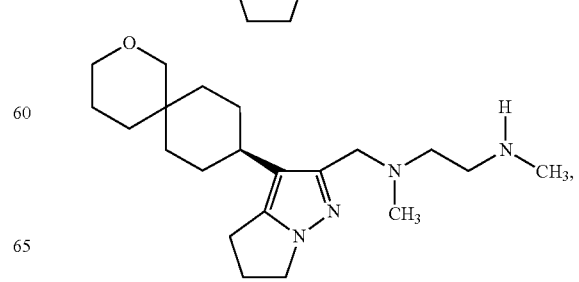

-continued

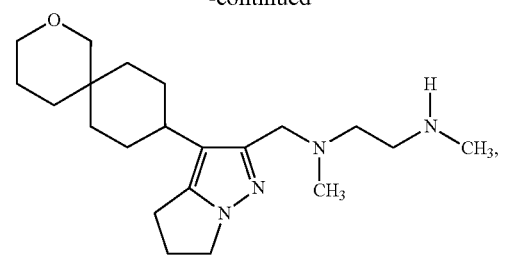

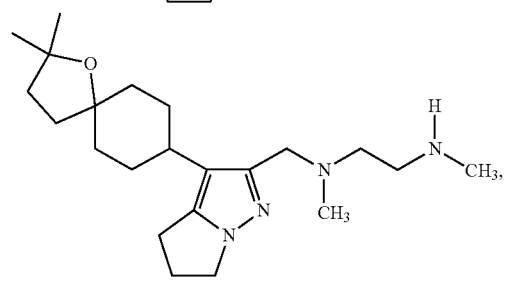

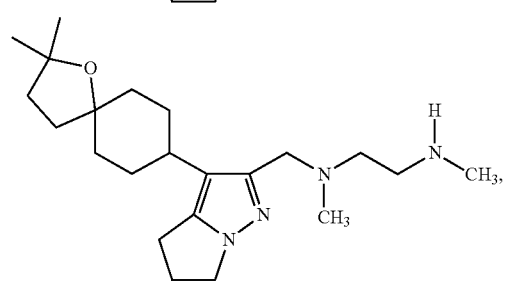

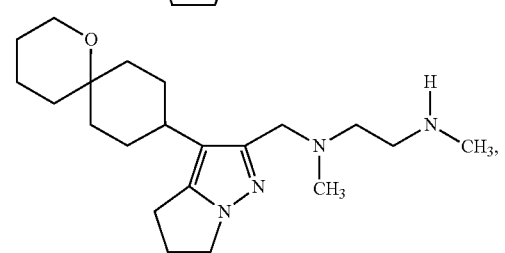

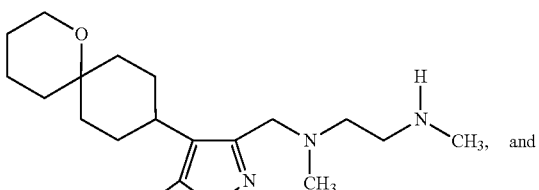

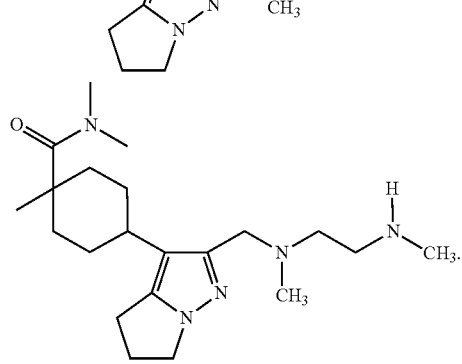

Embodiment C-32: A compound as recited in claim 1 for use as a medicament.

Embodiment C-33: A compound as recited in claim 1 for use in the treatment of cancer.

Embodiment C-34: A compound as recited in claim 1 for use in the manufacture of a medicament for the prevention or treatment of a disease or condition ameliorated by the inhibition of PRMT.

Embodiment C-35: A pharmaceutical composition comprising a compound as recited in claim 1 together with a pharmaceutically acceptable carrier.

Embodiment M-36: A method of inhibition of a PRMT comprising contacting PRMT with a compound as recited in Embodiment C-1.

Embodiment M-37: The method as recited in Embodiment M-36, wherein the PRMT is PRMT1.

Embodiment M-38: A method of modulating gene expression comprising contacting a cell with an effective dose of the compound as recited in Embodiment C-1, or a pharmaceutically acceptable salt thereof.

Embodiment M-39: A method of treatment of a PRMT-mediated disease comprising the administration of a therapeutically effective amount of a compound as recited in Embodiment C-1 to a patient in need thereof.

Embodiment M-40: The method of Embodiment M-39, wherein the disease is a proliferative disease.

Embodiment M-41: The method of Embodiment M-40, wherein the proliferative disease is cancer.

Embodiment M-42: The method of Embodiment M-41, wherein the cancer is chosen from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor.

Embodiment M-43: The method as recited in Embodiment M-41, further comprising the administration of a non-chemical method of cancer treatment.

Embodiment M-44: The method as recited in Embodiment M-43, wherein said non-chemical method of cancer treatment is chosen from surgery, radiation therapy, thermoablation, focused ultrasound therapy, and cryotherapy.

Embodiment M-45: A method of treatment of a PRMT-mediated disease comprising the administration of:
a. a therapeutically effective amount of a compound as recited in Embodiment C-1; and
b. another therapeutic agent.

Embodiment M-46: The method as recited in Embodiment M-45, wherein said other agent is a cytotoxic agent.

Embodiment M-47: The method as recited in Embodiment M-46, wherein said cytotoxic agent is chosen from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism.

Embodiment M-48: The method as recited in Embodiment M-39, wherein the disease is an autoimmune disease.

Embodiment M-49: The method as recited in Embodiment M-39, wherein the disease is amyotrophic lateral sclerosis.

Embodiment M-50: The method as recited in Embodiment M-39, wherein the disease is a muscular dystrophy.

Embodiment M-51: The method as recited in Embodiment M-39, wherein the disease is a vascular disease.

Embodiment M-52: The method as recited in Embodiment M-39, wherein the disease is a metabolic disorder.

Embodiment M-53: The method as recited in Embodiment M-52, wherein the metabolic disorder is diabetes.

Embodiment M-54: The method as recited in Embodiment M-52, wherein the metabolic disorder is a skeletal muscle metabolic disorder.

The disclosure provides the following further embodiments:

Embodiment I-2: The compound as recited in Embodiment 1, wherein A comprises 5 or 6 ring members.

Embodiment I-3: The compound as recited in Embodiment I-2, wherein each Y is —$CH_2$—.

Embodiment I-4: The compound as recited in Embodiment I-3, wherein Z is chosen from —$CH_2$—, —CHOH—, —CH($CF_3$), —C($CH_3$)$_2$—,

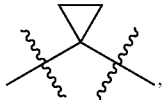 [SMILES: *C1(*)CC1]

—N($R^{5a}$)—, —N(COR$^{5a}$)—, —CH($CH_2$OH)—, —$CF_2$—, and —O—.

Embodiment I-5: The compound as recited in Embodiment I-4, wherein Z is chosen from —$CH_2$—, —C($CH_3$)$_2$—,

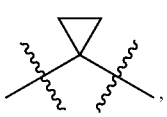 [SMILES: *C1(*)CC1 ; ","]

—$CF_2$—, and —O—.

Embodiment I-6: The compound as recited in Embodiment I-5, wherein $R^4$ is chosen from cycloalkyl and heterocycloalkyl, either of which is optionally substituted with 1, 2, or 3 $R^6$ groups.

Embodiment I-7: The compound as recited in Embodiment I-6, wherein at least one of $R^{1b}$ and $R^{1c}$ is H.

Embodiment I-8: The compound as recited in Embodiment I-7, wherein each $R^6$ is independently chosen from $C_{1-6}$alkyl, halo$C_{1-6}$alkyl, ($C_{1-6}$alkoxy)$C_{1-6}$alkyl, (aryl)$C_{1-6}$alkyl, COR$^7$, COOR$^7$, CONHR$^7$, CON(R$^7$)$_2$, NHCOR$^7$, $SO_2R^7$, NHSO$_2R^7$, halo, hydroxy, and oxo.

Embodiment I-9: The compound as recited in Embodiment I-8, wherein each $R^7$ is independently chosen from $C_{1-6}$alkylo, $C_{3-6}$cycloalkyl, (aryl)$C_{1-6}$alkyl, and (heteroaryl)$C_{1-6}$alkyl, any of which is optionally substituted with 1 or 2 $R^8$ groups.

Embodiment I-10: The compound as recited in Embodiment I-9, wherein $X^1$ is N and $X^2$ is C.

Embodiment II-12: The compound as recited in Embodiment 34, wherein A comprises 5 or 6 ring members.

Embodiment II-13: The compound as recited in Embodiment II-12, wherein each $R^6$ is independently chosen from $C_{1-6}$alkyl, halo$C_{1-6}$alkyl, ($C_{1-6}$alkoxy)$C_{1-6}$alkyl, (halo$C_{1-6}$alkoxy)$C_{1-6}$alkyl, ($C_{3-6}$cycloalkyl)$C_{1-6}$alkyl, (3-6 membered heterocycloalkyl)$C_{1-6}$alkyl, (aryl)$C_{1-6}$alkyl, (heteroaryl)$C_{1-6}$alkyl, (($C_{1-6}$alkyl)aryl)$C_{1-6}$alkyl, and (($C_{1-6}$alkyl)heteroaryl)$C_{1-6}$alkyl.

Embodiment II-14: The compound as recited in Embodiment II-13, wherein:
Z is chosen from —$CH_2$—, —C($CH_3$)$_2$—,

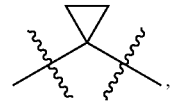

—CF—, and —O—; and
each Y is —$CH_2$—.

Embodiment II-15: The compound as recited in Embodiment II-14, wherein Z is chosen from —$CH_2$—, —C($CH_3$)$_2$—,

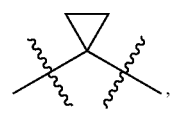 [SMILES: *C1(*)CC1 ; ","]

—CF—, and —O—.

Embodiment II-16: The compound as recited in Embodiment II-15, wherein $X^1$ is N and $X^2$ is C.

Embodiment II-17: The compound as recited in Embodiment II-16, wherein:
each $R^3$ is independently chosen from cyano, fluoro, hydroxy, $C_{1-6}$alkyl, $C_{1-6}$fluoroalkyl, and $C_{1-6}$hydroxyalkyl, or
any two $R^3$, when directly attached to the same atom, forms a 3-7 membered cycloalkyl ring.

Embodiment II-18: The compound as recited in Embodiment II-17, wherein $R^{4a}$ and $R^{4b}$, together with the atom to which they are attached, form a ring chosen from oxetane, tetrahydrofuran, oxane, azetidine, pyrrolidine, and piperidine, any of which is optionally substituted with 1 or 2 $R^6$ groups.

Embodiment II-19: The compound as recited in Embodiment II-17, wherein $R^{4a}$ and $R^{4b}$, together with the atom to which they are attached, form a ring chosen from cyclopentane and cyclohexane, either of which is optionally substituted with 1 or 2 $R^6$ groups.

Embodiment II-20: The compound as recited in Embodiment II-17, wherein $R^{4a}$ and $R^{4b}$, together with the atom to which they are attached, form a lactam ring, which is optionally substituted with 1 or 2 $R^6$ groups.

Embodiment IIb-22: The compound as recited in Embodiment 60, wherein B is chosen from:

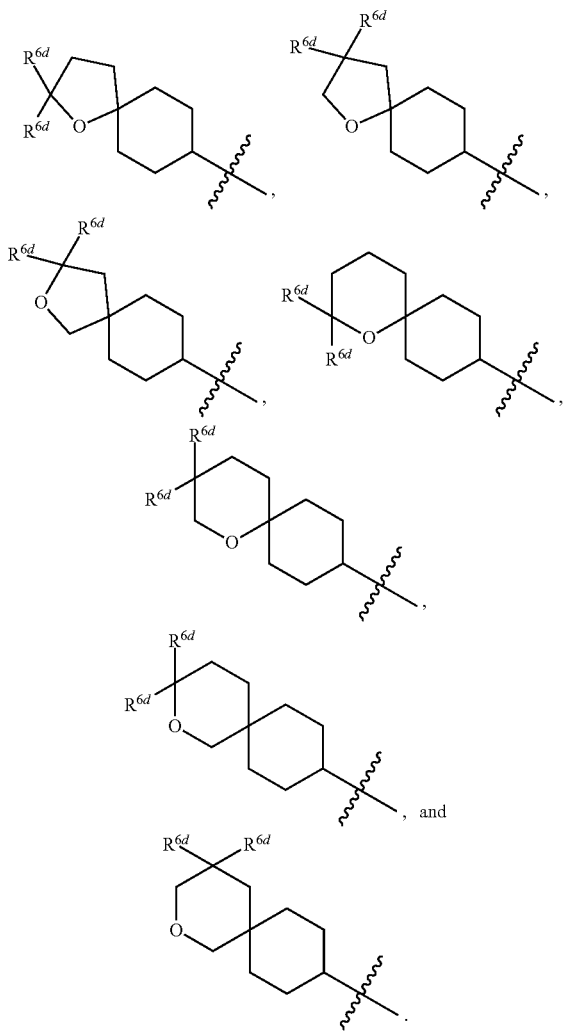

Embodiment III-24: The compound as recited in Embodiment 93, wherein $R^{6a}$ and $R^{6b}$ are independently chosen from H, $C_{1-6}$alkyl, halo$C_{1-6}$alkyl, ($C_{1-6}$alkoxy)$C_{1-6}$alkyl, (halo$C_{1-6}$alkoxy)$C_{1-6}$alkyl, $C_{3-6}$cycloalkyl, ($C_{3-6}$alkoxy)$C_{3-6}$cycloalkyl, $OR^7$, $COR^7$, COOH, $COOR^7$, $CONH_2$, $CONHR^7$, $CON(R^7)_2$, $HCOR_7$, $NHCONHR^7$, $NHCON(R^7)_2$, $SO_2R^7$, $SO_2NHR^7$, $SO_2N(R^7)_2$, $NHSO_2R^7$, cyano, halo, hydroxy, and oxo.

Embodiment III-25: The compound as recited in Embodiment III-24, wherein:
$R^{6a}$ and $R^{6b}$ are independently chosen from H, $C_{1-6}$alkyl, halo$C_{1-6}$alkyl, ($C_{1-6}$alkoxy)-$C_{1-6}$alkyl, (halo$C_{1-6}$alkoxy)$C_{1-6}$alkyl, $OR^7$, $COR^7$, $COOR^7$, $CONH_2$, $CONHR^7$, $CON(R^7)_2$, $SO_2R^7$, $SO_2NHR^7$, $SO_2N(R^7)_2$, $NHSO_2R^7$, cyano, halo, hydroxy, and oxo; and
each $R^7$ is independently chosen from $C_{1-6}$alkyl, halo$C_{1-6}$alkyl, $C_{3-6}$cycloalkyl, and $C_{3-6}$heterocycloalkyl.

Embodiment III-26: The compound as recited in Embodiment III-25, wherein:
Z is chosen from —$CH_2$—, —$C(CH_3)_2$—,

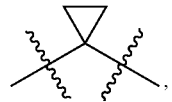

—CF—, and —O—;
p is 2; and
each Y is —$CH_2$—.

Embodiment III-27: The compound as recited in Embodiment III-26, wherein Z is chosen from —$CH_2$—, —$C(CH_3)_2$—,

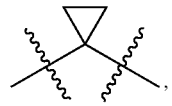 [SMILES: *C1(*)CC1 ; ","]

—$CF_2$—, and —O—.

Embodiment III-28: The compound as recited in Embodiment III-27, wherein:
each $R^3$ is independently chosen from cyano, fluoro, hydroxy, $C_{1-6}$alkyl, $C_{1-6}$fluoroalkyl, and $C_{1-6}$hydroxyalkyl, or
any two $R^3$, when directly attached to the same atom, forms a 3-7 membered cycloalkyl ring.

Embodiment III-29: The compound as recited in Embodiment III-28, wherein:
$R^{6a}$ and $R^{6b}$ are independently chosen from H, $C_{1-6}$alkyl, fluoro$C_{1-6}$alkyl, ($C_{1-6}$alkoxy)-$C_{1-6}$alkyl, (fluoro$C_{1-6}$alkoxy)$C_{1-6}$alkyl, $C_{3-6}$cycloalkyl, ($C_{3-6}$alkoxy)$C_{3-6}$cycloalkyl, $OR^7$, $COR^7$, COOH, and $COOR^7$; and
each $R^7$ is independently chosen from $C_{1-6}$alkyl and fluoro$C_{1-6}$alkyl.

Embodiment III-30: The compound as recited in Embodiment III-29, wherein $R^{6a}$ and $R^{6b}$ are independently chosen from $C_{1-6}$alkyl, fluoro$C_{1-6}$alkyl, ($C_{1-6}$alkoxy)$C_{1-6}$alkyl, (fluoro$C_{1-6}$alkoxy)$C_{1-6}$alkyl, and $OR^7$.

Embodiment III-31: The compound as recited in Embodiment III-30, wherein at least one of $R^{6a}$ and $R^{6b}$ is chosen from $C_{1-6}$alkyl, ($C_{1-6}$alkoxy)$C_{1-6}$alkyl, and (fluoro$C_{1-6}$alkoxy)$C_{1-6}$alkyl.

Embodiment III-32: The compound as recited in Embodiment III-31, wherein at least one of $R^{6a}$ and $R^{6b}$ is chosen from $C_{1-6}$alkoxymethyl, $C_{1-6}$alkoxyethyl, and fluoro$C_{1-6}$alkoxy-ethyl.

Embodiment IV-34: The compound as recited in Embodiment 100, wherein:
each $R^2$ and $R^3$ is independently chosen from cyano, halo, hydroxy, $C_{1-6}$alkyl, $C_{1-6}$haloalkyl, $C_{1-6}$hydroxyalkyl, ($C_{1-6}$alkoxy)$C_{1-6}$alkyl, or
any two $R^2$ or $R^3$, when directly attached to the same atom, forms a 3-6 membered cycloalkyl ring; and
$R^{6a}$ and $R^{6b}$ are chosen from H, $C_{1-6}$alkyl, $C_{1-6}$alkoxy, ($C_{1-6}$alkoxy)$C_{1-6}$alkyl, and (fluoro$C_{1-6}$alkoxy)$C_{1-6}$alkyl.

Also provided are embodiments, wherein any embodiment above may be combined with any one or more of these embodiments, provided the combination is not mutually exclusive.

As used herein, two embodiments are "mutually exclusive" when one is defined to be something which is different than the other. For example, an embodiment, wherein two groups combine to form a cycloalkyl is mutually exclusive with an embodiment in which one group is ethyl the other group is hydrogen. Similarly, an embodiment, wherein one group is —CH$_2$— is mutually exclusive with an embodiment, wherein the same group is —NH—.

Also provided is a compound chosen from the Examples disclosed herein.

The present invention also relates to a method of inhibiting at least one PRMT function comprising the step of contacting PRMT with a compound as described herein. The cell phenotype, cell proliferation, activity of PRMT, change in biochemical output produced by active PRMT, expression of PRMT, or binding of PRMT with a natural binding partner may be monitored. Such methods may be modes of treatment of disease, biological assays, cellular assays, biochemical assays, or the like.

Also provided herein is a method of treatment of a PRMT-mediated disease comprising the administration of a therapeutically effective amount of a compound as disclosed herein, or a salt thereof, to a patient in need thereof.

In certain embodiments, the disease is chosen from a vascular disease, a metabolic disease, an autoimmune disease, and a proliferative disease.

Also provided herein is a compound as disclosed herein for use as a medicament.

Also provided herein is a compound as disclosed herein for use as a medicament for the treatment of a PRMT-mediated disease.

Also provided is the use of a compound as disclosed herein as a medicament.

Also provided is the use of a compound as disclosed herein as a medicament for the treatment of a PRMT-mediated disease.

Also provided is a compound as disclosed herein for use in the manufacture of a medicament for the treatment of a PRMT-mediated disease.

Also provided is the use of a compound as disclosed herein for the treatment of a PRMT-mediated disease.

Also provided herein is a method of inhibition of type I PRMTs comprising contacting PRMT with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

Compounds of the present invention may be selective amongst the PRMT isoforms, e.g. PRMT1, PRMT3, CARM1, PRMT6, and PRMT8 in various ways. For example, compounds described herein may be selective for PRMT1 and/or PRMT6 over the other isoforms, be a pan-inhibitor of all the isoforms, or be selective for only one isoform. In certain embodiments, compounds of the present invention are selective for PRMT1 over other isoforms.

In certain embodiments, the PRMT-mediated disease is chosen from vascular disease, a metabolic disease, an autoimmune disease, and a proliferative disease.

Also provided is a method of modulation of a PRMT-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the pharmaceutical composition is formulated for intravenous administration.

In certain embodiments, the pharmaceutical composition is formulated for subcutaneous or intramuscular administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group, wherein the term alkyl is as defined above and, wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings, wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group, wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo [3.2.1]octane. "Cycloalkyl", as used herein, alone or in combination, encompasses "bicycloalkyl" and "spirocycloalkyl", as defined below.

The term "bicycloalkyl", as used herein, alone or in combination, refers to a cyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo [3.3.0]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "fluoroalkoxy," as used herein, alone or in combination, refers to a fluoroalkyl group attached to the parent molecular moiety through an oxygen atom. Specifically embraced are difluoromethoxy, trifluoromethoxy, pentafluoroethoxy, 2,2,2-trifluoroethoxy, 3,3,3-trifluoropropoxy, and (1,1,1,3,3,3-hexafluoroprop-2-yl)oxy.

The term "fluoroalkyl," as used herein, alone or in combination, refers to an alkyl group having the meaning as defined above, wherein one or more hydrogens are replaced with a fluorine. Specifically embraced are monofluoroalkyl, difluoroalkyl and polyfluoroalkyl groups. Examples of fluoroalkyl groups include fluoromethyl, difluoromethyl, trifluoromethyl, 2,2,2-trifluoroethyl, pentafluoroethyl, heptafluoropropyl, difluoroethyl, difluoropropyl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above, wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and, wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups, wherein heterocyclic rings are fused with aryl rings, wherein heteroaryl rings are fused with other heteroaryl rings, wherein heteroaryl rings are fused with heterocycloalkyl rings, or, wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited. The term "heterocycloalkyl", as used herein, alone or in combination, is understood to encompass "heterobicycloalkyl", as defined below. The term "heterocycloalkyl", as used herein, alone or in combination, is understood to encompass "lactone", as defined below. The term "heterocycloalkyl", as used herein, alone or in combination, is understood to encompass "lactam", as defined below. The term "heterocycloalkyl", as used herein, alone or in combination, is understood to encompass "spiroheterocycloalkyl", as defined below.

The term "azaheterocycloalkyl", as used herein, alone or in combination, refers to a heterocycloalkyl, wherein the ring members are chosen from carbon and nitrogen. By way of example, the term "azaheterocycloalkyl" is understood to encompass pyrroline, piperazine, 2-azaspiro[4.4]nonane, and 1,4-diazabicyclo[2.2.2]octane.

The term "oxaheterocycloalkyl", as used herein, alone or in combination, refers to a heterocycloalkyl, wherein the ring members are chosen from carbon and oxygen. By way of example, the term "oxaheterocycloalkyl" is understood to encompass tetrahydrofuran, 3,4-dihydro-2H-pyran, tetrahydropyran, and 6,10-dioxaspiro[4.5]decane.

The term "heterobicycloalkyl", as used herein, alone or in combination, refers to a heterocyclic alkyl system that is characterized by the presence of two atoms, termed "bridgehead atoms" that are connected to each other via three bond pathways. "Heterobicycloalkyl" thus encompasses, by way of example, 3-azabicyclo[3.1.0]hexane, 3,7-diazabicyclo[3.3.0]octane, and 1-aza-4,6-dioxabicyclo(3.3.0)octane.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The term "lactam" refers to a heterocycloalkyl ring which comprises a —C(=O)NH— moiety.

The term "lactone" refers to a heterocycloalkyl ring which comprises a —C(=O)O— moiety.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl).

Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycloalkyl", as used herein, alone or in combination, refers to an alkyl group having two rings that has a single atom common to both rings. Examples of spirocycloalkyl systems include spiro[3.3]heptane and spiro[4.4]nonane.

The term "spiroheterocycloalkyl", as used herein, alone or in combination, refers to a heteroalkyl group having two rings that has a single atom common to both rings. Examples of spiroheterocycloalkyl systems include 2-azaspiro[3.3]heptane and 3-azaspiro[4.4]nonane.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —SO—.

The term "sulfonyl," as used herein, alone or in combination, refers to —SO$_2$—.

The term "N-sulfonamido" refers to a RSO$_2$NR'— group with R and R' as defined herein.

The term "S-sulfonamido" refers to a —SO$_2$NRR', group, with R and R' as defined herein.

The terms "thia" and "thio," as used herein, alone or in combination, refer to a —S— group or an ether, wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X₃CSO₂NR— group with X is a halogen and R as defined herein.

The term "trihalomethanesulfonyl" refers to a X₃CSO₂— group where X is a halogen.

The term "trihalomethoxy" refers to a X₃CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group. Parentheses may be used to further clarify connectivity. For example, the terms "arylalkyl" and "(aryl)alkyl" are equivalent, and both refer to an aryl group attached to the parent molecule through an alkyl group. The term "(alkyl)aryl" refers to an alkyl group attached to the parent molecule through an aryl group, and may be described equivalently as an alkyl substituted aryl group. Similarly, the term "((alkyl)aryl)alkyl" refers to an ((alkyl)aryl) group attached to the parent molecule through an alkyl group, or equivalently as an alkyl substituted aryl group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N₃, SH, SCH₃, C(O)CH₃, CO₂CH₃, CO₂H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PRMT1 inhibitor" is used herein to refer to a compound that exhibits an IC50 with respect to PRMT1 activity of no more than about 100 μM and more typically not more than about 50 μM, as measured in the PRMT1 enzymatic assay described generally herein. "IC50" is that concentration of inhibitor which reduces the activity of an enzyme (e.g., PRMT1) to half-maximal level. Certain compounds disclosed herein have been discovered to exhibit inhibitory activity against PRMT1. In certain embodiments, compounds will exhibit an IC50 with respect to PRMT1 of no more than about 10 μM; in further embodiments, compounds will exhibit an IC50 with respect to PRMT1 of no more than about 2 μM; in yet further embodiments, compounds will exhibit an IC50 with respect to PRMT1 of not more than about 500 nM; in yet further embodiments, compounds will exhibit an IC50 with respect to PRMT1 of not more than about 200 nM; in yet further embodiments, compounds will exhibit an IC50 with respect to PRMT1 of not more than about 50 nM, as measured in the PRMT1 assay described herein.

The phrase "therapeutically effective" is intended to qualify the amount of active ingredients used in the treatment of a disease or disorder or on the effecting of a clinical endpoint.

The term "therapeutically acceptable" refers to those compounds which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VCHA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a PRMT inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide(TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatininb (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PRMT-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of PRMT-mediated disorders.

Specific diseases to be treated by the compounds, compositions, and methods disclosed herein include proliferative diseases, neurological diseases, amyotrophic lateral sclerosis, muscular dystrophies, autoimmune disorders, vascular disorders, and metabolic disorders.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations

Ac$_2$O=acetic anhydride; AcCl=acetyl chloride; AcOH=acetic acid; AIBN=azobisisobutyronitrile; aq.=aqueous; BPD=4,4,5,5-tetramethyl-2-(4,4,5,5-tetramethyl-1,3,2-dioxaborolan-2-yl)-1,3,2-dioxaborolane; Bu$_3$SnH=tributyltin hydride; CD$_3$OD=deuterated methanol; CDCl$_3$=deuterated chloroform; CDI=1,1'-Carbonyldiimidazole; DAST=diethylaminosulfur trifluoride; DBU=1,8-diazabicyclo[5.4.0]undec-7-ene; DCE=1,2-dichloroethane; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMP=Dess-Martin periodinane; DMSO-d$_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; Et$_2$O=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; IBX=2-iodoxybenzoic acid; i-PrOH=isopropanol; LAH=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chloro-succinimide; NMP=N-Methyl-2-pyrrolidone; Pd(Ph$_3$)$_4$=tetrakis(triphenylphosphine)-palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=TBDMS=tert-butyldimethylsilyl; TBSCl=TBDMSCl=tert-butyldimethylchlorosilane; TEA=Et$_3$N=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl.

GENERAL SYNTHETIC METHODS FOR PREPARING COMPOUNDS

The following schemes can be used to practice the present invention.

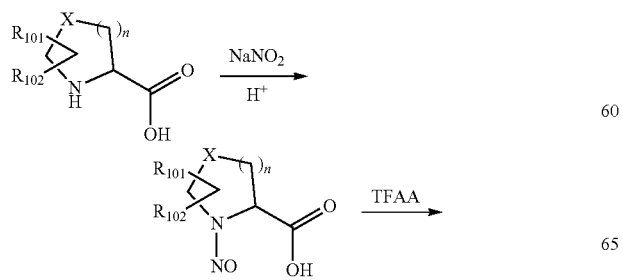

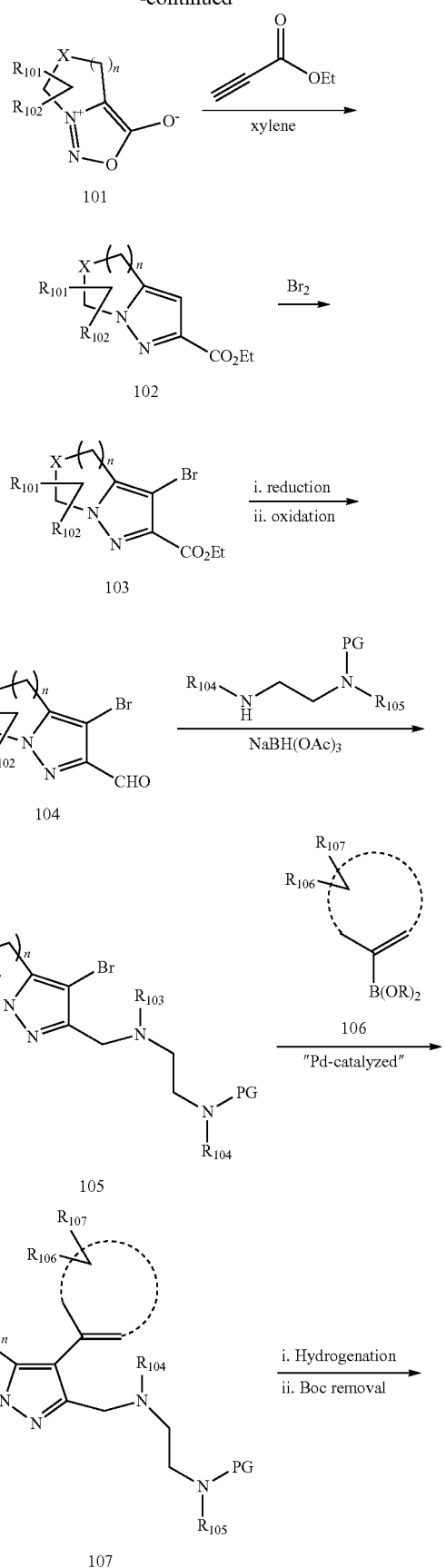

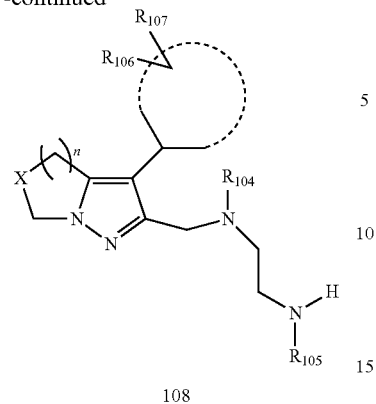

108 n = 1, 2; X = NR₁₀₃, O

Bicyclic-pyrazole compounds with a functionalized amino side-chain of general formula 108 can be prepared as shown in Scheme I. Nitration of a cyclic amino acid (e.g. a functionalized proline, or 2-carboxypiperazine, or 3-carboxymorpholine) can be performed in the presence of sodium nitrite in aqueous acid to give a corresponding nitroso intermediate. Treatment of the latter with a dehydrating agent, such as TFAA, in an appropriate solvent provides a zwitterionic intermediate of general formula 101. Dipolar cycloaddition of intermediate 101 with a suitable propiolate (e.g. ethyl propiolate) at elevated temperatures can yield the corresponding functionalized bicyclic pyrazole ester 102. Bromination of this bicyclic pyrazole intermediate with a bromination reagent (e.g. elemental bromine) in an appropriate organic solvent gives the bromo-ester of general formula 103. The corresponding bicyclic pyrazole carboxaldehyde 104 can be obtained from 103 by reduction to the hydroxymethyl derivative (e.g. with lithium aluminium hydride) and subsequent reaction with an oxidizing agent (e.g. Des-Martin periodinane) in the appropriate organic solvent. Installation of the amino side chain to the bicyclic pyrazole aldehyde can be accomplished through reductive amination with a suitably protected ethylendiamine derivative (e.g. PG can be Boc or Cbz). The amino side chain of interest can be reacted with the aldehyde of the bicyclic pyrazole in the presence of a reducing agent such as sodium triacetoxy borohydride to give the intermediate of general formula 105. A palladium mediated coupling can be utilized to install a highly functionalized cyclic alkene by reacting 105 with the boronic ester or acid 106 in the presence of a suitable catalyst (e.g. PdCl₂(dppf)) and a suitable base (e.g. K₂CO₃) with an appropriate organic solvent (e.g. dioxane) at elevated temperature, yielding di-substituted bicyclic pyrazoles of general structure 107. Functional bicyclic pyrazoles 108 can then be derived from 107 by reduction of the olefin with a suitable metal catalyst (e.g. palladium on carbon) under an atmosphere of hydrogen, followed by removal of the amino side chain protecting group.

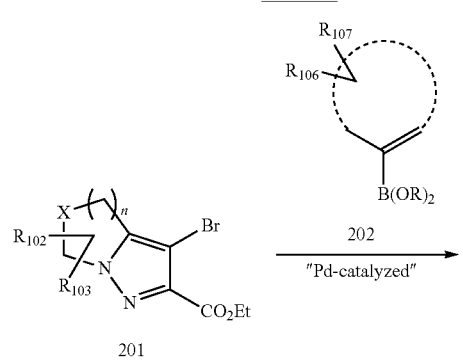

Scheme II

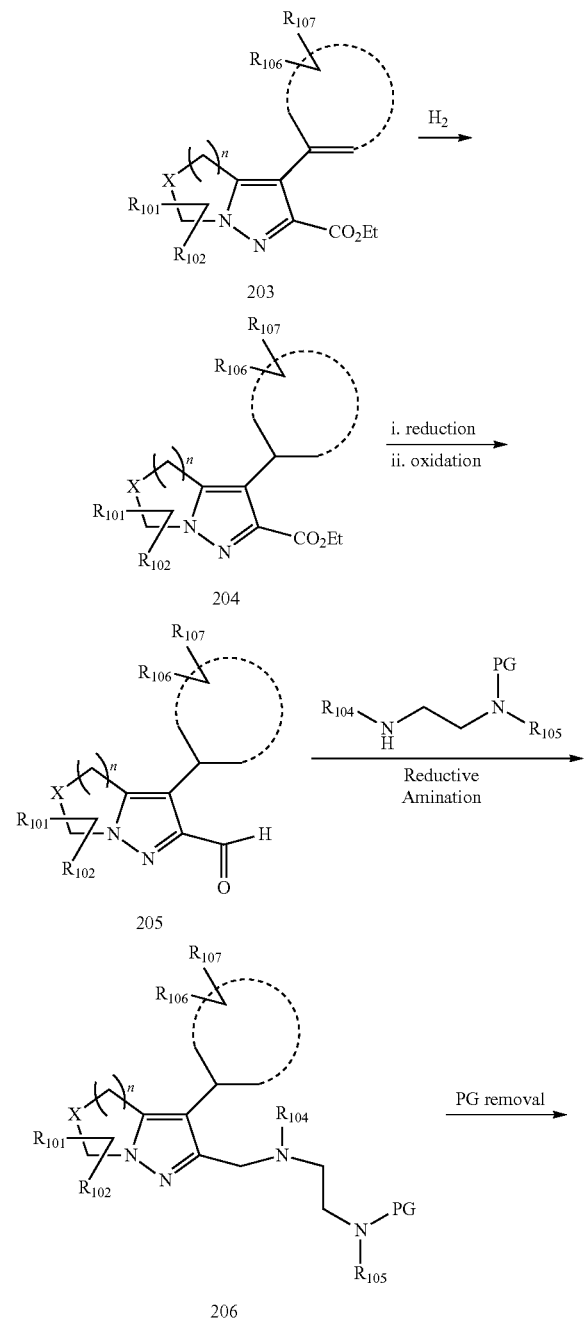

103

-continued

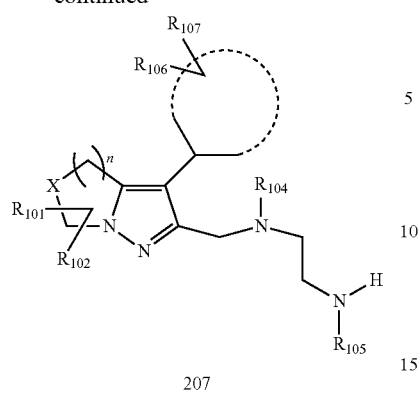

207 n = 1, 2; X = CHR₁₀₁, NR₁₀₁, O

104

-continued

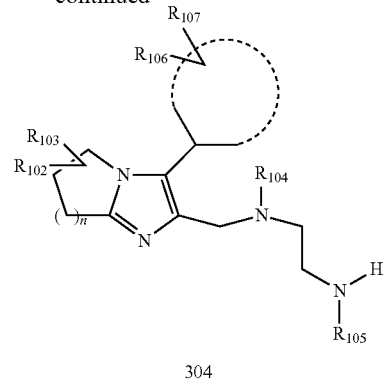

304 n = 1, 2

An alternative way to obtain bicyclic pyrazoles of structure 207 is described in Scheme II. A palladium mediated coupling can be employed to convert 201 into the highly functionalized 203 by reaction with a cyclic alkene boronic ester or acid 202 in the presence of a suitable catalyst (e.g. PdCl₂(dppf)) and a suitable base (e.g. K₂CO₃) with an appropriate organic solvent (e.g. dioxane) at elevated temperature. Reduction of the double bond under an atmosphere of H₂, in the presence of a metal catalyst can give esters of general structure 204. Functional group manipulation to obtain aldehyde 205, followed by reductive amination to install the functionalized ethylendiamine sidechain in 206 and final removal of the protecting groups can be employed to complete the synthesis of compounds 207.

A further way to prepare the compounds described in this invention is presented in Scheme III. Bicyclic imidazole derivatives of general structure 304 can be synthesized via conjugate addition of a substituted cyclic amine (e.g. functionalized pyrrolidine or piperidine) to a suitable propiolate (e.g. ethyl propiolate) in an appropriate solvent, to obtain the intermediate enamines of general structure 301. Reaction of such enamines with a diazonium salts (e.g. 4-nitrobenzenediazonium tetrafluoroborate) in the presence of an amine base (e.g. TEA) in an appropriate organic solvent at elevated temperature can give the desired bicycle intermediates 302. Bromination of the latter with a bromination reagent (e.g. elemental bromine) in an organic solvent affords the intermediates 303. Further manipulation to generate fully functionalized compounds of structure 304 can then be executed according the synthetic routes depicted in Scheme I or Scheme II.

Scheme III

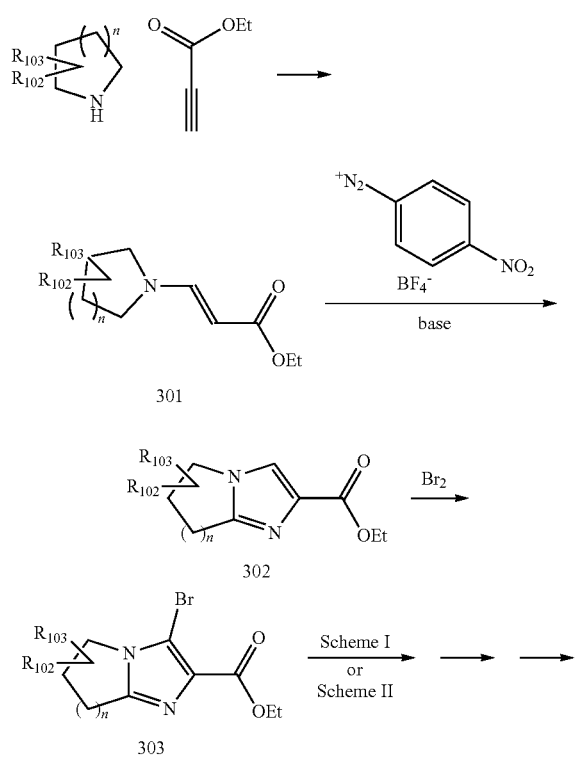

Scheme IV

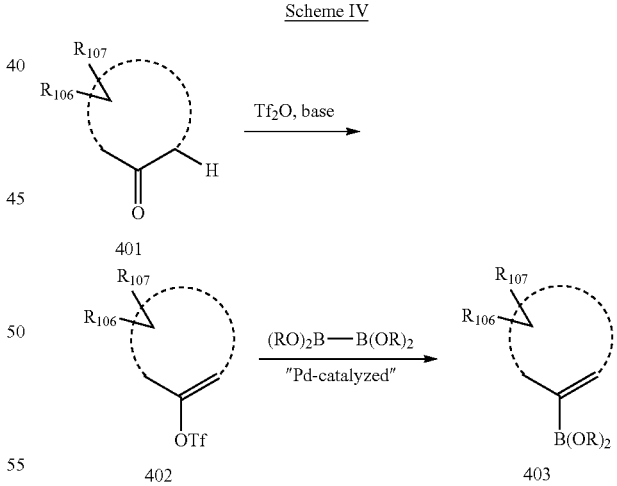

Boronic acids or esters of general structure 403 can be commercially available or can be prepared in a straightforward manner starting from the corresponding alkenyl bromides using a strong base such as BuLi, and reacting the resulting highly reactive lithium species with trimethyl borate. Alternatively, boronic acids or esters I-e can be prepared by the corresponding ketone 401, as described in Scheme IV. Ketone 401 can be converted to enol triflates 402 and further functionalized into boronates 403 via palladium mediated coupling reactions with suitable boron derivatives.

Scheme V

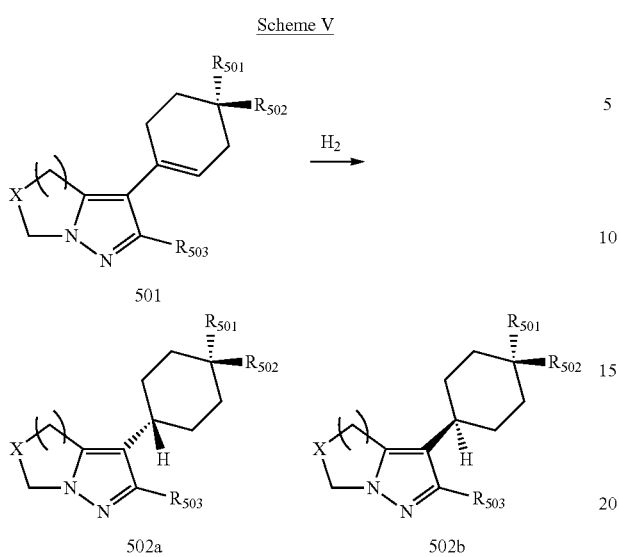

Certain compounds disclosed herein exist as diastereomers. The origin of a stereocenter for certain compounds can be seen in the reactivity depicted in Scheme V, which corresponds to the hydrogenation step of Scheme I ($R_{503}$=CH$_2$N(R$_{104}$)CH$_2$CH$_2$N(Boc)(R$_{105}$) or Scheme II ($R_{503}$=CO$_2$Et). Hydrogenation of disubstituted cyclohexene 501 proceeds at either face, giving cyclohexanes 502a and 502b. Because of the diastereomeric nature of the 502a/b pair, the ratio of diastereomers formed during the hydrogenation reaction may be different from 1:1. The two diastereomers can be separated immediately after the hydrogenation step, or the two diastereomers can be separated at the final purification of compounds. Alternatively, the mixture of diastereomers formed during synthesis may be carried forward.

This disclosure contemplates the use of selective hydrogenation methods to enrich a reduction product mixture in a certain diastereomer. Many methods are available for diastereoselective reduction, including the use of modified transition metal catalysts, and enantiopure ligands for metal catalysts.

In certain embodiments, compounds of Formula (II) or (III) have substituted cyclohexene moieties that are related to the structures depicted for 502a/b in Scheme V. This disclosure contemplates diastereomeric mixtures as well as compounds that have been separated into individual diastereomers. Examples 1, 3, 6, 7, 8, and 9 were separated into individual diastereomers. Examples 62 to 77, disclosed in Table 2, below, were separated into individual diastereomers.

In certain embodiments, the compounds are provided in an approximately 1:1 ratio of diastereomers. In certain embodiments, the compounds are provided in a 20% or greater diastereomeric excess of one diastereomer. In certain embodiments, the compounds are provided in a 50% or greater diastereomeric excess of one diastereomer. In certain embodiments, the compounds are provided in a 80% or greater diastereomeric excess of one diastereomer. In certain embodiments, the compounds are provided in a 90% or greater diastereomeric excess of one diastereomer. In certain embodiments, the compounds are provided in a 95% or greater diastereomeric excess of one diastereomer. In certain embodiments, the compounds are provided in a 99% or greater diastereomeric excess of one diastereomer. In certain embodiments, the compounds are provided in essentially diastereomerically pure form.

The following Intermediates are used to synthesize the Example compounds disclosed herein.

INTERMEDIATE A

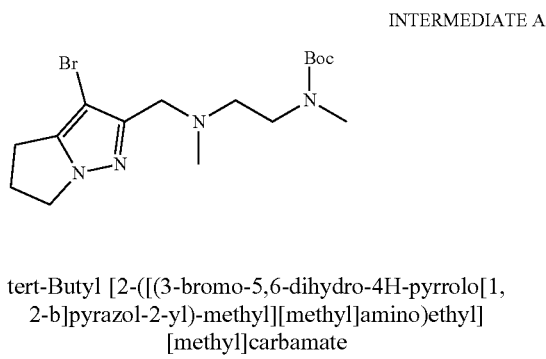

tert-Butyl [2-([(3-bromo-5,6-dihydro-4H-pyrrolo[1,2-b]pyrazol-2-yl)-methyl][methyl]amino)ethyl][methyl]carbamate

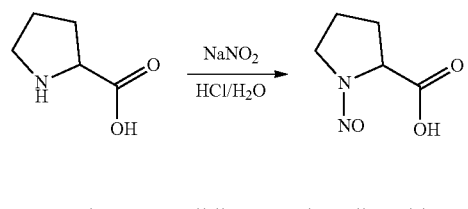

1-Nitrosopyrrolidine-2-carboxylic acid

To a solution of pyrrolidine-2-carboxylic acid (30.0 g, 260.6 mmol, 1.0 eq) in H$_2$O (250 mL) at 0° C. was added NaNO$_2$ (26.97 g, 390.9 mmol, 21.2 mL, 1.5 eq) followed by aqueous HCl (12 M, 26.06 mL, 1.20 eq), and the mixture was allowed to warm slowly to 15° C. and stirred for a further 12 hr. The reaction mixture was diluted with EtOAc (500 mL), the aqueous layer was separated. The organic layer was washed with brine (100 mL×2), dried over Na$_2$SO$_4$, filtered and concentrated under reduced pressure to afford the title compound (25 g) as a white solid. The product was used without further purification in the next step.

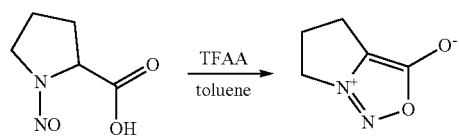

5,6-Dihydro-4H-pyrrolo[1,2-c]oxadiazol-7-ium-3-olate

To a solution of the product from the previous step (25.0 g, 173.4 mmol, 1.0 eq) in toluene (300 mL) at 0° C. was added dropwise TFAA (54.65 g, 260.2 mmol, 36.2 mL, 1.5 eq). The resulting mixture was stirred at 15° C. for 1 hr and then concentrated under reduced pressure. The residue was purified by SiO$_2$ gel chromatography (PE:EtOAc=5:1 to 1:1) to afford the title compound (20.5 g, 162.6 mmol, 93.7% yield) as a viscous oil. $^1$H NMR (400 MHz, CDCl$_3$): 4.39-4.43 (m, 2H), 2.81-2.91 (m, 2H), 2.75-2.79 (m, 2H).

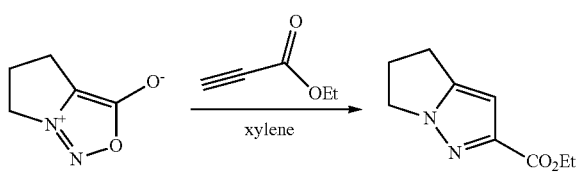

Ethyl 5,6-dihydro-4H-pyrrolo[1,2-b]pyrazole-2-carboxylate

A mixture of the product from the previous step (20.5 g, 162.6 mmol, 1.0 eq) and ethyl prop-2-ynoate (19.14 g, 195.1 mmol, 19.14 mL, 1.2 eq) in xylene (200 mL) was heated to 120° C. and stirred for 36 hr. The reaction mixture was concentrated under reduced pressure and the residue was purified by SiO$_2$ gel chromatography (PE:EtOAc=10:1 to 3:1) to afford the title compound (17.0 g, 94.3 mmol, 58% yield) as yellow solid. $^1$H NMR (400 MHz, CDCl$_3$): 6.52 (s, 1H), 4.34-4.40 (m, 2H), 4.18-4.20 (m, 2H), 2.89-2.93 (m, 2H), 2.59-2.63 (m, 2H), 1.36-1.40 (t, J=7.2 Hz, 3H).

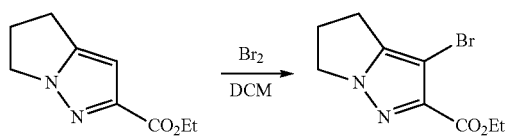

Ethyl 3-bromo-5,6-dihydro-4H-pyrrolo[1,2-b]pyrazole-2-carboxylate

To a solution of the product from the previous step (15 g, 83.2 mmol, 1.0 eq) in CH$_2$Cl$_2$ (200 mL) at 0° C. was added a solution of Br$_2$ (8.58 mL, 26.61 g, 166.48 mmol, 2.0 eq) in CH$_2$Cl$_2$ (15 mL). The resulting mixture was stirred at 0° C. for 2 hr and was then quenched by slow addition of NaHCO$_3$/Na$_2$S$_2$O$_3$ (200 mL, 1:1 v:v). The layers were separated, the aqueous layer was extracted with CH$_2$Cl$_2$ (100 mL×4), and the combined organic layers were washed with brine (100 mL), dried over Na$_2$SO$_4$, filtered and concentrated under reduced pressure. The residue was suspended in PE/EtOAc (220 mL, 10:1 v:v) and stirred for 2 hr. The solid was removed by filtration, and the filter cake was collected and dried to afford the title compound (14.0 g, 54.0 mmol, 64.9% yield) as a light brown solid. $^1$H NMR (400 MHz, CDCl$_3$): 4.39-4.44 (q, J=7.2 Hz, 2H), 4.23-4.27 (m, 2H), 2.90-2.94 (m, 2H), 2.62-2.69 (m, 2H), 1.40-1.43 (t, J=7.2 Hz, 3H).

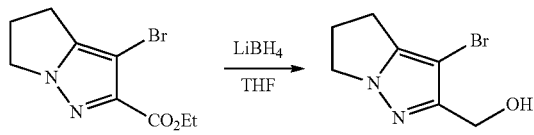

(3-Bromo-5,6-dihydro-4H-pyrrolo[1,2-b]pyrazol-2-yl)methanol

To a solution of the product from the previous step (4.0 g, 15.4 mmol, 1.0 eq) in THF (40 mL) at 15° C. was added portionwise LiBH$_4$ (673 mg, 30.9 mmol, 2.0 eq). The resulting mixture was heated to 60° C. and stirred for 6 hr. The reaction was then allowed to cool to RT and quenched by saturated aq. NH$_4$Cl solution (60 mL). The layers were separated, the aqueous layer was extracted with EtOAc (20 mL×4), and the combined organic layers were washed with brine (30 mL), dried over Na$_2$SO$_4$, filtered and concentrated under reduced pressure to afford the title compound (3.20 g, 14.7 mmol, 95.5% yield) as a white solid. $^1$H NMR (400 MHz, CDCl$_3$): 4.63-4.64 (m, 2H), 4.14-4.17 (m, 2H), 2.84-2.88 (m, 2H), 2.59-2.65 (m, 2H), 2.09 (s, 1H).

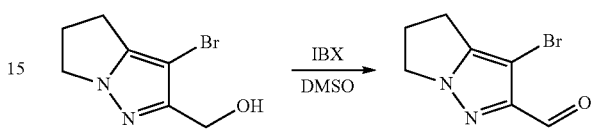

3-Bromo-5,6-dihydro-4H-pyrrolo[1,2-b]pyrazole-2-carbaldehyde

To a solution of the product from the previous step (1.60 g, 7.37 mmol, 1.0 eq) in DMSO (20 mL) at 20° C. was added portionwise IBX (4.13 g, 14.74 mmol, 2.0 eq). The mixture was stirred at 20° C. for 1 hr, then poured into H$_2$O (100 mL) and filtered. The filtrate was extracted with EtOAc (30 mL×4). The combined organic layers were washed with brine (30 mL), dried over Na$_2$SO$_4$, filtered and concentrated under reduced pressure to afford the title compound (1.60 g) as a white solid which was used in the next step without further purification. MS (ES$^+$) C$_7$H$_7$BrN$_2$O requires: 215. found: 215, 217 [M+H]$^+$.

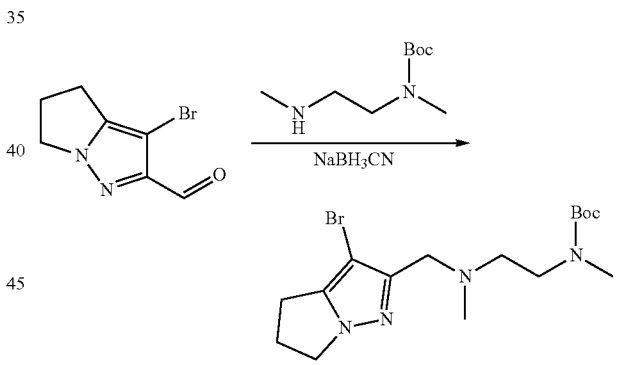

tert-Butyl-N-[2-[(3-bromo-5,6-dihydro-4H-pyrrolo[1,2-b]pyrazol-2-yl)methyl-methyl-amino]ethyl]-N-methyl-carbamate A mixture of the product from the previous step (1.60 g, 7.44 mmol, 1.0 eq) and tert-butyl N-methyl-N-[2-(methylamino)ethyl]carbamate (1.54 g, 8.18 mmol, 1.1 eq) in MeOH (20.00 mL) was stirred at 15° C. for 1 h. NaBH$_3$CN (935 mg, 14.9 mmol, 2.09 eq) and AcOH (446.8 mg, 7.4 mmol, 425 µL, 1.0 eq) were then added to the solution and the resulting mixture was stirred at 15° C. for 15 hr. Saturated aq. NaHCO$_3$ solution (80 mL) was slowly added to the reaction mixture, and the resulting suspension was concentrated under reduced pressure to remove MeOH. The residual aqueous solution was extracted with EtOAc (20 mL×5), the combined organic layers were washed with brine (30 mL), dried over Na$_2$SO$_4$, filtered and concentrated under reduced pressure. The residue was purified by SiO₂ gel chromatography (PE:EtOAc=10:1 to 3:1) to afford the title compound (1.6 g, 3.76 mmol, 50.5% yield) as a light yellow oil.

¹H NMR (400 MHz, CDCl₃): δ 4.12-4.16 (m, 2H), 3.53 (s, 2H), 3.34 (s, 2H), 2.87 (s, 3H), 2.82-2.85 (m, 2H), 2.55-2.62 (m, 4H), 2.32 (s, 3H), 1.44 (s, 9H). MS (ES⁺) C₁₆H₂₇BrN₄O₂ requires: 387, found: 387, 389 [M+H]⁺.

INTERMEDIATE B

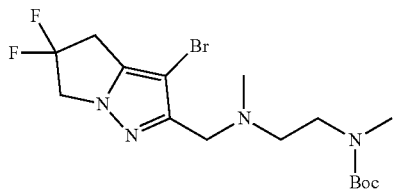

tert-Butyl (2-(((3-bromo-5,5-difluoro-5,6-dihydro-4H-pyrrolo[1,2-b]pyrazol-2-yl)-methyl)(methyl)amino)ethyl)(methyl)carbamate

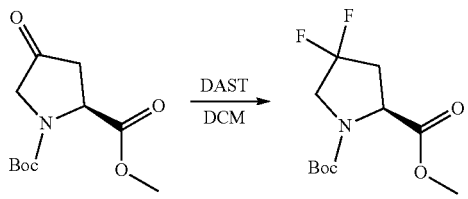

1-(tert-Butyl) 2-methyl (S)-4,4-difluoropyrrolidine-1,2-dicarboxylate

To a solution of 1-(tert-butyl) 2-methyl (S)-4-oxopyrrolidine-1,2-dicarboxylate (10 g, 41.1 mmol, 1.0 eq) in CH₂Cl₂ (80 mL) at 0° C. was added dropwise a solution of DAST (12.2 g, 75.7 mmol, 10.0 mL, 1.84 eq) in CH₂Cl₂ (20 mL). The resulting mixture was allowed to warm slowly to RT, stirred for a further 16 hr and quenched by dropwise addition of saturated aq. NaHCO₃ (50 mL) and H₂O (50 mL). The layers were separated, the aqueous phase was extracted with CH₂Cl₂ (50 mL×3) and the combined organic layers were dried over Na₂SO₄, filtered and concentrated under reduced pressure to give the title compound as a viscous oil (11 g). ¹H NMR (400 MHz, CDCl₃): δ 4.55-4.43 (m, 1H), 3.89-3.81 (m, 2H), 3.77 (s, 3H), 2.71-2.65 (m, 1H), 2.52-2.44 (m, 1H), 1.47 (s, 9H).

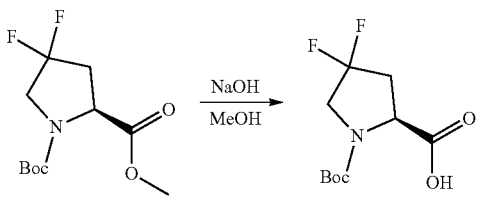

(2S)-1-tert-butoxycarbonyl-4,4-difluoro-pyrrolidine-2-carboxylic acid

To a solution of the product from the previous step (11 g, 41.47 mmol, 1.0 eq) in a mixture of THF (80 mL) and MeOH (80 mL) was added dropwise aqueous NaOH (2 M, 41.47 mL, 2.0 eq). The resulting mixture was stirred at 25° C. for 2 hr then concentrated under reduced pressure and partitioned between H₂O (40 mL) and EtOAc (30 mL). The layers were separated; the aqueous phase was adjusted to pH 6 by addition of 2M aq. HCl, then extracted with EtOAc (50 mL×5). The combined organic layers were dried over Na₂SO₄, filtered and concentrated under reduced pressure to give the title compound (9 g) as a viscous oil. ¹H NMR (400 MHz, CDCl₃): δ 6.15 (br, 1H), 4.55-4.53 (m, 1H), 3.86-3.73 (m, 2H), 2.72-2.65 (m, 2H), 1.48 (s, 9H).

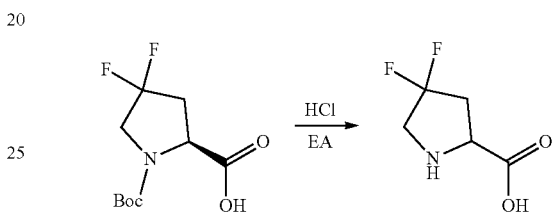

(2S)-4,4-Difluoropyrrolidine-2-carboxylic acid

To a solution of the product from the previous step (9 g, 35.8 mmol, 1.0 eq) in EtOAc (50 mL) at 0° C. was added dropwise HCl in EtOAc (4 M, 50 mL, 5.58 eq). The resulting suspension was stirred at 25° C. for 1 h, then filtered, the filter cake was washed with EtOAc (30 mL) and dried to give the title compound (4.8 g, 25.6 mmol, 71.4% yield) as a solid. ¹H NMR (400 MHz, DMSO): δ 11.11 (m, 1H), 4.69-4.64 (m, 1H), 3.77-3.66 (m, 2H), 2.71-2.65 (m, 2H).

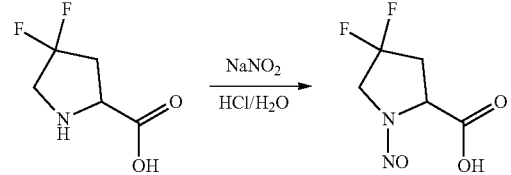

4,4-Difluoro-1-nitroso-pyrrolidine-2-carboxylic acid

To a solution of the product from the previous step (4.8 g, 25.59 mmol, 1.0 eq) in H₂O (50 mL) at 0° C. was added NaNO₂ (2.65 g, 38.39 mmol, 1.5 eq) followed by aq. HCl (12 M, 2.56 mL, 1.2 eq). The resulting solution was allowed to slowly reach RT and stirred for a further 1 h. The mixture was extracted with EtOAc (30 mL×5), the combined organic layers were washed with brine (20 mL), dried over Na₂SO₄, filtered and concentrated under reduced pressure to give the title compound (4.5 g) as a solid which was used in the next step without further purification.

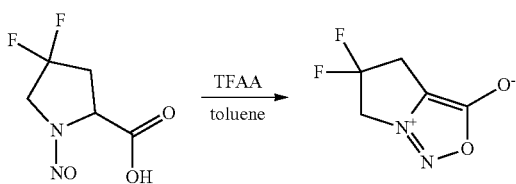

5,5-Difluoro-4,6-dihydropyrrolo[1,2-c]oxadiazol-7-ium-3-olate

To a solution of the product from the previous step (4.8 g, 26.6 mmol, 1.0 eq) in toluene (50 mL) at 0° C. was added dropwise TFAA (8.4 g, 40.0 mmol, 5.56 mL, 1.5 eq) and the resulting mixture was stirred at 25° C. for 1 h. The volatiles were removed under reduced pressure and the residue was purified by $SiO_2$ gel chromatography (PE:EtOAc=20:1 to 5:1) to give the title compound (3.7 g, 22.8 mmol, 86% yield) as a light yellow solid. $^1$H NMR (400 MHz, CDCl$_3$): δ 4.80 (t, J=12 Hz, 2H), 3.49 (t, J=12 Hz, 2H).

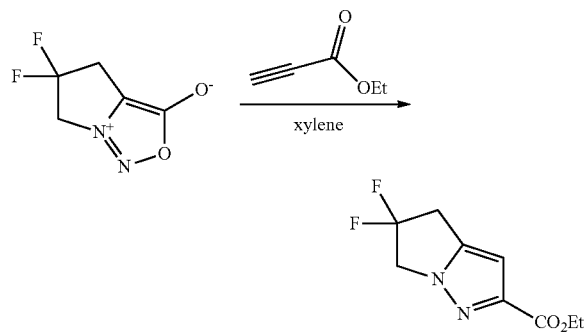

Ethyl 5,5-difluoro-4,6-dihydropyrrolo[1,2-b]pyrazole-2-carboxylate

A mixture of the product from the previous step (3.7 g, 22.8 mmol, 1.0 eq) and ethyl prop-2-ynoate (4.48 g, 45.6 mmol, 4.48 mL, 2.0 eq) in xylene (50 mL) was stirred at 120° C. for 16 hr. The reaction mixture was cooled to RT, the volatiles were removed under reduced pressure and the residue was purified by $SiO_2$ gel chromatography (PE:EtOAc=100:1 to 30:1) to give the title compound (2 g, 9.2 mmol, 40% yield) as a pale yellow solid. $^1$H NMR (400 MHz, CDCl$_3$): δ 6.67 (s, 1H), 4.58 (t, J=12 Hz, 2H), 4.43-4.38 (m, 2H), 3.50 (t, J=12 Hz, 2H), 1.42-1.39 (m, 3H).

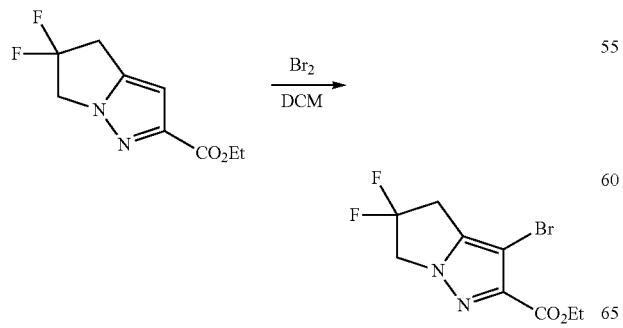

Ethyl 3-bromo-5,5-difluoro-4,6-dihydropyrrolo[1,2-b]pyrazole-2-carboxylate

To a solution of the product from the previous step (2.0 g, 9.25 mmol, 1.0 eq) in CH$_2$Cl$_2$ (20 mL) at 0° C. was added dropwise was added a solution of Br$_2$ (2.96 g, 18.50 mmol, 954 μL, 2.0 eq) in CH$_2$Cl$_2$ (10 ml). The resulting mixture was stirred at 25° C. for 2 hr, then quenched by slow addition of saturated aq. NaHCO$_3$/Na$_2$S$_2$O$_3$ (80 mL, 1:1 v:v), and filtered through a pad of celite. The layers were separated, and the aqueous phase was extracted with CH$_2$Cl$_2$ (20 mL×4). The combined organic layers were dried over Na$_2$SO$_4$, filtered and concentrated under reduced pressure to give the title compound (2.6 g) as a pale yellow solid. $^1$H NMR (400 MHz, CDCl$_3$): δ 4.62 (t, J=12 Hz, 2H), 4.42 (q, J=7.6 Hz, 2H), 3.49 (t, J=12 Hz, 2H), 1.42 (t, J=7.6 Hz, 3H).

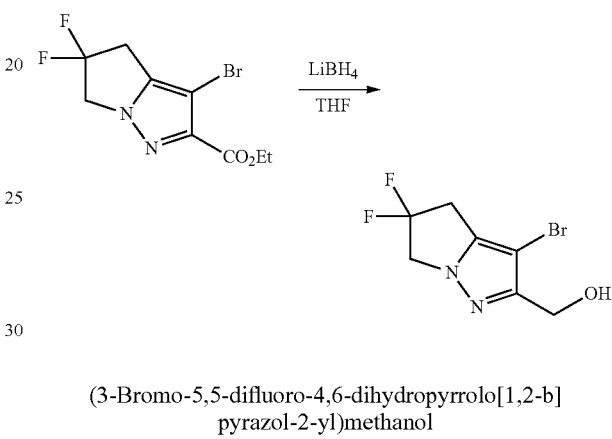

(3-Bromo-5,5-difluoro-4,6-dihydropyrrolo[1,2-b]pyrazol-2-yl)methanol

To a solution of the product from the previous step (1.3 g, 4.41 mmol, 1.0 eq) in THF (30 mL) was added LiBH$_4$ (240 mg, 11.0 mmol, 2.5 eq). The resulting mixture was heated to 45° C. and stirred for 4 hr. The reaction mixture was then cooled to RT, and quenched by slow addition of saturated aq. NH$_4$Cl (30 mL). The resulting suspension was extracted with EtOAc (20 mL×3), the combined organic layers were washed with brine (30 mL), dried over Na$_2$SO$_4$, filtered and concentrated under reduced pressure to give the title compound (1.1 g) as a pale yellow solid. $^1$H NMR (400 MHz, CDCl$_3$): δ 4.7 (s, 2H), 4.56-4.50 (m, 2H), 3.47-3.40 (m, 2H), 2.05 (s, 1H).

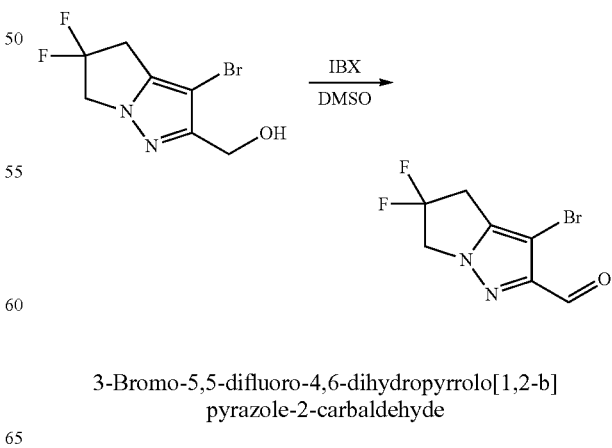

3-Bromo-5,5-difluoro-4,6-dihydropyrrolo[1,2-b]pyrazole-2-carbaldehyde

To a solution of the product from the previous step (1.1 g, 4.35 mmol, 1.0 eq) in DMSO (20 mL) was added IBX (2.43 g, 8.69 mmol, 2.0 eq) portionwise. The resulting mixture was stirred at 25° C. for 12 hr. H₂O (40 mL) and EtOAc (40 mL) were added and the mixture was filtered through a pad of CELITE(R), washing with EtOAc (30 mL). The layers were separated, the aqueous phase was extracted with EtOAc (20 mL×3), and the combined organic layers were washed with brine (30 mL×2), dried over Na₂SO₄, filtered and concentrated under reduced pressure to give the title compound (1 g) as a pale yellow solid. ¹H NMR (400 MHz, CDCl₃): δ 9.94 (s, 1H), 4.65 (t, J=12 Hz, 2H), 3.51 (t, J=12 Hz, 2H).

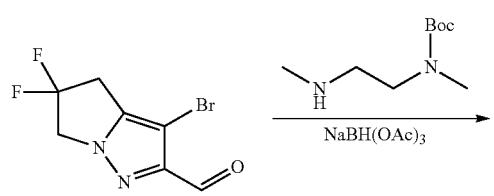

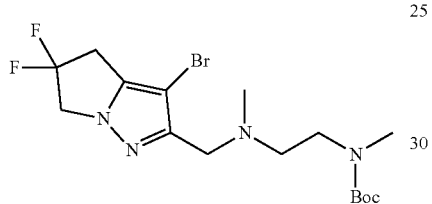

tert-Butyl [2-([(3-bromo-5,5-difluoro-5,6-dihydro-4H-pyrrolo[1,2-b]pyrazol-2-yl)methyl][methyl]amino)ethyl][methyl]carbamate To a solution of the product from the previous step (600 mg, 2.39 mmol, 1.0 eq) and tert-butyl N-methyl-N-[2-(methylamino)ethyl]-carbamate (495 mg, 2.63 mmol, 1.1 eq) in DCE (20 mL) at RT were added AcOH (71.8 mg, 1.20 mmol, 68 μL, 0.5 eq) and NaBH(OAc)₃ (1.01 g, 4.78 mmol, 2.0 eq). The resulting mixture was stirred at RT for 1 h. and quenched by careful addition of saturated aq. NaHCO₃ (40 mL). The suspension was extracted with CH₂Cl₂ (20 mL×3), the combined organic layers were dried over Na₂SO₄, filtered concentrated under reduced pressure and the residue was purified by SiO₂ gel chromatography (PE:EtOAc=20:1 to 3:1) to give the title compound (500 mg, 1.18 mmol, 49% yield) as a pale yellow oil.

¹H NMR (400 MHz, CDCl₃) δ 4.52 (t, J=12.8 Hz, 2H), 3.56 (s, 2H), 3.45-3.35 (m, 4H), 2.87 (s, 3H), 2.60 (s, 2H), 2.32 (s, 3H), 1.45 (s, 9H). MS (ES⁺) C₁₆H₂₅BrF₂N₄O₂, requires: 423, found: 423 and 425 [M+H].

INTERMEDIATE C

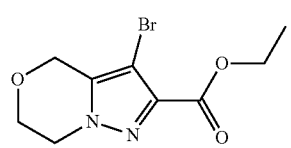

Ethyl-3-bromo-6,7-dihydro-4H-pyrazolo[5,1-c][1,4]oxazine-2-carboxylate

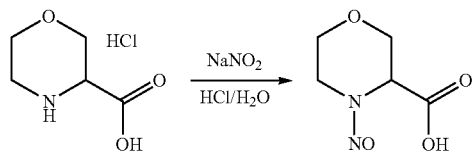

4-Nitrosomorpholine-1-carboxylic acid

To a solution of morpholine-3-carboxylic acid (5.0 g, 29.8 mmol, 1.0 eq) in H₂O (30 mL) was added NaNO₂ (3.09 g, 44.7 mmol, 2.4 mL, 1.50 eq). The mixture was cooled to 0-5° C. and aq. HCl (12 M, 4.97 mL, 2.00 eq) was slowly added. After addition, the mixture was allowed to reach 25° C. and stirred for a further 12 hr, then extracted with EtOAc (40 mL×5). The combined organic layers were dried over Na₂SO₄, filtered and concentrated under reduced pressure to afford the title compound (4.8 g) as a light yellow oil which was used in next step without further purification.

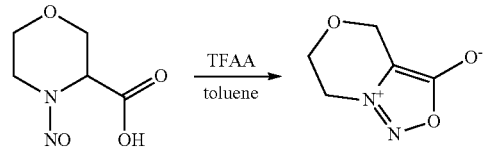

6,7-Dihydro-4H-[1,2,3]oxadiazolo[4,3-c][1,4]oxazin-8-ium-3-olate

To a solution of the product from the previous step (4.8 g, 29.98 mmol, 1.0 eq) in toluene (45 mL) at 0° C. was added TFAA (9.44 g, 44.96 mmol, 6.25 mL, 1.5 eq). The mixture was then stirred at 15° C. for 12 hr and concentrated under reduced pressure. The residue was purified by SiO₂ gel chromatography (PE:EtOAc=10/1 to 0:1) to afford the title compound (3.6 g, 25.33 mmol, 84% yield) as a pale yellow solid. ¹H NMR (400 MHz, CDCl₃) δ 4.62 (s, 2H), 4.36 (t, J=5.2 Hz, 2H), 4.09 (t, J=5.2 Hz, 2H).

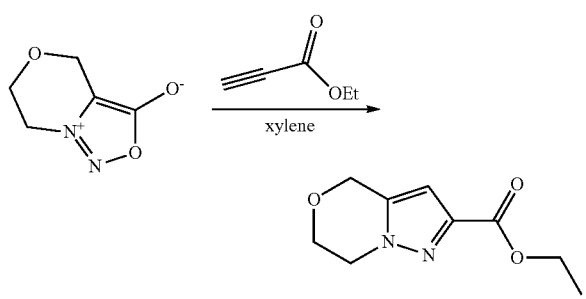

Ethyl-6,7-dihydro-4H-pyrazolo[5,1-c][1,4]oxazine-2-carboxylate

To a solution of 6,7-dihydro-4H-oxadiazolo[4,3-c][1,4]oxazin-8-ium-3-olate (3.6 g, 25.3 mmol, 1.0 eq) in xylene (45 mL) was added ethyl propiolate (3.23 g, 32.9 mmol, 3.23 mL, 1.3 eq). The mixture was stirred at 120° C. for 5 hr and concentrated under reduced pressure. The residue was purified by SiO₂ gel chromatography (PE:EtOAc=10/1 to 0:1) to afford the title compound (3.4 g, 17.3 mmol, 68% yield) as a light yellow solid. $^1$H NMR (400 MHz, CDCl₃) δ 6.56 (s, 1H), 4.84 (s, 2H), 4.38 (q, J=7.2 Hz, 2H), 4.27 (t, J=5.2 Hz, 2H), 4.12 (t, J=5.2 Hz, 2H), 1.39 (t, J=7.2 Hz, 2H).

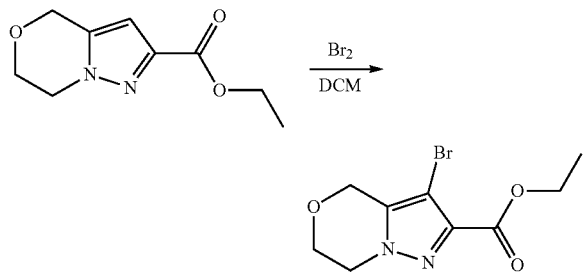

Ethyl-3-bromo-6,7-dihydro-4H-pyrazolo[5,1-c][1,4]oxazine-2-carboxylate

To a solution of the product from the previous step (3.4 g, 17.3 mmol, 1.0 eq) in CH₂Cl₂ (30 mL) at 0° C. was added a solution of Br₂ (5.54 g, 34.7 mmol, 1.79 mL, 2.0 eq) in CH₂Cl₂ (10 mL). The reaction mixture was stirred at 15° C. for 1 hr and was quenched by the addition of saturated aq. NaHCO₃ (15 mL) and saturated aq. Na₂S₂O₃ (15 mL). The mixture was then extracted with CH₂Cl₂ (20 mL×2), the combined organic layers were washed with brine (20 mL), dried over Na₂SO₄, filtered and concentrated under reduced pressure. The residue was triturated with PE:EtOAc (15:1, 30 mL) to afford the title compound (4.1 g, 14.9 mmol, 86% yield) as a white solid. $^1$H NMR (400 MHz, CDCl₃) δ 4.75 (s, 2H), 4.32 (q, J=7.2 Hz, 2H), 4.23 (t, J=5.2 Hz, 2H), 4.11 (t, J=5.2 Hz, 2H), 1.41 (t, J=7.2 Hz, 2H).

INTERMEDIATE C-1

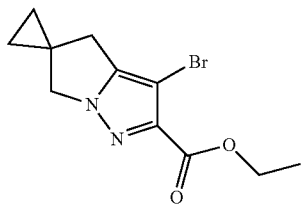

Ethyl 3-bromospiro-[4,6-dihydropyrrolo[1,2-b]pyrazole-5,1'-cyclopropane]-2-carboxylate The title compound was obtained as a white solid using the same procedure already described for Intermediate C, using 5-azaspiro[2.4]heptane-6-carboxylic acid as the starting material. $^1$H NMR (400 MHz, CDCl₃) δ 4.42 (q, J=7.2 Hz, 2H), 4.15 (s, 2H), 2.89 (s, 2H), 1.42 (t, J=7.2 Hz, 3H), 0.86 (s, 4H). MS (ES⁺) C₁₁H₁₃BrN₂O₂ requires 284, 286, found 285, 287 [M+H]⁺.

INTERMEDIATE C-2

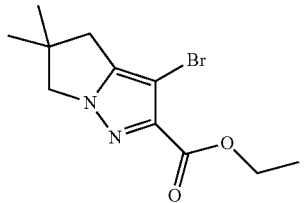

Ethyl 3-bromo-5,5-dimethyl-4,6-dihydropyrrolo[1,2-b]pyrazole-2-carboxylate

The title compound was obtained as a pale yellow oil using the same procedure already described for Intermediate C, using 4,4-dimethylpyrrolidine-2-carboxylic acid as the starting material. $^1$H NMR (400 MHz, CDCl₃) δ 4.42 (q, J=7.2 Hz, 2H), 3.98 (s, 2H), 2.71 (s, 2H), 1.42 (t, J=7.2 Hz, 3H), 1.32 (s, 6H). MS (ES⁺) C₁₁H₁₅BrN₂O₂ requires 286, 288, found 287, 289 [M+H]⁺.

INTERMEDIATE C-3

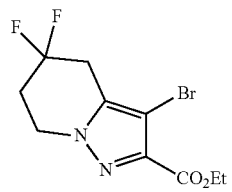

Ethyl-3-bromo-5,5-difluoro-6,7-dihydro-4H-pyrazolo[1,5-a]pyridine-2-carboxylate

The title compound was obtained as a pale yellow solid using the same procedure already described for ethyl 5,5-difluoro-4,6-dihydropyrrolo[1,2-b]pyrazole-2-carboxylate (Intermediate B, step 7), using 1-(tert-butyl) 2-methyl 4-oxopiperidine-1,2-dicarboxylate as the starting material instead of 1-(tert-butyl) 2-methyl (S)-4-oxopyrrolidine-1,2-dicarboxylate. $^1$H NMR (400 MHz, CDCl₃) δ 4.44-4.31 (m, 4H), 3.20 (t, J=13.7 Hz, 2H), 2.58-2.49 (m, 2H), 1.35 (t, J=7.1 Hz, 3H). MS (ES⁺) C₁₀H₁₁BrF₂N₂O₂ requires 308, 310, found 309, 311 [M+H]⁺.

INTERMEDIATE C-4

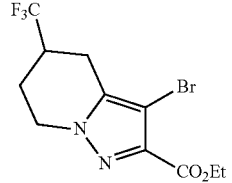

Ethyl 3-bromo-5-(trifluoromethyl)-4,5,6,7-tetrahydropyrazolo[1,5-a]pyridine-2-carboxylate The title compound was obtained as a white solid using the same procedure already described for Intermediate C, using 4-(trifluoromethyl)piperidine-2-carboxylic acid as the starting material. $^1$H NMR (400 MHz, CDCl₃) δ 4.52-4.48

(m, 1H), 4.46-4.41 (m, 2H), 4.19-4.11 (m, 1H), 3.16-3.10 (m, 1H), 2.78-2.71 (m, 1H), 2.68-2.64 (m, 1H), 2.44-2.39 (m, 1H), 2.15-2.08 (m, 1H), 1.44-1.40 (m, 3H). MS (ES⁺) $C_{11}H_{15}BrN_2O_2$ $C_{11}H_{12}BrF_3N_2O_2$ requires 340, 342, found 341, 343 [M+H]⁺.

INTERMEDIATE D

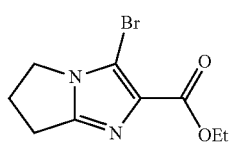

Ethyl 3-bromo-6,7-dihydro-5H-pyrrolo[1,2-a]imidazole-2-carboxylate

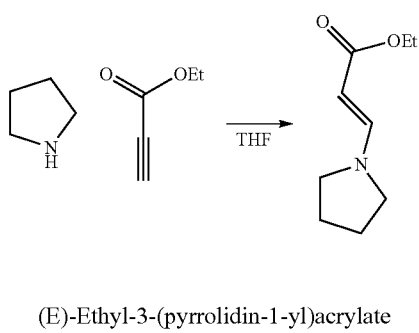

(E)-Ethyl-3-(pyrrolidin-1-yl)acrylate

To a solution of pyrrolidine (5.87 ml, 70.3 mmol) in THF (280 ml) at 10° C. was added ethyl propiolate (7.12 ml, 70.3 mmol) and the resulting mixture was stirred at 25° C. for 1 h. The volatiles were removed under reduced pressure to give the title compound (11.85 g, 70.0 mmol, 100% yield) as a yellow solid. ¹H NMR (600 MHz, CDCl₃) δ 7.65 (d, J=12.8 Hz, 1H), 4.48 (d, J=12.8 Hz, 1H), 4.13 (q, J=7.1 Hz, 2H), 3.51-2.94 (m, 4H), 1.96-1.90 (m, 4H), 1.26 (t, J=7.1 Hz, 3H).

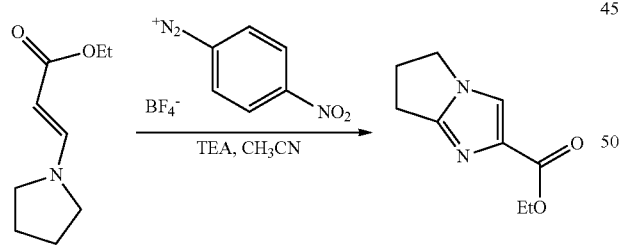

Ethyl 6,7-dihydro-5H-pyrrolo[1,2-a]imidazole-2-carboxylate

To a solution of the product from the previous step (5.94 g, 35.1 mmol) in acetonitrile (700 mL) was added 4-nitrobenzenediazonium tetrafluoroborate (8.32 g, 35.1 mmol) and the resulting mixture was stirred at 25° C. for 1 h. TEA (9.79 ml, 70.2 mmol) was then added and the reaction mixture was heated to reflux for 2 h. The reaction mixture was allowed to cool to RT and the volatiles were removed under reduced pressure. The residue was purified by SiO₂ gel chromatography (0-10% MeOH in CH₂Cl₂) to give the title compound (3.6 g, 19.98 mmol, 56.9% yield) as a viscous oil. MS (ES⁺) $C_9H_{12}N_2O_2$ requires: 180, found: 203 [M+Na]⁺.

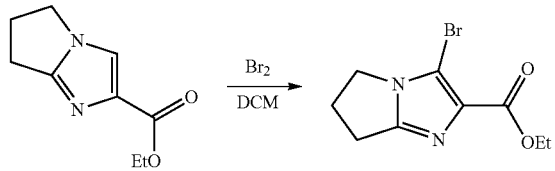

Ethyl 3-bromo-6,7-dihydro-5H-pyrrolo[1,2-a]imidazole-2-carboxylate

To a solution of the product from the previous step (1.0 g, 5.55 mmol) in CH₂Cl₂ (11 mL) at 0° C. was added a solution of Br₂ (0.286 ml, 5.55 mmol) in CH₂Cl₂ (11.1 ml). The resulting mixture was stirred at 0° C. for 1 h, quenched by addition of saturated aq. Na₂S₂O₃ (100 mL), and allowed to stir for 1 h while reaching RT. The layers were separated, the aqueous phase was extracted with CH₂Cl₂ (3×20 mL), and the combined organic layers were washed with sat NaHCO₃, then brine, dried over Na₂SO₄, filtered and concentrated under reduced pressure. The residue was purified by SiO₂ gel chromatography (0-10% MeOH in CH₂Cl₂ to give the title compound (436 mg, 1.68 mmol, 30% yield) as a light brown solid. MS (ES⁺) $C_9H_{11}BrN_2O_2$ requires: 259, found: 259, 260 [M+H]⁺.

INTERMEDIATE E

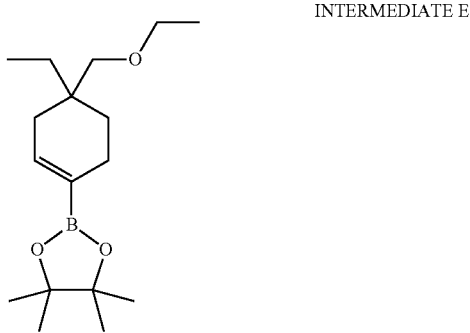 [SMILES: CCOCC1(CC)CC=C(B2OC(C)(C)C(C)(C)O2)CC1]

2-[4-(Ethoxymethyl)-4-ethyl-cyclohexen-1-yl]-4,4,5,5-tetramethyl-1,3,2-dioxaborolane

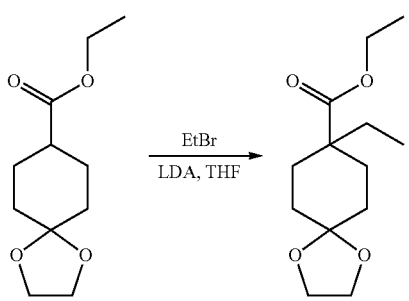 [SMILES: "EtBr" ; CCOC(=O)C1CCC2(CC1)OCCO2 ; "LDA, THF" ; CCOC(=O)C1(CC)CCC2(CC1)OCCO2]

Ethyl 8-ethyl-1,4-dioxaspiro[4.5]decane-8-carboxylate

To a solution of ethyl 1,4-dioxaspiro[4.5]decane-8-carboxylate (21 g, 98.0 mmol, 1.0 eq) in THF (250 mL) at −78° C. under N₂ atmosphere was added dropwise LDA (2 M in THF, 58.8 mL, 1.2 eq). The mixture was stirred at −78° C. for 1 hour, EtBr (19.22 g, 176.4 mmol, 1.8 eq) was slowly added at −78° C., and stirring was continued for 16 hour at −78° C. The reaction was quenched by dropwise addition of saturated aqueous NH₄Cl (30 mL) and allowed to warm to room temperature, then extracted with EtOAc (150 mL×3). The combined organic layers were washed with brine (50 mL×3), dried over Na₂SO₄, filtered and concentrated under reduced pressure. The residue was purified by SiO₂ gel chromatography (PE:EtOAc=100:0 to 30:1) to afford the title compound (11.5 g, 47.46 mmol, 48% yield) as pale yellow oil. ¹H NMR (400 MHz, d-CDCl₃, ppm): δ 4.16 (q, J=7.2 Hz, 2H), 3.94 (m, 4H), 2.16 (m, 2H), 1.60 (m, 6H), 1.47 (m, 2H), 1.26 (t, J=7.2 Hz, 3H), 0.82 (t, J=7.6 Hz, 3H).

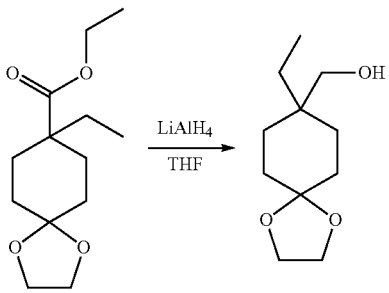 [SMILES: CCOC(=O)C1(CC)CCC2(CC1)OCCO2 ; "LiAlH4" ; CCC1(CO)CCC2(CC1)OCCO2 ; "THF"]

(8-Ethyl-1,4-dioxaspiro[4.5]decan-8-yl)methanol

To a suspension of LiAlH₄ (2.07 g, 54.48 mmol, 1.2 eq) in THF (100 mL) at 0° C. was added dropwise a solution of the product from the previous step (11 g, 45.40 mmol, 1.0 eq) in THF (50 mL). The mixture was stirred at 0-15° C. for 16 hr, cooled to 0° C. and quenched by addition of H₂O (2 mL), followed by 15% aqueous NaOH (2 mL). After stirring at room temperature for 0.5 hour, the mixture was diluted with H₂O (6 mL) and extracted with EtOAc (50 mL). The organic phase was dried over anhydrous MgSO₄, filtered and concentrated under reduced pressure. The residue was purified by SiO₂ gel chromatography (PE/EtOAc=10:1 to 0:1) to afford the title compound (8.2 g, 40.94 mmol, 90.19% yield) as a colorless oil. ¹H NMR (400 MHz, d-CDCl₃, ppm): δ 3.94 (m, 4H), 3.45 (d, J=4.4 Hz, 2H), 1.62 (m, 4H), 1.45 (m, 5H), 1.27 (m, 1H), 0.84 (t, J=7.6 Hz, 3H).

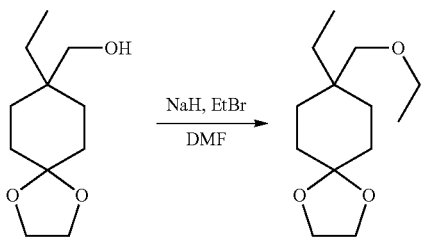

8-(ethoxymethyl)-8-ethyl-1,4-dioxaspiro[4.5]decane

To a solution of the product from the previous step (8.2 g, 40.94 mmol, 1 eq) in DMF (100 mL) at 0° C. was added NaH (4.09 g, 102.4 mmol, 60% weight, 2.5 eq) The mixture was stirred at 0° C. for 1 hour, EtBr (8.92 g, 81.89 mmol, 2 eq) was added and the mixture was stirred at 0-15° C. for a further 16 hr. The reaction mixture was quenched with saturated aqueous NH₄Cl (50 mL) and extracted with EtOAc (100 mL×3). The combined organic layers were washed with brine (50 mL×3), dried over Na₂SO₄, filtered and concentrated under reduced pressure. The residue was purified by SiO₂ gel chromatography (PE/EtOAc=100:0 to 50:1) to afford the title compound (6.1 g, 26.72 mmol, 65.25% yield) as a colorless oil. ¹H NMR (400 MHz, d-CDCl₃, ppm): δ 3.94 (s, 4H), 3.45 (q, J=9.2 Hz, 2H), 3.20 (s, 2H), 1.53 (m, 10H), 1.17 (t, J=6.8 Hz, 3H), 0.81 (t, J=7.6 Hz, 3H).

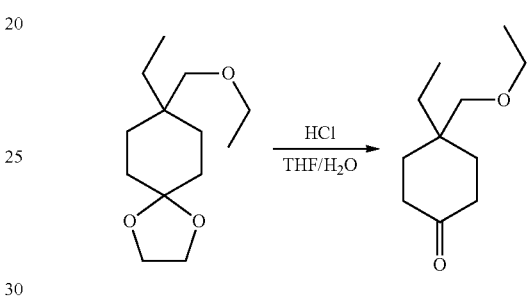

4-(Ethoxymethyl)-4-ethyl-cyclohexanone

To a solution of the product from the previous step (6.1 g, 26.72 mmol, 1 eq) in THF (50 mL) was added aq. HCl (4 M, 26.72 mL, 4 eq) and the resulting mixture was stirred at 40° C. for 16 hr. The reaction mixture was concentrated under reduced pressure and diluted with H₂O (10 mL), neutralized with saturated aqueous NaHCO₃ and extracted with EtOAc (80 mL×3). The combined organic layers were washed with brine (40 mL×2), dried over Na₂SO₄, filtered and concentrated under reduced pressure to give the title compound (4.7 g, 25.51 mmol, 95.5% yield) as a pale yellow oil. ¹H NMR (400 MHz, d-CDCl₃, ppm): δ 3.48 (q, J=7.2 Hz, 2H), 3.29 (s, 2H), 2.34 (t, J=6.8 Hz, 4H), 1.74 (m, 4H), 1.53 (m, 2H), 1.19 (t, J=6.8 Hz, 3H), 0.88 (t, J=7.6 Hz, 3H).

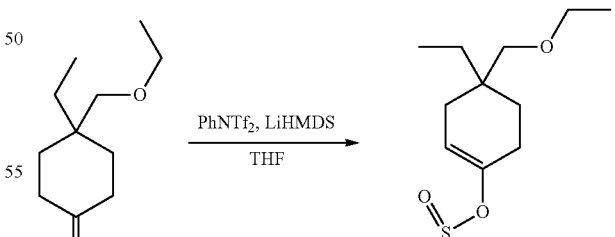

[4-(Ethoxymethyl)-4-ethyl-cyclohexen-1-yl] trifluoromethanesulfonate

To a solution of the product from the previous step (4.7 g, 25.51 mmol, 1 eq) in THF (100 mL) at −78° C. was added dropwise LiHMDS (1 M in THF, 30.61 mL, 1.2 eq) and the mixture was stirred for 1 hour. A solution of 1,1,1-trifluoro-N-phenyl-N-(trifluoromethylsulfonyl)methane-sulfonamide (9.57 g, 26.78 mmol, 1.05 eq) in THF (30 mL) was added at −78° C. and the resulting mixture was allowed to warm slowly to 0° C. An aqueous solution of KHSO$_4$ (1M, 30 mL) was added dropwise at 0° C., and the mixture was concentrated under reduced pressure. The residue was extracted with EtOAc (80 mL×3), and the combined organic layers were washed with aq. NaOH (0.5 M, 50 mL×2). The combined organic layers were washed with brine (50 mL), dried over Na$_2$SO$_4$, filtered and concentrated under reduced pressure. The residue was purified by SiO$_2$ gel chromatography (PE/EtOAc=1/0 to 100:1) to afford the title compound (6.5 g, 20.55 mmol, 80.56% yield) as a pale yellow oil. $^1$H NMR (400 MHz, d-CDCl$_3$, ppm): δ 5.67 (m, 1H), 3.46 (q, J=6.8 Hz, 2H), 3.19 (m, 2H), 2.31 (m, 2H), 2.02 (m, 2H), 1.76 (m, 1H), 1.60 (m, 1H), 1.41 (m, 2H), 1.18 (t, J=7.2 Hz, 3H), 0.84 (m, 3H).

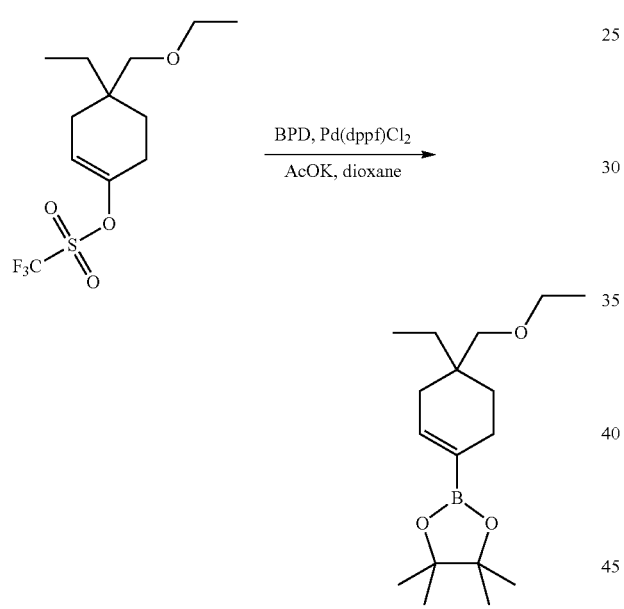

2-[4-(Ethoxymethyl)-4-ethyl-cyclohexen-1-yl]-4,4,5,5-tetramethyl-1,3,2-dioxaborolane A mixture of the product from the previous step (6.5 g, 20.55 mmol, 1.0 eq), BPD (5.74 g, 22.60 mmol, 1.1 eq), Pd(dppf)Cl$_2$ (752 mg, 1.03 mmol, 0.05 eq) and KOAc (6.05 g, 61.64 mmol, 3 eq) in dioxane (150 mL) was purged with N$_2$ for 3 times, and then stirred at 90° C. for 16 hr under N$_2$ atmosphere. The reaction mixture was concentrated under reduced pressure and the residue was partitioned between H$_2$O (30 mL) and EtOAc (100 mL×2). The combined organic layers were washed with brine (30 mL×2), dried over Na$_2$SO$_4$, filtered and concentrated under reduced pressure. The residue was purified by SiO$_2$ gel chromatography (PE/EtOAc=1/0 to 40:1) to afford the title compound (4.0 g, 13.59 mmol, 66% yield) was obtained as a pale yellow oil.

$^1$H NMR (400 MHz, d-CDCl$_3$, ppm): δ 6.5 (m, 1H), 3.44 (q, J=6.8 Hz, 2H), 3.15 (m, 2H), 2.10 (m, 2H), 1.92 (m, 2H), 1.51 (m, 1H), 1.37 (m, 3H), 1.27 (m, 12H), 1.17 (t, J=7.2 Hz, 3H), 0.81 (t, J=7.6 Hz, 3H).

INTERMEDIATE F

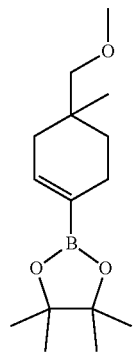

2-[4-(Methoxymethyl)-4-methyl-cyclohexen-1-yl]-4,4,5,5-tetramethyl-1,3,2-dioxaborolane

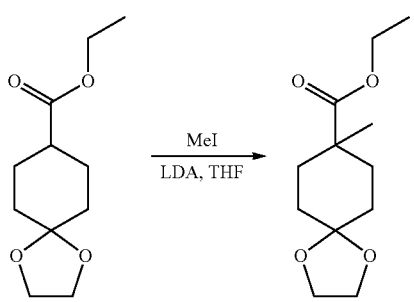 [SMILES: "MeI" ; CCOC(=O)C1CCC2(CC1)OCCO2 ; "LDA, THF" ; CCOC(=O)C1(C)CCC2(CC1)OCCO2]

Ethyl 8-methyl-1,4-dioxaspiro[4.5]decane-8-carboxylate

To a solution of ethyl 1,4-dioxaspiro[4.5]decane-8-carboxylate (25 g, 116.7 mmol, 1.0 eq) in THF (250 mL) at −78° C. under N$_2$ was added dropwise LDA (2 M in THF, 70.0 mL, 1.2 eq). The mixture was stirred at −78° C. for 1 hour, MeI (38.92 g, 274.2 mmol, 17.07 mL, 2.3 eq) was slowly added, and stirring was continued for 16 hour at −78° C. The reaction was quenched by dropwise addition of saturated aqueous NH$_4$Cl (30 mL), allowed to warm to room temperature and extracted with EtOAc (150 mL×3). The combined organic layers were washed with brine (50 mL×3), dried over Na$_2$SO$_4$, filtered and concentrated under reduced pressure. The residue was purified by SiO$_2$ gel chromatography (PE/EtOAc=50:1 to 10:1) to afford the title compound (20 g, 87.6 mmol, 75% yield) as a pale yellow oil. $^1$H NMR (400 MHz, CDCl$_3$, ppm): δ 4.15 (q, J=7.2 Hz, 2H), 3.94 (m, 4H), 2.14 (m, 2H), 1.63 (m, 4H), 1.51 (m, 2H), 1.26 (t, J=7.2 Hz, 3H), 1.19 (s, 3H).

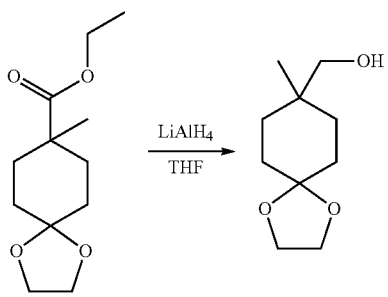 [SMILES: CCOC(=O)C1(C)CCC2(CC1)OCCO2 ; "LiAlH4" ; CC1(CO)CCC2(CC1)OCCO2 ; "THF"]

(8-Methyl-1,4-dioxaspiro[4.5]decan-8-yl)methanol

To a suspension of LiAlH₄ (6.65 g, 175.2 mmol, 2.0 eq) in THF (100 mL) 0° C. was added dropwise a solution of the product from the previous step (20 g, 87.61 mmol, 1.0 eq) in THF (250 mL). The mixture was stirred at 0-15° C. for 16 hr, cooled to 0° C. and quenched by addition of H₂O (20 mL), followed by 15% aqueous NaOH (20 mL). After stirring at room temperature for 0.5 hour, the mixture was diluted with H₂O (60 mL), filtered through a pad of Celite, and extracted with EtOAc (150 mL). The organic phase was dried over anhydrous MgSO₄, filtered and concentrated under reduced pressure. The residue was purified by SiO₂ gel chromatography (PE/EtOAc=10:1 to 0:1) to afford the title compound (15 g, 80.54 mmol, 92% yield) as a colorless oil. $^1$H NMR (400 MHz, CDCl₃, ppm): δ 3.95 (m, 4H), 3.40 (s, 2H), 1.65 (m, 4H), 1.55 (m, 2H), 1.40 (m, 3H), 0.97 (s, 3H).

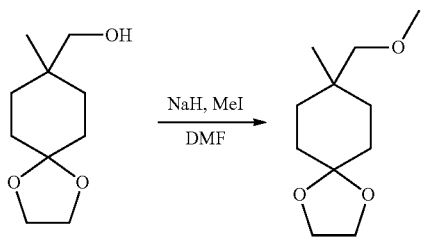

8-(Methoxymethyl)-8-methyl-1,4-dioxaspiro[4.5]decane

To a suspension of NaH (8.05 g, 201.3 mmol, 60% weight, 2.5 eq) in DMF (150 mL) at 0° C. was added the product from the previous step (15 g, 80.54 mmol, 1.0 eq). The mixture was stirred at 0° C. for 1 hour, and CH₃I (22.86 g, 161.08 mmol, 10.03 mL, 2.0 eq) was added. The mixture was stirred at 0-15° C. for 16 hr, then quenched with 50 mL of saturated aqueous NH₄Cl. The resulting solution was extracted with EtOAc (100 mL×3), the combined organic layers were washed with brine (50 mL×3), dried over Na₂SO₄, filtered and concentrated under reduced pressure. The residue was purified by SiO₂ gel chromatography (PE/EtOAc=50:1 to 20:1) to afford the title compound (14 g, 69.90 mmol, 87% yield) as a colorless oil. $^1$H NMR (400 MHz, CDCl₃, ppm): δ 3.94 (m, 4H), 3.34 (s, 3H), 3.13 (s, 2H), 1.61 (m, 6H), 1.41 (m, 2H), 0.97 (s, 3H).

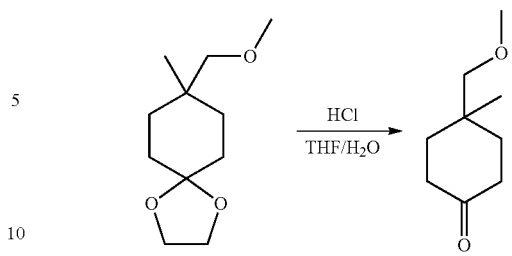

4-(Methoxymethyl)-4-methyl-cyclohexanone

To a solution of the product from the previous step (14 g, 69.90 mmol, 1.0 eq) in THF (150 mL) was added aq. HCl (4 M, 87.38 mL, 5.0 eq). The mixture was stirred at 40° C. for 16 hr then concentrated under reduced pressure. The residue was diluted with H₂O (10 mL), neutralized with saturated aqueous NaHCO₃ and extracted with EtOAc (100 mL×3). The combined organic layers were washed with brine (50 mL×2), dried over Na₂SO₄, filtered and concentrated under reduced pressure to give the title compound (10 g, 64.01 mmol, 91% yield) as a pale yellow oil. $^1$H NMR (400 MHz, CDCl₃, ppm): δ 3.37 (s, 3H), 3.23 (s, 2H), 2.36 (m, 4H), 1.82 (m, 2H), 1.66 (m, 2H), 1.12 (s, 3H).

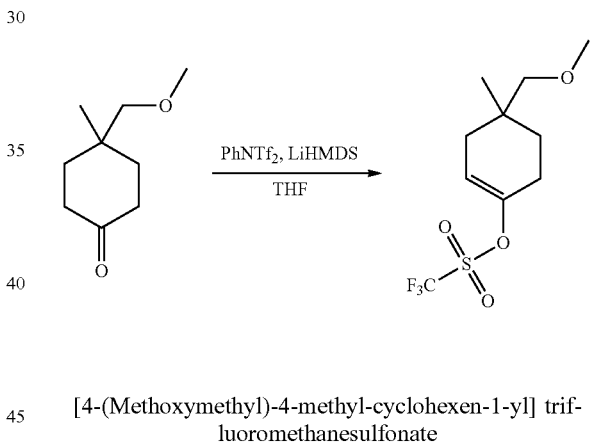

[4-(Methoxymethyl)-4-methyl-cyclohexen-1-yl] trifluoromethanesulfonate

To a solution of the product from the previous step (10 g, 64.01 mmol, 1.0 eq) in THF (200 mL) at −78° C. was added dropwise LiHMDS (1 M, 76.81 mL, 1.2 eq). The mixture was stirred at −78° C. for 1 hour, then a solution of 1,1,1-trifluoro-N-phenyl-N-(trifluoromethyl-sulfonyl)methanesulfonamide (24.01 g, 67.21 mmol, 1.05 eq) in THF (50 mL) was added and the resulting mixture was stirred at −78° C. for a further 16 hour. The mixture was warmed to 0° C., aqueous KHSO₄ (1M, 50 mL) was added drop-wise and the mixture was concentrated under reduced pressure. The residue was extracted with EtOAc (100 mL×3), and the combined organic layers were washed with aqueous NaOH (0.5 M, 100 mL×2). The organic layers were washed with brine (50 mL), dried over Na₂SO₄, filtered and concentrated under reduced pressure. The residue was purified by SiO₂ gel chromatography (PE/EtOAc=1:0 to 100:1) to afford the title compound (14 g, 48.56 mmol, 76% yield) as pale yellow oil. $^1$H NMR (400 MHz, CDCl₃, ppm): δ 5.69 (m, 1H), 3.35 (s, 3H), 3.13 (m, 2H), 2.34 (m, 2H), 2.18 (m, 1H), 1.90 (m, 1H), 1.74 (m, 1H), 1.51 (m, 1H), 0.98 (s, 3H).

125

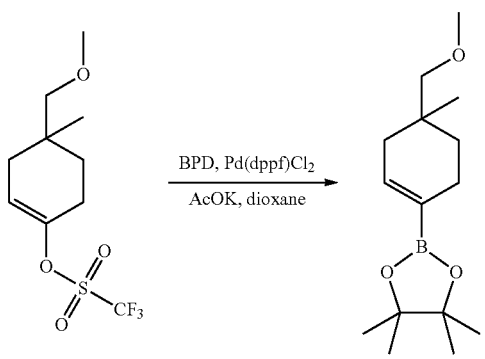

2-[4-(Methoxymethyl)-4-methyl-cyclohexen-1-yl]-4,4,5,5-tetramethyl-1,3,2-dioxaborolane A mixture of the product from the previous step (14 g, 48.56 mmol, 1.0 eq), BPD (13.57 g, 53.42 mmol, 1.1 eq), Pd(dppf)Cl$_2$ (1.78 g, 2.43 mmol, 0.05 eq), and KOAc (14.30 g, 145.69 mmol, 3 eq) in dioxane (300 mL) was degassed and purged with N$_2$ for 3 times, and stirred at 90° C. under N$_2$ for 16 hr. The reaction mixture was concentrated under reduced pressure, diluted with H$_2$O (30 mL) and extracted with EtOAc (100 mL×2). The combined organic layers were washed with brine (30 mL×2), dried over Na$_2$SO$_4$, filtered and concentrated under reduced pressure. The residue was purified by SiO$_2$ gel chromatography (PE/EtOAc=1:0 to 50:1) to afford 2-[4-(methoxymethyl)-4-methyl-cyclohexen-1-yl]-4,4,5,5-tetramethyl-1,3,2-dioxaborolane (9 g, 33.81 mmol, 70% yield) as a pale yellow oil. $^1$H NMR (400 MHz, CDCl$_3$, ppm): δ 6.51 (m, 1H), 3.33 (s, 3H), 3.09 (m, 2H), 2.13 (m, 2H), 2.04 (m, 1H), 1.81 (m, 1H), 1.48 (m, 1H), 1.35 (m, 1H), 1.27 (m, 12H), 0.92 (s, 3H).

INTERMEDIATE G

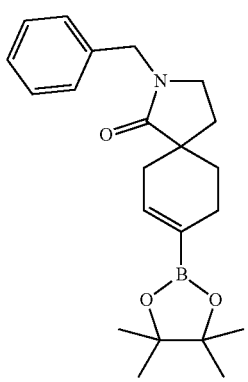

126

2-Benzyl-8-(4,4,5,5-tetramethyl-1,3,2-dioxaborolan-2-yl)-2-azaspiro[4.5]dec-7-en-1-one

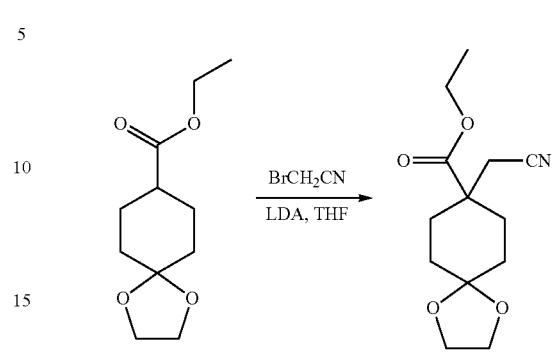

Ethyl 8-(cyanomethyl)-1,4-dioxaspiro[4.5]decane-8-carboxylate

To a solution of ethyl 1,4-dioxaspiro[4.5]decane-8-carboxylate (50 g, 233.36 mmol, 1.00 eq) in THF (500 mL) at −65° C. was added dropwise LDA (2 M in THF, 128.3 mL, 1.10 eq) and the mixture was stirred at −65° C. for 1 hr. A solution of 2-bromoacetonitrile (33.59 g, 280.04 mmol, 18.66 mL, 1.20 eq) and DMPU (14.96 g, 116.68 mmol, 14.11 mL, 0.50 eq) in THF (100 mL) were then added drop-wise to the reaction mixture at −65° C. The resulting solution was slowly warmed to 15° C. and stirred for 15 hr and quenched by saturated NH$_4$Cl (300 mL). The layers were separated, the aqueous layer was extracted with EtOAc (100 mL×3), and the combined organic layers were washed with brine (100 mL), dried over Na$_2$SO$_4$, filtered and concentrated under reduced pressure. The crude product was purified by silica gel chromatography (PE:EtOAc=50:1 to 5:1) to afford the title compound (27 g, 106.6 mmol, 46% yield) as a light yellow oil. $^1$H NMR (400 MHz, CDCl$_3$): δ 4.21-4.26 (q, J=7.2 Hz, 2H), 3.94-3.96 (m, 4H), 2.58 (s, 2H), 2.23-2.25 (m, 2H), 1.66-1.72 (m, 6H), 1.28-1.32 (t, J=7.2 Hz, 3H).

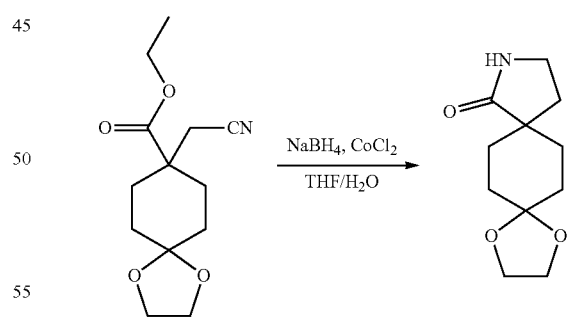

9,12-Dioxa-3-azadispiro[4.2.4$^8$.2$^5$]tetradecan-4-one

To a mixture of the product from the previous step (15 g, 59.22 mmol, 1.00 eq) and CoCl$_2$ (3.84 g, 29.61 mmol, 0.50 eq) in THF (300 mL) and H$_2$O (150 mL) at 15° C. was added NaBH$_4$ (11.20 g, 296.10 mmol, 5.00 eq) in portions. The resulting mixture was stirred at 15° C. for 6 hr. A second portion of CoCl$_2$ (1.92 g, 14.81 mmol, 0.25 eq) and NaBH$_4$ (5.60 g, 148.05 mmol, 2.50 eq) were added and the resulting mixture was stirred at 15° C. for a further 14 hr. A 25% aqueous NH₃ solution (15 mL) was added, the reaction mixture was filtered through a pad of CELITE(R), and washed with EtOAc/H₂O (2:1, 500 mL). The filtrate was separated and the aqueous layer was extracted with EtOAc (100 mL×5). The combined organic layers were dried over Na₂SO₄, filtered and concentrated under reduced pressure. The residue was washed with PE/EtOAc (50 mL, 10:1) and concentrated to afford the title compound (7 g, 33.14 mmol, 55% yield) as a white solid. ¹H NMR (400 MHz, CDCl₃): δ 5.96 (s, 1H), 3.95 (s, 4H), 3.30-3.34 (m, 2H), 2.00-2.06 (m, 4H), 1.96-1.99 (m, 2H), 1.56-1.60 (m, 4H).

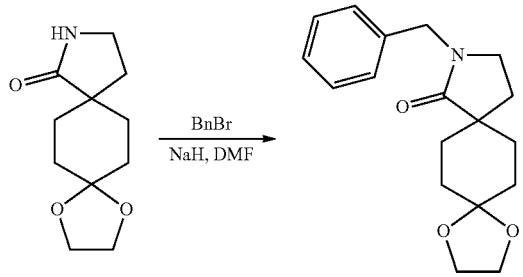

3-Benzyl-9,12-dioxa-3-azadispiro[4.2.4⁸.2⁵]tetradecan-4-one

To a solution of NaH (1.09 g, 29.60 mmol, 65% w/w, 2.5 eq) in DMF (40.00 mL) at 0° C. was added the product from the previous step (2.5 g, 11.83 mmol, 1.0 eq). The mixture was stirred at 0° C. for 1 hour. Benzyl bromide (4.05 g, 23.67 mmol, 2.81 mL, 2.0 eq) was added and the mixture was stirred at 0° C. for 16 hr, then quenched at 0° C. with H₂O (20 mL) and extracted with EtOAc (50 mL×2). The combined organic layers were washed with brine (15 mL×3), dried over Na₂SO₄, filtered and concentrated under reduced pressure. The residue was purified by SiO₂ gel chromatography (PE/EtOAc=10/1 to 1:1) to afford 3-benzyl-9,12-dioxa-3-azadispiro[4.2.4⁸.2⁵]tetradecan-4-one (3.5 g, 10.45 mmol, 88% yield) as a pale yellow oil. ¹H NMR (400 MHz, CDCl₃, ppm): δ 7.33 (m, 3H), 7.23 (d, J=6.8 Hz, 2H), 4.48 (s, 2H), 3.98 (m, 4H), 3.17 (t, J=6.8 Hz, 2H), 2.07 (m, 2H), 1.93 (m, 4H), 1.63 (m, 2H), 1.53 (m, 2H).

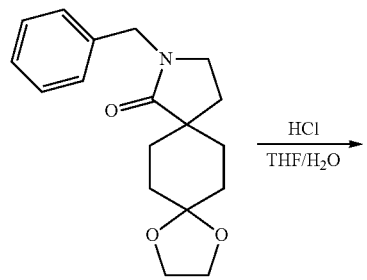

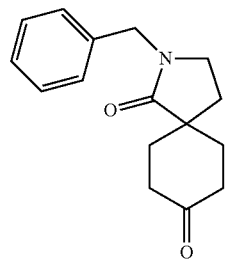

2-Benzyl-2-azaspiro[4.5]decane-1,8-dione

To a solution of the product from the previous step (3.5 g, 11.61 mmol, 1.0 eq) in THF (40 mL) at 15° C. was added aq. HCl (3 M, 23.23 mL, 6.0 eq). The reaction mixture was stirred at 15° C. for 16 hr, then concentrated under reduced pressure. The pH was adjusted to 8 by addition of saturated aq. NaHCO₃ (30 mL), and then extracted with CH₂Cl₂/MeOH=10:1(50 mL×2). The combined organic layers were washed with brine (20 mL), dried over Na₂SO₄, filtered and concentrated under reduced pressure to give the crude 2-benzyl-2-azaspiro[4.5]decane-1,8-dione (2.9 g, 10.14 mmol, 87% yield) as a pale yellow oil. ¹H NMR (400 MHz, CDCl₃, ppm): δ 7.35 (m, 3H), 7.25 (m, 2H), 4.50 (s, 2H), 3.26 (m, 2H), 2.76 (m, 2H), 2.36 (m, 2H), 2.22 (m, 2H), 2.06 (t, J=6.8 Hz, 2H), 1.84 (m, 2H).

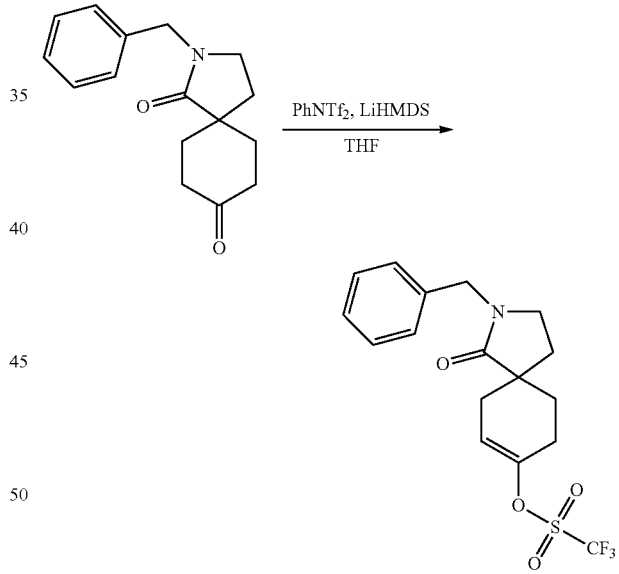

(2-Benzyl-1-oxo-2-azaspiro[4.5]dec-7-en-8-yl) trifluoromethanesulfonate

To a solution of the product from the previous step (2.90 g, 11.27 mmol, 1.0 eq) in THF (30 mL) at −78° C. was added dropwise LiHMDS (1 M in THF, 13.52 mL, 1.20 eq) over 10 min. After the addition, the mixture was stirred at −78° C. for 1 hr, and a solution of 1,1,1-trifluoro-N-phenyl-N-(trifluoromethylsulfonyl)methanesulfonamide (4.23 g, 11.83 mmol, 1.05 eq) in THF (10 mL) was added dropwise. The resulting mixture was stirred at −78° C. for 16 hr. The mixture was warmed to 0° C., aqueous KHSO₄ (1M, 14 mL)

was added dropwise, and the mixture was concentrated under reduced pressure. The residue was extracted with EtOAc (50 mL×2) and washed with NaOH aqueous (0.5 M, 50 mL×2). The organic layers were washed with brine (40 mL), dried over $Na_2SO_4$, filtered and concentrated under reduced pressure to give the title compound (4.2 g, 10.79 mmol, 96% yield) as a pale yellow oil. $^1$H NMR (400 MHz, $CDCl_3$, ppm): δ 7.16 (m, 3H), 7.05 (m, 2H), 5.6 (s, 1H), 4.31 (s, 2H), 3.05 (m, 2H), 2.27 (s, 2H), 1.90 (m, 4H), 1.73 (m, 2H).

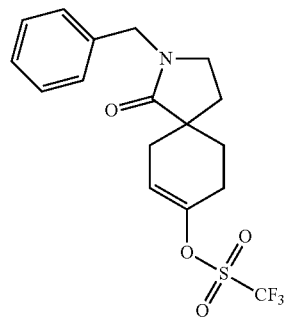

INTERMEDIATE H

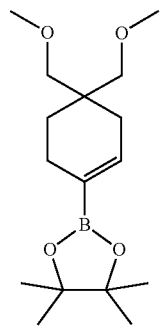

2-[4,4-Bis(methoxymethyl)cyclohexen-1-yl]-4,4,5,5-tetramethyl-1,3,2-dioxaborolane

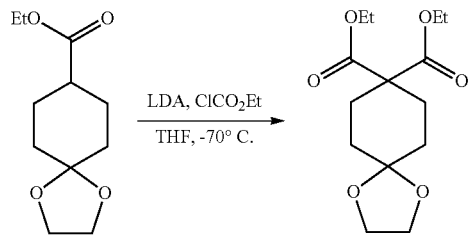 [SMILES: CCOC(=O)C1CCC2(CC1)OCCO2 ; "LDA, ClCO2Et" ; "THF, -70° C." ; CCOC(=O)C1(C(=O)OCC)CCC2(CC1)OCCO2]

Diethyl 1,4-dioxaspiro[4.5]decane-8,8-dicarboxylate

To a solution of ethyl 1,4-dioxaspiro[4.5]decane-8-carboxylate (10 g, 46.67 mmol) in THF (150 mL) at −70° C. was added dropwise LDA (2 M in THF, 25.67 mL, 1.10 eq), and the mixture was stirred at −70° C. for 1 hr. Ethyl chloroformate (5.32 g, 49.0 mmol, 4.67 mL, 1.05 eq) was then added dropwise, the mixture was slowly warmed to 15° C. and stirred for 11 hr. The reaction mixture was then poured into saturated aq. $NH_4Cl$ (200 mL), the layers were separated, and the aqueous layer was extracted with EtOAc (50 mL×4). The combined organic layers were washed with brine (200 mL), dried over $Na_2SO_4$ and concentrated. The residue was purified by $SiO_2$ gel chromatography (PE to PE:EtOAc=20:1) to afford the title compound as a light yellow oil (9.50 g, 33 mmol, 71% yield). $^1$H NMR (400 MHz, $CDCl_3$) δ 4.19 (q, J=7.2 Hz, 4H), 3.96-3.92 (m, 4H), 2.23-2.13 (m, 4H), 1.73-1.65 (m, 4H), 1.25 (t, J=7.2 Hz, 6H).

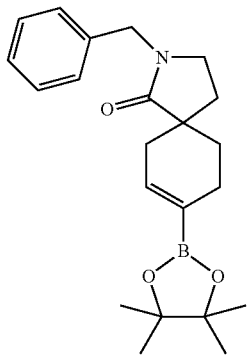

2-Benzyl-8-(4,4,5,5-tetramethyl-1,3,2-dioxaborolan-2-yl)-2-azaspiro[4.5]dec-7-en-1-one A mixture of the product from the previous step (4.2 g, 10.79 mmol, 1.0 eq), BPD (2.88 g, 11.33 mmol, 1.05 eq), Pd(dppf)Cl$_2$ (394.62 mg, 539.31 μmol, 0.05 eq) and KOAc (3.18 g, 32.36 mmol, 3.00 eq) in dioxane (35.00 mL) was degassed and purged with $N_2$ for 3 times, and the mixture was stirred at 90° C. for 16 hr. The reaction mixture was concentrated under reduced pressure, diluted with $H_2O$ (30 mL), and extracted with EtOAc (50 mL×2). The combined organic layers were washed with brine (20 mL×2), dried over $Na_2SO_4$, filtered and concentrated under reduced pressure. The residue was purified by $SiO_2$ gel chromatography (PE/EtOAc=10/1 to 5:1) to afford the title compound (1.8 g, 4.90 mmol, 45% yield) as a pale yellow oil. $^1$H NMR (400 MHz, $CDCl_3$, ppm): δ: 7.32 (m, 3H), 7.23 (m, 2H), 6.55 (dd, J=4.4, 2.4 Hz, 1H), 4.46 (m, 2H), 3.16 (m, 2H), 2.52 (m, 1H), 2.34 (m, 1H), 2.12 (m, 1H), 1.84 (m, 4H), 1.52 (m, 1H), 1.28 (s, 12H).

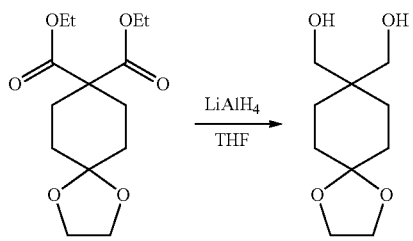 [SMILES: CCOC(=O)C1(C(=O)OCC)CCC2(CC1)OCCO2 ; "LiAlH4" ; OCC1(CO)CCC2(CC1)OCCO2 ; "THF"]

(1,4-Dioxaspiro[4.5]decane-8,8-diyl)dimethanol

To a suspension of LiAlH$_4$ (3.00 g, 79 mmol, 2.38 eq) in THF (100 mL) at 0° C. was added dropwise a solution of diethyl 1,4-dioxaspiro[4.5]decane-8,8-dicarboxylate (9.50 g, 33.2 mmol, 1.0 eq) in THF (50 mL). The resulting mixture was stirred for 1 hr at 15° C., then diluted with THF (200 mL), followed by dropwise addition of water (3 mL), 15% NaOH aqueous solution (3 mL) and water (9 mL). Anhydrous MgSO₄ was added and the mixture was stirred at RT for 0.5 h. The mixture was filtered through a pad of Celite and washed with EtOAc (100 mL). The filtrate was concentrated under reduced pressure to give the title compound as a white solid (6.20 g, 30.66 mmol, 92% yield) as white solid. ¹H NMR (400 MHz, CDCl₃) δ 4.30 (t, J=4.4 Hz, 2H), 3.82 (s, 4H), 3.27-3.21 (m, 4H), 1.49-1.46 (m, 4H), 1.42-1.36 (m, 4H).

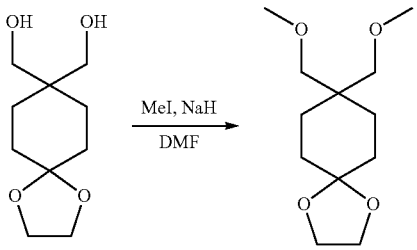

8,8-Bis(methoxymethyl)-1,4-dioxaspiro[4.5]decane

To a solution of [8-(hydroxymethyl)-1,4-dioxaspiro[4.5]decan-8-yl]methanol (6.20 g, 30.66 mmol) in DMF (70 mL) at 0° C. was added portionwise NaH (3.07 g, 76.65 mmol, 60% weight, 2.50 eq). The mixture was stirred at 0° C. for 1 h, MeI (11.4 g, 80.3 mmol, 5.0 mL, 2.62 eq) was added dropwise and the mixture was allowed to warm slowly to 15° C. while stirring for 15 hr. Saturated aq. NH₄Cl (100 mL) was added followed by water (200 mL). The mixture was extracted with EtOAc (150 mL×3), the combined organic layers were washed with brine (150 mL), dried over Na₂SO₄ and concentrated under reduced pressure. The residue was purified by SiO₂ gel chromatography (PE:EtOAc=100:1 to 30:1) to afford the title compound (5.0 g, 21.71 mmol, 71% yield) as colorless oil. ¹H NMR (400 MHz, CDCl₃) δ 3.93 (s, 4H), 3.30 (s, 6H), 3.25 (s, 4H), 1.63-1.60 (m, 4H), 1.55-1.52 (m, 4H).

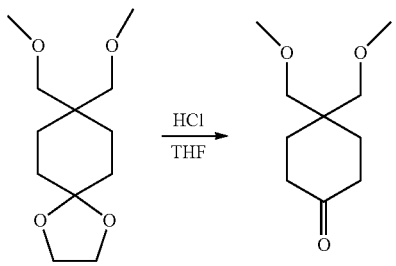

4,4-Bis(methoxymethyl)cyclohexanone

To a solution of 8,8-bis(methoxymethyl)-1,4-dioxaspiro[4.5]decane (5.0 g, 21.7 mmol) in THF (20 mL) at 15° C. was added HCl (4 M in dioxane, 20 mL, 3.68 eq). The resulting solution was stirred in a pressure safe closed reaction vessel at 40° C. for 12 hr, then cooled to RT and extracted with EtOAc (100 mL×3). The combined organic layers were washed with saturated aq NaHCO₃ (100 mL), brine (100 mL), dried (Na₂SO₄) and concentrated under reduced pressure to give 4,4-bis(methoxymethyl)cyclohexanone (3.50 g, 18.79 mmol, 86% yield) as pale yellow oil. ¹H NMR (400 MHz, CDCl₃) δ 3.35 (s, 6H), 3.33 (s, 4H), 2.36-2.32 (m, 4H), 1.79-1.75 (m, 4H).

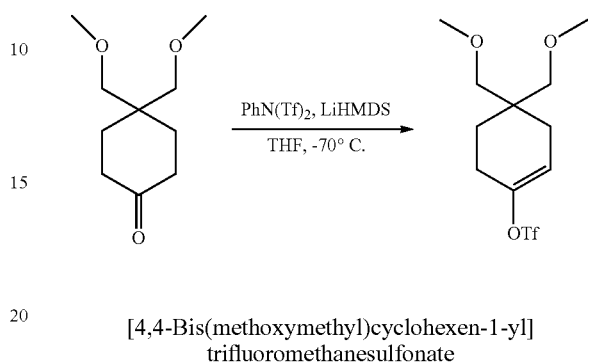

[4,4-Bis(methoxymethyl)cyclohexen-1-yl] trifluoromethanesulfonate

To a solution of 4,4-bis(methoxymethyl)cyclohexanone (1.50 g, 8.05 mmol) in THF (20 mL) at −70° C. was added dropwise LiHMDS (1 M in hexanes, 9.66 mL, 1.20 eq) and the mixture was stirred at −70° C. for 1 h. A solution of 1,1,1-trifluoro-N-phenyl-N-(trifluoromethylsulfonyl)methanesulfonamide (3.02 g, 8.45 mmol, 1.05 eq) in THF (10 mL) was added dropwise and the reaction mixture was slowly warmed to 15° C. while stirring for 15 hr. Saturated aq. NH₄Cl (80 mL) was added, the layers were separated and the aqueous layer was extracted with EtOAc (50 mL×4). The combined organic layers were washed with brine (100 mL), dried (Na₂SO₄) and concentrated under reduced pressure. The residue was purified by SiO₂ gel chromatography (PE to PE:EtOAc=100:1) to give the title compound (1.60 g, 5.03 mmol, 62% yield) as light yellow oil. ¹H NMR (400 MHz, CDCl₃) δ 5.69-5.67 (m, 1H), 3.35 (s, 6H), 3.25-3.19 (m, 4H), 2.31-2.29 (m, 2H), 2.09-2.06 (m, 2H), 1.74-1.69 (m, 2H).

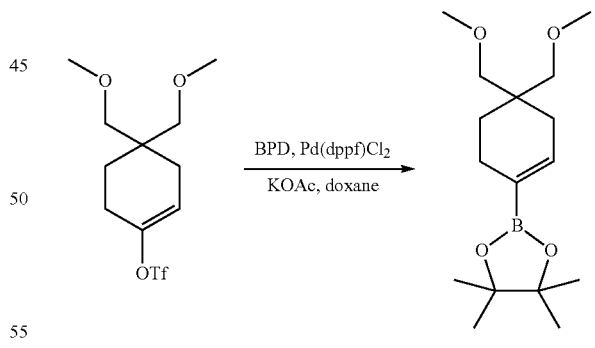

2-[4,4-Bis(methoxymethyl)cyclohexen-1-yl]-4,4,5,5-tetramethyl-1,3,2-dioxaborolane A mixture of [4,4-bis(methoxymethyl)cyclohexen-1-yl] trifluoromethanesulfonate (1.60 g, 5.03 mmol), bis(pinacolato)diboron (1.53 g, 6.04 mmol, 1.20 eq), AcOK (987.29 mg, 10.06 mmol, 2.00 eq) and Pd(dppf)Cl₂ (184.03 mg, 251.50 µmol, 0.05 eq) in dioxane (30 mL) was degassed and purged with N₂ for three times, and heated at 90° C. for 16 hr. The reaction mixture was diluted with EtOAc (50 mL), filtered through a pad of Celite and the filtrate was concentrated under reduced pressure. The residue was purified by SiO₂ gel chromatography (PE to PE:EtOAc=100:1) to give the title compound (1.10 g, 3.71 mmol, 74% yield) as a pale yellow oil. ¹H NMR (400 MHz, CDCl₃) δ 6.49-6.48 (m, 1H), 3.34 (s, 6H), 3.25-3.17 (m, 4H), 2.11-2.09 (m, 2H), 1.97-1.95 (m, 2H), 1.50-1.47 (m, 2H), 1.26 (s, 12H).

INTERMEDIATE I

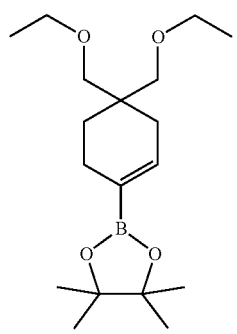

2-[4,4-Bis(ethoxymethyl)cyclohexen-1-yl]-4,4,5,5-tetramethyl-1,3,2-dioxaborolane The title compound was obtained using the same procedure already described for Intermediate H, using ethyl iodide instead of methyl iodide in step 3. ¹H NMR (400 MHz, CDCl₃) δ 6.51-6.50 (m, 1H), 3.45 (q, J=7.1 Hz, 4H), 3.31-3.20 (m, 4H), 2.14-2.08 (m, 2H), 2.01-1.95 (m, 2H), 1.51 (t, J=6.4 Hz, 2H), 1.27 (s, 12H), 1.16 (t, J=7.0 Hz, 6H).

INTERMEDIATE J

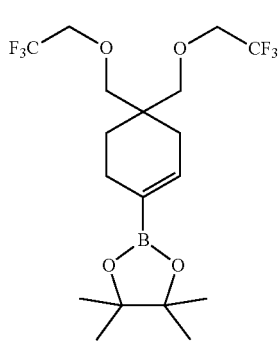

2-(4,4-Bis((2,2,2-trifluoroethoxy)methyl)cyclohexen-1-yl)-4,4,5,5-tetramethyl-1,3,2-dioxaborolane

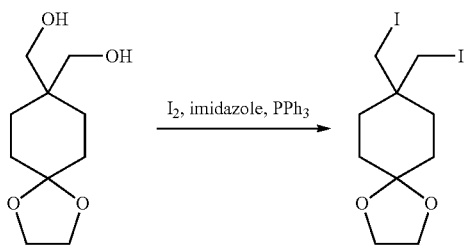 [SMILES: OCC1(CO)CCC2(CC1)OCCO2 ; "I2, imidazole, PPh3" ; ICC1(CI)CCC2(CC1)OCCO2]

8,8-Bis(iodomethyl)-1,4-dioxaspiro[4.5]decane

To a solution of [8-(hydroxymethyl)-1,4-dioxaspiro[4.5]decan-8-yl]methanol (Intermediate H, step 2; 7.5 g, 37.08 mmol) in toluene (150 mL) at RT were added PPh₃ (29.18 g, 111.25 mmol, 3 eq) and imidazole (7.57 g, 111.25 mmol, 3 eq). Iodine (28.24 g, 111.2 mmol, 3 eq) was then added portionwise, and the resulting mixture was stirred for 3 hr at 100° C., cooled to RT and concentrated under reduced pressure. The residue was purified by SiO₂ gel chromatography (PE to PE:EtOAc=50:1) to afford the title compound (9 g, 21.32 mmol, 57.5% yield) as white solid. ¹H NMR (400 MHz, DMSO-d₆) δ 3.84 (s, 4H), 3.39 (s, 4H), 1.65-1.62 (m, 4H), 1.54-1.51 (m, 4H).

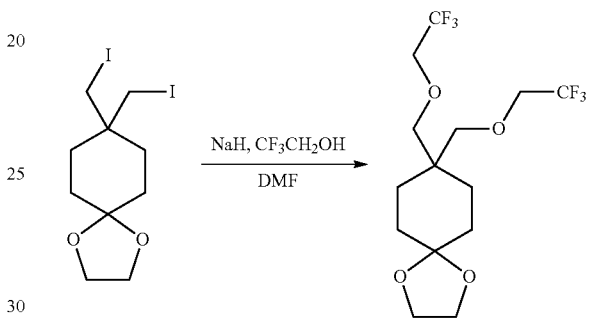

8,8-Bis(2,2,2-trifluoroethoxymethyl)-1,4-dioxaspiro[4.5]decane

To a solution of 2,2,2-trifluoroethanol (10.67 g, 106.6 mmol, 7.67 mL, 5 eq) in DMF (100 mL) at 0° C. was added NaH (5.12 g, 127.9 mmol, 60% weight, 6 eq) portionwise. The mixture was stirred at 0° C. for 1 h before adding 8,8-bis(iodomethyl)-1,4-dioxaspiro[4.5]decane (9 g, 21.32 mmol, 1 eq). The resulting mixture was stirred at 90° C. for 15 hr, cooled to RT and poured into saturated aq. NH₄Cl (300 mL). The suspension was extracted with EtOAc (100 mL×3), the combined organic layers were washed with brine (300 mL×3), dried (Na₂SO₄) and concentrated under reduced pressure. The residue was purified by SiO₂ gel chromatography (PE to PE:EtOAc=30:1) to give the title compound (5.1 g, 13.9 mmol, 65% yield) as a pale yellow oil. ¹H NMR (400 MHz, CDCl₃) δ 3.94 (s, 4H), 3.83-3.77 (m, 4H), 3.51 (s, 4H), 1.61-1.56 (m, 8H).

8,8-Bis(2,2,2-trifluoroethoxymethyl)-1,4-dioxaspiro[4.5]decane was progressed to Intermediate J according to the procedures already described for Intermediate H.

2-[4,4-Bis(2,2,2-trifluoroethoxymethyl)cyclohexen-1-yl]-4,4,5,5-tetramethyl-1,3,2-dioxaborolane (Intermediate J)

Pale yellow oil; (2.2 g, 5.09 mmol, 55.06% yield) as yellow oil. ¹H NMR (400 MHz, CDCl₃) δ 6.48-6.46 (m, 1H), 3.82-3.76 (m, 4H), 3.50-3.42 (m, 4H), 2.13-2.09 (m, 2H), 1.99-1.97 (m, 2H), 1.54-1.51 (m, 2H), 1.27 (s, 12H).

INTERMEDIATE K

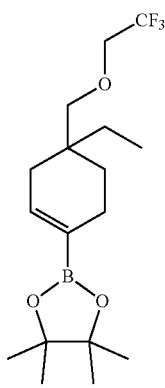

2-[4-Ethyl-4-(2,2,2-trifluoroethoxymethyl)cyclo-hexen-1-yl]-4,4,5,5-tetramethyl-1,3,2-dioxaborolane

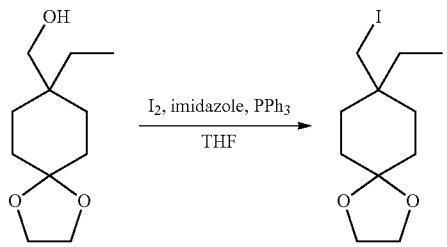

8-Ethyl-8-(iodomethyl)-1,4-dioxaspiro[4.5]decane

To a solution of (8-ethyl-1,4-dioxaspiro[4.5]decan-8-yl)methanol (Intermediate E, step 2; 9.8 g, 48.93 mmol) in THF (30 mL) at 0° C. were added PPh$_3$ (19.25 g, 73.40 mmol, 1.5 eq) and imidazole (6.66 g, 97.87 mmol, 2 eq), followed by iodine (19.87 g, 78.29 mmol, 1.6 eq), The mixture was stirred for 2 hr at 0-25° C., quenched at 0° C. by addition of H$_2$O (20 mL), and extracted with EtOAc (50 mL×3). The combined organic layers were washed with brine (100 mL), dried (Na$_2$SO$_4$), filtered and concentrated under reduced pressure. The residue was purified by SiO$_2$ gel chromatography (PE:EtOAc=75:1 to 50:1) to afford 8-ethyl-8-(iodomethyl)-1,4-dioxaspiro[4.5]decane (4.1 g, 12.56 mmol, 26% yield) as colorless oil. $^1$H NMR (400 MHz, CDCl$_3$): δ 3.94 (s, 4H), 3.25 (s, 2H), 1.68-1.58 (m, 8H), 1.44 (t, J=7.6 Hz, 2H), 0.79 (t, J=7.6 Hz, 3H).

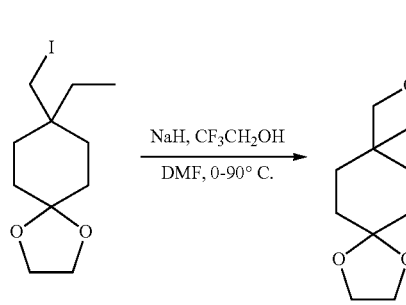

8-Ethyl-8-(2,2,2-trifluoroethoxymethyl)-1,4-dioxaspiro[4.5]decane

To a solution of 2,2,2-trifluoroethanol (3.31 g, 33.05 mmol, 2.38 mL, 2.5 eq) in DMF (50 mL) at 0° C. was added NaH (1.59 g, 39.66 mmol, 60% weight, 3 eq) and the suspension was stirred at 0° C. for 0.5 hr. A solution of 8-ethyl-8-(iodomethyl)-1,4-dioxaspiro[4.5]decane (4.1 g, 13.22 mmol, 1 eq) in DMF (10 mL) was added dropwise, and the reaction was stirred for 24 hr at 90° C., then cooled to 0° C., quenched by addition of saturated aq. NH$_4$Cl (25 mL), and extracted with EtOAc (50 mL×3). The combined organic layers were washed with brine (100 mL), dried (Na$_2$SO$_4$), filtered and concentrated under reduced pressure. The residue was purified by SiO$_2$ gel chromatography (PE:EtOAc=35:1 to 5:1) to afford the title compound (2.85 g, 10.1 mmol, 76% yield) as a colorless oil. $^1$H NMR (400 MHz, CDCl$_3$): δ 3.98-3.90 (m, 4H), 3.79 (q, J=8.8 Hz, 2H), 3.40 (s, 2H), 1.67-1.62 (m, 2H), 1.60-1.58 (m, 2H), 1.56-1.37 (m, 6H), 0.85-0.76 (m, 3H).

8-Ethyl-8-(2,2,2-trifluoroethoxymethyl)-1,4-dioxaspiro [4.5]decane was progressed to Intermediate K according to the procedures already described for Intermediate H.

2-[4-Ethyl-4-(2,2,2-trifluoroethoxymethyl)cyclo-hexen-1-yl]-4,4,5,5-tetramethyl-1,3,2-dioxaborolane (Intermediate K)

Pale yellow oil; (2.8 g, 8.04 mmol). $^1$H NMR (400 MHz, CDCl$_3$): δ 6.49-4.47 (m, 1H), 3.83-3.72 (m, 2H), 3.43-3.26 (m, 2H), 2.20-2.03 (m, 2H), 2.01-1.79 (m, 2H), 1.45-1.33 (m, 4H), 1.30-1.23 (m, 12H), 0.81 (t, J=7.6 Hz, 3H).

INTERMEDIATE L

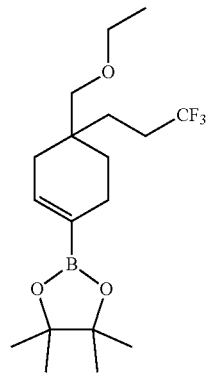

2-(4-(Ethoxymethyl)-4-(3,3,3-trifluoropropyl)cyclo-hexen-1-yl)-4,4,5,5-tetramethyl-1,3,2-dioxaborolane

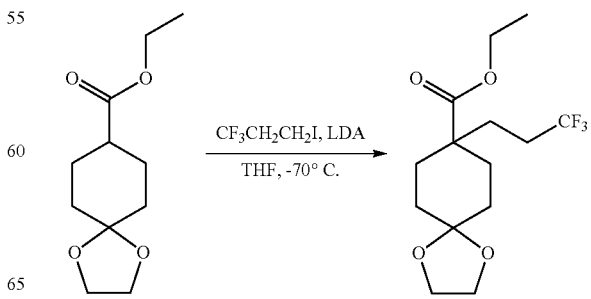

Ethyl 8-(3,3,3-trifluoropropyl)-1,4-dioxaspiro[4.5]decane-8-carboxylate

To a solution of N-isopropylpropan-2-amine (9.45 g, 93.35 mmol, 13.2 mL, 2 eq) in THF (100 mL) at −40° C. was added dropwise n-BuLi (2.5 M in hexanes, 28 mL, 1.5 eq) and the mixture was stirred at −10° C. for 1 h, then cooled to −70° C. A solution of ethyl 1,4-dioxaspiro[4.5]decane-8-carboxylate (10 g, 46.67 mmol, 1 eq) in THF (50 mL) was added dropwise and the reaction mixture was stirred at −70° C. for 1 h. A solution of 1,1,1-trifluoro-3-iodo-propane (15.68 g, 70.0 mmol, 8.21 mL, 1.5 eq) in THF (50 mL) was then added dropwise at −70° C. and the mixture was stirred for 14 hr at RT. The reaction was quenched by addition of saturated aq. NH$_4$Cl (200 mL) and extracted with EtOAc (100 mL×3). The combined organic layers were washed with brine (200 mL), dried (Na$_2$SO$_4$), and concentrated under reduced pressure. The residue was purified by SiO$_2$ gel chromatography (PE to PE:EtOAc=50:1) to give the title compound (10 g, 32.2 mmol, 69% yield) as a pale yellow oil. $^1$H NMR (400 MHz, CDCl$_3$): δ 4.20-4.15 (m, 2H), 3.93 (s, 4H), 2.18-2.13 (m, 2H), 2.03-1.96 (m, 2H), 1.78-1.73 (m, 2H), 1.67-1.66 (m, 2H), 1.60-1.57 (m, 2H), 1.54-1.48 (m, 2H), 1.28-1.25 (m, 3H).

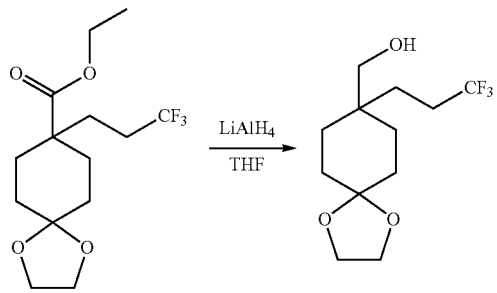 [SMILES: CCOC(=O)C1(CCC(F)(F)F)CCC2(CC1)OCCO2 ; "LiAlH4" ; OCC1(CCC(F)(F)F)CCC2(CC1)OCCO2 ; "THF"]

[8-(3,3,3-Trifluoropropyl)-1,4-dioxaspiro[4.5]decan-8-yl]methanol

A solution of ethyl 8-(3,3,3-trifluoropropyl)-1,4-dioxaspiro[4.5]decane-8-carboxylate (10 g, 32.2 mmol) in THF (50 mL) was added dropwise to a suspension of LiAlH$_4$ (2.50 g, 65.9 mmol, 2.04 eq) in THF (100 mL) at 0° C. The resulting mixture was stirred at 25° C. for 2 hr, cooled to 0° C. and carefully quenched by the sequential addition of water (2.5 mL), 15% aq. NaOH (2.5 mL), water (7.5 mL) and Na$_2$SO$_4$. The mixture was filtered through a pad of Celite and the filtrate concentrated under reduced pressure. The residue was purified by SiO$_2$ gel chromatography (PE:EtOAc=100:1 to 10:1) to give the title compound (6.6 g, 24.6 mmol, 76% yield) as a colorless oil. $^1$H NMR (400 MHz, DMSO-d$_6$): δ 4.60-4.57 (m, 1H), 3.82 (s, 4H), 3.22-3.19 (m, 2H), 2.19-2.12 (m, 2H), 1.53-1.31 (m, 10H).

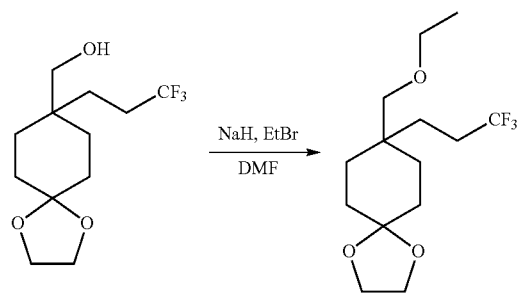

8-(Ethoxymethyl)-8-(3,3,3-trifluoropropyl)-1,4-dioxaspiro[4.5]decane

To a solution of [8-(3,3,3-trifluoropropyl)-1,4-dioxaspiro[4.5]decan-8-yl]methanol (6.6 g, 24.0 mmol) in DMF (50 mL) at 0° C. was added portionwise NaH (1.48 g, 36.9 mmol, 60% weight, 1.5 eq). The suspension was stirred at 0° C. for 1 hr, bromoethane (5.36 g, 49.2 mmol, 3.67 mL, 2 eq) was added and the resulting mixture was stirred for 15 hr at RT, then poured into saturated aq. NH$_4$Cl (150 mL) and extracted with EtOAc (100 mL×3). The combined organic layers were washed with brine (200 mL), dried (Na$_2$SO$_4$) and concentrated under reduced pressure. The residue was purified by SiO$_2$ gel chromatography (PE:EtOAc=100:1 to 10:1) to give the title compound (5 g, 16.87 mmol, 68% yield) as a pale yellow oil. $^1$H NMR (400 MHz, DMSO-d$_6$): δ 3.83 (s, 4H), 3.43-3.38 (m, 2H), 3.18 (s, 2H), 2.19-2.12 (m, 2H), 1.15-1.32 (m, 10H), 1.11-1.07 (m, 3H).

8-(Ethoxymethyl)-8-(3,3,3-trifluoropropyl)-1,4-dioxaspiro[4.5]decane was progressed to Intermediate L according to the procedures already described for Intermediate H.

2-(4-(Ethoxymethyl)-4-(3,3,3-trifluoropropyl)cyclohexen-1-yl)-4,4,5,5-tetramethyl-1,3,2-dioxaborolane (Intermediate L)

Pale yellow oil; (3.3 g, 9.1 mmol). $^1$H NMR (400 MHz, CDCl$_3$) δ 6.48-6.46 (m, 1H), 3.45-3.39 (m, 2H), 3.18-3.10 (m, 2H), 2.15-2.08 (m, 4H), 2.01-1.84 (m, 2H), 1.59-1.53 (m, 3H), 1.41-1.36 (m, 1H), 1.27 (s, 12H), 1.17-1.14 (m, 3H).

INTERMEDIATE M

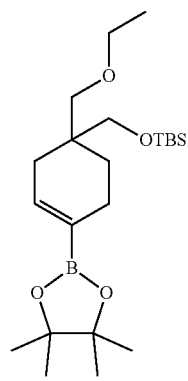

tert-Butyl((1-(ethoxymethyl)-4-(4,4,5,5-tetramethyl-1,3,2-dioxaborolan-2-yl)cyclohex-3-en-1-yl)methoxy)dimethylsilane

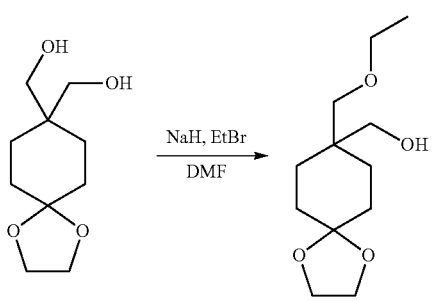

[8-(Ethoxymethyl)-1,4-dioxaspiro[4.5]decan-8-yl]methanol

To a solution of [8-(hydroxymethyl)-1,4-dioxaspiro[4.5]decan-8-yl]methanol (Intermediate H, step 2; 10 g, 49.44 mmol) in DMF (100 mL) at 0° C. was added NaH (2.18 g, 54.39 mmol, 60% weight, 1.1 eq). The mixture was stirred at 0° C. for 1 hr, and a solution of ethyl bromide (4.85 g, 44.5 mmol, 3.32 mL, 0.9 eq) in DMF (50 mL) was added at 0° C. After stirring at 20° C. for 3 hr, the reaction mixture was quenched by addition of saturated aq. NH$_4$Cl (80 mL), diluted with EtOAc (50 mL) and extracted with EtOAc (80 mL×3). The combined organic layers were washed with brine (150 mL), dried (Na$_2$SO$_4$), filtered and concentrated under reduced pressure. The residue was purified by SiO$_2$, (PE:EtOAc=10/1 to 3/1) to afford the title compound (3.7 g, 16.07 mmol, 32% yield) as pale yellow oil. $^1$H NMR (400 MHz, CDCl$_3$) δ 3.94 (s, 4H), 3.58 (d, J=5.6 Hz, 2H), 3.48 (q, J=7.2 Hz, 2H), 3.40 (s, 2H), 1.67-1.46 (m, 8H), 1.19 (t, J=6.8 Hz, 3H).

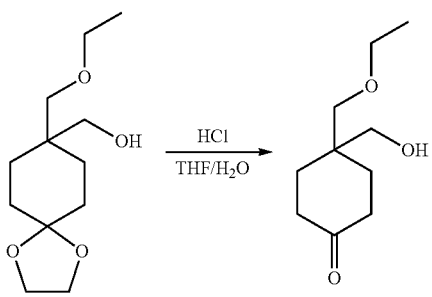

4-(Ethoxymethyl)-4-(hydroxymethyl)cyclohexanone

To a solution of [8-(ethoxymethyl)-1,4-dioxaspiro[4.5]decan-8-yl]methanol (1.1 g, 4.78 mmol) in THF (10 mL) was added aq. HCl (6 M, 1.59 mL, 2 eq). The mixture was stirred at 20° C. for 16 hr, partially concentrated under reduced pressure and extracted with EtOAc (100 mL×2). The combined organic layers were washed with saturated aq. NaHCO$_3$ (100 mL), brine (100 mL), dried (Na$_2$SO$_4$), filtered and concentrated under reduced pressure to give 4-(ethoxymethyl)-4-(hydroxymethyl)cyclohexanone (950 mg, 4.08 mmol, 85% yield) as a colorless oil. $^1$H NMR (400 MHz, CDCl$_3$) δ 3.71 (d, J=5.6 Hz, 2H), 3.56-3.50 (m, 2H), 3.48 (s, 2H), 2.94 (t, J=5.6 Hz, 1H), 2.43-2.28 (m, 4H), 1.90-1.80 (m, 2H), 1.77-1.66 (m, 2H), 1.27-1.19 (m, 3H).

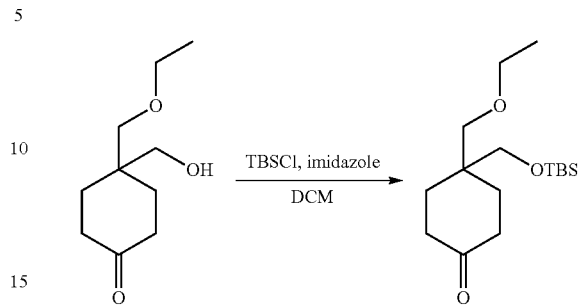

4-[[tert-Butyl(dimethyl)silyl]oxymethyl]-4-(ethoxymethyl)cyclohexanone

To a solution of 4-(ethoxymethyl)-4-(hydroxymethyl)cyclohexanone (450 mg, 2.42 mmol) in DCM (5 mL) at 0° C. were added imidazole (493 mg, 7.2 mmol, 3 eq) and TBSCl (400 mg, 2.66 mmol, 1.1 eq). The mixture was stirred at 20° C. for 3 hr, quenched by addition H$_2$O (20 mL), and extracted with EtOAc (30 mL×3). The combined organic layers were washed with brine (50 mL), dried (Na$_2$SO$_4$), filtered and concentrated under reduced pressure. The residue was purified by SiO$_2$ gel chromatography (PE to PE/EtOAc=40/1) to afford the title compound (550 mg, 1.83 mmol, 76% yield) as a colorless oil. $^1$H NMR (400 MHz, CDCl$_3$) δ 3.54 (s, 2H), 3.52-3.44 (m, 2H), 3.35 (s, 2H), 2.40-2.29 (m, 4H), 1.80-1.70 (m, 4H), 1.22-1.15 (m, 3H), 0.91 (s, 9H), 0.06 (s, 6H).

4-[[tert-Butyl(dimethyl)silyl]oxymethyl]-4-(ethoxymethyl)cyclohexanone was progressed to Intermediate M according to the procedures already described for Intermediate H.

tert-Butyl((1-(ethoxymethyl)-4-(4,4,5,5-tetramethyl-1,3,2-dioxaborolan-2-yl)cyclohex-3-en-1-yl)methoxy)dimethylsilane (Intermediate M). Colorless oil; (350 mg, 0.853 mmol). $^1$H NMR (400 MHz, CDCl$_3$) δ 6.51-6.50 (m, 1H), 3.48-3.37 (m, 4H), 3.29-3.11 (m, 2H), 2.13-2.08 (m, 2H), 1.95-1.95 (m, 2H), 1.53-1.41 (m, 2H), 1.31-1.21 (m, 12H), 1.16 (t, J=7.2 Hz, 3H), 0.88 (s, 9H), 0.02 (s, 6H).

INTERMEDIATE N

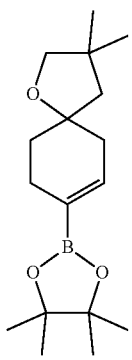

2-(3,3-dimethyl-1-oxaspiro[4.5]dec-7-en-8-yl)-4,4,5,5-tetramethyl-1,3,2-dioxaborolane

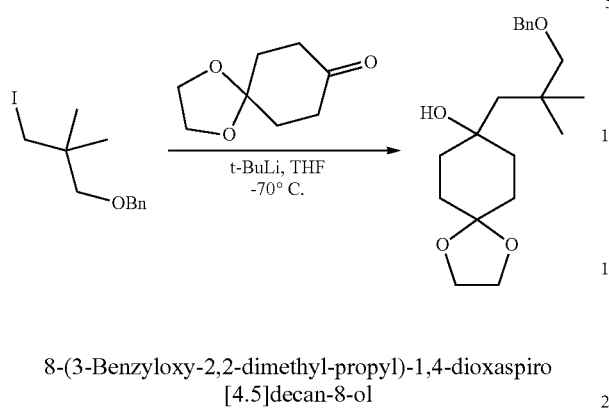

8-(3-Benzyloxy-2,2-dimethyl-propyl)-1,4-dioxaspiro[4.5]decan-8-ol

Tert-Butyl Lithium (1.3 M in pentane, 379.35 mL, 2.5 eq) was added dropwise to a flask containing THF (300 mL) at −70° C., under an atmosphere of $N_2$. A solution of (3-iodo-2,2-dimethyl-propoxy)methylbenzene (60 g, 197 mmol, 1 eq) in THF (300 mL) was added to the above solution dropwise at −70° C. The reaction mixture was stirred at −70° C. for 1 h, and a solution of 1,4-dioxaspiro[4.5]decan-8-one (46.21 g, 296 mmol, 1.5 eq) in THF (300 mL) was added dropwise at −70° C. The mixture was stirred at −70° C. for 2 hr, then slowly warmed to 0° C. and carefully quenched by addition of saturated aq. $NH_4Cl$ solution (500 mL). The layers were separated, the aqueous layer was extracted with EtOAc (150 mL×3). The combined organic layers were washed with brine (300 mL), dried ($Na_2SO_4$) and concentrated under reduced pressure. The residue was purified by $SiO_2$ gel chromatography (PE:EtOAc=100:1 to 5:1) to afford the title compound (50 g) as yellow oil. $^1$H NMR (400 MHz, DMSO-$d_6$): δ 7.36-7.27 (m, 5H), 4.45 (s, 2H), 3.94 (s, 2H), 3.91 (s, 1H), 3.81 (s, 4H), 3.21 (s, 2H), 2.37-2.33 (m, 2H), 1.94-1.90 (m, 2H), 1.72-1.70 (m, 2H), 1.63-1.60 (m, 2H), 1.52-1.48 (m, 2H), 1.43 (s, 2H), 0.99 (s, 6H).

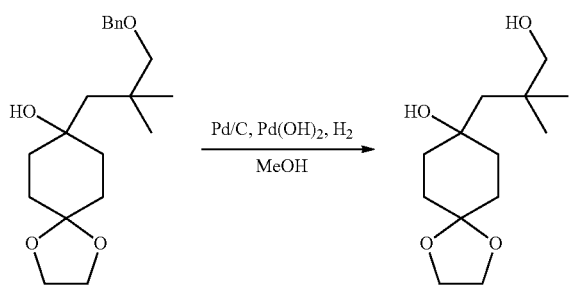 [SMILES: "MeOH" ; CC(C)(COCc1ccccc1)CC1(O)CCC2(CC1)OCCO2 ; "Pd/C, Pd(OH)2, H2" ; CC(C)(CO)CC1(O)CCC2(CC1)OCCO2]

8-(3-Hydroxy-2,2-dimethyl-propyl)-1,4-dioxaspiro[4.5]decan-8-ol

A Parr reaction vessel was charged with the product from the previous step (47 g, 140 mmol), Pd/C (2 g, 10% weight), Pd(OH)$_2$/C (2 g, 20% weight) and MeOH (500 mL). The suspension was degassed under vacuum and with $N_2$ three times, purged with $H_2$ and stirred under an atmosphere of $H_2$ (15 Psi) at 25° C. for 16 hr in a Parr shaker. The reaction mixture was then purged with $N_2$, filtered through a pad of Celite and concentrated under reduced pressure. The residue was purified by $SiO_2$ gel chromatography (PE:EtOAc=30:1 to 1:2) to afford the title compound (15 g, 61.4 mmol, 44% yield) as white solid. $^1$H NMR (400 MHz, DMSO-$d_6$) δ 4.87-4.84 (m, 1H), 4.49 (s, 1H), 3.81 (s, 4H), 3.17-3.16 (d, J=4 Hz, 2H), 1.77-1.69 (m, 2H), 1.66-1.62 (m, 2H), 1.53-1.49 (m, 2H), 1.42-1.38 (m, 4H), 0.90 (s, 6H).

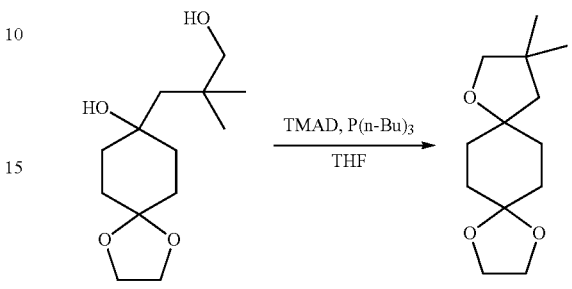

2,2-Dimethyl-4,9,12-trioxadispiro[4.2.4⁸.2⁵]tetradecane

To a mixture of 8-(3-hydroxy-2,2-dimethyl-propyl)-1,4-dioxaspiro[4.5]decan-8-ol (16 g, 65.49 mmol) and tributylphosphine (26.50 g, 130.97 mmol, 32 mL, 2 eq) in THF (400 mL) at −40° C. was added dropwise a solution of TMAD (22.5 g, 131 mmol, 2 eq) in THF (300 mL) dropwise. The mixture was stirred at −40° C. for 1 h, then slowly warmed to 25° C., stirred for 2 hr, filtered and washed with EtOAc (100 mL). The filtrate was concentrated under reduced pressure and the residue was purified by $SiO_2$ gel chromatography (PE to PE:EtOAc=20:1) to afford 2,2-dimethyl-4,9,12-trioxadispiro[4.2.4⁸.2⁵]tetradecane (11 g, 48.6 mmol, 74% yield) as colorless oil.

$^1$H NMR (400 MHz, DMSO-$d_6$): δ 3.83 (s, 4H), 3.38 (s, 2H), 1.72-1.64 (m, 4H), 1.60-1.55 (m, 2H), 1.52 (s, 2H), 1.49-1.44 (m, 2H), 1.03 (s, 6H).

2,2-Dimethyl-4,9,12-trioxadispiro[4.2.4⁸.2⁵]tetradecane was progressed to Intermediate N according to the procedures already described for Intermediate H.

2-(3,3-Dimethyl-1-oxaspiro[4.5]dec-7-en-8-yl)-4,4,5,5-tetramethyl-1,3,2-dioxaborolane (Intermediate N)

Pale yellow oil; $^1$H NMR (400 MHz, CDCl$_3$) δ 6.46-6.44 (m, 1H), 3.52 (s, 2H), 2.39-2.13 (m, 4H), 1.75-1.69 (m, 2H), 1.63-1.58 (m, 2H), 1.24 (s, 12H), 1.10-1.09 (d, J=4.0 Hz, 6H).

INTERMEDIATE O

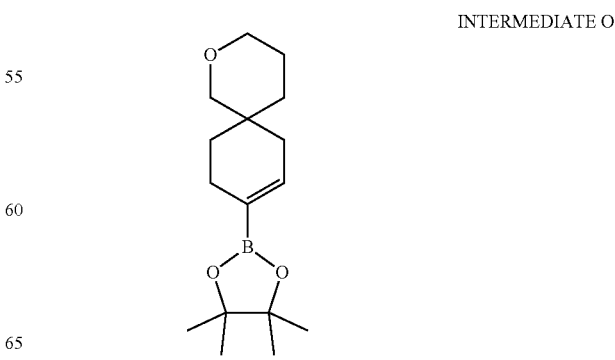

4,4,5,5-Tetramethyl-2-(2-oxaspiro[5.5]undec-8-en-9-yl)-1,3,2-dioxaborolane

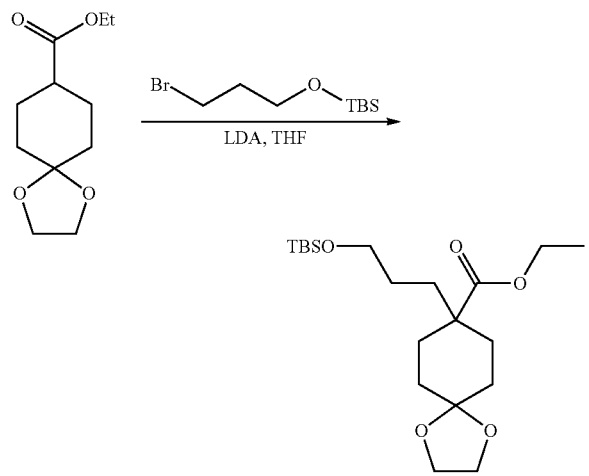

Ethyl 8-(3-((tert-butyldimethylsilyl)oxy)propyl)-1,4-dioxaspiro[4.5]decane-8-carboxylate To a solution of ethyl 1,4-dioxaspiro[4.5]decane-8-carboxylate (8 g, 37.34 mmol) and HMPA (3.35 g, 18.67 mmol, 3.28 mL, 0.5 eq) in THF (60 mL) at −78° C. was added LDA (2 M in THF, 24.27 mL, 1.3 eq) and the mixture was stirred at −78° C. for 1 hr. A solution of 3-bromopropoxy-tert-butyl-dimethyl-silane (10.4 g, 41.07 mmol, 1.1 eq) in THF (10 mL) was added dropwise, the mixture was warmed to 15° C. and stirred for further 12 hr. Saturated aq. NH$_4$Cl (100 mL) was added, and the mixture was extracted with EtOAc (100 mL×2). The combined organic layers were washed with brine (100 mL), dried (Na$_2$SO$_4$), filtered and concentrated under reduced pressure. The residue was purified by SiO$_2$ gel chromatography (PE:EtOAc=50/1 to 10/1) to afford the title compound (4.4 g, 11.38 mmol, 30.48% yield) as light yellow oil. $^1$H NMR (400 MHz, CDCl$_3$) δ 4.13 (q, J=5.2 Hz, 2H), 3.94-3.93 (m, 4H), 3.54 (t, J=6.0 Hz, 2H), 2.17-2.15 (m, 2H), 1.63-1.43 (m, 10H), 1.25 (t, J=7.2 Hz, 3H), 0.87 (s, 9H), 0.03 (s, 6H).

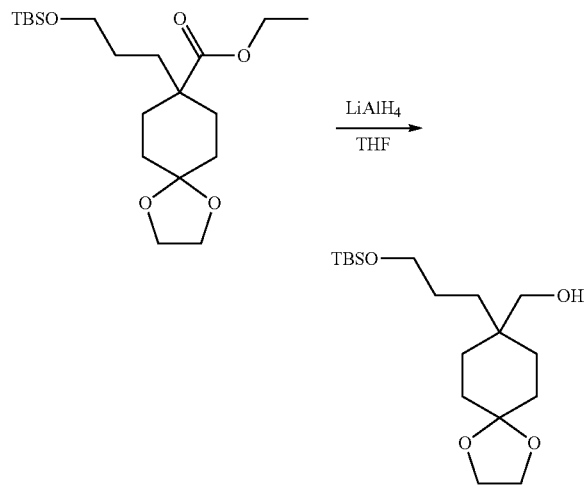

(8-(3-((tert-Butyldimethylsilyl)oxy)propyl)-1,4-dioxaspiro[4.5]decan-8-yl)methanol To a solution of the product from previous step (4.4 g, 11.38 mmol) in THF (30 mL) at 0° C. was added LiAlH$_4$ (431.92 mg, 11.38 mmol, 1 eq) and the suspension was stirred at 15° C. for 2 hr. To the reaction was carefully quenched by sequential addition of H$_2$O (500 mg), aq. NaOH (15%, 500 mg) and H$_2$O (1.5 g) at 0° C. The mixture was then stirred at 15° C. for 30 min, MgSO$_4$ was added and the mixture was filtered. The filtrate was concentrated under reduced pressure to give the title compound (3.6 g, 10.45 mmol, 92% yield) as a pale yellow solid. $^1$H NMR (400 MHz, CDCl$_3$) δ 3.94 (s, 4H), 3.61-3.58 (m, 2H), 3.45-3.43 (m, 2H), 2.05-2.04 (m, 1H) 1.62-1.41 (m, 12H), 0.89 (s, 9H), 0.05 (s, 6H).

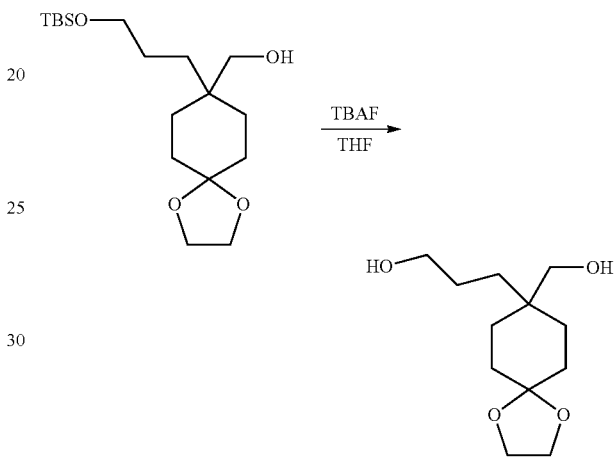

3-(8-(Hydroxymethyl)-1,4-dioxaspiro[4.5]decan-8-yl)propan-1-ol

To a solution of the product from previous step (3.6 g, 10.4 mmol) in THF (30 mL) at 0° C. was added TBAF (1 M in THF, 12.54 mL, 1.2 eq). After addition, the mixture was stirred at 15° C. for 16 hr, and concentrated under reduced pressure. The residue was purified by SiO$_2$ gel chromatography (PE:EtOAc=5/1 to 0/1) to afford 3-[8-(hydroxymethyl)-1,4-dioxaspiro[4.5]decan-8-yl]propan-1-ol (1.9 g, 8.25 mmol, 79% yield) as a colorless oil. $^1$H NMR (400 MHz, CDCl$_3$) δ 3.93 (s, 4H), 3.66-3.64 (m, 2H), 3.46 (d, J=4.4 Hz, 2H), 1.87 (s, 1H), 1.70 (s, 1H), 1.62-1.53 (m, 4H), 1.52-1.46(m, 8H).

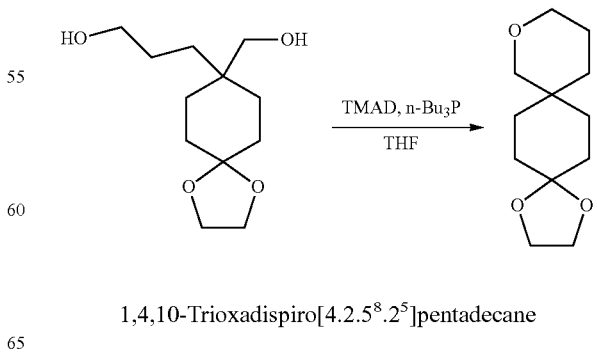

1,4,10-Trioxadispiro[4.2.5$^8$.2$^5$]pentadecane

To a solution of 3-[8-(hydroxymethyl)-1,4-dioxaspiro[4.5]decan-8-yl]propan-1-ol (1.9 g, 8.25 mmol) and tributylphosphine (1.84 g, 9.08 mmol, 1.1 eq) in THF (25 mL) at 0° C. was added TMAD (1.56 g, 9.08 mmol, 1.1 eq). The mixture was warmed to 15° C. and stirred at 15° C. for 12 hr, then filtered and the filtrate was concentrated under reduced pressure. The residue was purified by SiO$_2$ gel chromatography (PE to PE:EtOAc=10/1) to afford 1,4,10-trioxadispiro[4.2.5$^8$.2$^5$]pentadecane (820 mg, 3.86 mmol, 47% yield) as a colorless oil. $^1$H NMR (400 MHz, CDCl$_3$) δ 3.93 (s, 4H), 3.61 (t, J=5.2 Hz, 2H), 3.39 (s, 2H), 1.60-1.49 (m, 12H).

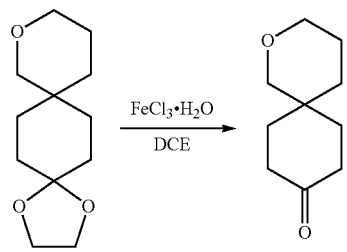

2-oxaspiro[5.5]undecan-9-one

To a solution of 1,4,10-trioxadispiro[4.2.5$^8$.2$^5$]pentadecane (820 mg, 3.86 mmol) in DCE (10 mL) was added FeCl$_3$·6H$_2$O (2.09 g, 7.73 mmol, 2 eq) and the mixture was stirred at 15° C. for 3 hr. To the reaction mixture was partitioned between H$_2$O (15 mL) and DCM (15 mL×2). The combined organic layers were washed with brine (20 mL), dried (Na$_2$SO$_4$), filtered and concentrated under reduced pressure to give 2-oxaspiro[5.5]undecan-9-one (620 mg) as a light yellow oil. $^1$H NMR (400 MHz, CDCl$_3$) δ 3.73-3.67 (m, 2H), 3.49 (s, 2H), 2.35-2.33(m, 4H), 1.78-1.73 (m, 4H), 1.65-1.63 (m, 4H).

2-oxaspiro[5.5]undecan-9-one was progressed to Intermediate O according to the procedures already described for Intermediate H.

4,4,5,5-tetramethyl-2-(2-oxaspiro[5.5]undec-8-en-9-yl)-1,3,2-dioxaborolane (Intermediate O)

Colorless oil; (520 mg, 1.50 mmol). $^1$H NMR (400 MHz, CDCl$_3$) δ 6.49-6.47 (m, 1H), 3.68-3.54 (m, 2H), 3.38-3.28 (m, 2H), 2.13-1.90 (m 4H), 1.60-1.57 (m, 2H), 1.47-1.41 (m, 4H), 1.25 (s, 12H).

INTERMEDIATE P

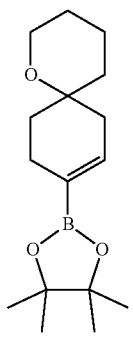

4,4,5,5-Tetramethyl-2-(1-oxaspiro[5.5]undec-8-en-9-yl)-1,3,2-dioxaborolane

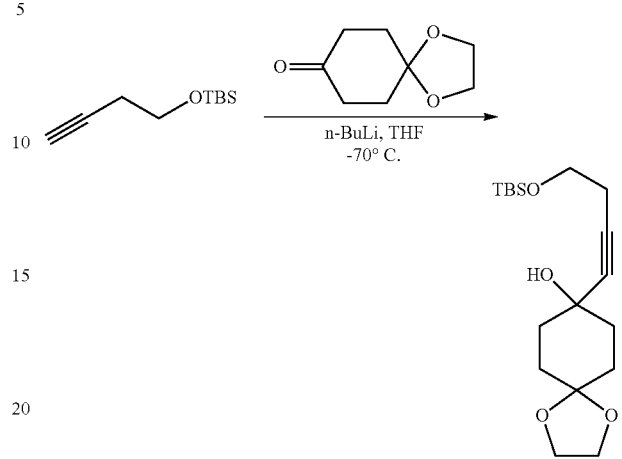

8-(4-((tert-Butyldimethylsilyl)oxy)but-1-yn-1-yl)-1,4-dioxaspiro[4.5]decan-8-ol

A 3-necked round-bottom flask was charged with tert-butyl-but-3-ynoxy-dimethyl-silane (57 g, 309 mmol, 1.2 eq) and THF (500 mL) and purged with N$_2$. The solution was cooled at −70° C. and n-BuLi (2.5 M in hexanes, 133 mL, 1.3 eq) was added dropwise. The resulting mixture was stirred at −70° C. for 1 hr, and a solution of 1,4-dioxaspiro[4.5]decan-8-one (40 g, 256.12 mmol, 1 eq) in THF (200 mL) was added drop-wise at −70° C. After stirring for 16 h at 25° C. the reaction mixture was quenched at 0° C. by the addition of saturated aq. NH$_4$Cl (800 mL), and extracted with EtOAc (800 mL×3). The combined organic layers were washed with brine (800 mL), filtered, dried (Na$_2$SO$_4$), and concentrated under reduced pressure. The residue was purified by SiO$_2$ gel chromatography (PE:EtOAc=20/1 to 5/1) to give the title compound (36 g, 105 mmol, 41% yield) as a colorless oil. $^1$H NMR (400 MHz, CDCl$_3$) δ 3.99 (s, 4H), 3.71 (t, J=7.2 Hz, 2H), 2.43 (t, J=7.2 Hz, 2H), 1.98-1.83 (m, 4H), 1.82-1.69 (m, 4H), 0.96-0.83 (m, 9H), 0.13-0.02 (m, 6H)

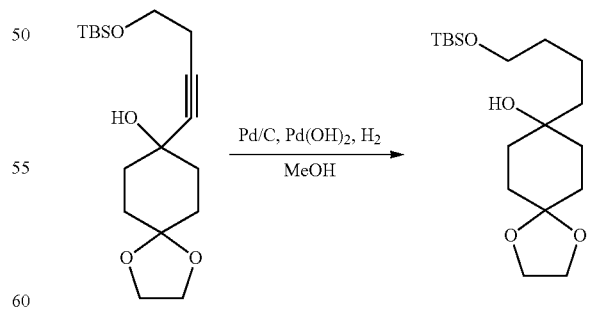

8-(3-Benzyloxy-2,2-dimethyl-propyl)-1,4-dioxaspiro[4.5]decan-8-ol

A Parr reaction vessel was charged with the product from the previous step (36 g, 105.72 mmol), Pd/C (2 g, 10% purity), Pd(OH)$_2$/C (2 g, 10% purity) and MeOH (200 mL). The suspension was degassed under vacuum and with N$_2$ three times, purged with H$_2$ and stirred under an atmosphere of H$_2$ (15 Psi) at 25° C. for 3 hr in a Parr shaker. The reaction mixture was then purged with N$_2$, filtered through a pad of Celite and concentrated under reduced pressure. The residue was purified by SiO$_2$ gel chromatography (PE:EtOAc=30:1 to 1:2) to afford the title compound as colorless oil. $^1$H NMR (400 MHz, CDCl$_3$) δ 4.00-3.88 (m, 4H), 3.63 (t, J=6.4 Hz, 2H), 1.96-1.82 (m, 2H), 1.72-1.25 (m, 12H), 0.96-0.84 (m, 9H), 0.12-0.01 (m, 6H).

4,4,5,5-Tetramethyl-2-(1-oxaspiro[5.5]undec-8-en-9-yl)-1,3,2-dioxaborolane (Intermediate P)

Pale yellow oil; $^1$H NMR (400 MHz, CDCl$_3$): δ 6.45-6.44 (m, 1H), 3.69-3.66 (m, 2H), 2.23-2.21 (m, 3H), 2.13-2.11 (m, 1H), 1.65-1.55 (m, 1H), 1.54-1.52 (m, 1H), 1.51-1.49 (m, 4H), 1.48-1.43 (m, 2H), 1.26 (s, 12H).

INTERMEDIATE Q

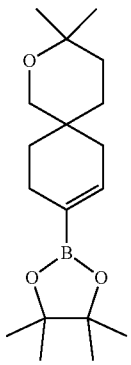

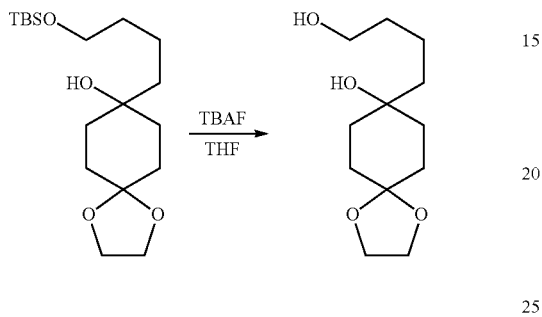

8-(4-Hydroxybutyl)-1,4-dioxaspiro[4.5]decan-8-ol

To a solution of 8-[4-[tert-butyl(dimethyl)silyl]oxybutyl]-1,4-dioxaspiro[4.5]decan-8-ol (62 g, 179.9 mmol) in THF (600 mL) at 0° C. was added TBAF (1 M in THF, 215 mL, 1.19 eq). The mixture was stirred at 25° C. for 16 hr and concentrated under reduced pressure, the residue was purified by SiO$_2$ gel chromatography (PE:EtOAc=3/1 to 1/2) to give 8-(4-hydroxybutyl)-1,4-dioxaspiro[4.5] decan-8-ol (30 g, 130.26 mmol, 72% yield) as a light yellow solid. $^1$H NMR (400 MHz, CDCl$_3$): δ 4.03-3.79 (m, 4H), 3.69-3.48 (m, 2H), 1.93-1.78 (m, 2H), 1.71-1.36 (m, 12H).

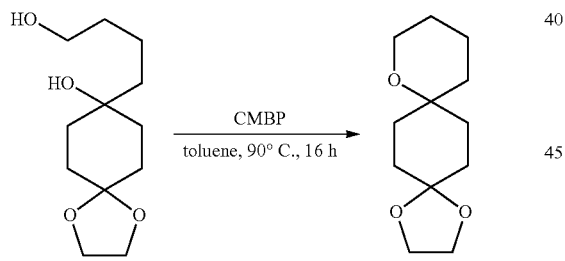

1,4,9-Trioxadispiro[4.2.5$^8$.2$^5$]pentadecane

To a solution of 8-(4-hydroxybutyl)-1,4-dioxaspiro[4.5] decan-8-ol (20 g, 86.84 mmol) in toluene (200 mL) was added cyanomethylene)tributylphosphorane (23.06 g, 95.53 mmol, 1.1 eq). The mixture was stirred at 90° C. for 16 hr, concentrated under reduced pressure and the residue was purified by SiO$_2$ gel chromatography (PE to PE:EtOAc=50/1) to afford 1,4,9-trioxadispiro[4.2.5$^8$.2$^5$]pentadecane (17 g, 80 mmol, 92% yield) as a yellow oil. $^1$H NMR (400 MHz, CDCl$_3$): δ 4.02-3.86 (m, 4H), 3.68-3.55 (m, 2H), 2.01-1.92 (m, 2H), 1.90-1.79 (m, 2H), 1.68-1.59 (m, 2H), 1.56-1.42 (m, 8H).

1,4,9-Trioxadispiro[4.2.5$^8$.2$^5$]pentadecane was progressed to Intermediate P according to the procedures already described for Intermediate H.

2-(3,3-Dimethyl-2-oxaspiro[5.5]undec-9-en-9-yl)-4,4,5,5-tetramethyl-1,3,2-dioxaborolane

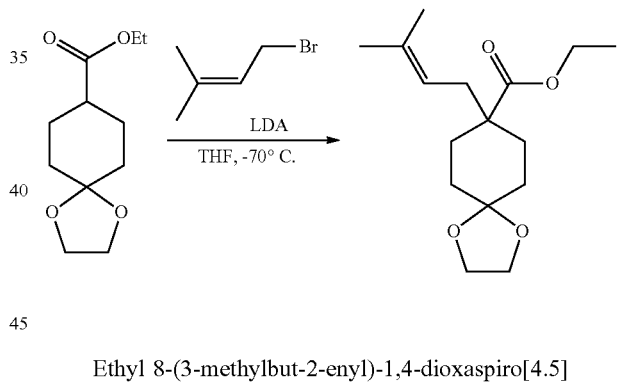

Ethyl 8-(3-methylbut-2-enyl)-1,4-dioxaspiro[4.5] decane-8-carboxylate

To a solution of ethyl 1,4-dioxaspiro[4.5]decane-8-carboxylate (20 g, 93.35 mmol) in THF (300 mL) at −70° C. was added dropwise LDA (2 M in THF, 56 mL, 1.2 eq), and the mixture was stirred at this temperature for 1 hr. A solution of 1-bromo-3-methyl-but-2-ene (20.87 g, 140 mmol, 1.5 eq) in THF (50 mL) was then added dropwise at −70° C. and the resulting mixture was stirred at 25° C. for 11 hr, quenched at 0° C. by addition of saturated aq. NH$_4$Cl (150 mL) and then extracted with EtOAc (500 mL×3). The combined organic layers were washed with brine (500 mL), dried (Na$_2$SO$_4$), filtered and concentrated under reduced pressure. The residue was purified by SiO$_2$ gel chromatography (PE:EtOAc=100:1 to 25:1) to afford the title compound (19.39 g, 68.7 mmol, 73% yield) as a pale yellow oil. $^1$H NMR (400 MHz, CDCl$_3$) δ 4.97 (t, J=7.6 Hz, 1H), 4.09-4.02 (m, 2H), 3.86 (s, 4H), 2.17-2.03 (m, 4H), 1.64-1.49 (m, 10H), 1.48-1.38 (m, 2H), 1.21-1.14 (m, 3H).

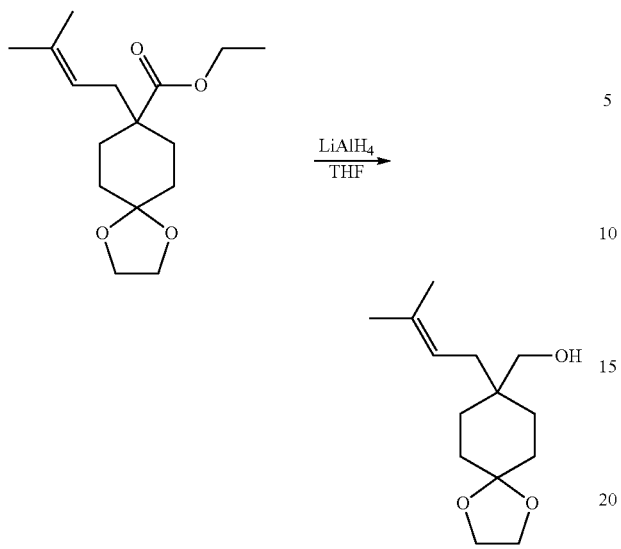

[8-(3-Methylbut-2-enyl)-1,4-dioxaspiro[4.5]decan-8-yl]methanol

To a solution of ethyl 8-(3-methylbut-2-enyl)-1,4-dioxaspiro[4.5]decane-8-carboxylate (19 g, 67 mmol) in THF (250 mL) at 0° C. was added LiAlH$_4$ (3.06 g, 80.74 mmol, 1.2 eq) and the suspension was stirred at 25° C. for 2 hr. The reaction mixture was quenched at 0° C. by sequential addition of H$_2$O (3 mL), 15% aq. NaOH (3 mL), H$_2$O (9 mL) and MgSO$_4$. The suspension was filtered, concentrated under reduced pressure and the residue was purified by SiO$_2$ gel chromatography (PE:EtOAc=10:1 to 1:1) to afford the title compound (13.78 g, 57.3 mmol, 85% yield) as a pale yellow oil. $^1$H NMR (400 MHz, CDCl$_3$) δ 5.19 (t, J=7.6 Hz, 1H), 3.93 (s, 4H), 3.51-3.37 (m, 2H), 2.06 (d, J=7.6 Hz, 2H), 1.71 (s, 3H), 1.54-1.43 (m, 7H), 1.26-1.23 (m, 4H).

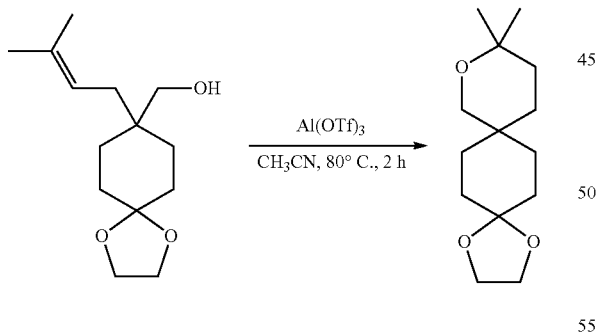

11,11-Dimethyl-1,4,10-trioxadispiro[4.2.5$^8$.2$^5$]pentadecane

To a solution of [8-(3-methylbut-2-enyl)-1,4-dioxaspiro[4.5]decan-8-yl]methanol (14.5 g, 60.3 mmol) in CH$_3$CN (200 mL) was added aluminum-trifluoromethanesulfonate (2.86 g, 6.03 mmol, 0.1 eq), and the mixture was stirred at 80° C. for 2 hr, then concentrated under reduced pressure. The residue was purified by SiO$_2$ gel chromatography (PE:EtOAc=15:1 to 5:1) to afford the title compound (8.3 g, 34.53 mmol, 57% yield) as a white solid. $^1$H NMR (400 MHz, CDCl$_3$) δ 3.94 (s, 4H), 3.43 (s, 2H), 1.59-1.64 (m, 4H), 1.43-1.57 (m, 8H), 1.20 (s, 6H).

11,11-Dimethyl-1,4,10-trioxadispiro[4.2.5$^8$.2$^5$]pentadecane was progressed to Intermediate Q according to the procedures already described for Intermediate H.

2-(3,3-Dimethyl-2-oxaspiro[5.5]undec-9-en-9-yl)-4,4,5,5-tetramethyl-1,3,2-dioxaborolane (Intermediate Q)

Colorless oil (7 g, 22.86 mmol). $^1$H NMR (400 MHz, CDCl$_3$) δ 6.51-6.49 (m, 1H), 3.40-3.30 (m, 2H), 2.18-2.02 (m, 3H), 1.86-1.85 (m, 1H), 1.53-1.38 (m, 6H), 1.28-1.24 (m, 12H), 1.20 (s, 6H).

INTERMEDIATE R

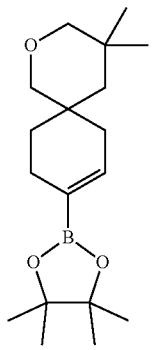

2-(4,4-Dimethyl-2-oxaspiro[5.5]undec-8-en-9-yl)-4,4,5,5-tetramethyl-1,3,2-dioxaborolane

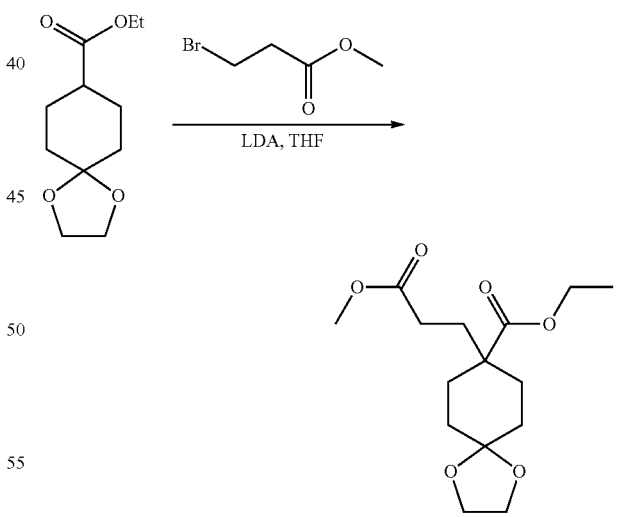

Ethyl 8-(3-methoxy-3-oxopropyl)-1,4-dioxaspiro[4.5]decane-8-carboxylate

To a solution of ethyl 1,4-dioxaspiro[4.5]decane-8-carboxylate (20 g, 93.35 mmol) in THF (200 mL) at −60° C. was added a solution of LDA (2 M in THF, 46.67 mL, 1 eq). The reaction was stirred at −60° C. for 1 h, a solution of methyl 3-bromopropanoate (15.59 g, 93.35 mmol, 1 eq) in THF (50 mL) was added dropwise. The mixture was stirred at 25° C. for 16 hr, then quenched at 0° C. by addition of saturated aq. NH₄Cl (200 mL), and extracted with EtOAc (250 mL×3). The combined organic layers were washed with brine (400 mL), dried (Na₂SO₄), filtered and concentrated under reduced pressure. The residue was purified by SiO₂ gel chromatography (PE to PE:EtOAc=10/1) to give the title compound (5.3 g) as yellow oil, which was used without further purification. ¹H NMR (400 MHz, CDCl₃) δ 4.18-4.17 (m, 2H), 3.96-3.88 (m, 4H), 3.65 (s, 3H), 2.30-2.19 (m, 2H), 2.16-2.13 (m, 2H), 1.88-1.84 (m, 2H), 1.71-1.44 (m, 6H), 1.26 (t, J=7.1 Hz, 3H).

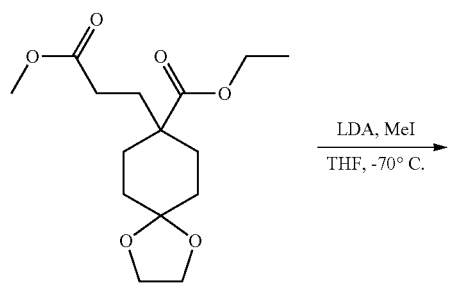

Ethyl 8-(3-methoxy-2-methyl-3-oxopropyl)-1,4-dioxaspiro[4.5]decane-8-carboxylate To a solution of ethyl 8-(3-methoxy-3-oxo-propyl)-1,4-dioxaspiro[4.5] decane-8-carboxylate (1.4 g, 4.66 mmol) in THF (20 mL) at −70° C. was added dropwise LDA (2 M in THF, 7.0 mL, 3.0 eq) and the mixture was stirred at −70° C. for 1.5 hr. MeI (2.65 g, 18.65 mmol, 1.16 mL, 4 eq) was added dropwise at −70° C. and the mixture was stirred at 25° C. for 6 hr. The reaction was quenched at 0° C. by addition of saturated aq. NH₄Cl (20 mL) and extracted with EtOAc (50 mL×3). The combined organic layers were washed with brine (100 mL), dried (Na₂SO₄), filtered and concentrated under reduced pressure. The residue was purified by SiO₂ gel chromatography (PE to PE:EtOAc=20/1) to give the title compound (1 g, 3.18 mmol, 68% yield) as a pale yellow oil. ¹H NMR (400 MHz, CDCl₃) δ 4.17-4.07 (m, 2H), 3.95-3.89 (m, 4H), 3.64 (s, 3H), 2.56-2.44 (m, 1H), 2.20-2.06 (m, 3H), 1.65-1.41 (m, 7H), 1.26 (t, J=7.1 Hz, 3H), 1.12 (d, J=7.1 Hz, 3H).

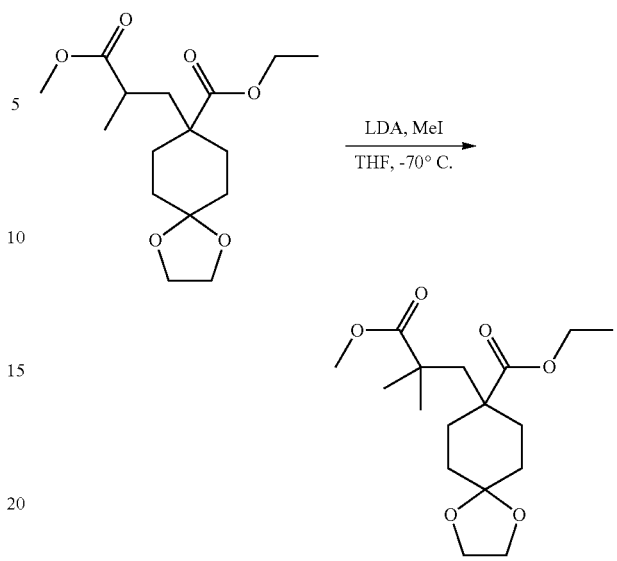

Ethyl 8-(3-methoxy-2,2-dimethyl-3-oxopropyl)-1,4-dioxaspiro[4.5]decane-8-carboxylate The product from previous step (4 g, 12.72 mmol) was subjected to a second methylation procedure performed in the same conditions described above, to give the title compound (4.15 g, 12.6 mmol, 99% yield) as a pale yellow oil after SiO₂ gel chromatography. ¹H NMR (400 MHz, CDCl₃) δ 4.13 (q, J=7.1 Hz, 2H), 3.94-3.88 (m, 4H), 3.66 (s, 3H), 2.12-2.04 (m, 2H), 1.99 (s, 2H), 1.65-1.60 (m, 4H), 1.55-1.45 (m, 2H), 1.30-1.25 (m, 3H), 1.16 (s, 6H).

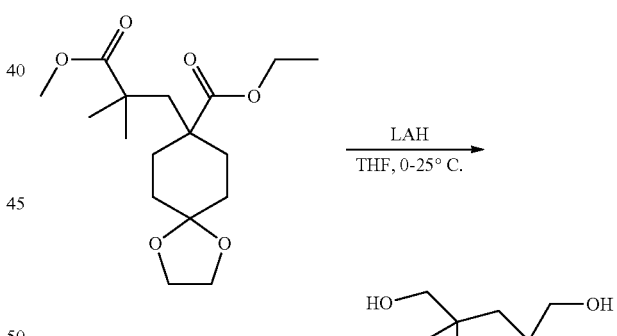

3-(8-(Hydroxymethyl)-1,4-dioxaspiro[4.5]decan-8-yl)-2,2-dimethylpropan-1-ol

To a suspension of LiAlH₄ (1.44 g, 37.91 mmol, 3 eq) in THF (40 mL) at 0° C. was added dropwise a solution of ethyl 8-(3-methoxy-2,2-dimethyl-3-oxo-propyl)-1,4-dioxaspiro [4.5]decane-8-carboxylate (4.15 g, 12.64 mmol, 1 eq) in THF (10 mL). After addition, the mixture was stirred at 0° C. for 1 h, and then quenched at 0° C. by sequential addition of H₂O (1.4 mL), 15% aq. NaOH (1.4 mL), H₂O (4.2 mL) and MgSO₄ (~10 g). The suspension was filtered and the filtrate was concentrated under reduced pressure, the residue was purified by SiO₂ gel chromatography (PE to PE:EtOAc=2/1) to give the title compound (2.1 g, 8.13 mmol, 64% yield) as a colorless oil. ¹H NMR (400 MHz, CDCl₃) δ 4.01-3.93 (m, 4H), 3.65 (s, 2H), 3.48 (s, 2H), 3.06 (br s, 2H), 1.74-1.61 (m, 8H), 1.45 (s, 2H), 0.99 (s, 6H).

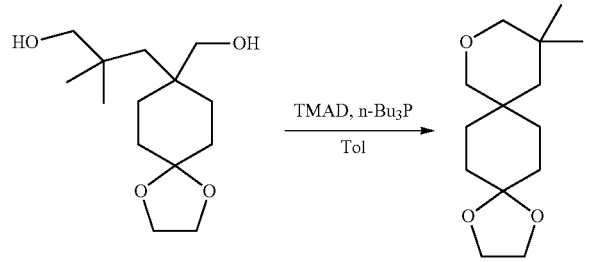

12,12-Dimethyl-1,4,10-trioxadispiro[4.2.5⁸.2⁵]pentadecane

To a solution of 3-[8-(hydroxymethyl)-1,4-dioxaspiro[4.5]decan-8-yl]-2,2-dimethyl-propan-1-ol (2.96 g, 11.46 mmol) in toluene (30 mL) were added tributylphosphine (3.48 g, 17.19 mmol, 4.24 mL, 1.5 eq) and N,N,N',N'-Tetramethylazodicarboxamide (2.96 g, 17.19 mmol, 1.5 eq). The mixture was stirred at 25° C. for 3 h, then at 60° C. for 15 hr. The reaction was filtered and the filtrate was concentrated under reduced pressure, the residue was purified by SiO₂ gel column chromatography (PE to PE:EtOAc=20/1) to give the title compound (0.9 g, 3.74 mmol, 33% yield) as a white solid. ¹H NMR (400 MHz, CDCl₃) δ 3.97-3.92 (m, 4H), 3.41 (s, 2H), 3.28 (s, 2H), 1.68-1.60 (m, 4H), 1.59-1.53 (m, 4H), 1.34 (s, 2H), 0.96 (s, 6H). 12,12-Dimethyl-1,4,10-trioxadispiro[4.2.5⁸.2⁵]pentadecane was progressed to Intermediate R according to the procedures already described for Intermediate H.

2-(4,4-Dimethyl-2-oxaspiro[5.5]undec-8-en-9-yl)-4,4,5,5-tetramethyl-1,3,2-dioxaborolane (Intermediate R)

Colorless oil (1.05 g, 3.43 mmol). ¹H NMR (400 MHz, CDCl₃) δ 6.48-6.47 (m, 1H), 3.47-3.45 (m, 1H), 3.35-3.32 (m, 1H), 3.22-3.20 (m, 2H), 2.28-2.22 (m, 1H), 2.15-2.06 (m, 2H), 1.92-1.87 (m, 1H), 1.59-1.47 (m, 2H), 1.43-1.33 (m, 2H), 1.27 (s, 12H), 0.99 (s, 3H), 0.93 (s, 3H).

INTERMEDIATE S

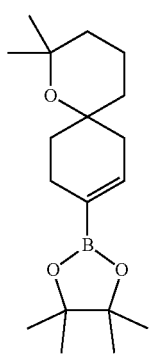

2-(2,2-Dimethyl-1-oxaspiro[5.5]undec-8-en-9-yl)-4,4,5,5-tetramethyl-1,3,2-dioxaborolane

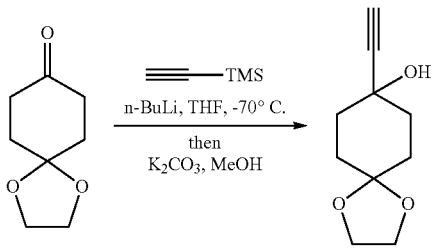

8-ethynyl-1,4-dioxaspiro[4.5]decan-8-ol

To a solution of ethynyl(trimethyl)silane (7.55 g, 76.84 mmol, 10.64 mL, 1.2 eq) in THF (120 mL) at −70° C. was added n-BuLi (2.5 M in hexanes, 30.7 mL, 1.2 eq) dropwise over 20 min, and the mixture was stirred at −70° C. for 0.5 hr. A solution of 1,4-dioxaspiro[4.5]decan-8-one (10 g, 64.03 mmol, 1 eq) in THF (40 mL) was then added dropwise and the mixture was stirred at −70° C. for 1.5 h. The reaction was quenched at 0° C. by addition of saturated aq. NH₄Cl (200 mL), and extracted with EtOAc (200 mL×3). The combined organic layers were washed with brine (300 mL), dried (Na₂SO₄), filtered and concentrated under reduced pressure. The residue was dissolved in MeOH (120 mL), K₂CO₃ (26 g) was added and the resulting suspension was stirred for 0.5 h. The volatiles were removed under reduced pressure, the residue was partitioned between H₂O (200 mL) and EtOAc (300 mL). The organic layer was washed with brine (200 mL), dried (Na₂SO₄), filtered and concentrated under reduced pressure. The residue purified by SiO₂ gel column chromatography (PE to PE:EtOAc=5/1) to give 8-ethynyl-1,4-dioxaspiro[4.5]decan-8-ol (11.5 g, 63.11 mmol, 98% yield) as a yellow oil. ¹H NMR (400 MHz, CDCl₃) δ 3.95 (s, 4H), 2.49 (s, 1H), 2.02-1.97 (m, 5H), 1.94-1.93 (m, 1H), 1.82-1.79 (m, 2H).

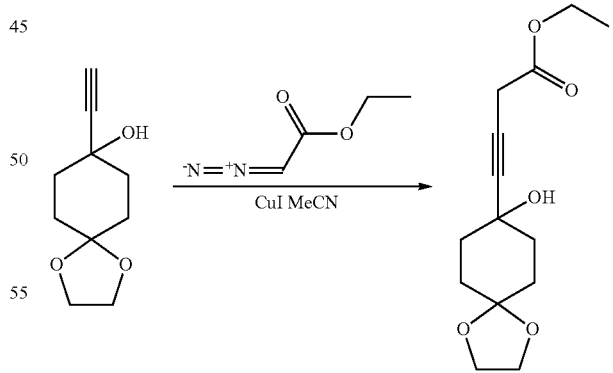

Ethyl 4-(8-hydroxy-1,4-dioxaspiro[4.5]decan-8-yl)but-3-ynoate

To a solution of 8-ethynyl-1,4-dioxaspiro[4.5]decan-8-ol (11.5 g, 63.11 mmol) in anhydrous MeCN (100 mL) were added CuI (1.20 g, 6.31 mmol, 0.1 eq) and ethyl 2-diazoacetate (7.92 g, 69.42 mmol, 1.1 eq), and the mixture was stirred at RT for 16 h. The suspension was filtered, the filtrate concentrated under reduced pressure and the residue was purified by SiO₂ gel chromatography (PE to E:EtOAC=5/1) to give the title compound (13.3 g, 49.57 mmol, 78% yield) as a yellow oil. ¹H NMR (400 MHz, CDCl₃) δ 5.81-5.75 (m, 1H), 4.23-4.13 (m, 2H), 3.98-3.91 (m, 4H), 3.30 (s, 2H), 1.96-1.78 (m, 8H), 1.31-1.27 (m, 3H).

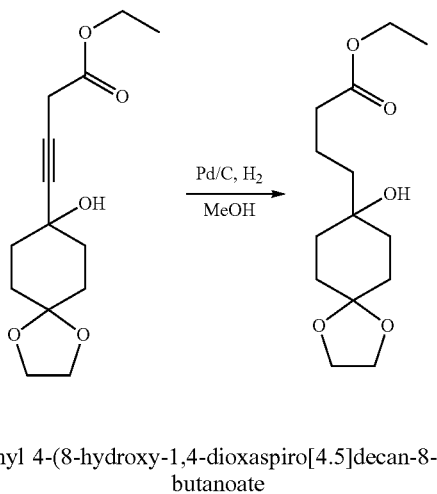

Ethyl 4-(8-hydroxy-1,4-dioxaspiro[4.5]decan-8-yl) butanoate

A Parr reaction vessel was charged with ethyl 4-(8-hydroxy-1,4-dioxaspiro[4.5]decan-8-yl)but-3-ynoate (6 g, 22.36 mmol), Pd/C (400 mg, 10% weight), Pd(OH)₂/C (400 mg, 20% weight) and MeOH (10 mL). The suspension was degassed under vacuum and with N₂ three times, purged with H₂ and stirred under an atmosphere of H₂ (15 Psi) at 25° C. for 16 hr in a Parr shaker. The reaction mixture was then purged with N₂, filtered through a pad of Celite and concentrated under reduced pressure to give the title compound. The residue was purified by SiO₂ gel chromatography (PE to PE:EtOAc=2/1) to give ethyl 4-(8-hydroxy-1,4-dioxaspiro[4.5]decan-8-yl)butanoate (4.8 g, 17.63 mmol, 78% yield) as a yellow oil. ¹H NMR (400 MHz, CDCl₃) δ 4.13 (q, J=7.1 Hz, 2H), 3.97-3.93 (m, 4H), 2.32 (t, J=7.3 Hz, 2H), 1.93-1.86 (m, 2H), 1.77-1.58 (m. 8H). 1.52-1.50 (m, 2H). 1.28-1.24 (m. 3H).

at 0° C. were added TEA (1.45 g, 14.3 mmol, 1.99 mL, 3 eq), DMAP (58.3 mg, 477 μmol, 0.1 eq) and TMSCl (778 mg, 7.16 mmol, 909 μL, 1.5 eq). The reaction mixture was stirred at 30° C. for 5 hr, then partitioned between H₂O (80 mL) and EtOAc (100 mL). The organic layer was washed with brine (80 mL), dried (Na₂SO₄), filtered and concentrated under reduced pressure. The residue was purified by SiO₂ gel chromatography (PE to PE:EtOAc=50/1) to give ethyl 4-(8-trimethylsilyloxy-1,4-dioxaspiro[4.5]decan-8-yl)butanoate (1.6 g, 4.64 mmol, 97% yield) as a yellow oil. ¹H NMR (400 MHz, CDCl₃) δ 4.13 (q, J=7.2 Hz, 2H), 3.96-3.92 (m, 4H), 2.29 (t, J=7.5 Hz, 2H), 1.89-1.81 (m, 2H), 1.72-1.51 (m, 10H), 1.26 (t, J=7.1 Hz, 3H), 0.13 (s, 9H).

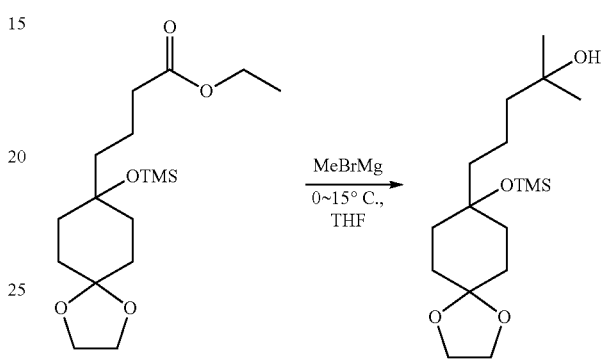

2-Methyl-5-(8-((trimethylsilyl)oxy)-1,4-dioxaspiro[4.5]decan-8-yl)pentan-2-ol

To a solution of the product from previous step (4.2 g, 12.19 mmol, 18.38 mL) in THF (40 mL) at 0° C. was added dropwise MeMgBr (3 M in THF, 21 mL, 5.17 eq) and the mixture was stirred at 15° C. for 2 hr. The reaction was quenched at 0° C. by addition of saturated aq. NH₄Cl (100 mL), and extracted with EtOAc (100 mL×3). The combined organic layers were washed with brine (200 mL), dried (Na₂SO₄), filtered and concentrated under reduced pressure. The residue was purified by SiO₂ gel chromatography (PE to PE:EtOAc=8/1) to give the title compound (3.8 g, 11.50 mmol, 94% yield) as white solid. ¹H NMR (400 MHz, CDCl₃) δ 4.98-3.92 (m, 4H), 1.91-1.83 (m, 2H), 1.70-1.42 (m, 13H), 1.23 (s, 6H), 0.13 (m, 9H).

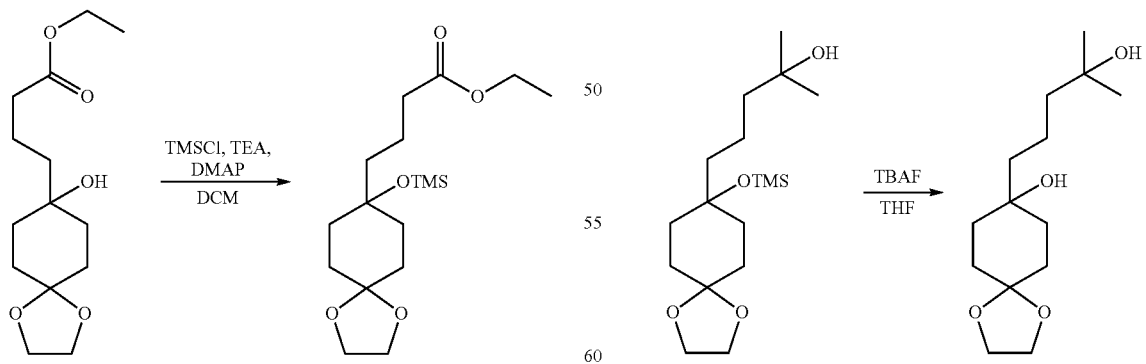

Ethyl 4-(8-((trimethylsilyl)oxy)-1,4-dioxaspiro[4.5]decan-8-yl)butanoate 8-(4-Hydroxy-4-methylpentyl)-1,4-dioxaspiro[4.5]decan-8-ol To a solution of ethyl 4-(8-hydroxy-1,4-dioxaspiro[4.5]decan-8-yl)butanoate (1.3 g, 4.77 mmol) in DCM (10 mL)

To a solution of 2-methyl-5-(8-trimethylsilyloxy-1,4-dioxaspiro[4.5]decan-8-yl)pentan-2-ol (5.6 g, 16.94 mmol) in THF (50 mL) at 0° C. was added TBAF (1 M in THF, 20.33 mL, 1.2 eq). The mixture was stirred at 35° C. for 3 hr, and concentrated under reduced pressure. The residue was purified by SiO₂ gel chromatography (PE:EtOAc=2/1 to 1/1) to give the title compound (4.3 g, 16.64 mmol, 98% yield) as a white solid. ¹H NMR (400 MHz, CDCl₃) δ 3.99-3.92 (m, 4H), 1.94-1.87 (m, 2H), 1.69-1.58 (m, 7H), 1.50-1.47 (m, 6H), 1.23 (s, 6H).

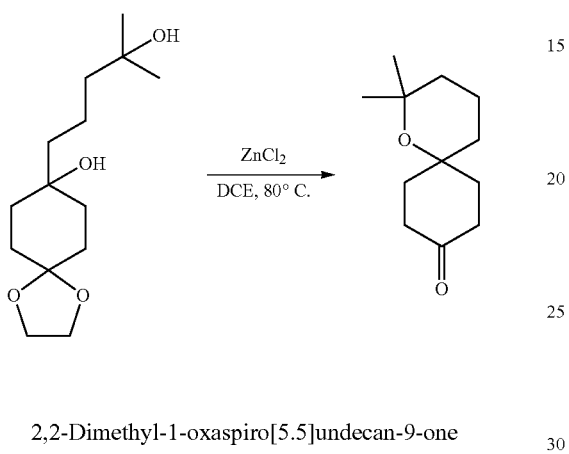

2,2-Dimethyl-1-oxaspiro[5.5]undecan-9-one

To a solution of 8-(4-hydroxy-4-methyl-pentyl)-1,4-dioxaspiro[4.5]decan-8-ol (3.8 g, 14.71 mmol) in dichloroethane (30 mL) was added ZnCl₂ (5.01 g, 36.77 mmol, 1.72 mL, 2.5 eq), and the mixture was stirred at 80° C. for 3 hr. The reaction was cooled to RT, quenched by addition of H₂O (50 mL), and extracted with EtOAc (100 mL×3). The combined organic layers were washed with brine (200 mL), dried (Na₂SO₄), filtered and concentrated under reduced pressure. The residue was purified by SiO₂ gel chromatography (PE to PE:EtOAc=50/1) to give the title compound (2.1 g, 10.7 mmol, 72% yield) as a colorless oil. ¹H NMR (400 MHz, CDCl₃) δ 2.78-2.69 (m, 2H), 2.21-2.12 (m, 4H), 1.73-1.59 (m, 4H), 1.52-1.47 (m, 4H), 1.26 (s, 6H).

2,2-Dimethyl-1-oxaspiro[5.5]undecan-9-one was progressed to Intermediate S according to the procedures already described for Intermediate H.

2-(2,2-Dimethyl-1-oxaspiro[5.5]undec-8-en-9-yl)-4,4,5,5-tetramethyl-1,3,2-dioxaborolane (Intermediate S)

Colorless oil; (2.1 g, 6.86 mmol). ¹H NMR (400 MHz, CDCl₃) δ 6.41 (d, J=2.4 Hz, 1H), 2.44-2.39 (m, 1H), 2.33-2.27 (m, 1H), 2.22-2.09 (m, 2H), 1.76-1.59 (m, 4H), 1.54-1.39 (m, 4H), 1.26 (s, 12H), 1.22 (s, 6H).

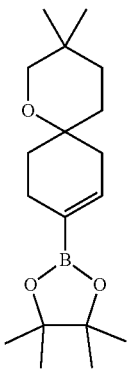

INTERMEDIATE T

2-(3,3-Dimethyl-1-oxaspiro[5.5]undec-9-en-9-yl)-4,4,5,5-tetramethyl-1,3,2-dioxaborolane

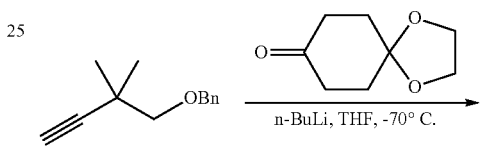

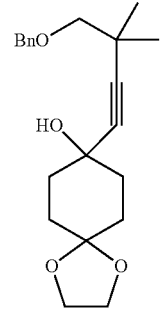

8-(4-Benzyloxy-3,3-dimethyl-but-1-ynyl)-1,4-dioxaspiro[4.5]decan-8-ol

To a solution of 2,2-dimethylbut-3-yn-oxymethylbenzene (15 g, 79.67 mmol) in THF (300 mL) at −70° C. was added dropwise n-BuLi (2.5 M in hexanes, 38.24 mL, 1.2 eq) and the mixture was stirred at −70° C. for 1 hr. A solution of 1,4-dioxaspiro[4.5]decan-8-one (11.82 g, 75.69 mmol, 0.95 eq) in THF (100 mL) was added dropwise at −70° C. and the resulting mixture was slowly warmed to 20° C. and stirred for 3 hr. The reaction was quenched at 0° C. by the addition of saturated aq. NH₄Cl (100 mL), and extracted with EtOAc (100 mL×3). The combined organic layers were washed with brine (150 mL), dried (Na₂SO₄), and concentrated under reduced pressure. The residue was purified by SiO₂ gel chromatography (PE:EtOAc=50:1 to 10:1) to afford the title compound (23 g) as a yellow oil. ¹H NMR (400 MHz, DMSO-d₆) δ 7.35-7.26 (m, 5H), 5.18 (s, 1H), 4.55 (s, 2H), 3.83 (s, 4H), 3.27 (s, 2H), 1.74-1.62 (m, 8H), 1.16 (s, 6H).

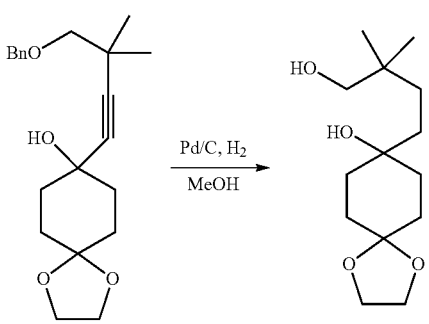 [SMILES: "MeOH" ; CC(C)(C#CC1(O)CCC2(CC1)OCCO2)COCc1ccccc1 ; "Pd/C, H2" ; CC(C)(CO)CCC1(O)CCC2(CC1)OCCO2]

8-(4-Hydroxy-3,3-dimethyl-butyl)-1,4-dioxaspiro[4.5]decan-8-ol

A Parr reaction vessel was charged with the product from the previous step (20 g, 58.06 mmol), Pd/C (1 g, 10% weight), Pd(OH)$_2$/C (1 g, 10% weight) and MeOH (200 mL). The suspension was degassed under vacuum and with N$_2$ three times, purged with H$_2$ and stirred under an atmosphere of H$_2$ (15 Psi) at 25° C. for 16 hr in a Parr shaker. The reaction mixture was then purged with N$_2$, filtered through a pad of Celite and concentrated under reduced pressure to give the title compound. The residue was purified by SiO$_2$ gel chromatography (PE:EtOAc=10:1 to 0:1) to afford the title compound (10 g, 38.71 mmol, 66% yield) as colorless oil. $^1$H NMR (400 MHz, DMSO-d$_6$) δ 4.40-4.37 (m, 1H), 3.91 (s, 1H), 3.81 (s, 4H), 3.06-3.05 (d, J=4 Hz, 2H), 1.76-1.70 (m, 2H), 1.47-1.39 (m, 6H), 1.29-1.23 (m, 2H), 1.21-1.17 (m, 2H), 0.75 (s, 6H).

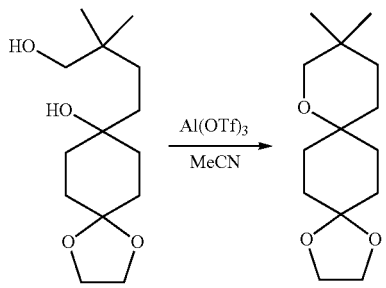 [SMILES: "MeCN" ; CC(C)(CO)CCC1(O)CCC2(CC1)OCCO2 ; CC1(C)CCC2(CCC3(CC2)OCCO3)OC1 ; "Al(OTf)3"]

11,11-Dimethyl-1,4,9-trioxadispiro[4.2.5$^8$.2$^5$]pentadecane

To a solution of 8-(4-hydroxy-3,3-dimethyl-butyl)-1,4-dioxaspiro[4.5]decan-8-ol (9.6 g, 37.16 mmol) in MeCN (150 mL) was added aluminum-trifluoromethanesulfonate (3.52 g, 7.43 mmol, 0.2 eq). The resulting mixture was stirred at 80° C. for 2 hr, then concentrated under reduced pressure. The residue was purified by SiO$_2$ gel chromatography (PE to PE:EtOAc=50:1) to afford the title compound (3 g) as a colorless oil. $^1$H NMR (400 MHz, DMSO-d$_6$) δ 3.83 (s, 4H), 3.13 (s, 2H), 2.46-2.36 (m, 1H), 2.17-2.10 (m, 1H), 1.86-1.81 (m, 2H), 1.47-1.31 (m, 8H), 0.85 (s, 6H). 11,11-Dimethyl-1,4,9-trioxadispiro[4.2.5$^8$.2$^5$]pentadecane was progressed to Intermediate T according to the procedures already described for Intermediate H.

2-(3,3-Dimethyl-1-oxaspiro[5.5]undec-9-en-9-yl)-4,4,5,5-tetramethyl-1,3,2-dioxaborolane (Intermediate T)

Pale yellow oil; (1.6 g, 5.22 mmol). $^1$H NMR (400 MHz, CDCl$_3$) δ 6.46-6.44 (m, 1H), 3.27 (s, 2H), 2.30-2.20 (m, 2H), 2.18-2.11 (m, 2H), 1.96-1.92 (m, 1H), 1.60-1.55 (m, 1H), 1.50-1.37 (m, 4H), 1.25 (s, 12H), 0.93-0.89 (m, 6H).

The invention is further illustrated by the following examples.

Example 1 a/b

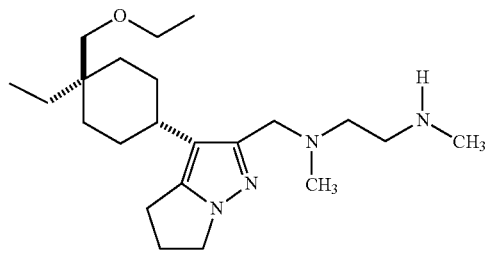

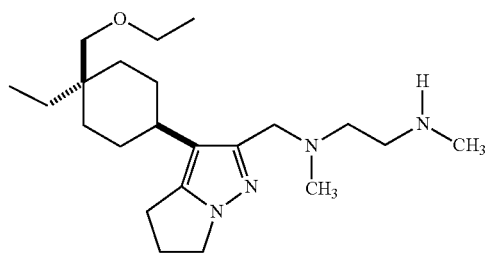

N$^1$-((3-((1r,4r)-4-(ethoxymethyl)-4-ethylcyclohexyl)-5,6-dihydro-4H-pyrrolo[1,2-b]-pyrazol-2-yl)methyl)-N$^1$,N$^2$-dimethylethane-1,2-diamine and N$^1$-((3-((1s,4s)-4-(ethoxymethyl)-4-ethylcyclohexyl)-5,6-dihydro-4H-pyrrolo[1,2-b]pyrazol-2-yl)methyl)-N$^1$,N$^2$-dimethylethane-1,2-diamine

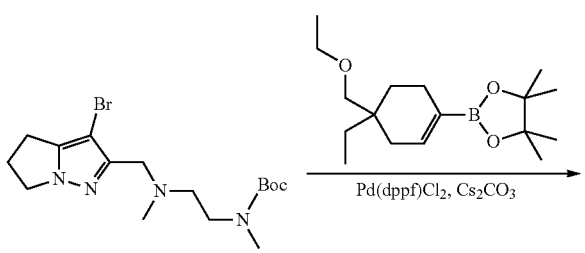

161

-continued

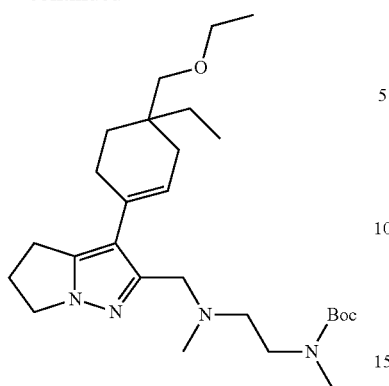

tert-Butyl-(2-(((3-(4-(ethoxymethyl)-4-ethylcyclo-hex-1-en-1-yl)-5,6-dihydro-4H-pyrrolo[1,2-b]pyrazol-2-yl)methyl)(methyl)amino)ethyl)(methyl)carbamate To a solution of Intermediate A (200 mg, 516.4 μmol, 1.0 eq) in dioxane (5 mL) and H$_2$O (1 mL) were added Intermediate E (243 mg, 826 μmol, 1.6 eq), Pd(dppf)Cl$_2$ (37.78 mg, 51.64 μmol, 0.1 eq) and Cs$_2$CO$_3$ (336.49 mg, 1.03 mmol, 2 eq). The mixture was stirred at 90° C. for 15 hr, cooled to RT, diluted with H$_2$O (30 mL) and extracted with EtOAc (20 mL×3). The combined organic layers were concentrated under reduced pressure and the residue was purified by prep-HPLC (column: Phenomenex Gemini 150× 25 mm×10 um; mobile phase: [A: H$_2$O (0.05% NH$_4$OH v/v); B: ACN]; B %: 75%-100%, 12 min) to give the title compound (95 mg, 120 μmol, 23% yield) as a pale yellow oil. MS (ES$^+$) C$_{27}$H$_{46}$N$_4$O$_3$, requires: 474, found: 475 [M+H]$^+$.

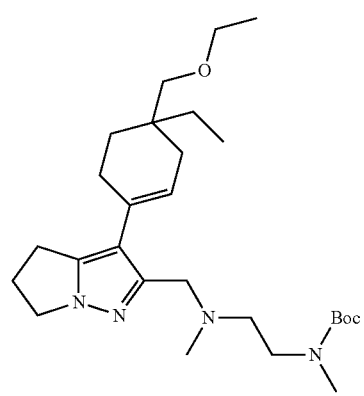

H$_2$, Pd(OH)$_2$/C
—————→
MeOH

162

-continued

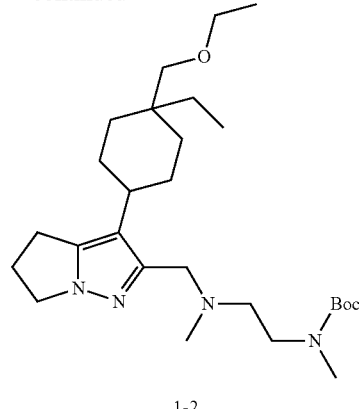

1-2 tert-Butyl(2-(((3-(4-(ethoxymethyl)-4-ethylcyclo-hexyl)-5,6-dihydro-4H-pyrrolo[1,2-b]pyrazol-2-yl)methyl)(methyl)amino)ethyl)(methyl)carbamate A Parr reaction vessel was charged with the product from the previous step (95 mg, 200 μmol, 1.0 eq), Pd(OH)$_2$ (190 mg, 676 μmol, 50% w/w, 3.38 eq) and MeOH (1.0 mL). The suspension as degassed with N$_2$, purged with H$_2$ and stirred under an atmosphere of H$_2$ (15 psi) at RT for 12 hr in the Parr shaker. The reaction mixture was then purged with N$_2$, filtered through a pad of CELITE(R) and concentrated under reduced pressure to give the title compound (94 mg) as a pale yellow oil, which was used in the next step without further purification. MS (ES$^+$) C$_{27}$H$_{48}$N$_4$O$_3$, requires: 476, found: 477 [M+H]$^+$.

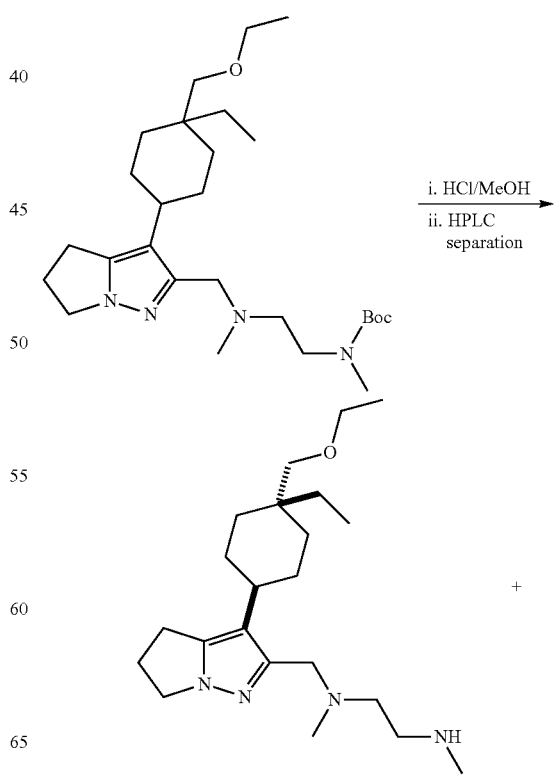

i. HCl/MeOH
ii. HPLC separation

-continued

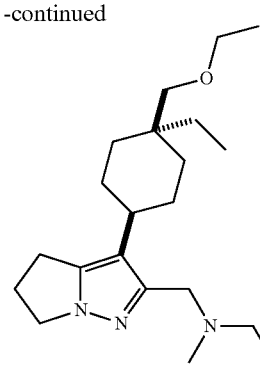

N$^1$-((3-((1r,4r)-4-(ethoxymethyl)-4-ethylcyclo-hexyl)-5,6-dihydro-4H-pyrrolo[1,2-b]pyrazol-2-yl)methyl)-N$^1$,N$^2$-dimethylethane-1,2-diamine and N$^1$-((3-((1s,4s)-4-(ethoxymethyl)-4-ethylcyclohexyl)-5,6-dihydro-4H-pyrrolo[1,2-b]pyrazol-2-yl)methyl)-N$^1$,N$^2$-dimethylethane-1,2-diamine To a solution of the product from the previous step (50 mg, 105 μmol, 1.0 eq) in MeOH (1.0 mL) was added a solution of HCl in MeOH (4 M, 1.0 mL, 38.1 eq). The mixture was stirred at 20° C. for 1 hr and then concentrated under reduced pressure. The residue was purified by prep-HPLC (column: Venusil XBP C8 150×25×10 um; mobile phase: [A: H$_2$O (0.225% FA); B: ACN]; B %: 8%-38%, 10 min) to give the title compound as two distinct diastereoisomeric products of undefined stereochemistry.

Example 1a 4.9 mg, 10.3 μmol, 9.8% yield, colorless oil; $^1$H NMR (400 MHz, Methanol-d$_4$) δ: 3.91 (t, J=7.2 Hz, 2H), 3.57-3.41 (m, 5H), 3.04-3.03 (m, 2H), 2.86 (m, 2H), 2.67 (m, 2H), 2.55 (s, 3H), 2.52-2.43 (m, 2H), 2.37 (m, 1H), 2.18 (s, 3H), 1.60-1.37 (m, 7H), 1.23-1.04 (m, 7H), 0.74-0.70 (t, 3 H). MS (ES$^+$) C$_{22}$H$_{40}$N$_4$O requires: 376, found: 377[M+H]$^+$.

Example 1b 8.6 mg, 19.6 μmol, 19% yield, colorless oil; $^1$H NMR (400 MHz, Methanol-d$_4$) δ: 8.34 (br s, 2H), 3.98-3.85 (m, 2H), 3.55-3.39 (m, 5H), 3.13 (s, 1H), 3.04 (m, 2H), 2.91-2.80 (m, 2H), 2.74-2.63 (m, 2H), 2.54 (s, 3H), 2.51-2.41 (m, 2H), 2.40-2.27 (m, 1H), 2.19 (s, 3H), 1.44-1.16 (m, 8H), 1.11-1.07(m, 7H), 0.72-0.68 (t, 3 H). MS (ES$^+$) C$_{22}$H$_{40}$N$_4$O requires: 376, found: 377[M+H]$^+$.

Example 2

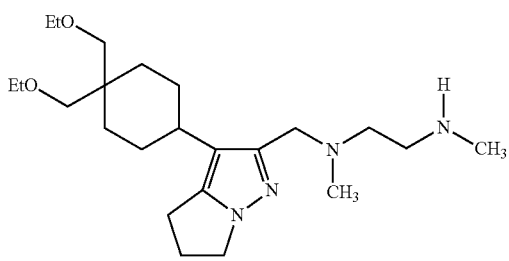 [SMILES: CCOCC1(COCC)CCC(c2c(CN(C)CCNC)nn3c2CCC3)CC1]

N$^1$-((3-(4,4-bis(ethoxymethyl)cyclohexyl)-5,6-dihydro-4H-pyrrolo[1,2-b]pyrazol-2-yl)methyl)-N$^1$,N$^2$-dimethylethane-1,2-diamine

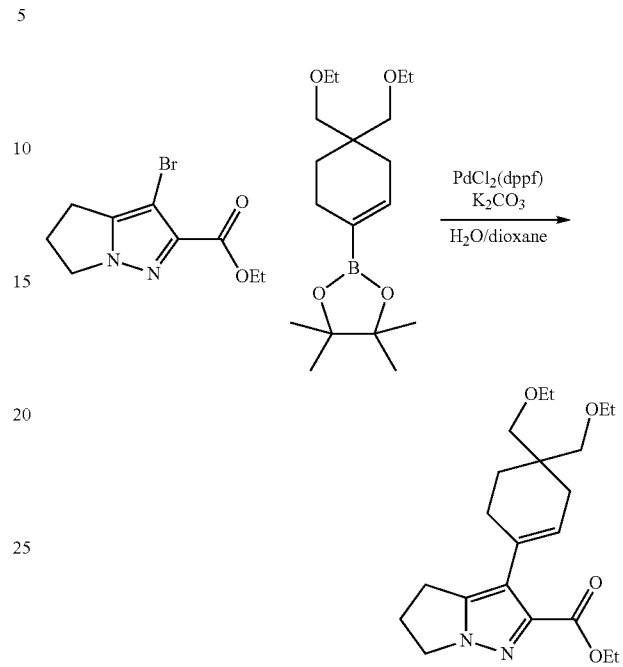

Ethyl 3-(4,4-bis(ethoxymethyl)cyclohex-1-en-1-yl)-5,6-dihydro-4H-pyrrolo[1,2-b]pyrazole-2-carboxylate A mixture of ethyl 3-bromo-5,6-dihydro-4H-pyrrolo[1,2-b]pyrazole-2-carboxylate (131 mg, 0.506 mmol), 2-(4,4-bis(ethoxymethyl)cyclohex-1-en-1-yl)-4,4,5,5-tetramethyl-1,3,2-dioxaborolane (197 mg, 0.607 mmol) and K$_2$CO$_3$ (217 mg, 1.567 mmol) in dioxane (3 mL)/H$_2$O (0.3 mL) was degassed with N$_2$ for 2 min. PdCl$_2$(dppf)-CH$_2$Cl$_2$ adduct (83 mg, 0.101 mmol) was added and the mixture was degassed with N$_2$ for an additional 1 min. The reaction mixture was heated to 100° C. and stirred for 5 hr, allowed to cool to room temperature, filtered through a pad of CELITE(R), and the filtrate was concentrated under reduced pressure. The residue was purified via SiO$_2$ gel chromatography (10 to 50% EtOAc in hexanes) to give the title compound (185 mg, 0.49 mmol, 97% yield) as a pale yellow oil.

$^1$H NMR (300 MHz, CDCl$_3$) δ 5.68-5.58 (m, 1H), 4.36 (q, J=7.1 Hz, 2H), 4.17 (dd, J=7.9, 6.7 Hz, 2H), 3.49 (q, J=7.0 Hz, 4H), 3.42-3.27 (m, 4H), 2.91-2.82 (m, 2H), 2.65-2.53 (m, 2H), 2.33-2.23 (m, 2H), 2.04 (dd, J=4.0, 2.3 Hz, 2H), 1.96 (s, 2H), 1.38 (t, J=7.1 Hz, 3H), 1.18 (t, J=7.0 Hz, 6H). MS (ES$^+$) C$_{21}$H$_{32}$N$_2$O$_4$ requires: 376, found: 377 [M+H]$^+$.

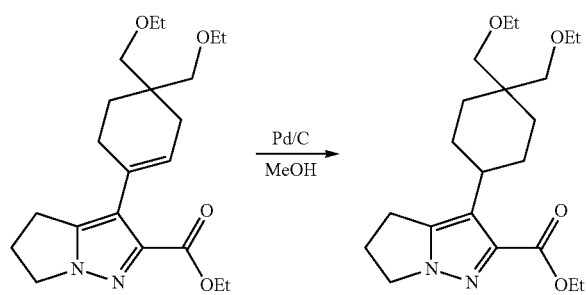 [SMILES: "MeOH" ; CCOCC1(COCC)CC=C(c2c(C(=O)OCC)nn3c2CCC3)CC1 ; "Pd/C" ; CCOCC1(COCC)CCC(c2c(C(=O)OCC)nn3c2CCC3)CC1]

Ethyl 3-(4,4-bis(ethoxymethyl)cyclohexyl)-5,6-dihydro-4H-pyrrolo[1,2-b]pyrazole-2-carboxylate A reaction vessel was charged with the product from the previous step (185 mg, 0.491 mmol), Pd/C (52.3 mg, 0.049 mmol) and MeOH (3.2 mL) under an atmosphere of $N_2$. The suspension was degassed with $N_2$ for 2 min and purged with $H_2$ for 1 min. The reaction mixture was stirred under an atmosphere of $H_2$ at 1 atm for 4 h, then purged with $N_2$, filtered through a pad of Celite and concentrated under reduced pressure. The residue was used without further purification in the next step. MS ($ES^+$) $C_{21}H_{34}N_2O_4$ requires: 378, found: 379 $[M+H]^+$.

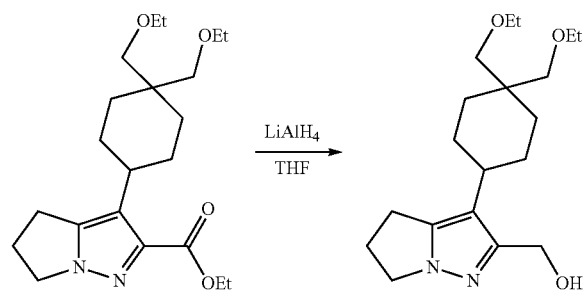 [SMILES: CCOCC1(COCC)CCC(c2c(C(=O)OCC)nn3c2CCC3)CC1 ; "LiAlH4" ; CCOCC1(COCC)CCC(c2c(CO)nn3c2CCC3)CC1 ; "THF"]

(3-(4,4-bis(Ethoxymethyl)cyclohexyl)-5,6-dihydro-4H-pyrrolo[1,2-b]pyrazol-2-yl)methanol To a solution of the product from the previous step (185 mg, 0.489 mmol) in THF (4.8 mL) at 0° C. was added LiAlH$_4$ (1 M in THF, 0.53 mL, 0.538 mmol). The resulting mixture was stirred at 25° C. for 2 h, solid Na$_2$SO$_4$*10H$_2$O was added and the resulting mixture was allowed to stir for a further 2 h. The reaction mixture was filtered through a pad of CELITE(R), and the filtrate was concentrated under reduced pressure. The residue was purified via SiO$_2$ gel chromatography (0 to 5% MeOH in CH$_2$Cl$_2$) to give the title compound (100 mg, 0.297 mmol, 60.8% yield) as a white solid.

$^1$H NMR (600 MHz, CDCl$_3$) δ 4.61 (d, J=5.2 Hz, 2H), 4.05 (t, J=7.3 Hz, 2H), 3.52-3.44 (m, 4H), 3.42 (s, 2H), 3.19 (s, 2H), 2.92-2.84 (m, 2H), 2.59-2.53 (m, 2H), 2.52-2.43 (m, 1H), 1.95 (t, J=5.8 Hz, 1H), 1.75-1.64 (m, 4H), 1.57-1.47 (m, 2H), 1.37-1.27 (m, 2H), 1.22-1.15 (m, 6H). MS (ES$^+$) C$_{19}$H$_{32}$N$_2$O$_3$ requires: 336, found: 337 $[M+H]^+$

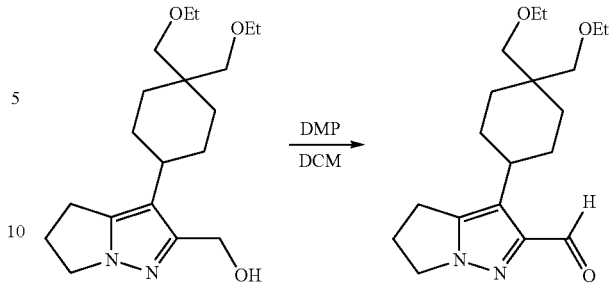

3-(4,4-bis(Ethoxymethyl)cyclohexyl)-5,6-dihydro-4H-pyrrolo[1,2-b]pyrazole-2-carbaldehyde To a solution of the product from the previous step (50 mg, 0.149 mmol) in CH$_2$Cl$_2$ (1.5 mL) was added Dess-Martin periodinane (69.3 mg, 0.163 mmol) and the resulting mixture was stirred at 25° C. for 2 h. The reaction was quenched with saturated aq. Na$_2$S$_2$O$_3$ (1 mL), saturated aq. NaHCO$_3$ (1 mL), and allowed to stir for 30 min. The mixture was then diluted with CH$_2$Cl$_2$ (5 mL) and the layers were separated. The organic layer was washed with brine (10 mL), dried over Na$_2$SO$_4$, filtered and concentrated under reduced pressure. The residue was purified via SiO$_2$ gel chromatography (0 to 5% MeOH) in CH$_2$Cl$_2$ to give the title compound (29 mg, 0.087 mmol, 58.3% yield) as a colorless oil.

$^1$H NMR (600 MHz, CDCl$_3$) δ 9.92 (s, 1H), 4.16 (t, J=7.4 Hz, 2H), 3.55-3.42 (m, 6H), 3.19 (s, 2H), 3.09-3.00 (m, 1H), 2.96 (t, J=7.4 Hz, 2H), 2.71-2.58 (m, 2H), 1.76 1.64 (m, 4H), 1.59-1.48 (m, 2H), 1.40-1.31 (m, 2H), 1.18 (q, J=7.4 Hz, 6H). MS (ES$^+$) C$_{19}$H$_{30}$N$_2$O$_3$ requires: 334, found: 335 $[M+H]^+$.

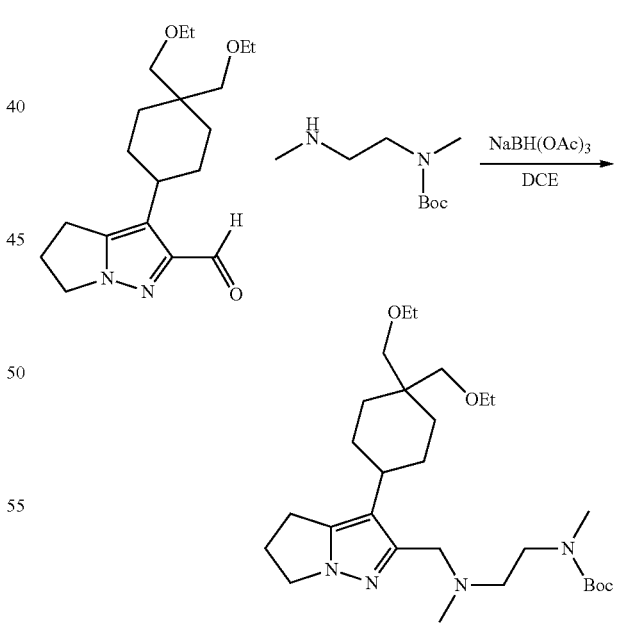

tert-Butyl (2-(((3-(4,4-bis(ethoxymethyl)cyclohexyl)-5,6-dihydro-4H-pyrrolo[1,2-b]pyrazol-2-yl)methyl)(methyl) amino)ethyl)(methyl)carbamate A mixture of the product from the previous step (29 mg, 0.087 mmol) and tert-butyl methyl(2-(methylamino)-ethyl)

carbamate (19.6 mg, 0.104 mmol) in DCE (0.9 mL) was stirred for 30 min at RT. NaBH(CN)$_3$ (23.89 mg, 0.113 mmol) was added, the resulting mixture was stirred at 25° C. for 2 h, then quenched with saturated aq. NaHCO$_3$ (1 mL). The layers were separated, the aqueous phase was extracted with CH$_2$Cl$_2$ (3×5 mL), and the combined organic layers were dried over Na$_2$SO$_4$, filtered and concentrated under reduced pressure. The residue was purified via SiO$_2$ gel chromatography (0 to 10% MeOH in CH$_2$Cl$_2$) to give the title compound (39 mg, 0.077 mmol, 89% yield) as a colorless oil.

$^1$H NMR (600 MHz, CDCl$_3$) δ 4.03 (t, J=7.2 Hz, 2H), 3.52-3.41 (m, 8H), 3.41-3.24 (m, 2H), 3.19 (s, 2H), 2.90-2.81 (m, 5H), 2.60-2.44 (m, 5H), 2.24 (s, 3H), 1.74-1.61 (m, 5H), 1.52-1.39 (m, 11H), 1.32-1.23 (m, 2H), 1.18 (q, J=7.0 Hz, 6H). MS (ES$^+$) C$_{28}$H$_{50}$N$_4$O$_4$ requires: 506, found: 507 [M+H]$^+$.

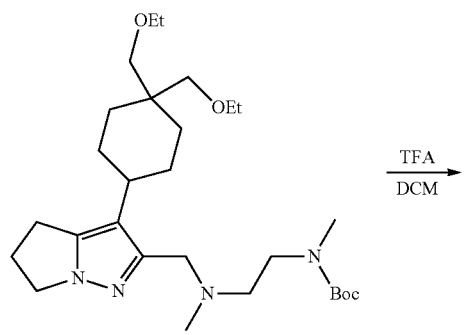

N$^1$-((3-(4,4-bis(ethoxymethyl)cyclohexyl)-5,6-dihydro-4H-pyrrolo[1,2-b]pyrazol-2-yl)methyl)-N$^1$,N$^2$-dimethylethane-1,2-diamine To a solution of the product from the previous step (39 mg, 0.077 mmol) in CH$_2$Cl$_2$ (770 μl) was added TFA (89 μl, 1.154 mmol) and the resulting mixture was stirred at 25° C. for 3 h. The volatiles were removed under reduced pressure to give the title compound (48 mg, 0.076 mmol, 98% yield) as a pale yellow oil.

$^1$H NMR (600 MHz, Methanol-d$_4$) δ 4.36 (s, 2H), 4.08 (t, J=7.3 Hz, 2H), 3.60-3.54 (m, 2H), 3.54-3.43 (m, 8H), 3.20 (s, 2H), 3.00-2.91 (m, 5H), 2.79 (s, 3H), 2.68-2.58 (m, 2H), 2.52-2.43 (m, 1H), 1.76-1.70 (m, 2H), 1.64-1.54 (m, 4H), 1.42-1.33 (m, 2H), 1.17 (dt, J=13.0, 7.0 Hz, 6H). MS (ES$^+$) C$_{23}$H$_{42}$N$_4$O$_2$ requires: 406, found: 407 [M+H]$^+$.

Example 3 a/b

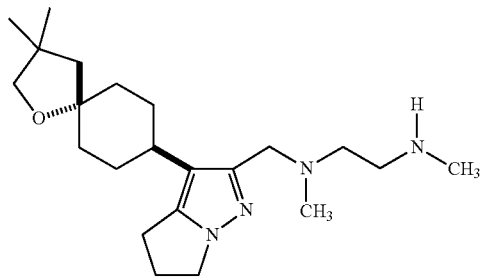

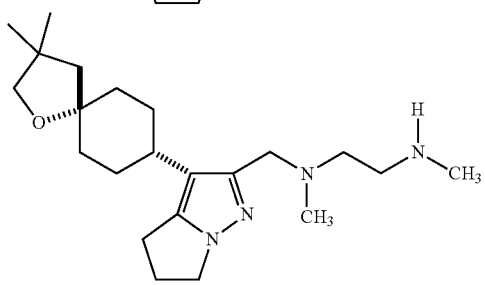

N$^1$-((3-((5r,8r)-3,3-dimethyl-1-oxaspiro[4.5]decan-8-yl)-5,6-dihydro-4H-pyrrolo[1,2-b]-pyrazol-2-yl)methyl)-N$^1$,N$^2$-dimethylethane-1,2-diamine and N$^1$-((3-((5s,8s)-3,3-dimethyl-1-oxaspiro[4.5]decan-8-yl)-5,6-dihydro-4H-pyrrolo[1,2-b]-pyrazol-2-yl)methyl)-N$^1$,N$^2$-dimethylethane-1,2-diamine

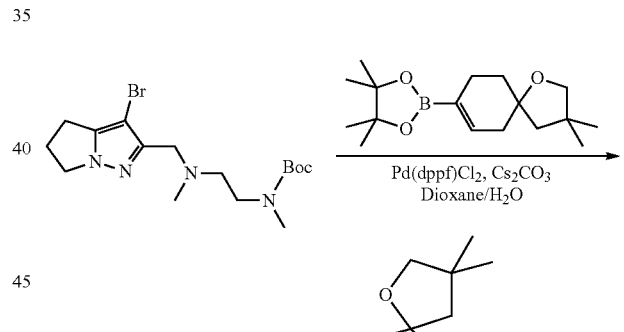

tert-Butyl (2-(((3-(3,3-dimethyl-1-oxaspiro[4.5]dec-7-en-8-yl)-5,6-dihydro-4H-pyrrolo[1,2-b]pyrazol-2-yl)methyl)(methyl)amino)ethyl)(methyl)carbamate A mixture of Intermediate A (150 mg, 387 μmol, 1.0 eq), 2-(3,3-dimethyl-1-oxaspiro[4.5]dec-7-en-8-yl)-4,4,5,5-tetramethyl-1,3,2-dioxaborolane (147.12 mg, 503 μmol, 1.3 eq), Cs$_2$CO$_3$ (378.55 mg, 1.16 mmol, 3.0 eq) and Pd(dppf)

Cl₂ (28.34 mg, 38.73 μmol, 0.1 eq) in dioxane (5 mL) and H₂O (1 mL) was degassed with N₂ for 2 min, and stirred at 90° C. for 16 hr. The mixture was cooled to RT, diluted with EtOAc (40 mL) and filtered through a pad of Celite. The filtrate was concentrated under reduced pressure, and the residue was purified by preparative TLC (EtOAc: MeOH=10:1, Rf=0.4) to give the title compound (100 mg) as a pale yellow oil. The product was used in the next step without further purification. MS (ES⁺) $C_{27}H_{44}N_4O_3$, requires: 472, found: 473 [M+H]⁺.

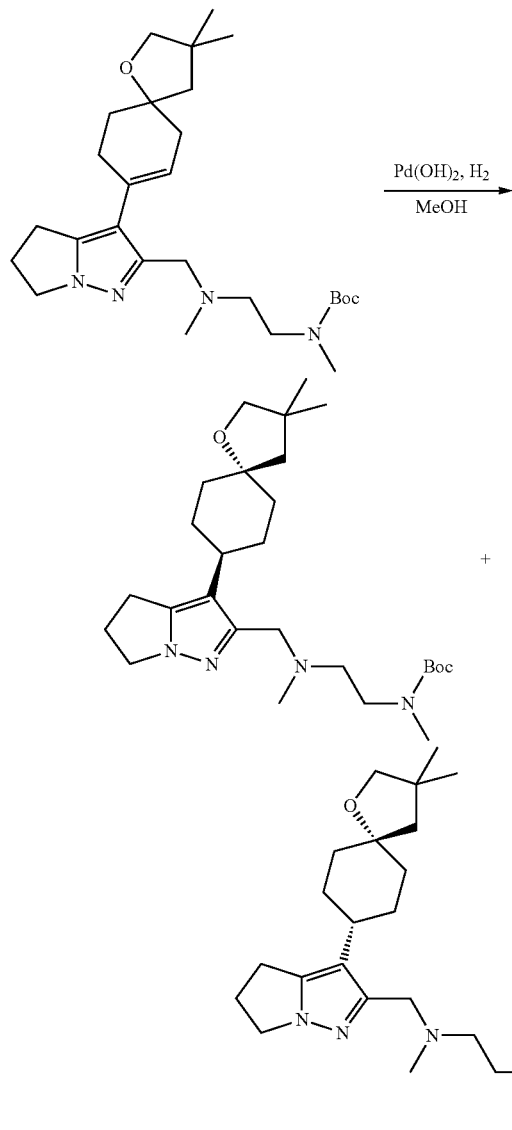

tert-Butyl (2-(((3-((5r,8r)-3,3-dimethyl-1-oxaspiro [4.5]decan-8-yl)-5,6-dihydro-4H-pyrrolo[1,2-b]pyrazol-2-yl)methyl)(methyl)amino)ethyl)(methyl)carbamate and tert-butyl (2-(((3-((5s,8s)-3,3-dimethyl-1-oxaspiro[4.5]decan-8-yl)-5,6-dihydro-4H-pyrrolo-[1,2-b]pyrazol-2-yl)methyl)(methyl)amino)ethyl) (methyl)carbamate (Compounds 3-2 a/b)

A Parr reaction vessel was charged with the product from the previous step (100 mg, 211.6 mol, 1.0 eq), Pd(OH)₂/C (50 mg, 10% w/w) and MeOH (10 mL). The suspension as degassed with N₂, purged with H₂ and stirred under an atmosphere of H₂ (15 psi) at 30° C. for 16 hr in the Parr shaker. The reaction mixture was then purged with N₂, filtered through a pad of Celite and concentrated under reduced pressure. The residue was purified by prep-HPLC (column: Boston Green ODS 150×30 5u; mobile phase: [A: H₂O (0.225% FA)-B: ACN]; B %: 30%-54%, 10 min) to give the title compound as two distinct diastereoisomeric products of undefined stereochemistry.

Compound 3-2a: 40 mg, 75 μmol, 35.6% yield; pale yellow oil; ¹H NMR (400 MHz, MeOD): δ 4.05-3.76 (m, 4H), 3.53-3.43 (m, 4H), 3.10-3.08 (m, 1H), 2.95-2.92 (m, 2H), 2.82-2.69 (m, 6H), 2.62-2.49 (m, 4H), 1.92-1.73 (m, 4H), 1.63-1.51 (m, 6H), 1.45 (s, 9H), 1.10 (s, 6H). MS (ES⁺) $C_{27}H_{46}N_4O_3$ requires: 474, found: 475 [M+H]⁺.

Compound 3-2b: 8 mg, 13.5 μmol, 6.4% yield; pale yellow oil; ¹H NMR (400 MHz, MeOD): δ 4.75-4.06 (m, 4H), 3.53-3.43 (m, 4H), 3.10-3.02 (m, 1H), 2.93-2.89 (m, 2H), 2.87-2.69 (m, 6H), 2.61-2.50 (m, 4H), 1.86-1.83 (m, 4H), 1.73 (s, 2H), 1.62-1.50 (m, 4H), 1.45 (s, 9H), 1.13 (s, 6H). MS (ES⁺) $C_{27}H_{46}N_4O_3$ requires: 474, found: 475 [M+H]⁺.

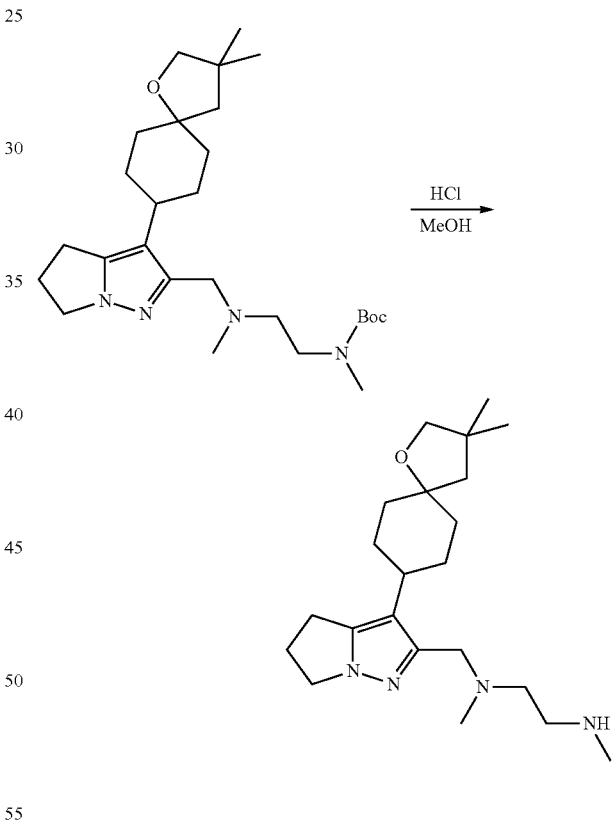

N¹-((3-(3,3-dimethyl-1-oxaspiro[4.5]decan-8-yl)-5, 6-dihydro-4H-pyrrolo[1,2-b]-pyrazol-2-yl)methyl)-N¹,N²-dimethylethane-1,2-diamine (Example 3a)

To a solution of Compound 3-2a (20 mg, 37.64 mol, 1.0 eq) in MeOH (2 mL) at 15° C. was added dropwise HCl (4 M in MeOH, 0.5 mL, 53 eq) and the resulting mixture was stirred at 15° C. for a further 4 hr. The volatiles were removed under reduced pressure, the residue was dissolved in H₂O (2 mL) and lyophilized to afford the title compound as a single stereoisomer of undefined stereochemistry.

Example 3a (15 mg, 32.85 μmol, 87% yield), white solid; $^1$H NMR (400 MHz, MeOD): δ 4.41 (s, 2H), 4.11-4.07 (m, 2H), 3.61-3.51 (m, 6H), 2.99-2.95 (m, 5H), 2.79 (s, 3H), 2.64-2.57 (m, 3H), 1.92-1.89 (m, 2H), 1.90-1.75 (m, 2H), 1.65-1.55 (m, 6H), 1.11 (s, 6H). MS (ES$^+$) $C_{22}H_{38}N_4O$ requires: 374, found: 375 [M+H]$^+$.

Reaction of Compound 3-2b in a similar manner gave Example 3b (6 mg, 12.7 μmol, 94% yield) white solid; $^1$H NMR (400 MHz, MeOD): δ 4.40 (s, 2H), 4.11-4.08 (m, 2H), 3.60-3.51 (m, 6H), 2.97-2.93 (m, 5H), 2.79 (s, 3H), 2.64-2.58 (m, 3H), 1.86-1.84 (m, 4H), 1.74 (s, 2H), 1.66-1.60 (m, 2H), 1.52-1.46 (m, 2H), 1.13 (s, 6H). MS (ES$^+$) $C_{22}H_{38}N_4O$ requires: 374, found: 375 [M+H]$^+$.

Example 4

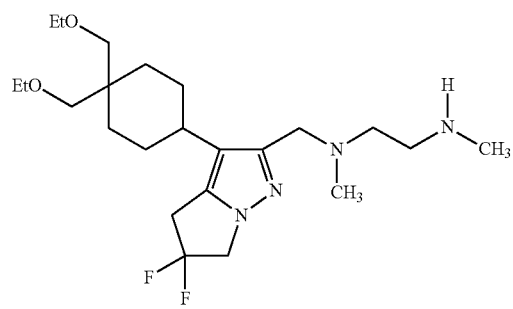 [SMILES: CCOCC1(COCC)CCC(c2c(CN(C)CCNC)nn3c2CC(F)(F)C3)CC1]

$N^1$-((3-(4,4-bis(ethoxymethyl)cyclohexyl)-5,5-difluoro-5,6-dihydro-4H-pyrrolo-[1,2-b]pyrazol-2-yl)methyl)-$N^1$,$N^2$-dimethylethane-1,2-diamine

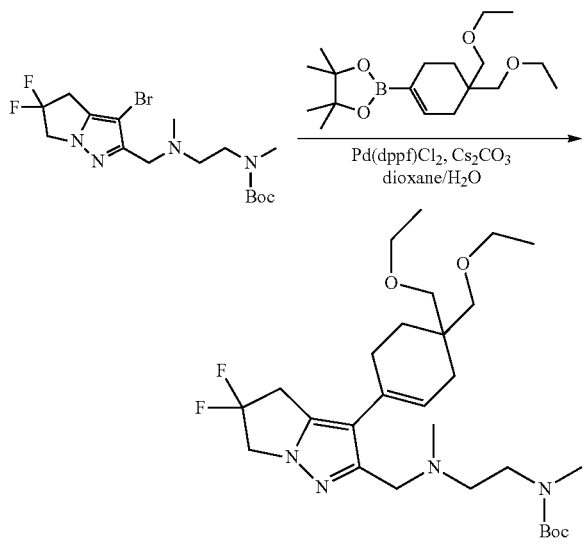

tert-Butyl (2-(((3-(4,4-bis(ethoxymethyl)cyclohex-1-en-1-yl)-5,5-difluoro-5,6-dihydro-4H-pyrrolo[1,2-b]pyrazol-2-yl)methyl)(methyl)amino)ethyl)(methyl)carbamate To a solution of 2-(4,4-bis(ethoxymethyl)cyclohex-1-en-1-yl)-4,4,5,5-tetramethyl-1,3,2-dioxaborolane (0.996 g, 3.07 mmol) in dioxane (21.5 ml) and H$_2$O (2.2 ml) under N$_2$ were added PdCl$_2$(dppf) (0.216 g, 0.295 mmol), K$_2$CO$_3$ (0.882 g, 6.38 mmol) and Intermediate B (1.0 g, 2.362 mmol) and the resulting mixture was stirred at 100° C. for 16 h. The mixture was filtered through a pad of CELITE(R) and the filtrate was concentrated under reduced pressure. The residue was purified via SiO$_2$ gel chromatography (0 to 5% MeOH in CH$_2$Cl$_2$) to give the title compound (1.2 g, 2.2 mmol, 94% yield) as a viscous oil.

$^1$H NMR (600 MHz, Methanol-d$_4$) δ 5.98-5.87 (m, 1H), 4.49 (t, J=12.7 Hz, 2H), 3.56-3.45 (m, 8H), 3.37 (s, 1H), 3.29 (s, 1H), 2.83-2.73 (m, 3H), 2.56-2.48 (m, 2H), 2.31-2.21 (m, 5H), 2.05 (s, 2H), 1.65 (t, J=6.6 Hz, 2H), 1.44-1.42 (m, 4H), 1.20 (s, 9H), 1.19-1.15 (m, 6H). MS (ES$^+$) $C_{28}H_{46}F_2N_4O_4$ requires: 540, found 541 [M+H]$^+$.

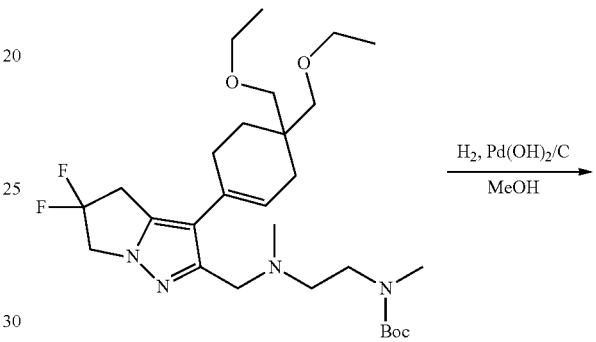

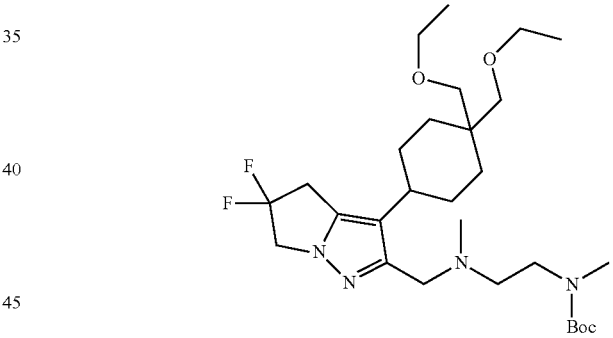

tert-Butyl (2-(((3-(4,4-bis(ethoxymethyl)cyclohexyl)-5,5-difluoro-5,6-dihydro-4H-pyrrolo[1,2-b]pyrazol-2-yl)methyl)(methyl)amino)ethyl)(methyl)carbamate A Parr reaction vessel was charged with the product from the previous step (0.8 g, 1.48 mmol), Pd(OH)$_2$/C (0.208 g, 0.148 mmol) and MeOH (15 ml) under an atmosphere of N$_2$. The suspension was degassed with N$_2$ for 2 min and purged with H$_2$ for 2 min and stirred under an atmosphere of H$_2$ (45 psi) for 22 h in a Parr shaker. The reaction mixture was purged with N$_2$, filtered through a pad of Celite and concentrated under reduced pressure. The residue was purified by preparative HPLC (Column C18; Mobile phase: A=0.1% TFA/H$_2$O, B=0.1% TFA/MeCN; Gradient: B=30-70%; 16 min;) to give the title compound (750 mg, 1.14 mmol, 77% yield) as a colorless liquid. MS (ES$^+$) $C_{28}H_{48}F_2N_4O_4$ requires: 542, found 543 [M+H]$^+$.

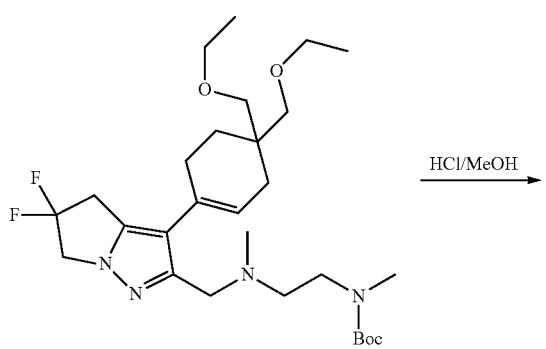

HCl/MeOH →

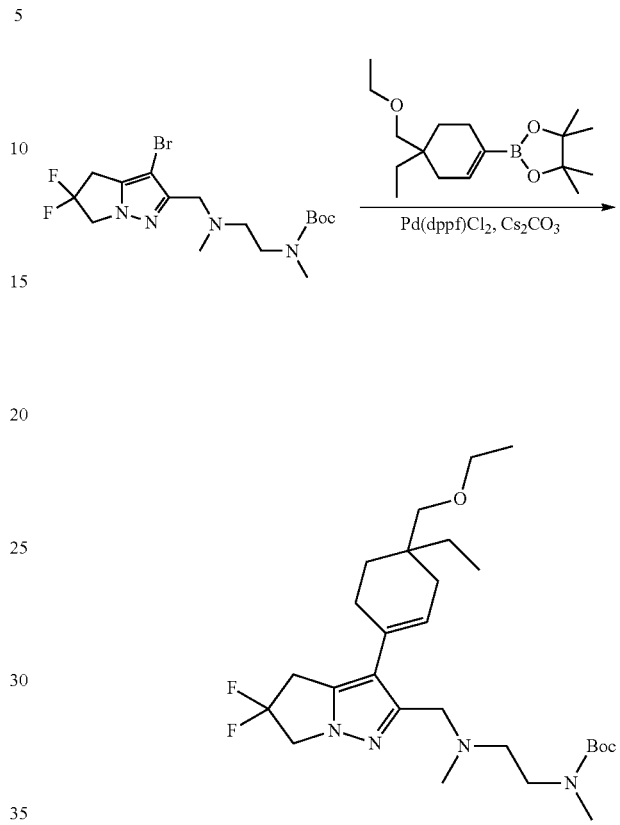

N¹-((3-(4,4-bis(ethoxymethyl)cyclohexyl)-5,5-difluoro-5,6-dihydro-4H-pyrrolo-[1,2-b]pyrazol-2-yl)methyl)-N¹,N²-dimethylethane-1,2-diamine To a solution of the product from the previous step (112 mg, 0.206 mmol) in $CH_2Cl_2$ (2 mL) was added TFA (238 μl, 3.10 mmol) and the resulting mixture was stirred at 25° C. for 3 h. The volatiles were removed under reduced pressure to give the title compound (128 mg, 0.191 mmol, 92% yield) as a colorless oil.

$^1$H NMR (600 MHz, Methanol-$d_4$) δ 4.57 (t, J=12.7 Hz, 2H), 4.45 (s, 2H), 3.70-3.57 (m, 4H), 3.57-3.43 (m, 8H), 3.21 (s, 2H), 2.98 (s, 3H), 2.79 (s, 3H), 2.60-2.52 (m, 1H), 1.77-1.71 (m, 2H), 1.71-1.64 (m, 2H), 1.60-1.50 (m, 2H), 1.45-1.36 (m, 2H), 1.18 (dt, J=14.5, 7.0 Hz, 6H). MS (ES⁺) $C_{23}H_{40}F_2N_4O_2$ requires: 442, found: 443 [M+H]⁺.

Example 5

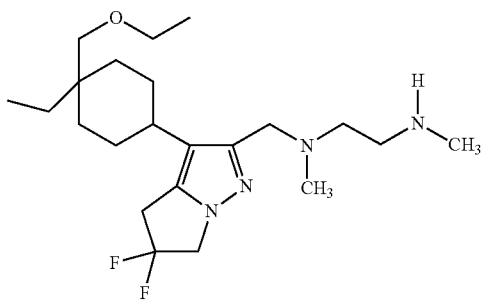 [SMILES: CCOCC1(CC)CCC(c2c(CN(C)CCNC)nn3c2CC(F)(F)C3)CC1]

N¹-((3-(4-(ethoxymethyl)-4-ethylcyclohexyl)-5,5-difluoro-5,6-dihydro-4H-pyrrolo-[1,2-b]pyrazol-2-yl)methyl)-N¹,N²-dimethylethane-1,2-diamine tert-Butyl (2-(((3-(4-(ethoxymethyl)-4-ethylcyclohex-1-en-1-yl)-5,5-difluoro-5,6-dihydro-4H-pyrrolo[1,2-b]pyrazol-2-yl)methyl)(methyl)amino)ethyl)(methyl)carbamate A mixture of Intermediate B (500 mg, 1.18 mmol, 1.0 eq), Intermediate E (382.31 mg, 1.30 mmol, 1.1 eq), $Cs_2CO_3$ (1.15 g, 3.54 mmol, 3.0 eq) and Pd(dppf)Cl₂ (86.43 mg, 118 μmol, 0.1 eq) in dioxane (10 mL) and $H_2O$ (2 mL) was degassed with $N_2$ for 2 min, then stirred at 80° C. for 16 hr. The reaction mixture was diluted with EtOAc (50 mL), dried over $Na_2SO_4$, filtered and concentrated under reduced pressure. The residue was purified by $SiO_2$ gel chromatography (PE:EtOAc=30:1 to 5:1) to give the title compound (350 mg, 637 μmol, 54% yield) as a pale yellow oil.

$^1$H NMR (400 MHz, CDCl₃): δ 5.89-5.88 (bs, 1H), 4.48-4.42 (t, J=12 Hz, 2H), 3.56-3.47 (m, 2H), 3.44-3.40 (m, 2H), 3.35-3.27 (m, 2H), 3.24-3.16 (m, 2H), 2.83 (s, 3H), 2.60-2.52 (m, 2H), 2.27 (s, 3H), 2.21-2.19 (m, 2H), 2.05-1.93 (m, 2H), 1.68-1.59 (s, 4H), 1.43 (s, 9H), 1.25 (s, 2H), 1.20-1.17 (t, J=7.2 Hz, 3H), 0.86-0.83 (t, J=7.6 Hz, 3H). MS (ES⁺) $C_{27}H_{44}F_2N_4O_3$, requires: 510, found: 511 [M+H].

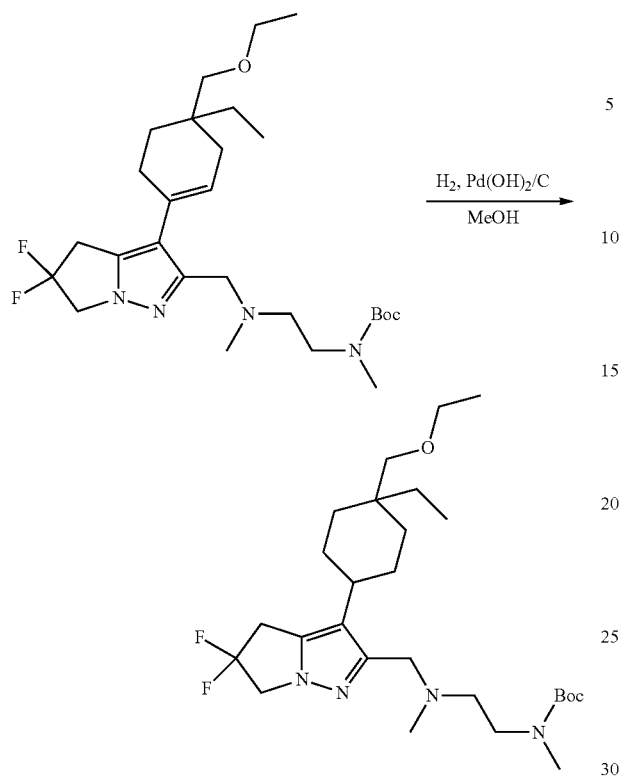
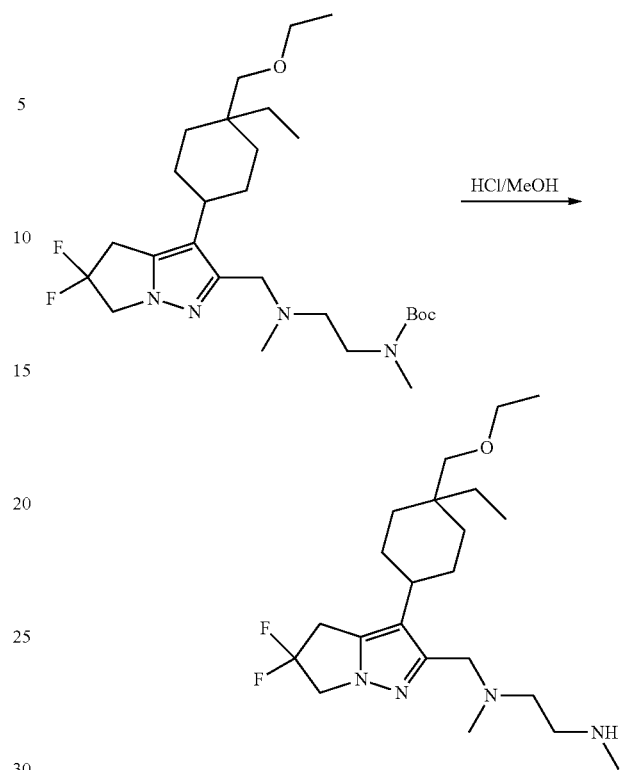

tert-Butyl (2-(((3-(4-(ethoxymethyl)-4-ethylcyclohexyl)-5,5-difluoro-5,6-dihydro-4H-pyrrolo[1,2-b]pyrazol-2-yl)methyl)(methyl)amino)ethyl)(methyl)carbamate A Parr reaction vessel was charged with the product from the previous step (350 mg, 637 μmol, 1.0 eq), Pd(OH)$_2$/C (100 mg, 10% w/w) and MeOH (10 mL). The mixture was degassed with N$_2$ and purged with H$_2$ for three times. The mixture was stirred in the Parr shaker under H$_2$ (15 psi) at 20° C. for 32 hr, then purged with N$_2$, filtered through a pad of CELITE(R) and concentrated under reduced pressure. The residue was purified by prep-HPLC (column: Phenomenex Synergi C18 150×25×10 um; mobile phase: [A: H$_2$O (0.1% TFA)-B: ACN]; B %: 35%-65%, 10 min) to give the title compound (250 mg, 391 μmol, 61% yield) as a colorless oil.

$^1$H NMR (400 MHz, CDCl$_3$): δ 4.58-4.52 (t, J=12 Hz, 2H), 4.42-4.39 (m, 2H), 3.68-3.57 (m, 4H), 3.53-3.44 (m, 4H), 3.41 (s, 1H), 3.13 (s, 1H), 2.96 (s, 3H), 2.90 (s, 3H), 2.51-2.47 (m, 1H), 1.77-1.74 (m, 1H), 1.63-1.53 (m, 6H), 1.47 (s, 9H), 1.40-1.25 (m, 3H), 1.21-1.15 (m, 3H), 0.86-0.82 (m, 3H). MS (ES$^+$) C$_{27}$H$_{46}$F$_2$N$_4$O$_3$ requires: 512, found: 513 [M+H].

N$^1$-((3-(4-(ethoxymethyl)-4-ethylcyclohexyl)-5,5-difluoro-5,6-dihydro-4H-pyrrolo[1,2-b]pyrazol-2-yl)methyl)-N$^1$,N$^2$-dimethylethane-1,2-diamine To a solution of the product from the previous step (250 mg, 399 μmol, 1.0 eq) in EtOAc (5 mL) at 0° C. was added HCl (4 M in EtOAc, 2 mL, 20 eq). The resulting solution was stirred at 20° C. for 2 hr and concentrated under reduced pressure. The residue was dissolved in H$_2$O (2 mL) and lyophilized to afford the title compound (120 mg, 244.7 μmol, 61% yield) as a white solid.

$^1$H NMR (400 MHz, D$_2$O): δ 4.61-4.54 (t, J=12 Hz, 2H), 4.42 (s, 2H), 3.70-3.50 (m, 9H), 3.23 (s, 1H), 2.90 (s, 3H), 2.78 (s, 3H), 2.46-2.43 (m, 1H), 1.66-1.46 (m, 7H), 1.30-1.26 (m, 3H), 1.19-1.17 (m, 3H), 0.81-0.76 (m, 3H). MS (ES$^+$) C$_{22}$H$_{38}$F$_2$N$_4$O requires: 412, found: 413 [M+H].

Example 5 a/b

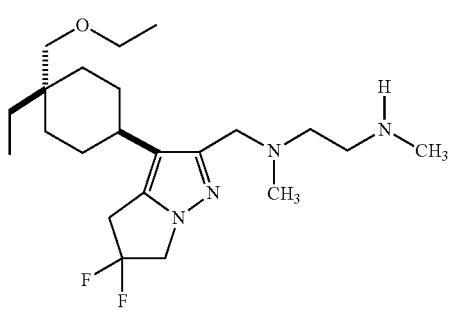

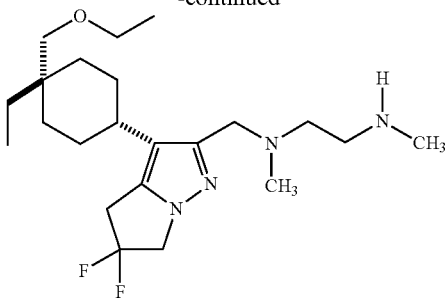

N$^1$-((3-((1r,4r)-4-(ethoxymethyl)-4-ethylcyclo-hexyl)-5,5-difluoro-5,6-dihydro-4H-pyrrolo-[1,2-b]pyrazol-2-yl)methyl)-N$^1$,N$^2$-dimethylethane-1,2-diamine and N$^1$-((3-((1s,4s)-4-(ethoxymethyl)-4-ethylcyclohexyl)-5,5-difluoro-5,6-dihydro-4H-pyrrolo-[1,2-b]pyrazol-2-yl)methyl)-N$^1$,N$^2$-dimethylethane-1,2-diamine The title compounds were obtained using the same procedures described below for Example 7 a/b, using ethyl 3-bromo-5,5-difluoro-5,6-dihydro-4H-pyrrolo[1,2-b]pyrazole-2-carboxylate (Intermediate A, Step 7) as the starting material.

Compound 5a. Colorless oil (60 mg, 0.0937 mmol); $^1$H NMR (400 MHz, CD$_3$OD) δ 4.57-4.50 (m, 2H), 4.21 (s, 2H), 3.62-3.55 (m, 2H), 3.48-3.37 (m, 6H), 3.13 (s, 2H), 2.79-2.76 (m, 6H), 2.50-2.45 (m, 1H), 1.63-1.52 (m, 8H), 1.42-1.35 (m, 2H), 1.18-1.15 (m, 3H), 0.85-0.82 (m, 3H); MS (ES$^+$) C$_{22}$H$_{38}$F$_2$N$_4$O, requires: 412, found: 413 [M+H]$^+$.

Compound 5b. Colorless oil (110 mg, 0.172 mmol); $^1$H NMR (400 MHz, CD$_3$OD) δ 4.57-4.50 (m, 2H), 4.14 (s, 2H), 3.62-3.55 (m, 2H), 3.53-3.48 (m, 2H), 3.41-3.37 (m, 4H), 2.75-2.74 (m, 6H), 2.51-2.45 (m, 1H), 1.77-1.73 (m, 2H), 1.64-1.52 (m, 4H), 1.37-1.24 (m, 4H), 1.20-1.17 (m, 3H), 0.86-0.82 (m, 3H); MS (ES$^+$) C$_{22}$H$_{38}$F$_2$N$_4$O, requires: 412, found: 413 [M+H]$^+$.

Example 6 a/b

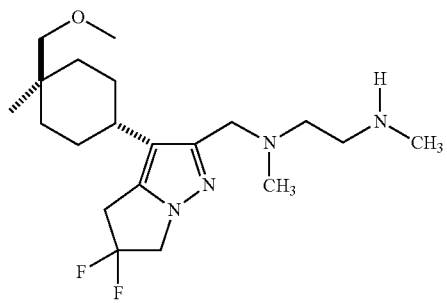

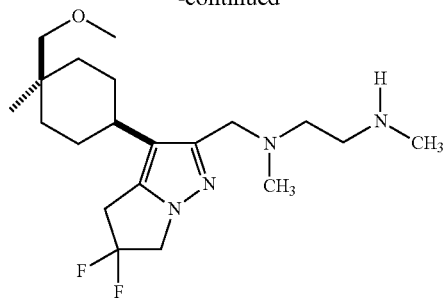

N$^1$-((5,5-difluoro-3-((1r,4r)-4-(methoxymethyl)-4-methylcyclohexyl)-5,6-dihydro-4H-pyrrolo[1,2-b]pyrazol-2-yl)methyl)-N$^1$,N$^2$-dimethylethane-1,2-diamine and N$^1$-((5,5-difluoro-3-((1s,4s)-4-(methoxymethyl)-4-methylcyclohexyl)-5,6-dihydro-4H-pyrrolo[1,2-b]pyrazol-2-yl)methyl)-N$^1$,N$^2$-dimethylethane-1,2-diamine)

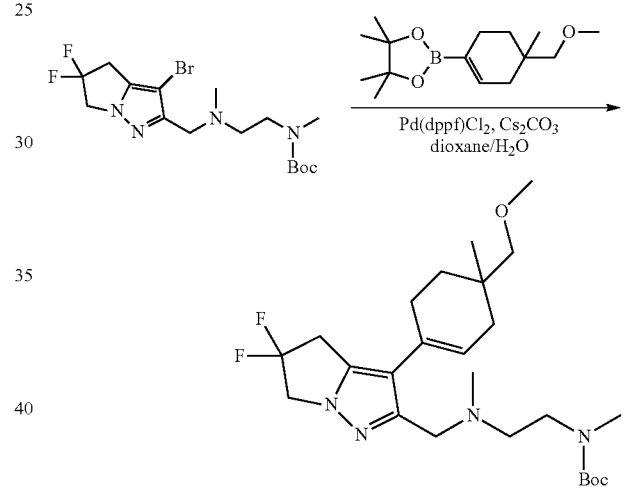

tert-Butyl (2-(((5,5-difluoro-3-(4-(methoxymethyl)-4-methylcyclohex-1-en-1-yl)-5,6-dihydro-4H-pyrrolo[1,2-b]pyrazol-2-yl)methyl)(methyl)amino)ethyl)(methyl)carbamate A mixture of Intermediate B (500 mg, 1.18 mmol, 1.0 eq), Intermediate F (346 mg, 1.30 mmol, 1.1 eq), Cs$_2$CO$_3$ (1.15 g, 3.54 mmol, 3.0 eq) and Pd(dppf)Cl$_2$ (86.43 mg, 118 μmol, 0.1 eq) in dioxane (10 mL) and H$_2$O (2 mL) was degassed with N$_2$ and stirred at 85° C. for 16 hr. The mixture was diluted with EtOAc (60 mL), filtered through a pad of CELITE(R) and concentrated under reduced pressure. The residue was purified by SiO$_2$ gel chromatography (PE:EtOAc=20:1 to 5:1) to give the title compound (500 mg, 1.0 mmol, 86% yield) as a pale yellow oil.

$^1$H NMR (400 MHz, CDCl$_3$): δ 5.93-5.85 (m, 1H), 4.51-4.41 (m, 2H), 3.52-3.43 (m, 4H), 3.35 (s, 3H), 3.32-3.29 (m, 2H), 3.14-3.11 (m, 2H), 2.82 (s, 3H), 2.59-2.52 (m, 2H), 2.30 (s, 3H), 2.24-2.20 (m, 2H), 2.16-2.09 (m, 1H), 1.92-1.85 (m, 1H), 1.69-1.62 (m, 2H), 1.43 (s, 9H), 0.97 (s, 3H). MS (ES$^+$) C$_{25}$H$_{40}$F$_2$N$_4$O$_3$, requires: 482, found: 483 [M+H]$^+$.

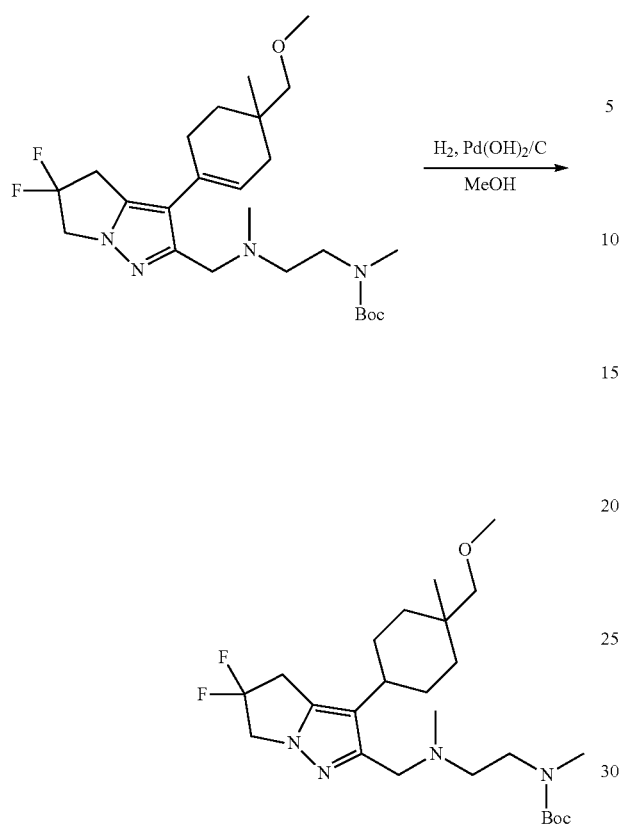

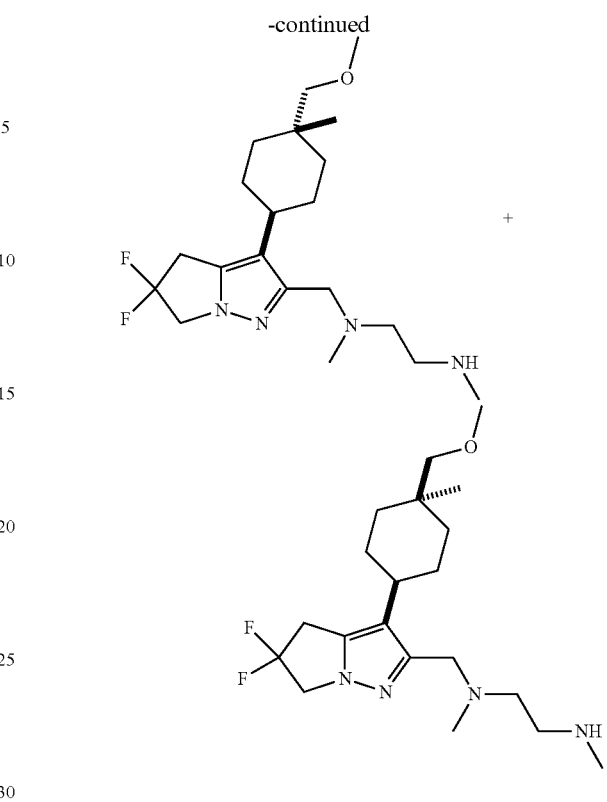

tert-Butyl (2-(((5,5-difluoro-3-(4-(methoxymethyl)-4-methylcyclohexyl)-5,6-dihydro-4H-pyrrolo[1,2-b]pyrazol-2-yl)methyl)(methyl)amino)ethyl)(methyl)carbamate A Parr vessel was charged with the product from the previous step (500.20 mg, 1.02 mmol, 1.0 eq), Pd(OH)$_2$/C (100 mg, 10% w/w) and MeOH (10 mL). The mixture was degassed with N$_2$ and purged with H$_2$ for three times, and stirred in the Parr shaker under H$_2$ (15 psi) at 25° C. for 16 hr. The reaction was then purged with N$_2$, filtered through a pad of Celite and concentrated under reduced pressure to give the title compound as a mixture of stereoisomers (480 mg, 990.5 μmol, 97% yield) as a pale yellow oil. MS (ES$^+$) C$_{25}$H$_{42}$F$_2$N$_4$O$_3$, requires: 484, found: 485 [M+H]$^+$.

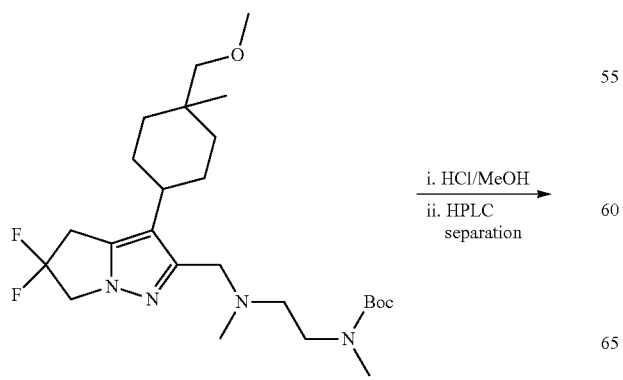

i. HCl/MeOH
ii. HPLC separation

N$^1$-((5,5-difluoro-3-((1r,4r)-4-(methoxymethyl)-4-methylcyclohexyl)-5,6-dihydro-4H-pyrrolo[1,2-b]pyrazol-2-yl)methyl)-N$^1$,N$^2$-dimethylethane-1,2-diamine and N$^1$-((5,5-difluoro-3-((1s,4s)-4-(methoxymethyl)-4-methylcyclohexyl)-5,6-dihydro-4H-pyrrolo[1,2-b]pyrazol-2-yl)methyl)-N$^1$,N$^2$-dimethylethane-1,2-diamine (Example 6a/b)

To a solution of the product from the previous step (480 mg, 990.5 μmol, 1.0 eq) in EtOAc (10 mL) at 0° C. was added dropwise HCl (4 M in EtOAc, 3 mL, 12.12 eq). The resulting solution was stirred at 25° C. for 2 hr and concentrated under reduced pressure. The residue was purified by prep-HPLC (column: Phenomenex Synergi C18 150×25×10 um; mobile phase: [A: H$_2$O (0.05% HCl)-B: ACN]; B %: 8%-28%, 7.8 min) to give the title compound as two distinct diastereoisomeric products of undefined stereochemistry.

Example 6a 79.3 mg, 173 μmol, 17% yield; $^1$H NMR (400 MHz, MeOD): δ 4.61-4.54 (m, 2H), 4.46 (s, 2H), 3.65-3.53 (m, 6H), 3.36 (s, 3H), 3.34 (s, 2H), 2.98 (s, 3H), 2.79 (s, 3H), 2.57-2.53 (m, 1H), 1.76-1.72 (m, 2H), 1.66-1.60 (m, 2H), 1.56-1.52 (m, 2H), 1.35-1.28 (m, 2H), 0.94 (s, 3H). MS (ES$^+$) C$_{20}$H$_{34}$F$_2$N$_4$O, requires: 384, found: 385 [M+H]$^+$.

Example 6b 52.2 mg, 114.12 μmol, 11.52% yield; $^1$H NMR (400 MHz, MeOD): δ 4.61-4.55 (m, 2H), 4.46 (s, 2H), 3.66-3.55 (m, 6H), 3.32 (s, 3H), 3.08 (s, 2H), 2.99 (s, 3H), 2.79 (s, 3H), 2.55-2.49 (m, 1H), 1.71-1.45 (m, 8H), 1.01 (s, 3H). MS (ES$^+$) C$_{20}$H$_{34}$F$_2$N$_4$O, requires: 384, found: 385 [M+H]$^+$.

Example 7 a/b

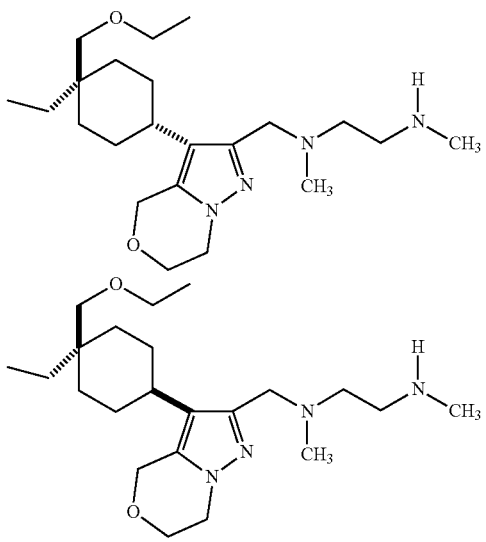

N[1]-((3-((1r,4r)-4-(ethoxymethyl)-4-ethylcyclohexyl)-6,7-dihydro-4H-pyrazolo[5,1-c][1,4]oxazin-2-yl)methyl)-N[1],N[2]-dimethylethane-1,2-diamine and N[1]-((3-((1s,4s)-4-(ethoxymethyl)-4-ethylcyclohexyl)-6,7-dihydro-4H-pyrazolo[5,1-c][1,4]oxazin-2-yl)methyl)-N[1],N[2]-dimethylethane-1,2-diamine

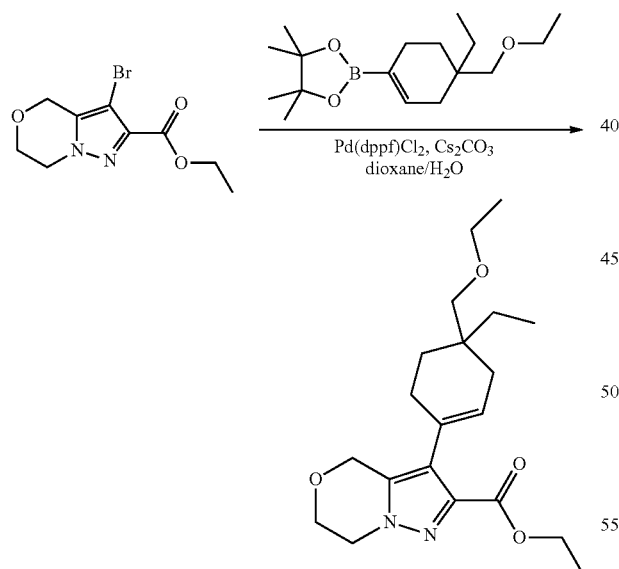

Ethyl-3-(4-(ethoxymethyl)-4-ethylcyclohex-1-en-1-yl)-6,7-dihydro-4H-pyrazolo[5,1-c][1,4]oxazine-2-carboxylate A mixture of Intermediate C (600 mg, 2.18 mmol, 1.0 eq), Intermediate E (770 mg, 2.62 mmol, 1.2 eq), Pd(dppf)Cl$_2$ (159.59 mg, 218.00 μmol, 0.1 eq) and Cs$_2$CO$_3$ (2.13 g, 6.54 mmol, 3 eq) in dioxane (10 mL) and H$_2$O (2 mL) was degassed with N$_2$ and stirred at 90° C. for 14 hr. The mixture was diluted with H$_2$O (10 mL) and extracted with EtOAc (12 mL×3). The combined organic layers were washed with brine (15 mL), dried over Na$_2$SO$_4$, filtered and concentrated under reduced pressure. The residue was purified by SiO$_2$ gel chromatography (PE/EtOAc=10/1 to 1:1) to afford the title compound (710 mg, 1.80 mmol, 83% yield) as a light yellow solid. MS (ES$^+$) C$_{20}$H$_{30}$N$_2$O$_4$, requires: 362, found: 363 [M+H]$^+$.

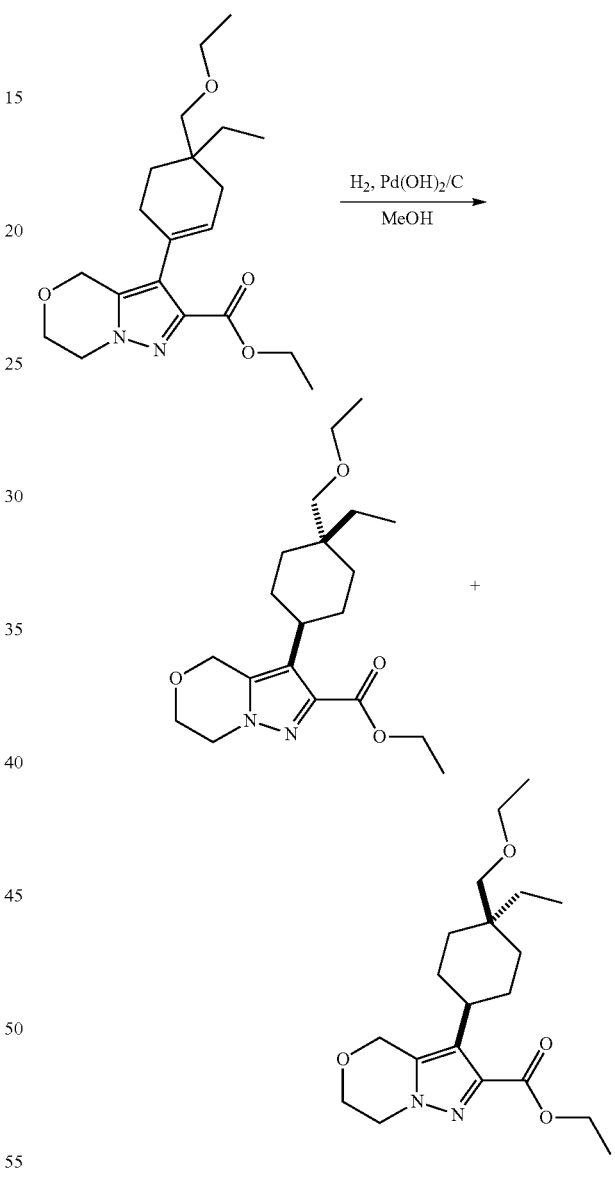

Ethyl 3-((1r,4r)-4-(ethoxymethyl)-4-ethylcyclohexyl)-6,7-dihydro-4H-pyrazolo-[5,1-c][1,4]oxazine-2-carboxylate and ethyl 3-((1s,4s)-4-(ethoxymethyl)-4-ethylcyclohexyl)-6,7-dihydro-4H-pyrazolo[5,1-c][1,4]oxazine-2-carboxylate
(Compound 7-2 a/b)

A Parr reaction vessel was charged with the product from the previous step (710 mg, 1.96 mmol, 1.0 eq), Pd(OH)$_2$/C (200 mg, 10% w/w, 1.00 eq) and MeOH (15 mL). The suspension was degassed with $N_2$ and purged with $H_2$ several times. The mixture was stirred in a Parr shaker under $H_2$ (50 psi) at 30° C. for 24 hr. The reaction was then purged with $N_2$, filtered through a pad of Celite and concentrated under reduced pressure. The residue was purified by prep-HPLC (column: Boston pH-lex 150×25 10 um; mobile phase: [A: $H_2O$ (0.1% TFA)-B: ACN]; B %: 58%-88%, 10 min) to give two distinct stereoisomer products of undefined stereochemistry, as light yellow solids.

Compound 7-2a: 310 mg, 842 mol, 43% yield; $^1$H NMR (400 MHz, $CDCl_3$) δ 4.90 (s, 2H), 4.37 (q, J=7.2 Hz, 2H), 4.26 (t, J=4.8 Hz, 2H), 4.08 (t, J=5.2 Hz, 2H), 3.45 (q, J=7.2 Hz, 2H), 3.18-3.11 (m, 1H), 3.09 (s, 2H), 1.63-1.55 (m, 4H), 1.52-1.45 (m, 4H), 1.38 (t, J=7.2 Hz, 3H), 1.35-1.12 (m, 2H), 1.17 (t, J=7.2 Hz, 3H), 0.80 (t, J=7.2 Hz, 3H). MS (ES$^+$) $C_{20}H_{32}N_2O_4$, requires 364: found: 365 [M+H]$^+$.

Compound 7-2b: 320 mg, 869 mol, 44% yield; $^1$H NMR (400 MHz, $CDCl_3$) δ 4.90 (s, 2H), 4.36 (q, J=7.2 Hz, 2H), 4.27 (t, J=4.8 Hz, 2H), 4.08 (t, J=5.2 Hz, 2H), 3.50 (q, J=7.2 Hz, 2H), 3.37 (s, 2H), 3.16-3.08 (m, 1H), 1.70-1.48 (m, 6H), 1.38 (t, J=7.2 Hz, 3H), 1.34-1.24 (m, 4H), 1.20 (t, J=7.2 Hz, 3H), 0.80 (t, J=7.2 Hz, 3H). MS (ES$^+$) $C_{20}H_{32}N_2O_4$, requires 364: found: 365 [M+H]$^+$.

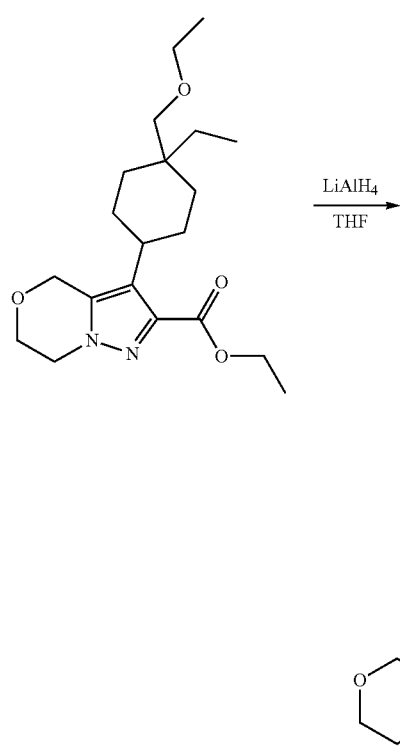

(3-(4-(Ethoxymethyl)-4-ethylcyclohexyl)-6,7-di-hydro-4H-pyrazolo[5,1-c][1,4]-oxazin-2-yl)methanol (Compound 7-3a)

To a solution of Compound 7-2a (300 mg, 823.1 μmol, 1.0 eq) in THF (5 mL) at 0° C. was added $LiAlH_4$ (62.48 mg, 1.65 mmol, 2.0 eq). After addition, the mixture was stirred at 20° C. for 12 hr, then cooled to 0° C. and quenched by addition of $H_2O$ (1 mL), followed by 15% aq. NaOH (1 mL) and $H_2O$ (3 mL). The mixture was filtered through a pad of Celite and extracted with EtOAc (10 mL). The organic layer was dried ($Na_2SO_4$), filtered and concentrated under reduced pressure to give the title compound (260 mg) as colorless oil, which was used without further purification in the next step. MS (ES$^+$) $C_{18}H_{30}N_2O_3$, requires: 322, found: 323 [M+H]$^+$.

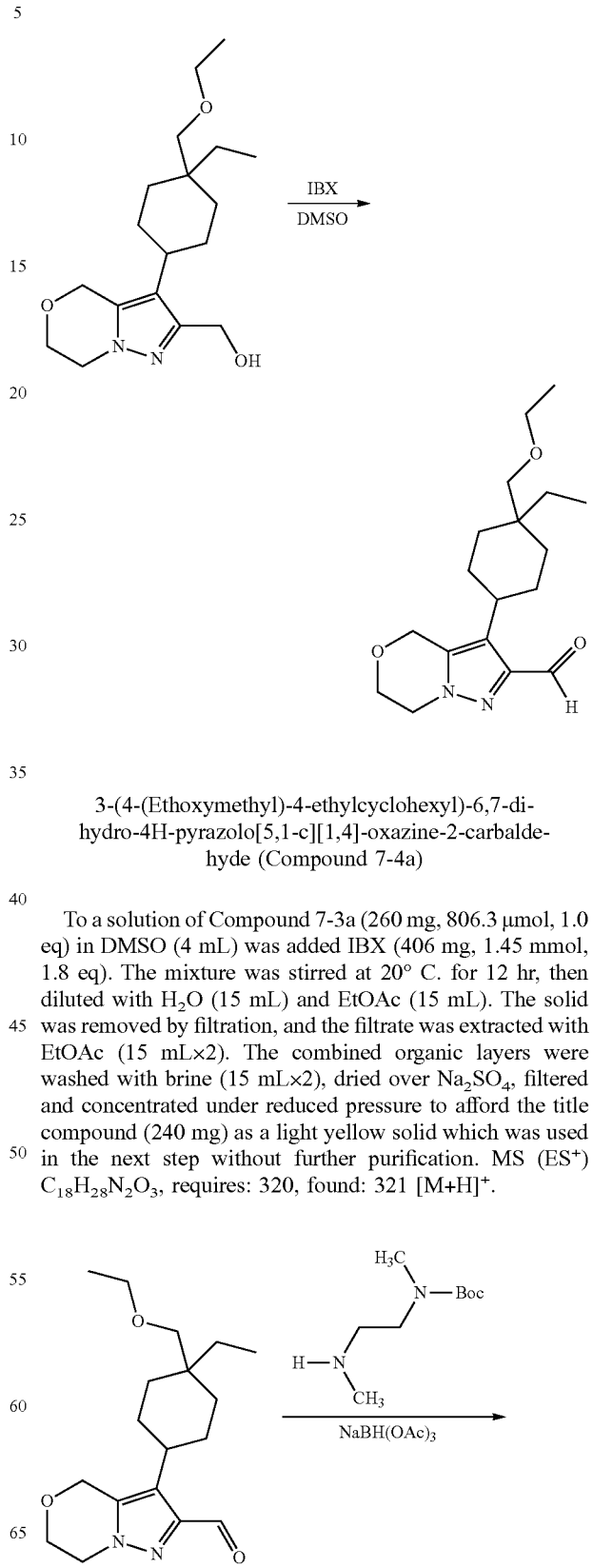

3-(4-(Ethoxymethyl)-4-ethylcyclohexyl)-6,7-di-hydro-4H-pyrazolo[5,1-c][1,4]-oxazine-2-carbalde-hyde (Compound 7-4a)

To a solution of Compound 7-3a (260 mg, 806.3 μmol, 1.0 eq) in DMSO (4 mL) was added IBX (406 mg, 1.45 mmol, 1.8 eq). The mixture was stirred at 20° C. for 12 hr, then diluted with $H_2O$ (15 mL) and EtOAc (15 mL). The solid was removed by filtration, and the filtrate was extracted with EtOAc (15 mL×2). The combined organic layers were washed with brine (15 mL×2), dried over $Na_2SO_4$, filtered and concentrated under reduced pressure to afford the title compound (240 mg) as a light yellow solid which was used in the next step without further purification. MS (ES$^+$) $C_{18}H_{28}N_2O_3$, requires: 320, found: 321 [M+H]$^+$.

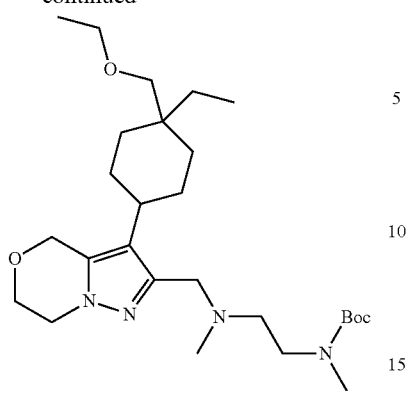

tert-Butyl (2-(((3-(4-(ethoxymethyl)-4-ethylcyclohexyl)-6,7-dihydro-4H-pyrazolo-[5,1-c][1,4]oxazin-2-yl)methyl)(methyl)amino)ethyl)(methyl)carbamate (Compound 7-5a)

To a solution of Compound 7-4a (240 mg, 749 μmol, 1.0 eq) and tert-butyl N-methyl-N-[2-(methylamino)ethyl]carbamate (197.42 mg, 1.05 mmol, 1.4 eq) in DCE (4 mL) was added $CH_3COOH$ (45 mg, 749 μmol, 43 μL, 1.0 eq), and the mixture was stirred at 20° C. for 30 min. then cooled to 0° C. $NaBH(OAc)_3$ (317 mg, 1.50 mmol, 2.0 eq) was added, the mixture was stirred at RT for 12 hr, then carefully diluted with saturated aq. $NaHCO_3$ (6 mL) and extracted with DCE (15 mL×3). The combined organic layers were washed with brine (10 mL), dried over $Na_2SO_4$, filtered and concentrated under reduced pressure. The residue was purified by $SiO_2$ gel chromatography (PE/EtOAc=10/1 to 0:1) to afford the title compound (230 mg, 420 μmol, 56% yield) as a light yellow solid. MS (ES$^+$) $C_{27}H_{48}N_4O_4$, requires 492: found: 493 [M+H]$^+$.

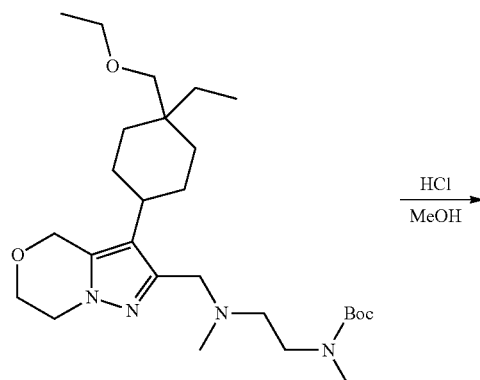

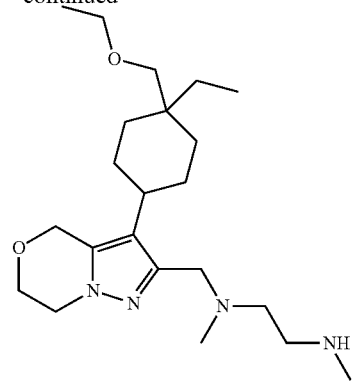

$N^1$-((3-(4-(ethoxymethyl)-4-ethylcyclohexyl)-6,7-dihydro-4H-pyrazolo[5,1-c][1,4]-oxazin-2-yl)methyl)-$N^1$,$N^2$-dimethylethane-1,2-diamine (Example 7a/b)

To a solution of Compound 7-5a (230 mg, 467 mol, 1.0 eq) in MeOH (2 mL) at 0° C. was added HCl (4 M in MeOH, 2 mL, 17.14 eq). The mixture was stirred at 20° C. for 2 hr and concentrated under reduced pressure. The residue was purified by Prep-HPLC (column: Phenomenex Synergi C18 150×25×10 um; mobile phase: [A: $H_2O$ (0.05% HCl)-B: ACN]; B %: 15%-35%, 7.8 min) to afford the title compound (95 mg, 204 μmol, 44% yield) as a white solid.

Example 7a $^1$H NMR (400 MHz, $CD_3OD$) δ 4.90 (s, 2H), 4.44 (s, 2H), 4.17 (t, J=5.2 Hz, 1H), 4.08 (t, J=5.2 Hz, 1H), 3.64 (br, 1H), 3.56(t, J=6.0 Hz, 1H), 3.44 (q, J=7.2 Hz, 2H), 3.11 (s, 2H), 2.97 (s, 3H), 2.79 (s, 3H), 2.55~2.49 (m, 1H), 1.61~1.45 (m, 8H), 1.41~1.35 (m, 2H), 1.15 (t, J=7.2 Hz 3H), 0.83 (t, J=7.2 Hz, 3H). MS (ES$^+$) $C_{22}H_{40}N_4O_2$, requires: found: 393 [M+H]$^+$.

In a similar manner, Example 7b was obtained from Compound 7-2b using the same procedures described to obtain Example 7a from Compound 7-2a.

Example 7b 98 mg, 210 mol, 43% yield; $^1$H NMR (400 MHz, $CD_3OD$) δ 4.91 (s, 2H), 4.44 (s, 2H), 4.17 (t, J=5.2 Hz, 1H), 4.08 (t, J=5.2 Hz, 1H), 3.65 (br, 1H), 3.56 (t, J=6.0 Hz, 1H), 3.50 (q, J=7.2 Hz, 2H), 3.40 (s, 2H), 2.97 (s, 3H), 2.79 (s, 3H), 2.58~2.49 (m, 1H), 1.72 (d, J=13.6 Hz, 2H), 1.61~1.49 (m, 4H), 1.35~1.22 (m, 4H), 1.18 (t, J=7.2 Hz 3H), 0.83 (t, J=7.2 Hz, 3H). MS (ES$^+$) $C_{22}H_{40}N_4O_2$, requires: found: 393 [M+H]$^+$.

Example 8 a/b

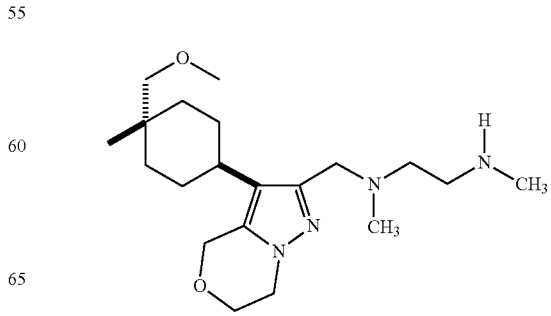

-continued

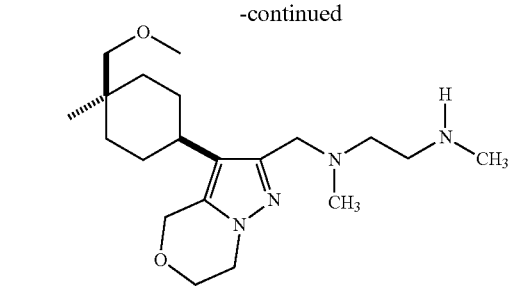

N¹-((3-((1r,4r)-4-(methoxymethyl)-4-methylcyclohexyl)-6,7-dihydro-4H-pyrazolo[5,1-c]-[1,4]oxazin-2-yl)methyl)-N¹,N²-dimethylethane-1,2-diamine and N¹-((3-((1s,4s)-4-(methoxymethyl)-4-methylcyclohexyl)-6,7-dihydro-4H-pyrazolo[5,1-c]-[1,4]oxazin-2-yl)methyl)-N¹,N²-dimethylethane-1,2-diamine

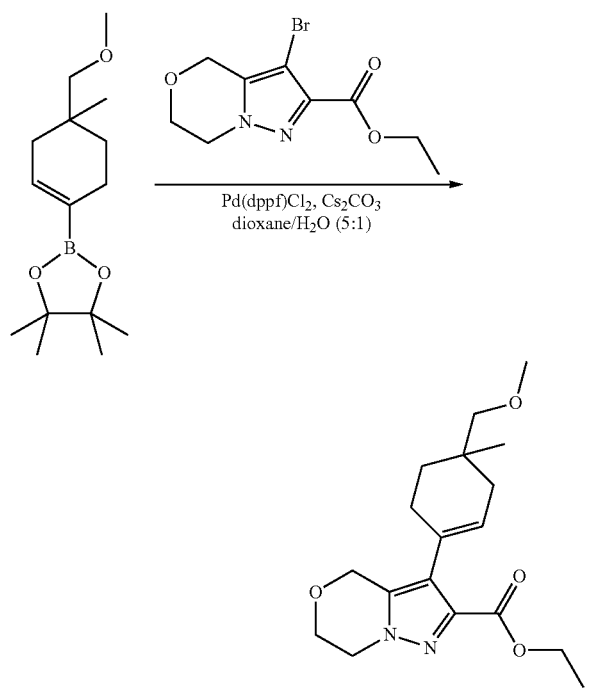

Ethyl 3-(4-(methoxymethyl)-4-methylcyclohex-1-en-1-yl)-6,7-dihydro-4H-pyrazolo[5,1-c][1,4]oxazine-2-carboxylate A mixture of Intermediate C (400 mg, 1.45 mmol, 1.0 eq), Intermediate F (464 mg, 1.74 mmol, 1.2 eq), Pd(dppf)Cl₂ (106 mg, 145.4 μmol, 0.1 eq) and Cs₂CO₃ (1.42 g, 4.36 mmol, 3.0 eq) in dioxane (6 mL) and H₂O (1.2 mL) was degassed with N₂ and heated to 90° C. for 14 hr. The mixture was diluted with H₂O (6 mL) and extracted with EtOAc (6 mL×3). The combined organic layers were washed with brine (15 mL), dried over Na₂SO₄, filtered and concentrated under reduced pressure. The residue was purified by SiO₂ gel chromatography (PE/EtOAc=10/1 to 1:1) to afford the title compound (450 mg, 1.29 mmol, 89% yield) as a light yellow oil. MS (ES⁺) C₁₈H₂₆N₂O₄, requires: 334, found: 335 [M+H]⁺.

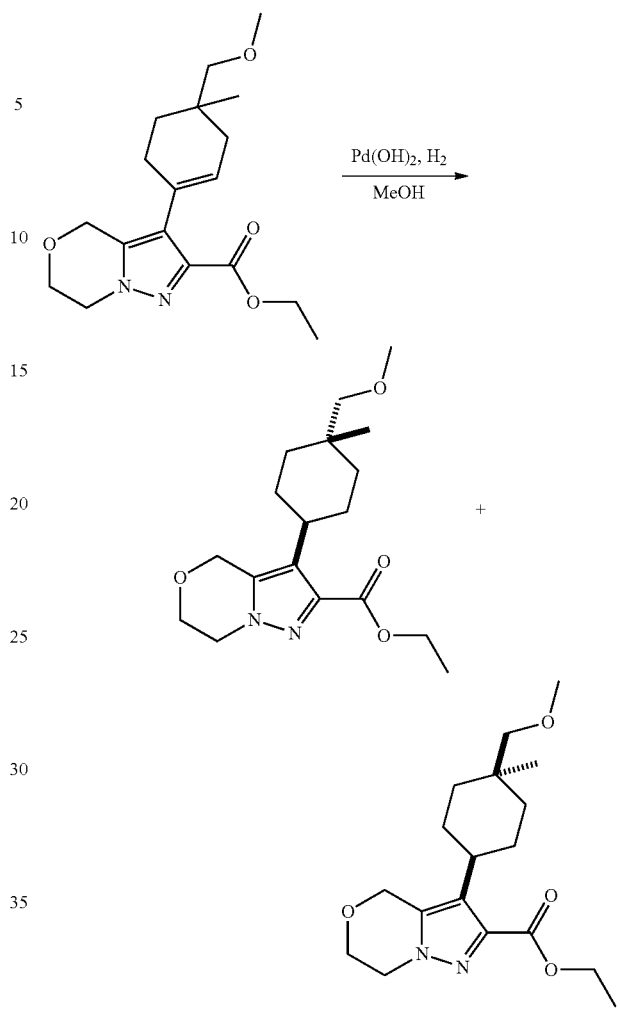

Ethyl 3-((1r,4r)-4-(methoxymethyl)-4-methylcyclohexyl)-6,7-dihydro-4H-pyrazolo[5,1-c][1,4]oxazine-2-carboxylate and ethyl 3-((1s,4s)-4-(methoxymethyl)-4-methylcyclohexyl)-6,7-dihydro-4H-pyrazolo[5,1-c][1,4]oxazine-2-carboxylate (Compound 8-2 a/b)

A Parr reaction vessel was charged with the product from the previous step (450 mg, 1.35 mmol, 1.0 eq) Pd(OH)₂/C (200 mg, 10% w/w) and MeOH (12 mL). The suspension was degassed with N₂ and purged with H₂ several times. The mixture was stirred in a Parr shaker under H₂ (50 psi) at 30° C. for 24 hr. The reaction was then purged with N₂, filtered through a pad of Celite and concentrated under reduced pressure. The residue was purified by Prep-HPLC (column: Boston pH-lex 150×25 10 um; mobile phase: [A: H₂O (0.1% TFA)-B: ACN]; B %: 47%-77%, 10 min). to give the title compound as two distinct stereoisomer products of undefined stereochemistry.

Compound 8-2a: 155 mg, 414 mol, 31% yield; ¹H NMR (400 MHz, CD₃OD) δ 4.91 (s, 2H), 4.32 (q, J=7.2 Hz, 2H), 4.15 (d, J=5.2 Hz, 2H), 4.10 (d, J=5.2 Hz, 2H), 3.32 (s, 3H), 3.06 (s, 2H), 3.06~3.02 (m, 1H), 1.66~1.60 (m, 4H), 1.46~1.30 (m, 7H), 1.06 (s, 3H). MS (ES⁺) C₁₈H₂₈N₂O₄, requires: found: 337 [M+H]⁺.

Compound 8-2b: 152 mg, 379 mol, 28% yield; $^1$H NMR (400 MHz, CD$_3$OD) δ 4.91 (s, 2H), 4.33 (q, J=7.2 Hz, 2H), 4.15 (d, J=5.2 Hz, 2H), 4.10 (d, J=5.2 Hz, 2H), 3.36 (s, 5H), 3.06~3.02 (m, 1H), 1.73~1.64 (m, 6H), 1.36 (t, J=7.2 Hz, 3H), 1.22 (t, J=4.0 Hz, 2H), 0.91 (s. 3H). MS (ES$^+$) C$_{20}$H$_{32}$N$_2$O$_4$, requires: found: 363 [M+H]$^+$.

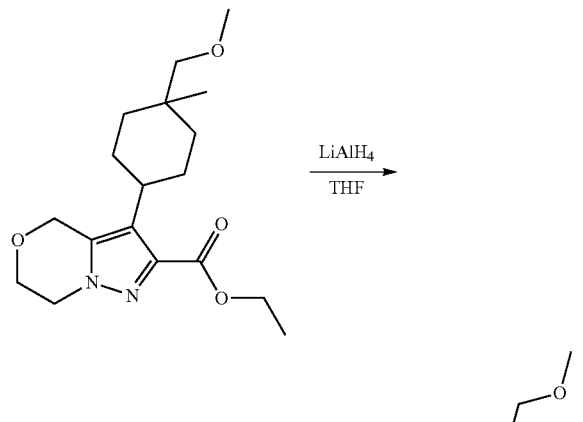

(3-(4-(Methoxymethyl)-4-methylcyclohexyl)-6,7-dihydro-4H-pyrazolo[5,1-c]-[1,4]oxazin-2-yl)methanol (Compound 8-3a)

To a solution of Compound 8-2a (150 mg, 446 μmol, 1.0 eq) in THF (3 mL) at 0° C. was added LiAlH$_4$ (34 mg, 892 μmol, 2.0 eq). then cooled to 0° C. and quenched by addition of H$_2$O (0.5 mL), followed by 15% aq. NaOH (0.5 mL) and H$_2$O (1.5 mL). The mixture was filtered through a pad of Celite and extracted with EtOAc (10 mL). The organic layer was dried (Na$_2$SO$_4$), filtered and concentrated under reduced pressure to give the title compound (140 mg,) as pale yellow solid which was used directly in next step. MS (ES$^+$) C$_{16}$H$_{26}$N$_2$O$_3$, requires: 294, found: 295 [M+H]$^+$.

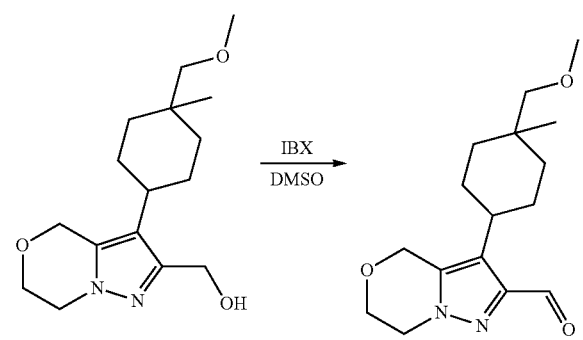

3-(4-(Methoxymethyl)-4-methylcyclohexyl)-6,7-dihydro-4H-pyrazolo[5,1-c]-[1,4]oxazine-2-carbaldehyde (Compound 8-4a)

To a solution of Compound 8-3a (140 mg, 475 μmol, 1.0 eq) in DMSO (2 mL) was added IBX (266 mg, 951 μmol, 2.0 eq). The mixture was stirred at 20° C. for 12 hr, then diluted with H$_2$O (15 mL) and EtOAc (15 mL). The solid was removed by filtration, and the filtrate was extracted with EtOAc (15 mL×2). The combined organic layers were washed with brine (15 mL×2), dried over Na$_2$SO$_4$, filtered and concentrated under reduced pressure to afford the title compound (125 mg) as a light yellow solid which was used in the next step without further purification. MS (ES$^+$) C$_{16}$H$_{24}$N$_2$O$_3$, requires: 292, found: 293 [M+H]$^+$.

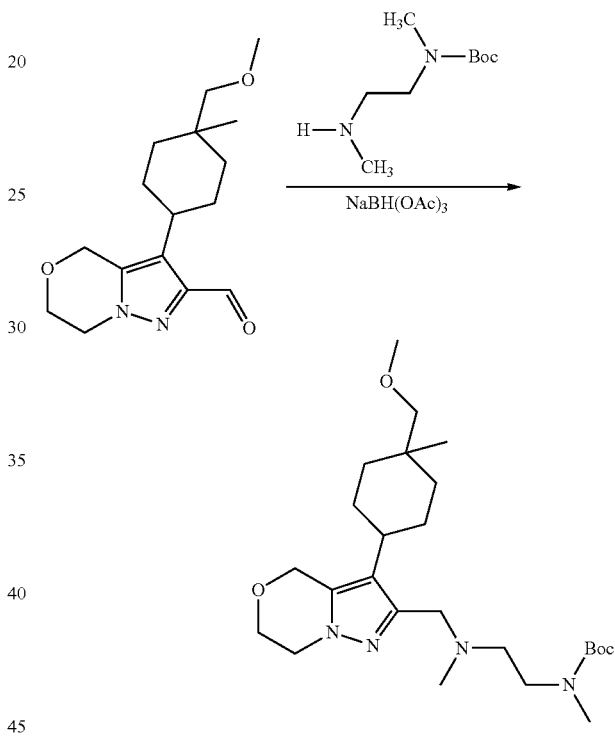

tert-Butyl (2-(((3-(4-(methoxymethyl)-4-methylcyclohexyl)-6,7-dihydro-4H-pyrazolo[5,1-c][1,4]oxazin-2-yl)methyl)(methyl)amino)ethyl)(methyl)carbamate (Compound 8-5a) To a mixture of Compound 8-4a (120 mg, 410 mol, 1.0 eq), tert-butyl N-methyl-N-[2-(methylamino)ethyl]carbamate (116 mg, 615 μmol, 1.5 eq) and CH$_3$COOH (25 mg, 410 μmol, 23 μL, 1.0 eq) in DCE (2 mL) at 0° C. was added NaBH(OAc)$_3$ (87 mg, 410 μmol, 1.0 eq). The mixture was stirred at RT for 12 hr, then carefully diluted with saturated aq. NaHCO$_3$ (6 mL) and extracted with DCE (15 mL×3). The combined organic layers were washed with brine (10 mL), dried over Na$_2$SO$_4$, filtered and concentrated under reduced pressure. The residue was purified by prep-HPLC (column: Phenomenex Synergi C18 150×25×10 um; mobile phase: [A: H$_2$O (0.1% TFA)-B: ACN]; B %: 22%-52%, 13 min) to give the title compound (180 mg, 298 μmol, 73% yield) as a light yellow solid. MS (ES$^+$) C$_{25}$H$_{44}$N$_4$O$_4$, requires: 464, found: 465 [M+H]$^+$.

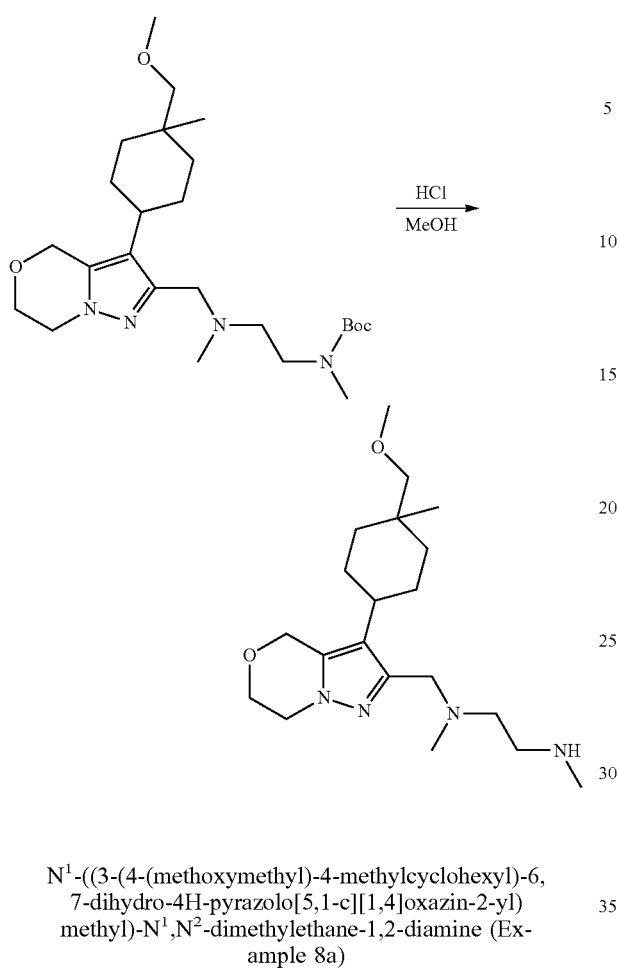

N[1]-((3-(4-(methoxymethyl)-4-methylcyclohexyl)-6,7-dihydro-4H-pyrazolo[5,1-c][1,4]oxazin-2-yl)methyl)-N[1],N[2]-dimethylethane-1,2-diamine (Example 8a)

To a solution of Compound 8-5a (180 mg, 372 mol, 1.0 eq) in MeOH (1 mL) at 0° C. was added HCl (4 M in MeOH, 1.00 mL, 10.8 eq) and the mixture was stirred at 15° C. for 2 hr. The volatiles were removed under reduced pressure, and the residue was purified by prep-HPLC (column: Phenomenex Synergi C18 150×25×10 um; mobile phase: [A: H$_2$O (0.1% TFA)-B: ACN]; B %: 2%-32%, 11 min) to give the title compound as a white solid.

Example 8a 55 mg, 90.96 μmol, 24% yield; $^1$H NMR (400 MHz, CD$_3$OD) δ 4.39 (s, 2H), 4.31 (s, 2H), 4.13 (t, J=5.2 Hz, 2H), 4.07 (t, J=5.2 Hz, 2H), 3.51~3.45 (m, 4H), 3.37 (s, 3H), 3.35 (s, 2H), 2.87 (s, 3H), 2.77 (s, 3H), 2.49~2.43 (m, 1H), 1.72 (d, J=6.8 Hz, 2H), 1.58~1.52 (m, 4H), 1.28~1.22 (m, 2H), 0.92 (s, 3H). MS (ES$^+$) C$_{20}$H$_{36}$N$_4$O$_2$, requires: found: 365 [M+H]$^+$ In a similar manner, Example 8b was obtained from Compound 8-2b using the same procedures described to obtain Example 8a from Compound 8-2a.

Example 8b 95 mg, 153 μmol, 43.9% yield; $^1$H NMR (400 MHz, CD$_3$OD) δ 4.91 (s, 2H), 4.35 (s, 2H), 4.12 (t, J=5.2 Hz, 2H), 4.07 (t, J=5.2 Hz, 2H), 3.54~3.50 (m, 4H), 3.31 (s, 3H), 3.06 (s, 2H), 2.92 (s, 3H), 2.78 (s, 3H), 2.45~2.41 (m, 1H), 1.59~1.56 (m, 4H), 1.46~1.44 (m, 4H), 0.92 (s, 3H). MS (ES$^+$) C$_{20}$H$_{36}$N$_4$O$_2$, requires: found: 365 [M+H]$^+$.

Example 9 a/b

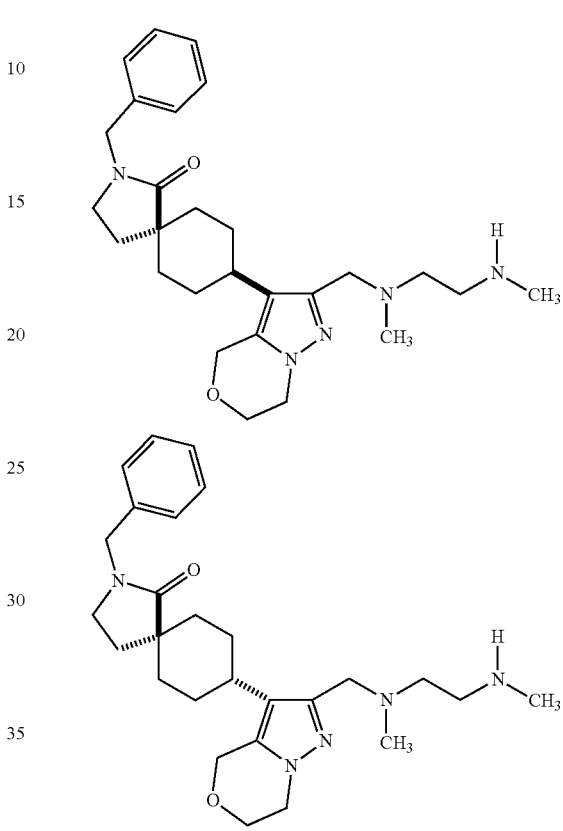

(5s,8s)-2-Benzyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one and (5r,8r)-2-Benzyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one

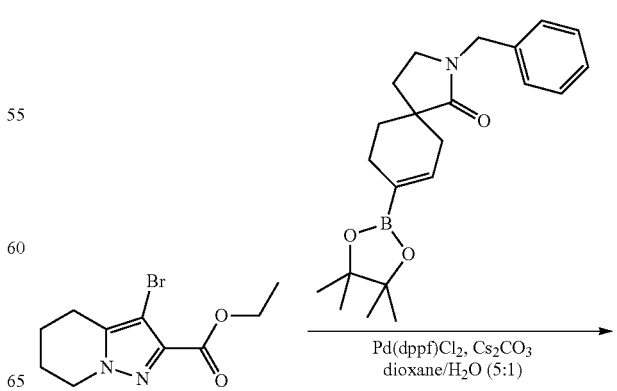

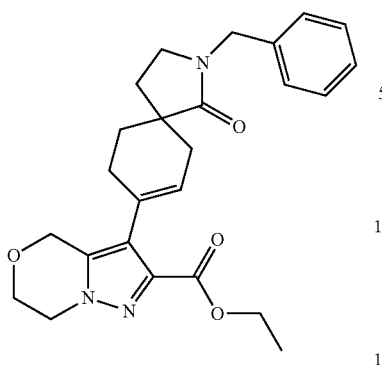

Ethyl 3-(2-benzyl-1-oxo-2-azaspiro[4.5]dec-7-en-8-yl)-6,7-dihydro-4H-pyrazolo[5,1-c][1,4]oxazine-2-carboxylate A mixture of Intermediate C (600 mg, 2.18 mmol, 1.0 eq), Intermediate G (801 mg, 2.18 mmol, 1.0 eq), Pd(dppf)Cl$_2$ (160 mg, 218 μmol, 0.1 eq) and Cs$_2$CO$_3$ (2.13 g, 6.54 mmol, 3.0 eq) in dioxane (10 mL) and H$_2$O (2 mL) was degassed with N$_2$ and heated to 90° C. for 12 hr. The mixture was diluted with H$_2$O (10 mL) and extracted with EtOAc (10 mL×3). The combined organic layers were washed with brine (15 mL), dried over Na$_2$SO$_4$, filtered and concentrated under reduced pressure. The residue was purified by SiO$_2$ gel chromatography (PE/EtOAc=10/1 to 1:2). to afford the title compound (380 mg, 855 μmol, 39% yield) as a light yellow gum. MS (ES$^+$) C$_{25}$H$_{29}$N$_3$O$_4$, requires: 435, found: 436 [M+H]$^+$.

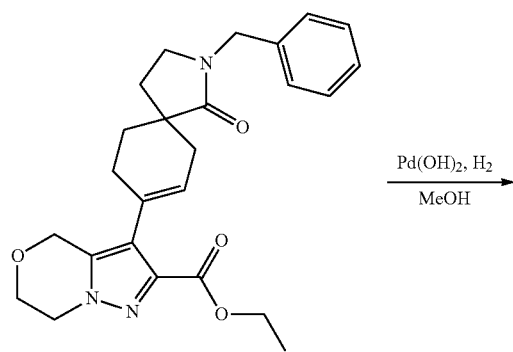

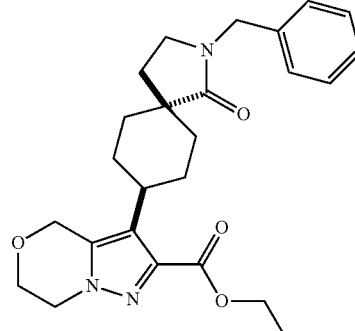

Ethyl 3-((5s,8s)-2-benzyl-1-oxo-2-azaspiro[4.5]decan-8-yl)-6,7-dihydro-4H-pyrazolo[5,1-c][1,4]oxazine-2-carboxylate and ethyl 3-((5r,8r)-2-benzyl-1-oxo-2-azaspiro[4.5]decan-8-yl)-6,7-dihydro-4H-pyrazolo[5,1-c][1,4]oxazine-2-carboxylate A Parr reaction vessel was charged with the product from the previous step (360 mg, 826 μmol, 1.0 eq), Pd(OH)$_2$/C (200 mg, 10% w/w) and MeOH (10 mL). The suspension was degassed with N$_2$ and purged with H$_2$ several times, then stirred in a Parr shaker under H$_2$ (15 psi) at 20° C. for 12 hr. The reaction was then purged with N$_2$, filtered through a pad of Celite and concentrated under reduced pressure. The residue was purified by prep-TLC (PE:EtOAc=1:2, Rf=0.20 and 0.28) to afford the title compound as two distinct stereoisomer products as white solids.

Compound 9-2a: 240 mg, 532 μmol, 64% yield; $^1$H NMR (400 MHz, CD$_3$Cl) δ 7.32-7.19 (m, 5H), 5.06 (s, 2H), 4.42 (s, 2H), 4.39 (q, J=7.2 Hz, 2H), 4.24 (t, J=5.2 Hz, 2H), 4.07 (t, J=5.2 Hz, 2H), 3.43-3.36 (m, 1H), 3.14 (t, J=6.8 Hz, 2H), 2.27-2.16 (m, 2H), 1.96-1.92 (m, 2H), 1.77 (t, J=6.8 Hz, 2H), 1.69-1.62 (m, 4H), 1.40 (t, J=7.2 Hz, 3H). MS (ES$^+$) C$_{25}$H$_{31}$N$_3$O$_4$, requires: found: 438 [M+H]$^+$.

Compound 9-2b: 90 mg, 181 μmol, 22% yield; $^1$H NMR (400 MHz, CD$_3$Cl) δ 7.32-7.20 (m, 5H), 4.85 (s, 2H), 4.65 (s, 2H), 4.39 (q, J=7.2 Hz, 2H), 4.23 (t, J=5.2 Hz, 2H), 4.07 (t, J=5.2 Hz, 2H), 3.18-3.07 (m, 3H), 1.99 (t, J=6.8 Hz, 2H), 1.91-1.85 (m, 2H), 1.78-1.74 (m, 2H), 1.65-1.52 (m, 4H), 1.40 (t, J=7.2 Hz, 3H). MS (ES$^+$) C$_{25}$H$_{31}$N$_3$O$_4$, requires: found: 438 [M+H]$^+$.

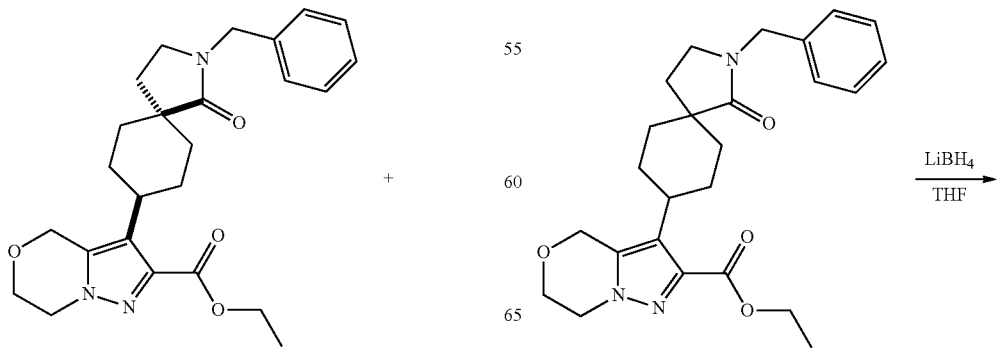

-continued

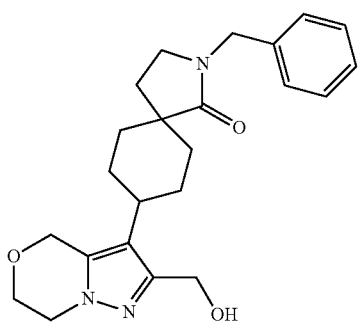

2-Benzyl-8-(2-(hydroxymethyl)-6,7-dihydro-4H-pyrazolo[5,1-c][1,4]oxazin-3-yl)-2-azaspiro[4.5]decan-1-one (Compound 9-3a)

To a solution of Compound 9-2a (56 mg, 128 µmol, 1.0 eq) in THF (5 mL) at 0° C. was added LiBH₄ (5.6 mg, 256 µmol, 2.0 eq). The mixture was then stirred at RT for 1 h, at 40° C. for another 1 hour, then cooled 0° C. again and quenched by addition H₂O (8 mL). The mixture was extracted with EtOAc (20 mL×3), the combined organic layers were washed with brine (15 mL×2), dried over Na₂SO₄, filtered and concentrated under reduced pressure to give the title compound (50 mg) as a white solid, which was used without further purification in the next step. MS (ES⁺) $C_{23}H_{29}N_3O_3$, requires: 395, found: 396 [M+H]⁺.

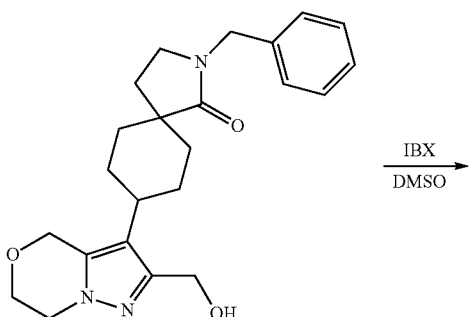

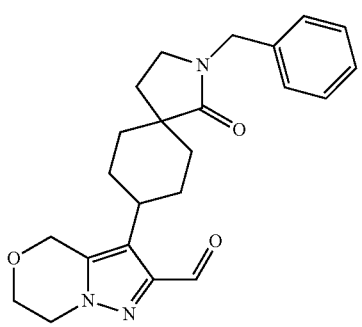

3-(2-Benzyl-1-oxo-2-azaspiro[4.5]decan-8-yl)-6,7-dihydro-4H-pyrazolo[5,1-c]-[1,4]oxazine-2-carbaldehyde (Compound 9-4a)

To a solution of Compound 9-3a (50 mg, 126 µmol, 1.0 eq) in DMSO (2 mL) was added IBX (71 mg, 253 µmol, 2.0 eq). The mixture was stirred at 25° C. for 16 hr, quenched by addition H₂O (10 mL) and extracted with EtOAc (20 mL×3). The combined organic layers were washed with brine (20 mL×3), dried over Na₂SO₄, filtered and concentrated under reduced pressure to give the title compound (48 mg) as a white solid, which was used without further purification in the next step. MS (ES⁺) $C_{23}H_{27}N_3O_3$, requires: 393, found: 394 [M+H]⁺.

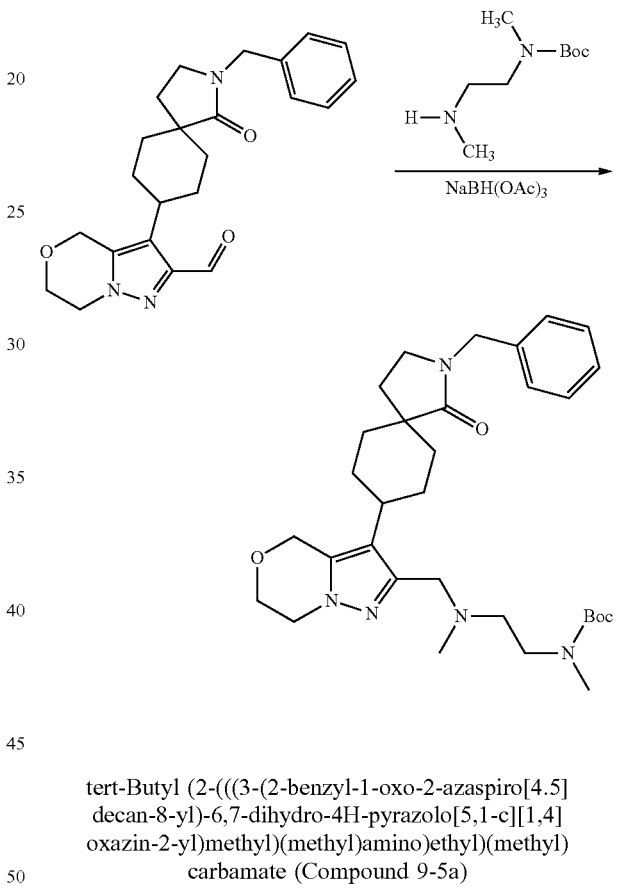

tert-Butyl (2-(((3-(2-benzyl-1-oxo-2-azaspiro[4.5]decan-8-yl)-6,7-dihydro-4H-pyrazolo[5,1-c][1,4]oxazin-2-yl)methyl)(methyl)amino)ethyl)(methyl)carbamate (Compound 9-5a)

To a solution of Compound 9-4a (48 mg, 98 mol, 1.0 eq) and tert-butyl N-methyl-N-[2-(methylamino)ethyl]carbamate (22 mg, 117 µmol, 1.2 eq) in DCE (2 mL) were added NaBH(OAc)₃ (62 mg, 293 µmol, 3.0 eq) and AcOH (6 µL, 98 µmol, 1.0 eq). The mixture was stirred at 25° C. for 16 hr, quenched by H₂O (10 mL) and extracted with EtOAc (20 mL×3). The combined organic layers were washed with brine (15 mL×2), dried over Na₂SO₄, filtered and concentrated under reduced pressure. The residue was purified by prep-HPLC (column: Boston Green ODS 150×30 5 u; mobile phase: [A: H₂O (0.225% FA)-B: ACN]; B %: 35%-62%, 10 min) to give the title compound (20 mg, 32 µmol, 32% yield) as a colorless oil. MS (ES⁺) $C_{32}H_{47}N_5O_4$, requires: 565, found: 566 [M+H]⁺.

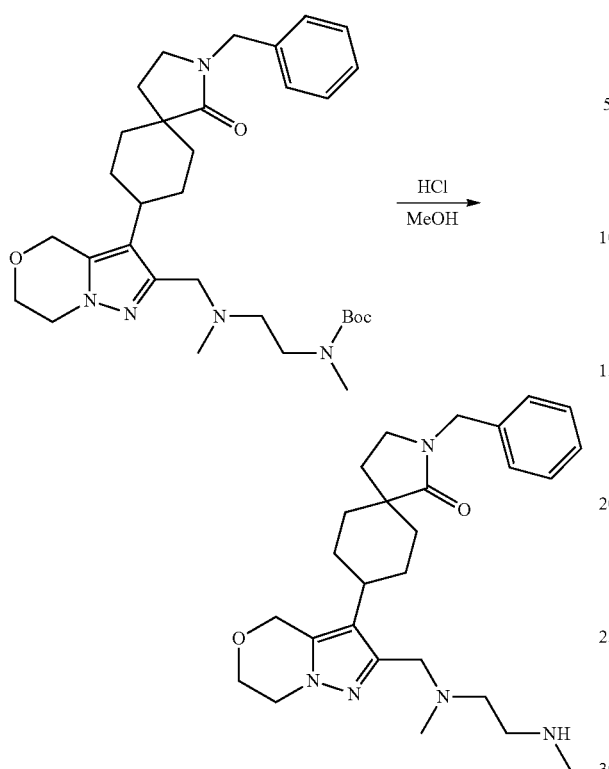

2-Benzyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one (Example 9a)

To a solution of Compound 9-5a (20 mg, 32.69 mol, 1 eq) in MeOH (2 mL) was added HCl/MeOH (4 M, 81.73 μL, 10 eq). The mixture was stirred at 25° C. for 12 hr. LC-MS showed the starting material was consumed completely and one main peak with desired MS was detected. The reaction mixture was concentrated under reduced pressure to remove solvent to give the residue. The residue was dissolved in H$_2$O (2 mL) and lyophilized to the title compound as a white solid.

Example 9a 13 mg, 23.9 73% yield; $^1$H NMR (400 MHz, d-H$_2$O, ppm): δ: 7.36 (m, 3H), 7.24 (d, J=6.8 Hz, 2H), 4.99 (s, 2H), 4.42 (d, J=5.2 Hz, 4H), 4.14 (m, 4H), 3.55 (m, 4H), 3.27 (t, J=6.8 Hz, 2H), 2.89 (s, 3H), 2.76 (s, 3H), 2.53 (m, 1H), 1.98 (m, 4H), 1.83 (t, J=6.8 Hz, 2H), 1.53 (m, 4H). MS (ES$^+$) C$_{27}$H$_{39}$N$_5$O$_2$, requires 465: found: 466 [M+H]$^+$.

In a similar manner, Example 9b was obtained from Compound 9-2b using the same procedures described to obtain Example 9a from Compound 9-2a.

Example 9b 26 mg, 46 μmol, 79% yield; $^1$H NMR (400 MHz, D$_2$O) δ 7.43-7.36 (m, 3H), 7.27 (d, J=7.2 Hz, 2H), 5.00 (s, 2H), 4.46 (d, J=8.0 Hz, 4H), 4.20-4.15 (m, 4H), 3.63-3.55 (m, 4H), 3.35 (t, J=7.2 Hz, 2H), 2.92 (s, 3H), 2.81 (s, 3H), 2.61-2.55 (m, 1H), 2.07 (t, J=6.8 Hz, 2H), 1.76-1.61 (m, 6H), 1.54-1.44 (m, 2H). MS (ES$^+$) C$_{27}$H$_{39}$N$_5$O$_2$, requires 465: found: 466 [M+H]$^+$.

Example 10

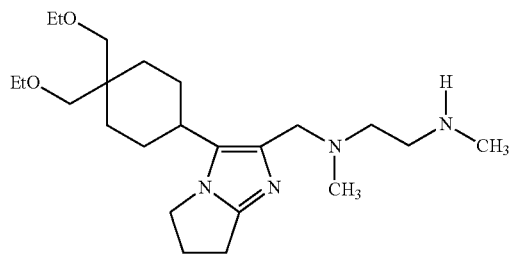 [SMILES: CCOCC1(COCC)CCC(c2c(CN(C)CCNC)nc3n2CCC3)CC1]

N$^1$-((3-(4,4-bis(ethoxymethyl)cyclohexyl)-6,7-dihydro-5H-pyrrolo-[1,2-a]imidazol-2-yl)methyl)-N$^1$,N$^2$-dimethylethane-1,2-diamine

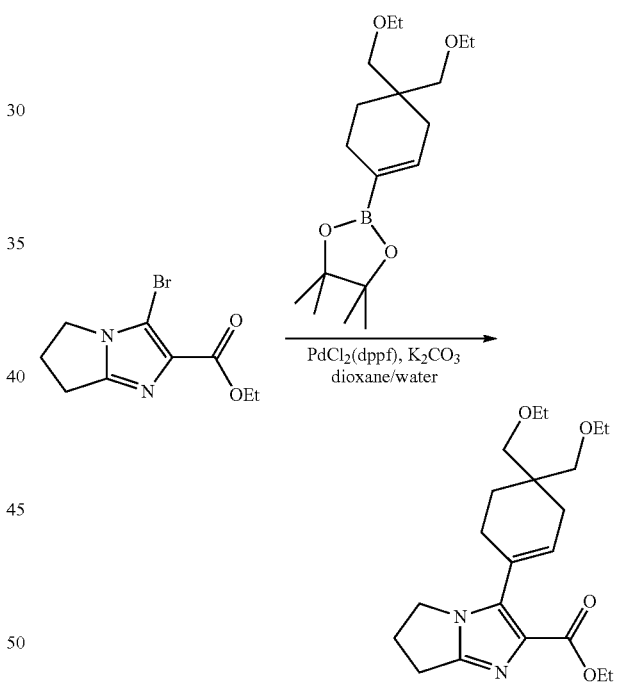

Ethyl 3-(4,4-bis(ethoxymethyl)cyclohex-1-en-1-yl)-6,7-dihydro-5H-pyrrolo[1,2-a]imidazole-2-carboxylate A mixture of Intermediate D (150 mg, 0.58 mmol), 2-(4,4-bis(ethoxymethyl)cyclohex-1-en-1-yl)-4,4,5,5-tetramethyl-1,3,2-dioxaborolane (225 mg, 0.69 mmol) and K$_2$CO$_3$ (248 mg, 1.79 mmol) in dioxane (3 ml)/H$_2$O (0.3 ml) was degassed with N$_2$ for 2 min. PdCl$_2$(dppf)-CH$_2$Cl$_2$ adduct (95 mg, 0.116 mmol) was added and the mixture was degassed with N$_2$ for an additional 1 min. The reaction mixture was heated to 100° C. and stirred for 5 h, then allowed to cool to room temperature and filtered through a pad of Celite. The filtrate was concentrated under reduced pressure and the residue was purified via silica gel chromatography (10-50% EtOAc in hexanes) to give the title compound (185 mg, 0.491 mmol, 85% yield) as a yellow liquid. MS (ES$^+$) $C_{21}H_{32}N_2O_4$ requires: 376, found: 377 [M+H]$^+$.

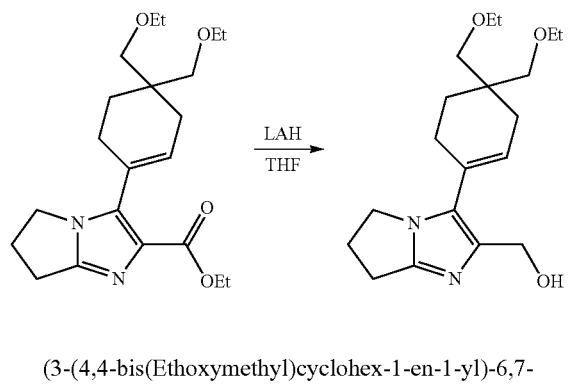

(3-(4,4-bis(Ethoxymethyl)cyclohex-1-en-1-yl)-6,7-dihydro-5H-pyrrolo[1,2-a]imidazol-2-yl)methanol To a solution of ethyl 3-(4,4-bis(ethoxymethyl)cyclohex-1-en-1-yl)-6,7-dihydro-5H-pyrrolo[1,2-a]imidazole-2-carboxylate (144 mg, 0.38 mmol) in THF (2 mL) at 0° C. was added LiAlH$_4$ (16 mg, 0.421 mmol). The resulting mixture was stirred at 25° C. for 2 h, quenched by addition of solid Na$_2$SO$_4$·10H$_2$O and stirred for a further 1 h. The reaction mixture was filtered through a pad of Celite, and the filtrate was concentrated under reduced pressure to give the title compound (128 mg) as a viscous oil. The product was used without further purification. MS (ES$^+$) $C_{19}H_{30}N_2O_3$ requires: 334, found: 335 [M+H]$^+$.

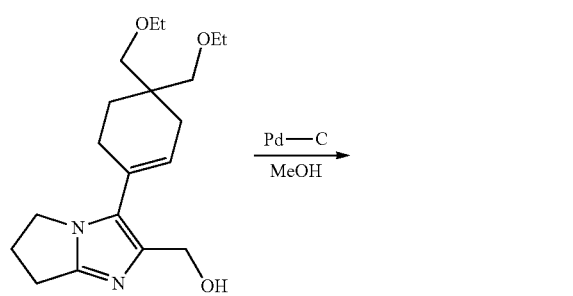

(3-(4,4-bis(Ethoxymethyl)cyclohexyl)-6,7-dihydro-5H-pyrrolo[1,2-a]imidazol-2-yl)methanol A reaction vessel was charged with (3-(4,4-bis(ethoxymethyl)cyclohex-1-en-1-yl)-6,7-dihydro-5H-pyrrolo[1,2-a]imidazol-2-yl)methanol (128 mg, 0.38 mmol), Pd/C (40.7 mg, 0.038 mmol) and MeOH (3 ml) under an atmosphere of N$_2$. The suspension was degassed with N$_2$ for 2 min and purged with H$_2$ for 1 min, then stirred under an atmosphere of H$_2$ at 1 atm for 6 h. The reaction mixture was then purged with N$_2$, filtered through a pad of Celite and concentrated under reduced pressure to give the title compound (120 mg) as a pale yellow oil. The product was used without further purification. MS (ES$^+$) $C_{19}H_{32}N_2O_3$ requires: 336, found: 337 [M+H]$^+$.

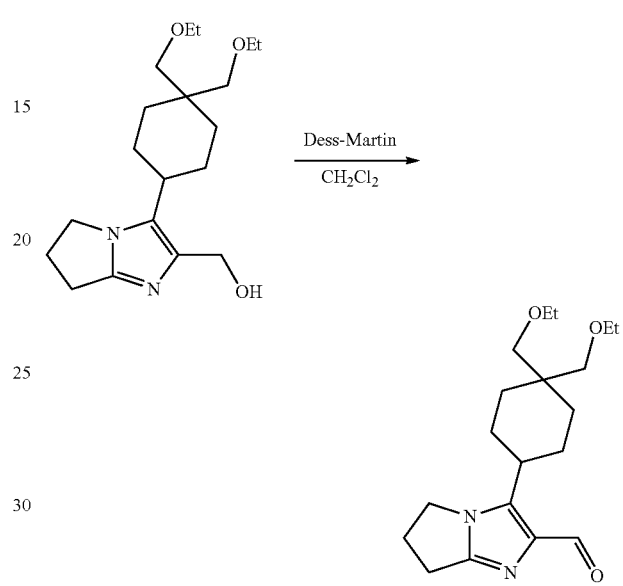

3-(4,4-bis(Ethoxymethyl)cyclohexyl)-6,7-dihydro-5H-pyrrolo[1,2-a]imidazole-2-carbaldehyde To a solution of (3-(4,4-bis(ethoxymethyl)cyclohexyl)-6,7-dihydro-5H-pyrrolo[1,2-a]imidazol-2-yl)methanol (120 mg, 0.36 mmol) in CH$_2$Cl$_2$ (3 ml) was added Dess-Martin periodinane (166 mg, 0.39 mmol) and the resulting mixture was stirred at 25° C. for 1 h. Saturated aq. Na$_2$S$_2$O$_3$ (10 mL) and NaHCO$_3$ (10 mL) were added and the reaction mixture was stirred for 30 min. The layers were separated, the aqueous phase was extracted with CH$_2$Cl$_2$ (3×15 mL), and the combined organic layers were washed with sat NaHCO$_3$, dried over Na$_2$SO$_4$, filtered and concentrated under reduced pressure to give the title compound (112 mg). The product was used without further purification. MS (ES$^+$) $C_{19}H_{30}N_2O_3$ requires: 334, found: 335 [M+H]$^+$.

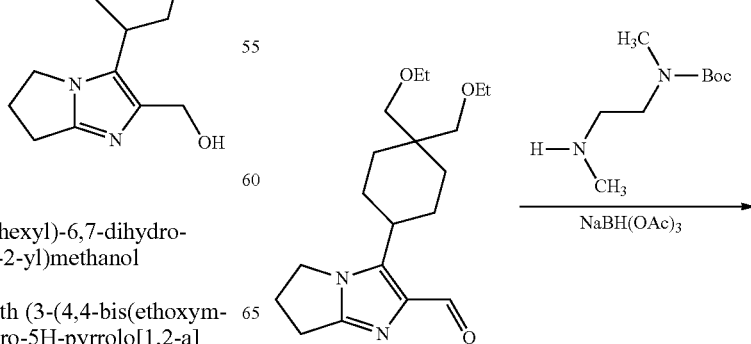

-continued

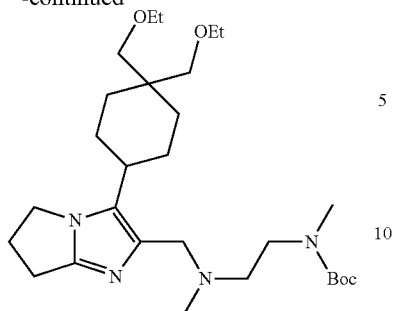

tert-Butyl (2-(((3-(4,4-bis(ethoxymethyl)cyclo-hexyl)-6,7-dihydro-5H-pyrrolo[1,2-a]imidazol-2-yl)methyl)(methyl)amino)ethyl)(methyl)carbamate To a solution of 3-(4,4-bis(ethoxymethyl)cyclohexyl)-6,7-dihydro-5H-pyrrolo[1,2-a]imidazole-2-carbaldehyde (50 mg, 0.149 mmol) in DCE (1.5 ml) were added tert-butyl methyl(2-(methylamino)ethyl)-carbamate (34 mg, 0.179 mmol) and, 30 min. later, sodium triacetoxyborohydride (41.2 mg, 0.194 mmol). The resulting mixture was stirred at 25° C. for 1 h, saturated aq. NaHCO$_3$ (0.5 mL) was added, and the layers were separated. The aqueous phase was extracted with CH$_2$Cl$_2$ (3×3 mL), the combined organic layers were washed with brine, dried over Na$_2$SO$_4$, filtered and concentrated under reduced pressure. The residue was purified by mass-triggered preparative HPLC (Mobile phase: A=0.1% TFA/H$_2$O, B=0.1% TFA/MeCN; Gradient: B=20-50%; 12 min; Column: C18) to give the title compound (11 mg, 0.022 mmol, 14% yield) as a colorless oil. MS (ES$^+$) C$_{28}$H$_{50}$N$_4$O$_4$ requires: 506, found: 507 [M+H]$^+$.

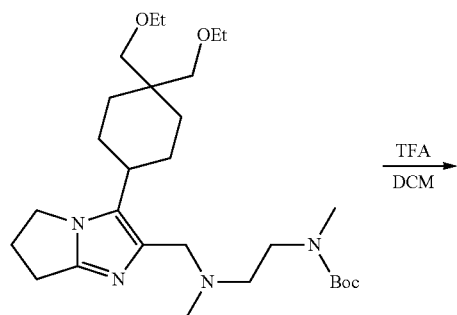

-continued

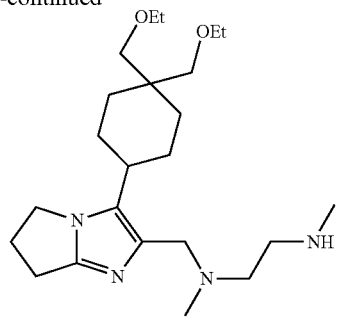

N$^1$-((3-(4,4-bis(ethoxymethyl)cyclohexyl)-6,7-dihydro-5H-pyrrolo[1,2-a]imidazol-2-yl)methyl)-N$^1$,N$^2$-dimethylethane-1,2-diamine To a solution of tert-butyl (2-(((3-(4,4-bis(ethoxymethyl)cyclohexyl)-6,7-dihydro-5H-pyrrolo[1,2-a]imidazol-2-yl)methyl)-(methyl)amino)ethyl)(methyl)carbamate (11 mg, 0.022 mmol) in CH$_2$Cl$_2$ (0.2 ml) was added TFA (33 µl, 0.43 mmol) and the resulting mixture was stirred at 25° C. for 3 h. The volatiles were removed under reduced pressure to give the title compound (12 mg, 0.019 mmol, 87% yield) as a pale yellow oil.

$^1$H NMR (600 MHz, DMSO-d$_6$) 4.25 (t, J=7.3 Hz, 2H), 3.71 (s, 2H), 3.51-3.37 (m, 6H), 3.14 (s, 4H), 3.08-3.00 (m, 2H), 2.80-2.69 (m, 3H), 2.67-2.58 (m, 6H), 2.32-2.18 (m, 3H), 1.74-1.60 (m, 4H), 1.57-1.49 (m, 2H), 1.40-1.31 (m, 2H), 1.12 (dt, J=16.5, 7.0 Hz, 6H). MS (ES$^+$) C$_{23}$H$_{42}$N$_4$O$_2$ requires: 406, found: 407 [M+H]$^+$.

The following Example compounds were prepared using the methods disclosed above. Unless otherwise noted, diastereomeric mixtures were not separated into diastereomerically pure compounds.

TABLE 1

Example compounds 11-61.

| Ex | Structure | IUPAC Name | MWt/[M + H] | Ex. Method |
|---|---|---|---|---|
| 11 | 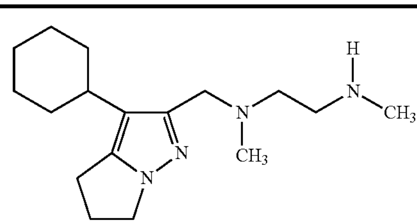 | N$^1$-((3-cyclohexyl-5,6-dihydro-4H-pyrrolo[1,2-b]pyrazol-2-yl)-methyl)-N$^1$,N$^2$-dimethylethane-1,2-diamine | 290/291 | 1 |

TABLE 1-continued

Example compounds 11-61.

| Ex | Structure | IUPAC Name | MWt/ [M + H] | Ex. Method |
|---|---|---|---|---|
| 12 | 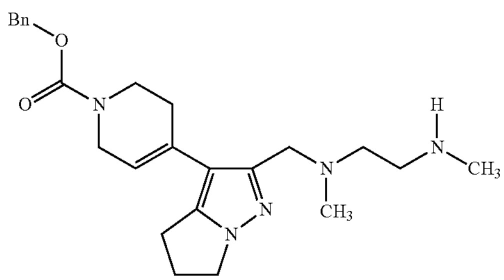 [SMILES: CNCCN(C)Cc1nn2c(c1C1=CCN(C(=O)OCc3ccccc3)CC1)CCC2] | Benzyl 4-(2-((methyl-(2-(methylamino)ethyl)amino)methyl)-5,6-dihydro-4H-pyrrolo[1,2-b]pyrazol-3-yl)-3,6-dihydropyridine-1(2H)-carboxylate | 423/424 | 1 |
| 13 | 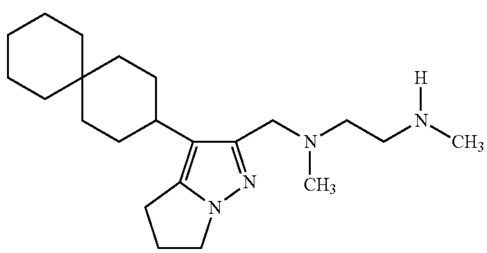 | $N^1,N^2$-dimethyl-$N^1$-((3-(spiro[5.5]undecan-3-yl)-5,6-dihydro-4H-pyrrolo[1,2-b]pyrazol-2-yl)methyl)ethane-1,2-diamine | 358/359 | 1 |
| 14 | 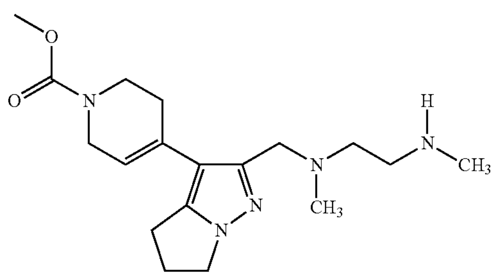 [SMILES: CNCCN(C)Cc1nn2c(c1C1=CCN(C(=O)OC)CC1)CCC2] | 1-(4-(2-((Methyl(2-(methylamino)ethyl)amino)methyl)-5,6-dihydro-4H-pyrrolo[1,2-b]pyrazol-3-yl)-3,6-dihydropyridin-1(2H)-yl)propan-1-one | 347/348 | 1 |
| 15 | 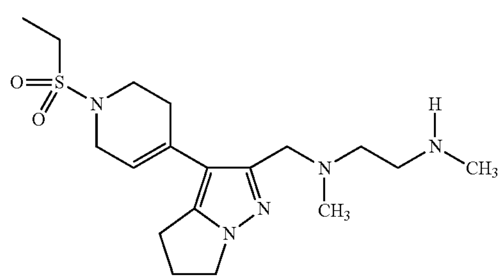 [SMILES: CCS(=O)(=O)N1CC=C(c2c(CN(C)CCNC)nn3c2CCC3)CC1] | $N^1$-((3-(1-(ethylsulfonyl)-1,2,3,6-tetrahydropyridin-4-yl)-5,6-dihydro-4H-pyrrolo[1,2-b]pyrazol-2-yl)-methyl)-$N^1,N^2$-dimethylethane-1,2-diamine | 383/384 | 1 |
| 16 | 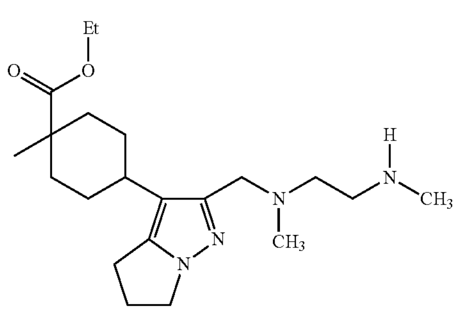 | Ethyl 1-methyl-4-(2-((methyl(2-(methylamino)ethyl)amino)methyl)-5,6-dihydro-4H-pyrrolo[1,2-b]pyrazol-3-yl)cyclohexane-1-carboxylate | 376/377 | 1 |

TABLE 1-continued

Example compounds 11-61.

| Ex | Structure | IUPAC Name | MWt/ [M + H] | Ex. Method |
|---|---|---|---|---|
| 17 | 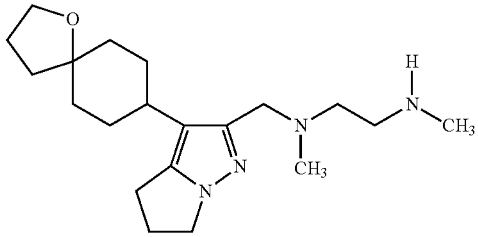 [SMILES: CNCCN(C)Cc1nn2c(c1C1CCC3(CCCO3)CC1)CCC2] | $N^1$-((3-(1-oxaspiro[4.5]decan-8-yl)-5,6-dihydro-4H-pyrrolo[1,2-b]pyrazol-2-yl)methyl)-$N^1$,$N^2$-dimethylethane-1,2-diamine | 346/347 | 3 |
| 18 | 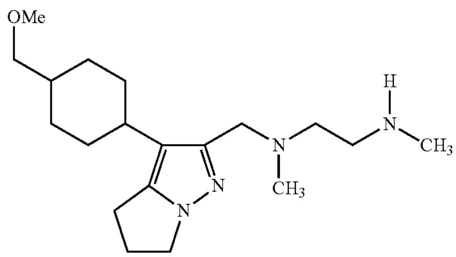 [SMILES: CNCCN(C)Cc1nn2c(c1C1CCC(COC)CC1)CCC2] | $N^1$-((3-(4-(methoxymethyl)cyclohexyl)-5,6-dihydro-4H-pyrrolo[1,2-b]pyrazol-2-yl)methyl)-$N^1$,$N^2$-dimethylethane-1,2-diamine | 334/335 | 1 |
| 19 | 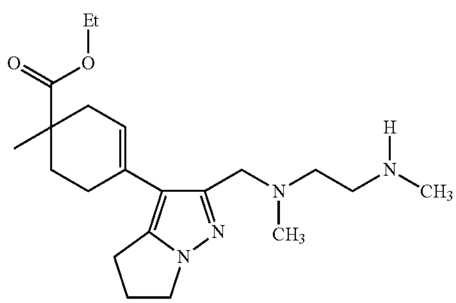 | Ethyl 1-methyl-4-(2-((methyl(2-(methylamino)ethyl)amino)methyl)-5,6-dihydro-4H-pyrrolo[1,2-b]pyrazol-3-yl)cyclohex-3-ene-1-carboxylate | 374/375 | 1 |
| 20 | 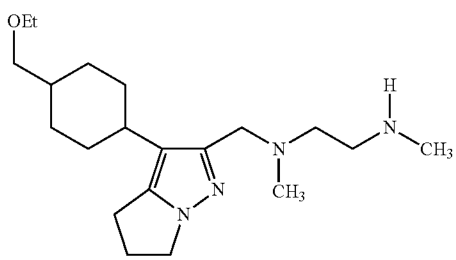 [SMILES: CCOCC1CCC(c2c(CN(C)CCNC)nn3c2CCC3)CC1] | $N^1$-((3-(4-(ethoxymethyl)cyclohexyl)-5,6-dihydro-4H-pyrrolo[1,2-b]pyrazol-2-yl)methyl)-$N^1$,$N^2$-dimethylethane-1,2-diamine | 348/349 | 1 |
| 21 | 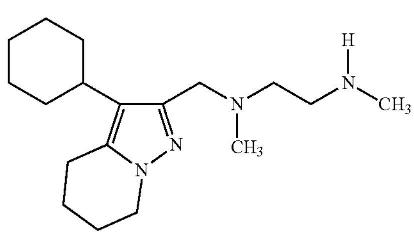 [SMILES: CNCCN(C)Cc1nn2c(c1C1CCCCC1)CCCC2] | $N^1$-((3-cyclohexyl-4,5,6,7-tetrahydropyrazolo[1,5-a]pyridin-2-yl)methyl)-$N^1$,$N^2$-dimethylethanediamine | 304/305 | 1 |
| 22 | 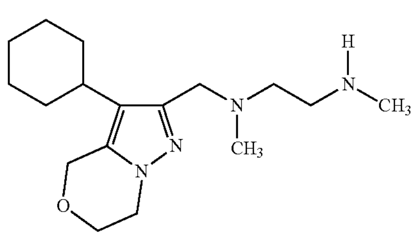 | $N^1$-((3-cyclohexyl-6,7-dihydro-4H-pyrazolo[5,1-c][1,4]oxazin-2-yl)methyl)-$N^1$$N^2$-dimethylethane-1,2-diamine | 306/307 | 7 |

TABLE 1-continued

Example compounds 11-61.

| Ex | Structure | IUPAC Name | MWt/ [M + H] | Ex. Method |
|---|---|---|---|---|
| 23 | 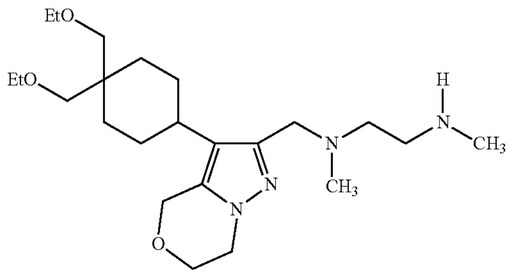 [SMILES: CCOCC1(COCC)CCC(c2c(CN(C)CCNC)nn3c2COCC3)CC1] | $N^1$-((3-(4,4-bis(ethoxymethyl)cyclohexyl)-6,7-dihydro-4H-pyrazolo[5,1-c][1,4]oxazin-2-yl)methyl)-$N^1$,$N^2$-dimethylethane-1,2-diamine | 422/423 | 7 |
| 24 | 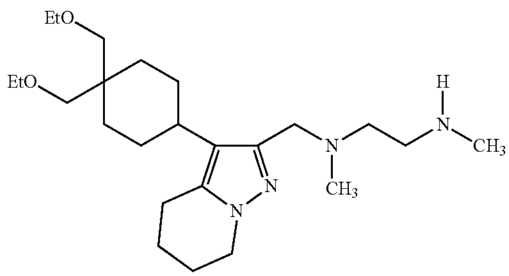 [SMILES: CCOCC1(COCC)CCC(c2c(CN(C)CCNC)nn3c2CCCC3)CC1] | $N^1$-((3-(4,4-bis(ethoxymethyl)cyclohexyl)-4,5,6,7-tetrahydropyrazolo[1,5-a]pyridin-2-yl)methyl)-$N^1$,$N^2$-dimethylethanediamine | 420/421 | 2 |
| 25 | 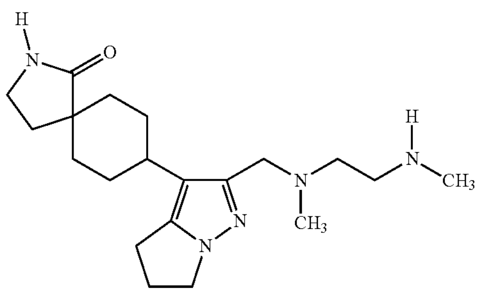 [SMILES: CNCCN(C)Cc1nn2c(c1C1CCC3(CCNC3=O)CC1)CCC2] | 8-(2-((Methyl(2-(methylamino)ethyl)amino)methyl)-5,6-dihydro-4H-pyrrolo[1,2-b]pyrazol-3-yl)-2-azaspiro[4.5]decan-1-one | 359/360 | 9 |
| 26 | 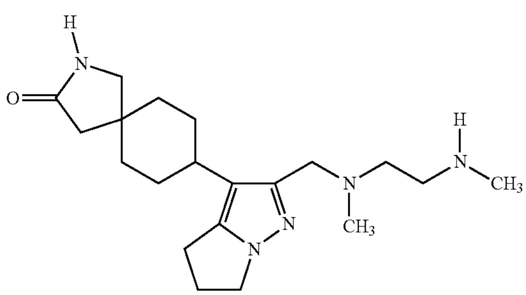 [SMILES: CNCCN(C)Cc1nn2c(c1C1CCC3(CC1)CNC(=O)C3)CCC2] | 8-(2-((Methyl(2-(methylamino)ethyl)amino)methyl)-5,6-dihydro-4H-pyrrolo[1,2-b]pyrazol-3-yl)-2-azaspiro[4.5]decan-3-one | 359/360 | 9 |
| 27 | 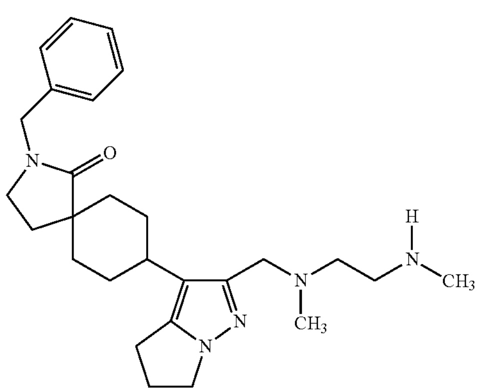 [SMILES: CNCCN(C)Cc1nn2c(c1C1CCC3(CC1)CCN(Cc1ccccc1)C3=O)CCC2] | 2-Benzyl-8-(2-((methyl(2-(methylamino)ethyl)amino)methyl)-5,6-dihydro-4H-pyrrolo[1,2-b]pyrazol-3-yl)-2-azaspiro[4.5]decan-1-one | 449/450 | 9 |

TABLE 1-continued

Example compounds 11-61.

| Ex | Structure | IUPAC Name | MWt/ [M + H] | Ex. Method |
|---|---|---|---|---|
| 28 | 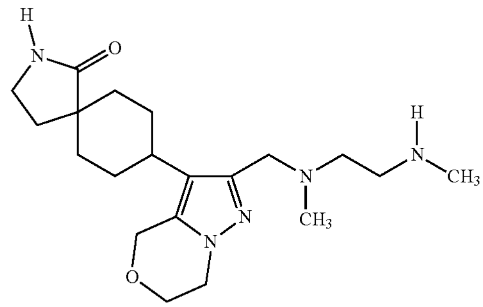 [SMILES: CNCCN(C)Cc1nn2c(c1C1CCC3(CCNC3=O)CC1)COCC2] | 8-(2-((Methyl(2-(methylamino)ethyl)-amino)methyl)-6,7-dihydro-4H-pyrazolo[5,1-c][1,4]oxazin-3-yl)-2-azaspiro[4.5]decan-1-one | 375/376 | 9 |
| 29 | 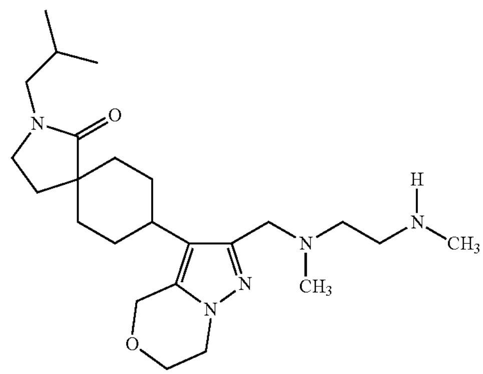 [SMILES: CNCCN(C)Cc1nn2c(c1C1CCC3(CC1)CCN(CC(C)C)C3=O)COCC2] | 2-Isobutyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one | 431/432 | 9 |
| 30 | 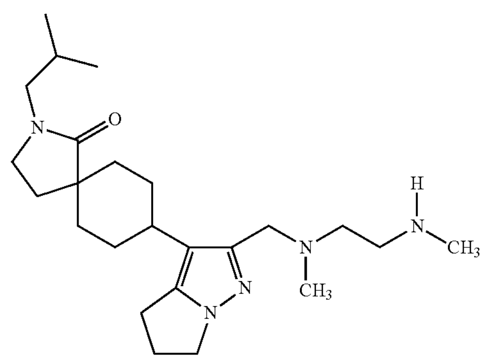 [SMILES: CNCCN(C)Cc1nn2c(c1C1CCC3(CC1)CCN(CC(C)C)C3=O)CCC2] | 2-Isobutyl-8-(2-((methyl(2-(methylamino)ethyl)amino)methyl)-5,6-dihydro-4H-pyrrolo[1,2-b]pyrazol-3-yl)-2-azaspiro[4.5]decan-1-one | 415/416 | 9 |
| 31 | 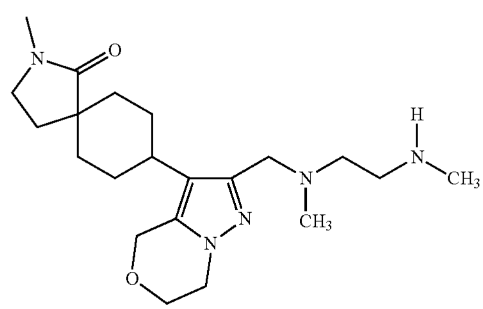 [SMILES: CNCCN(C)Cc1nn2c(c1C1CCC3(CC1)CCN(C)C3=O)COCC2] | 2-Methyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one | 389/390 | 9 |

TABLE 1-continued

Example compounds 11-61.

| Ex | Structure | IUPAC Name | MWt/ [M + H] | Ex. Method |
|---|---|---|---|---|
| 32 | 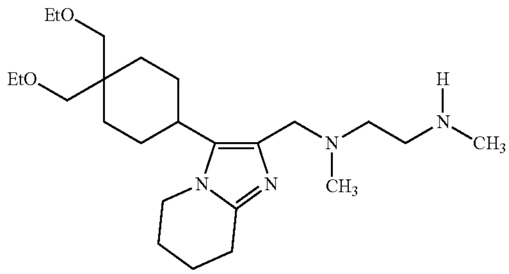 [SMILES: CCOCC1(COCC)CCC(c2c(CN(C)CCNC)nc3n2CCCC3)CC1] | $N^1$-((3-(4,4-bis(ethoxymethyl)cyclohexyl)-5,6,7,8-tetrahydroimidazo[1,2-a]pyridin-2-yl)methyl)-$N^1$,$N^2$-dimethylethane-1,2-diamine | 420/421 | 10 |
| 33 | 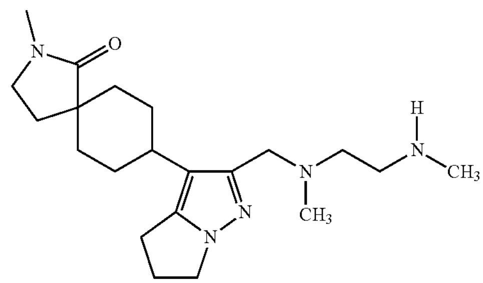 [SMILES: CNCCN(C)Cc1nn2c(c1C1CCC3(CC1)CCN(C)C3=O)CCC2] | 2-Methyl-8-(2-((methyl(2-(methylamino)ethyl)amino)methyl)-5,6-dihydro-4H-pyrrolo[1,2-b]pyrazol-3-yl)-2-azaspiro[4.5]decan-1-one | 373/374 | 9 |
| 34 | 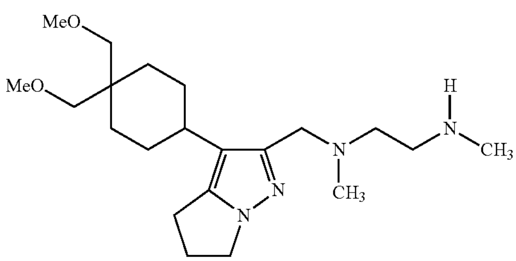 [SMILES: CNCCN(C)Cc1nn2c(c1C1CCC(COC)(COC)CC1)CCC2] | $N^1$-((3-(4,4-bis-(methoxymethyl)-cyclohexyl)-5,6-dihydro-4H-pyrrolo[1,2-b]pyrazol-2-yl)methyl)-$N^1$,$N^2$-dimethylethane-1,2-diamine | 378/379 | 2 |
| 35 | 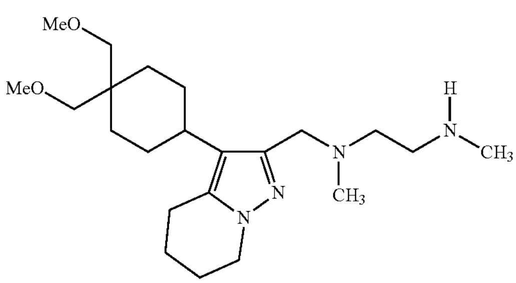 [SMILES: CNCCN(C)Cc1nn2c(c1C1CCC(COC)(COC)CC1)CCCC2] | $N^1$-((3-(4,4-bis-(methoxymethyl)-cyclohexyl)-4,5,6,7-tetrahydropyrazolo[1,5-a]pyridin-2-yl)-methyl)-$N^1$,$N^2$-dimethylethane-1,2-diamine | 392/393 | 2 |
| 36 | 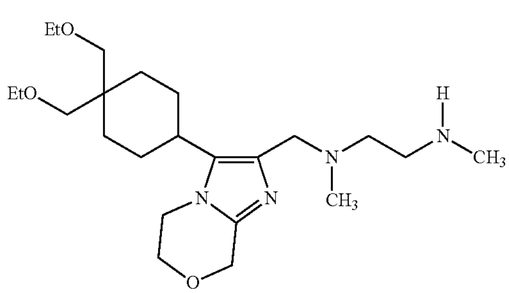 [SMILES: CCOCC1(COCC)CCC(c2c(CN(C)CCNC)nc3n2CCOC3)CC1] | $N^1$-((3-(4,4-bis(ethoxymethyl)cyclohexyl)-5,6-dihydro-8H-imidazo[2,1-c][1,4]oxazin-2-yl)methyl)-$N^1$,$N^2$-dimethylethane-1,2-diamine | 422/423 | 10 |

TABLE 1-continued

Example compounds 11-61.

| Ex | Structure | IUPAC Name | MWt/ [M + H] | Ex. Method |
|---|---|---|---|---|
| 37 | 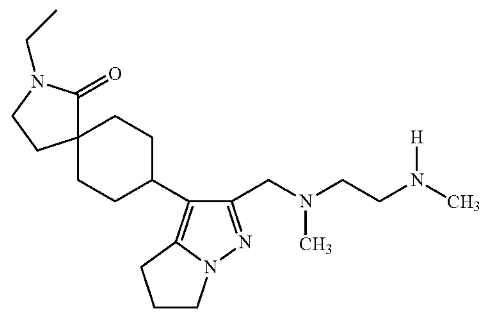 [SMILES: CCN1CCC2(CCC(c3c(CN(C)CCNC)nn4c3CCC4)CC2)C1=O] | 2-Ethyl-8-(2-((methyl-(2-(methylamino)-ethyl)amino)methyl)-5,6-dihydro-4H-pyrrolo[1,2-b]pyrazol-3-yl)-2-azaspiro[4.5]decan-1-one | 387/388 | 9 |
| 38 | 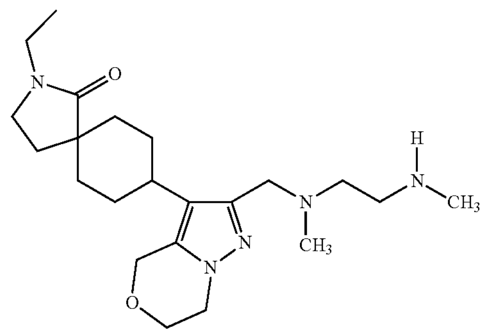 [SMILES: CCN1CCC2(CCC(c3c(CN(C)CCNC)nn4c3COCC4)CC2)C1=O] | 2-Ethyl-8-(2-((methyl-(2-(methylamino)-ethyl)amino)methyl)-6,7-dihydro-4H-pyrazolo[5,1-c][1,4]oxazin-3-yl)-2-azaspiro[4.5]decan-1-one | 403/404 | 9 |
| 39 | 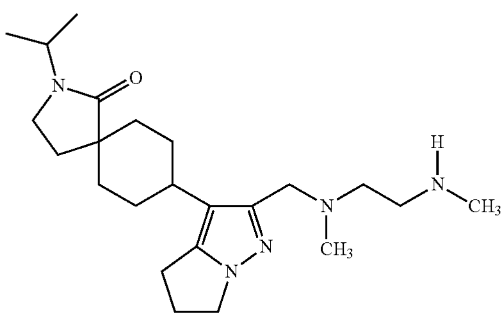 [SMILES: CNCCN(C)Cc1nn2c(c1C1CCC3(CC1)CCN(C(C)C)C3=O)CCC2] | 2-Isopropyl-8-(2-((methyl(2-(methylamino)ethyl)amino)methyl)-5,6-dihydro-4H-pyrrolo[1,2-b]pyrazol-3-yl)-2-azaspiro[4.5]decan-1-one | 401/402 | 9 |
| 40 | 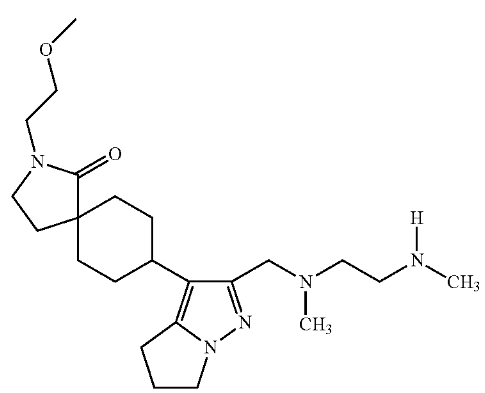 [SMILES: CNCCN(C)Cc1nn2c(c1C1CCC3(CC1)CCN(CCOC)C3=O)CCC2] | 2-(2-Methoxyethyl)-8-(2-((methyl(2-(methylamino)ethyl)amino)methyl)-5,6-dihydro-4H-pyrrolo[1,2-b]pyrazol-3-yl)-2-azaspiro[4.5]decan-1-one | 417/418 | 9 |

TABLE 1-continued

Example compounds 11-61.

| Ex | Structure | IUPAC Name | MWt/ [M + H] | Ex. Method |
|---|---|---|---|---|
| 41 | 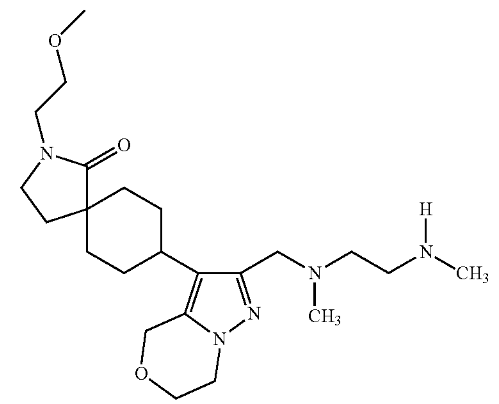 [SMILES: CNCCN(C)Cc1nn2c(c1C1CCC3(CC1)CCN(CCOC)C3=O)COCC2] | 2-(2-Methoxyethyl)-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one | 433/434 | 9 |
| 42 | 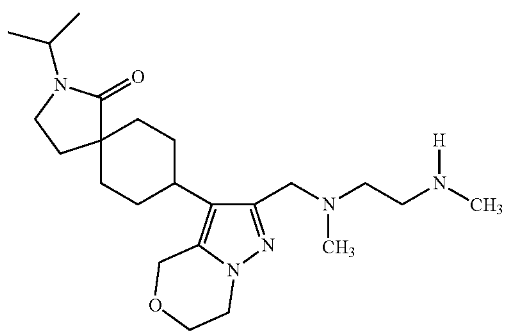 [SMILES: CNCCN(C)Cc1nn2c(c1C1CCC3(CC1)CCN(C(C)C)C3=O)COCC2] | 2-Isopropyl-8-(2-((methyl(2-(methylamino)ethyl)amino)methyl)-6,7-dihydro-4H-pyrazolo[5,1-c][1,4]oxazin-3-yl)-2-azaspiro[4.5]decan-1-one | 417/418 | 9 |
| 43 | 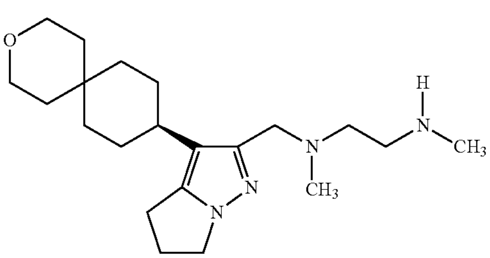 | $N^1$-((3-(3-oxaspiro[5.5]undecan-9-yl)-5,6-dihydro-4H-pyrrolo[1,2-b]pyrazol-2-yl)methyl)-$N^1$,$N^2$-dimethylethane-1,2-diamine | 360/361 | 1 |
| 44 | 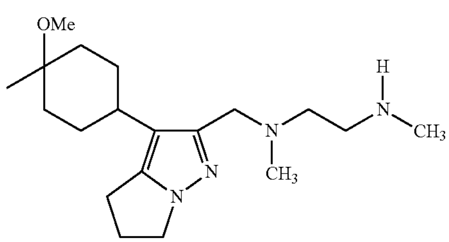 | $N^1$-((3-(4-methoxy-4-methylcyclohexyl)-5,6-dihydro-4H-pyrrolo[1,2-b]pyrazol-2-yl)methyl)-$N^1$,$N^2$-dimethylethane-1,2-diamine | 334/335 | 1 |
| 45 | 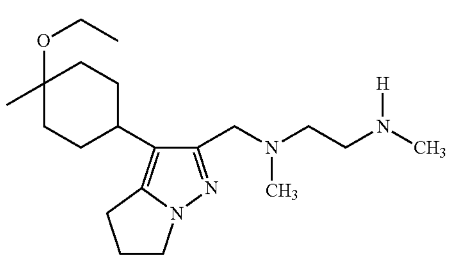 | $N^1$-((3-(4-ethoxy-4-methylcyclohexyl)-5,6-dihydro-4H-pyrrolo[1,2-b]pyrazol-2-yl)-methyl)-$N^1$,$N^2$-dimethylethane-1,2-diamine | 348/349 | 1 |

TABLE 1-continued

Example compounds 11-61.

| Ex | Structure | IUPAC Name | MWt/ [M + H] | Ex. Method |
|---|---|---|---|---|
| 46 | 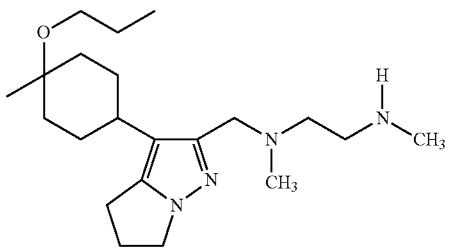 | N¹,N²-dimethyl-N¹-((3-(4-methyl-4-propoxycyclohexyl)-5,6-dihydro-4H-pyrrolo[1,2-b]pyrazol-2-yl)methyl)ethane-1,2-diamine | 362/363 | 1 |
| 47 | 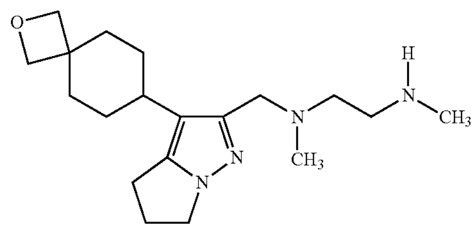 [SMILES: CNCCN(C)Cc1nn2c(c1C1CCC3(CC1)COC3)CCC2] | N¹-((3-(2-oxaspiro[3.5]nonan-7-yl)-5,6-dihydro-4H-pyrrolo[1,2-b]pyrazol-2-yl)-methyl)-N¹,N²-dimethylethane-1,2-diamine | 332/333 | 1 |
| 48 | 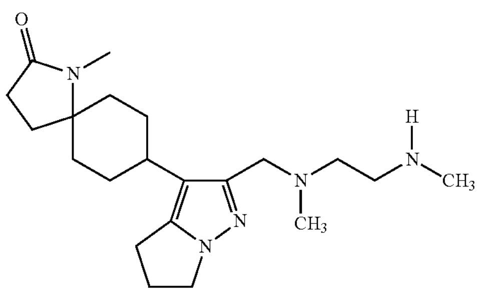 [SMILES: CNCCN(C)Cc1nn2c(c1C1CCC3(CCC(=O)N3C)CC1)CCC2] | 1-Methyl-8-(2-((methyl(2-(methylamino)ethyl)amino)methyl)-5,6-dihydro-4H-pyrrolo[1,2-b]pyrazol-3-yl)-1-azaspiro[4.5]decan-2-one | 373/374 | 9 |
| 49 | 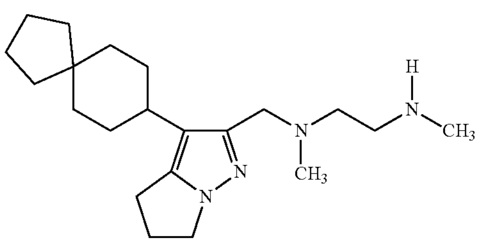 [SMILES: CNCCN(C)Cc1nn2c(c1C1CCC3(CCCC3)CC1)CCC2] | N¹,N²-dimethyl-N¹-((3-(spiro[4.5]decan-8-yl)-5,6-dihydro-4H-pyrrolo[1,2-b]pyrazol-2-yl)methyl)ethane-1,2-diamine | 344/345 | 1 |
| 50 | 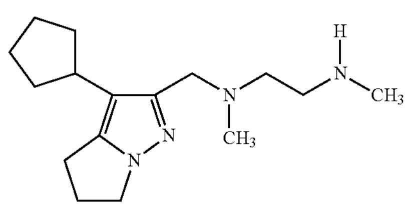 [SMILES: CNCCN(C)Cc1nn2c(c1C1CCCC1)CCC2] | N¹-((3-cyclopentyl-5,6-dihydro-4H-pyrrolo[1,2-b]pyrazol-2-yl)methyl)-N¹,N²-dimethylethane-1,2-diamine | 276/277 | 1 |
| 51 | 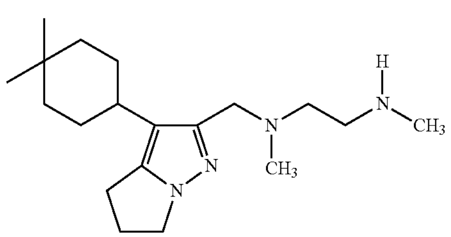 | N¹-((3-(4,4-dimethylcyclohexyl)-5,6-dihydro-4H-pyrrolo[1,2-b]pyrazol-2-yl)methyl)-N¹N²-dimethylethane-1,2-diamine | 318/319 | 1 |

TABLE 1-continued

Example compounds 11-61.

| Ex | Structure | IUPAC Name | MWt/ [M + H] | Ex. Method |
|---|---|---|---|---|
| 52 | 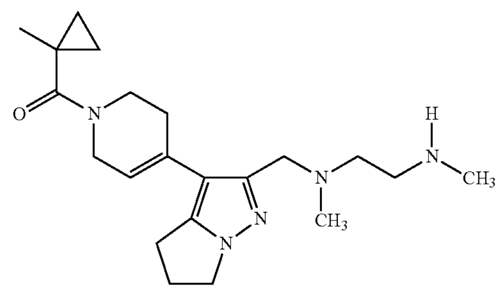 [SMILES: CNCCN(C)Cc1nn2c(c1C1=CCN(C(=O)C3(C)CC3)CC1)CCC2] | (4-(2-((Methyl(2-(methylamino)ethyl)amino)methyl)-5,6-dihydro-4H-pyrrolo[1,2-b]pyrazol-3-yl)-3,6-dihydropyridin-1(2H)-yl)(1-methylcyclopropyl)-methanone | 373/374 | 1 |
| 53 | 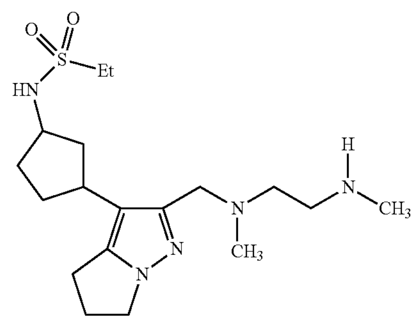 [SMILES: CCS(=O)(=O)NC1CCC(c2c(CN(C)CCNC)nn3c2CCC3)C1] | N-(3-(2-((methyl(2-(methylamino)ethyl)-amino)methyl)-5,6-dihydro-4H-pyrrolo[1,2-b]pyrazol-3-yl)-cyclopentyl)ethanesulfonamide | 383/384 | 1 |
| 54 | 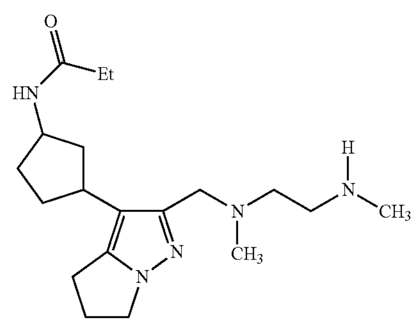 [SMILES: CCC(=O)NC1CCC(c2c(CN(C)CCNC)nn3c2CCC3)C1] | N-(3-(2-((methyl(2-(methylamino)ethyl)-amino)methyl)-5,6-dihydro-4H-pyrrolo[1,2-b]pyrazol-3-yl)-cyclopentyl)-propionamide | 347/348 | 1 |
| 55 | 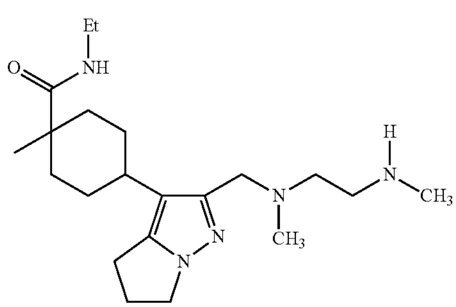 | N-ethyl-1-methyl-4-(2-((methyl(2-(methylamino)ethyl)amino)methyl)-5,6-dihydro-4H-pyrrolo[1,2-b]pyrazol-3-yl)cyclohexane-1-carboxamide | 375/376 | 1 |
| 56 | 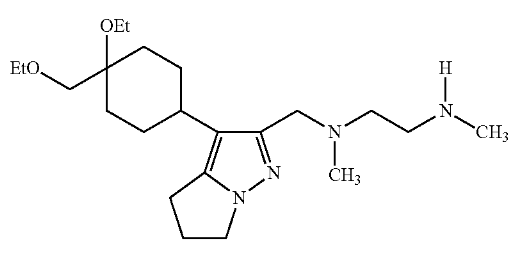 [SMILES: CCOCC1(OCC)CCC(c2c(CN(C)CCNC)nn3c2CCC3)CC1] | $N^1$-((3-(4-ethoxy-4-(ethoxymethyl)cyclohexyl)-5,6-dihydro-4H-pyrrolo[1,2-b]pyrazol-2-yl)methyl)-$N^1$,$N^2$-dimethylethane-1,2-diamine | 378/379 | 1 |

TABLE 1-continued

Example compounds 11-61.

| Ex | Structure | IUPAC Name | MWt/ [M + H] | Ex. Method |
|---|---|---|---|---|
| 57 | 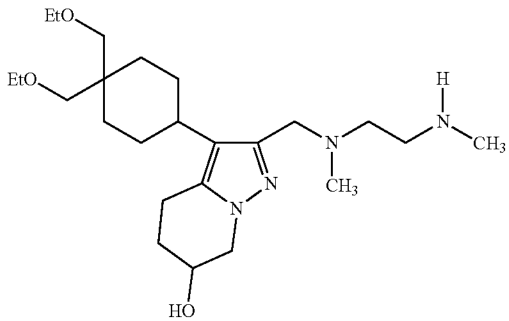 [SMILES: CCOCC1(COCC)CCC(c2c(CN(C)CCNC)nn3c2CCC(O)C3)CC1] | 3-(4,4-bis(Ethoxymethyl)cyclohexyl)-2-((methyl(2-(methylamino)ethyl)amino)methyl)-4,5,6,7-tetrahydropyrazolo[1,5-a]pyridin-6-ol | 436/437 | 2 |
| 58 | 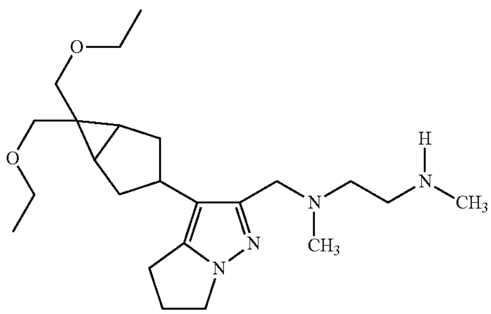 [SMILES: CCOCC1(COCC)C2CC(c3c(CN(C)CCNC)nn4c3CCC4)CC21] | $N^1$-((3-(6,6-bis(ethoxymethyl)bicyclo[3.1.0]hexan-3-yl)-5,6-dihydro-4H-pyrrolo[1,2-b]pyrazol-2-yl)methyl)-$N^1$,$N^2$-dimethylethane-1,2-diamine | 404/405 | 1 |
| 59 | 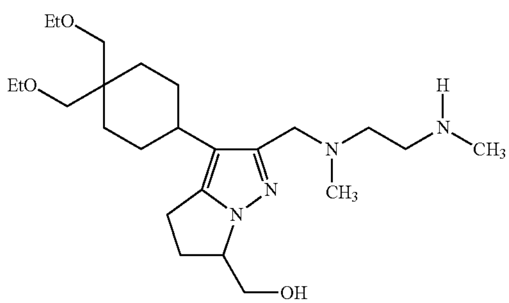 [SMILES: CCOCC1(COCC)CCC(c2c(CN(C)CCNC)nn3c2CCC3CO)CC1] | (3-(4,4-bis(Ethoxymethyl)cyclohexyl)-2-((methyl(2-(methylamino)ethyl)amino)methyl)-5,6-dihydro-4H-pyrrolo[1,2-b]pyrazol-6-yl)methanol | 436/437 | 2 |
| 60 | 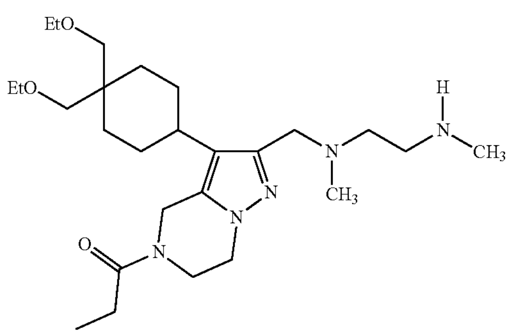 [SMILES: CCOCC1(COCC)CCC(c2c(CN(C)CCNC)nn3c2CN(C(=O)CC)CC3)CC1] | 1-(3-(4,4-bis(Ethoxymethyl)cyclohexyl)-2-((methyl(2-(methylamino)ethyl)amino)methyl)-6,7-dihydropyrazolo[1,5-a]pyrazin-5(4H)-yl)-propan-1-one | 477/478 | 2 |

TABLE 1-continued

Example compounds 11-61.

| Ex | Structure | IUPAC Name | MWt/ [M + H] | Ex. Method |
|---|---|---|---|---|
| 61 | 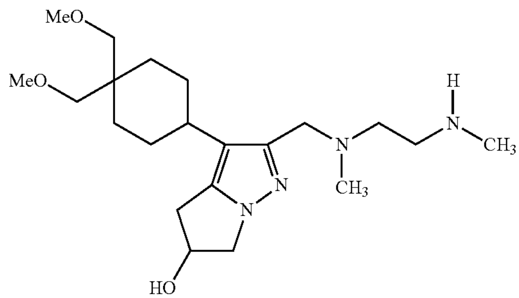 [SMILES: CNCCN(C)Cc1nn2c(c1C1CCC(COC)(COC)CC1)CC(O)C2] | 3-(4,4-bis(Methoxymethyl)cyclohexyl)-2-((methyl(2-(methylamino)ethyl)amino)methyl)-5,6-dihydro-4H-pyrrolo[1,2-b]pyrazol-5-ol | 422/423 | 2 |

The following Example compounds were prepared using the methods disclosed above. Compounds were separated into individual diastereomers; the configuration of individual diastereomers was not assigned.

TABLE 2

Example compounds 62a/b to 77a/b

| Ex | Structure | IUPAC Name | MWt/ [M + H] | Ex. Method |
|---|---|---|---|---|
| 62 a/b | 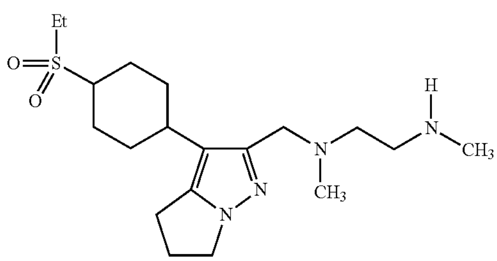 [SMILES: CCS(=O)(=O)C1CCC(c2c(CN(C)CCNC)nn3c2CCC3)CC1] | $N^1$-((3-(4-(ethyl-sulfonyl)cyclohexyl)-5,6-dihydro-4H-pyrrolo[1,2-b]pyrazol-2-yl)methyl)-$N^1$,$N^2$-dimethylethane-1,2-diamine | 382/383 | 1 |
| 63 a/b | 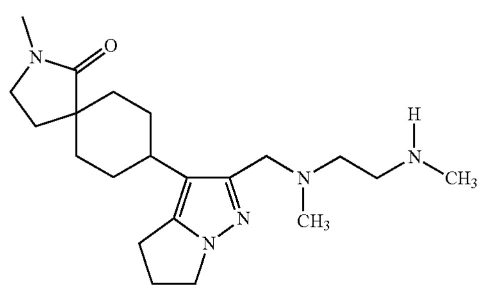 [SMILES: CNCCN(C)Cc1nn2c(c1C1CCC3(CC1)CCN(C)C3=O)CCC2] | 2-Methyl-8-(2-((methyl(2-(methyl-amino)ethyl)amino)-methyl)-5,6-dihydro-4H-pyrrolo[1,2-b]-pyrazol-3-yl)-2-aza-spiro[4.5]decan-1-one | 373/374 | 9 |
| 64 a/b | 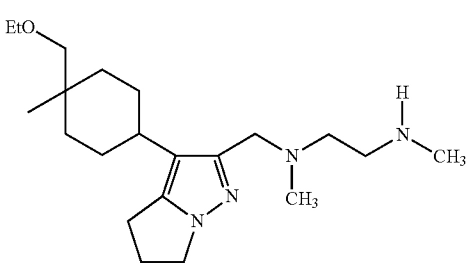 | $N^1$-((3-(4-(ethoxy-methyl)-4-methyl-cyclohexyl)-5,6-dihydro-4H-pyrrolo-[1,2-b]pyrazol-2-yl)-methyl)-$N^1$,$N^2$-dimethylethane-1,2-diamine | 362/363 | 6 |

TABLE 2-continued

Example compounds 62a/b to 77a/b

| Ex | Structure | IUPAC Name | MWt/ [M + H] | Ex. Method |
|---|---|---|---|---|
| 65 a/b | 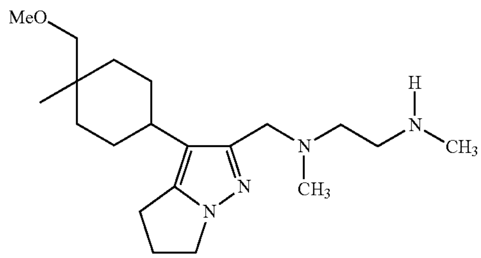 | N¹-((3-(4-(methoxy-methyl)-4-methyl-cyclohexyl)-5,6-dihydro-4H-pyrrolo-[1,2-b]pyrazol-2-yl)-methyl)-N¹,N²-dimethylethane-1,2-diamine | 348/ 349 | 6 |
| 66 a/b | 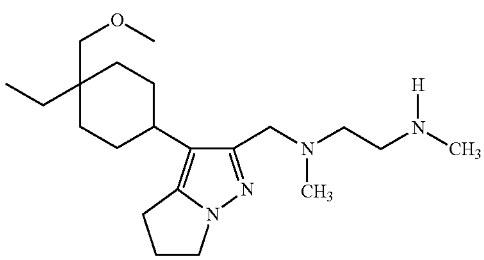 [SMILES: CCC1(COC)CCC(c2c(CN(C)CCNC)nn3c2CCC3)CC1] | N¹-((3-(4-ethyl-4-(methoxymethyl)-cyclohexyl)-5,6-dihydro-4H-pyrrolo-[1,2-b]pyrazol-2-yl)methyl)-N¹,N²-dimethylethane-1,2-diamine | 362/ 363 | 1 |
| 67 a/b | 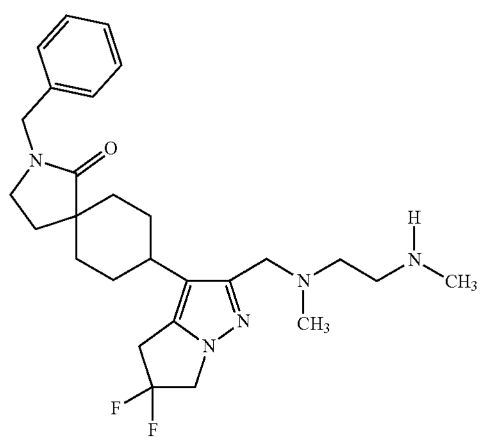 [SMILES: CNCCN(C)Cc1nn2c(c1C1CCC3(CC1)CCN(Cc1ccccc1)C3=O)CC(F)(F)C2] | 2-Benzyl-8-(5,5-difluoro-2-((methyl(2-(methylamino)ethyl)-amino)methyl)-5,6-dihydro-4H-pyrrolo-[1,2-b]pyrazol-3-yl)-2-azaspiro[4.5]decan-1-one | 485/ 486 | 9 |
| 68 a/b | 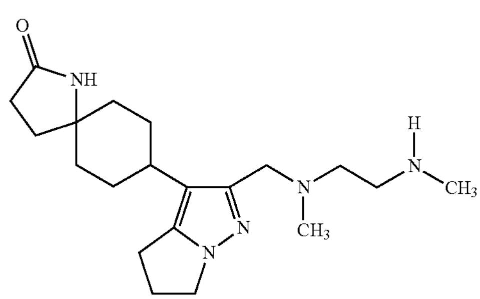 [SMILES: CNCCN(C)Cc1nn2c(c1C1CCC3(CCC(=O)N3)CC1)CCC2] | 8-(2-((Methyl(2-(methylamino)ethyl)-amino)methyl)-5,6-dihydro-4H-pyrrolo-[1,2-b]pyrazol-3-yl)-1-azaspiro[4.5]decan-2-one | 359/ 360 | 9 |
| 69 a/b | 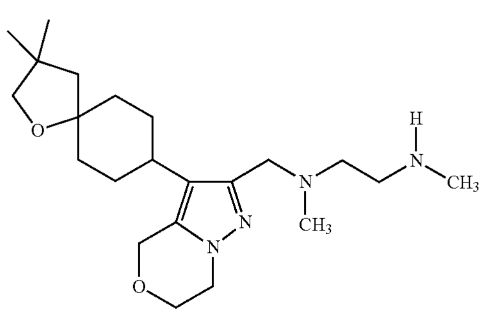 | N¹-((3-(3,3-dimethyl-1-oxaspiro[4.5]decan-8-yl)-6,7-dihydro-4H-pyrazolo[5,1-c][1,4]-oxazin-2-yl)methyl)-N¹,N²-dimethylethane-1,2-diamine | 390/ 391 | 3 |

TABLE 2-continued

Example compounds 62a/b to 77a/b

| Ex | Structure | IUPAC Name | MWt/ [M + H] | Ex. Method |
|---|---|---|---|---|
| 70 a/b | 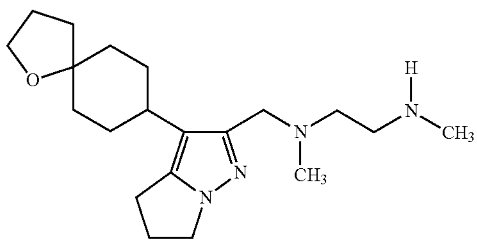 [SMILES: CNCCN(C)Cc1nn2c(c1C1CCC3(CCCO3)CC1)CCC2] | $N^1$-((3-(1-oxaspiro-[4.5]decan-8-yl)-5,6-dihydro-4H-pyrrolo-[1,2-b]pyrazol-2-yl)-methyl)-$N^1$,$N^2$-dimethylethane-1,2-diamine | 346/ 347 | 3 |
| 71 a/b | 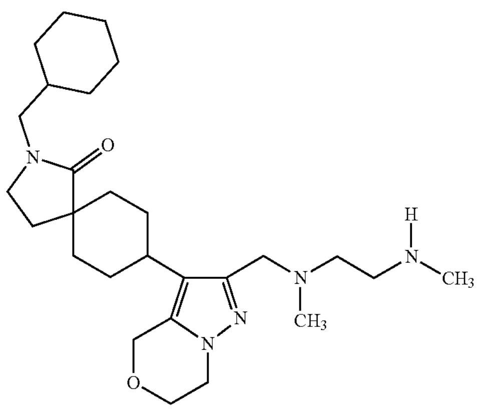 [SMILES: CNCCN(C)Cc1nn2c(c1C1CCC3(CC1)CCN(CC1CCCCC1)C3=O)COCC2] | 2-(Cyclohexylmethyl)-8-(2-((methyl(2-(methylamino)ethyl)-amino)methyl)-6,7-dihydro-4H-pyrazolo[5,1-c][1,4]oxazin-3-yl)-2-azaspiro[4.5]-decan-1-one | 471/ 472 | 9 |
| 72 a/b | 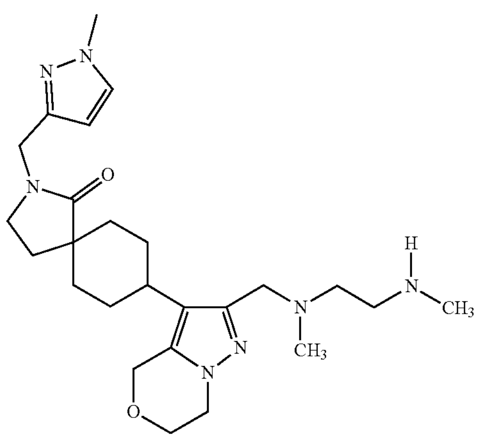 [SMILES: CNCCN(C)Cc1nn2c(c1C1CCC3(CC1)CCN(Cc1ccn(C)n1)C3=O)COCC2] | 8-(2-((Methyl(2-(methylamino)ethyl)-amino)methyl)-6,7-dihydro-4H-pyrazolo-[5,1-c][1,4]oxazin-3-yl)-2-((1-methyl-1H-pyrazol-3-yl)methyl)-2-azaspiro[4.5]decan-1-one | 469/ 470 | 9 |
| 73 a/b | 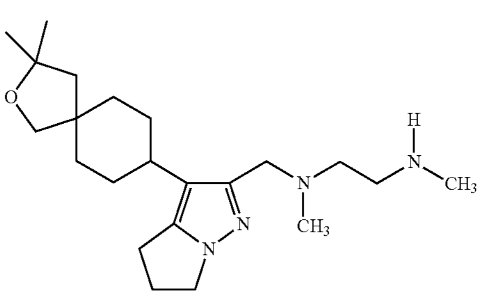 | $N^1$-((3-(3,3-dimethyl-2-oxaspiro[4.5]decan-8-yl)-5,6-dihydro-4H-pyrrolo[1,2-b]pyrazol-2-yl)methyl)-$N^1$,$N^2$-dimethylethane-1,2-diamine | 374/ 375 | 3 |

TABLE 2-continued

Example compounds 62a/b to 77a/b

| Ex | Structure | IUPAC Name | MWt/ [M + H] | Ex. Method |
|---|---|---|---|---|
| 74 a/b | 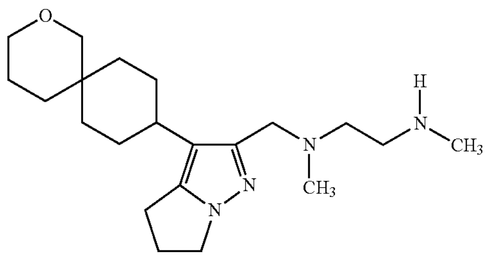 [SMILES: CNCCN(C)Cc1nn2c(c1C1CCC3(CCCOC3)CC1)CCC2] | N$^1$-((3-(2-oxaspiro-[5.5]undecan-9-yl)-5,6-dihydro-4H-pyrrolo[1,2-b]pyrazol-2-yl)methyl)-N$^1$,N$^2$-dimethylethane-1,2-diamine | 360/ 361 | 1 |
| 75 a/b | 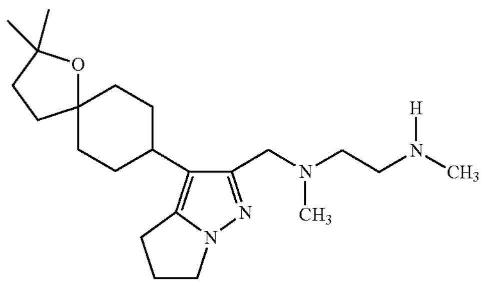 | N$^1$-((3-(2,2-dimethyl-1-oxaspiro[4.5]decan-8-yl)-5,6-dihydro-4H-pyrrolo[1,2-b]pyrazol-2-yl)methyl)-N$^1$,N$^2$-dimethylethane-1,2-diamine | 374/ 375 | 3 |
| 76 a/b | 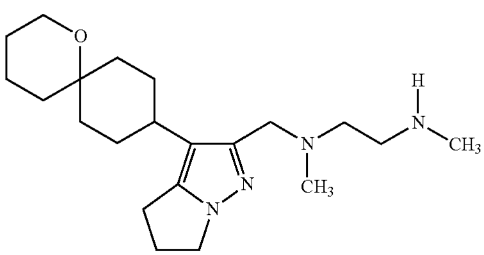 [SMILES: CNCCN(C)Cc1nn2c(c1C1CCC3(CCCCO3)CC1)CCC2] | N$^1$-((3-(1-oxaspiro-[5.5]undecan-9-yl)-5,6-dihydro-4H-pyrrolo[1,2-b]pyrazol-2-yl)methyl)-N$^1$,N$^2$-dimethylethane-1,2-diamine | 360/ 361 | 1 |
| 77 a/b | 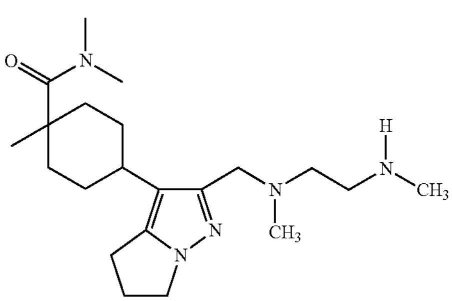 [SMILES: CNCCN(C)Cc1nn2c(c1C1CCC(C)(C(=O)N(C)C)CC1)CCC2] | (1r,4r)-N,N,1-trimethyl-4-(2-((methyl-(2-(methylamino)-ethyl)amino)methyl)-5,6-dihydro-4H-pyrrolo[1,2-b]pyrazol-3-yl)cyclohexane-1-carboxamide | 375/ 376 | 1 |

Example 78 a/b

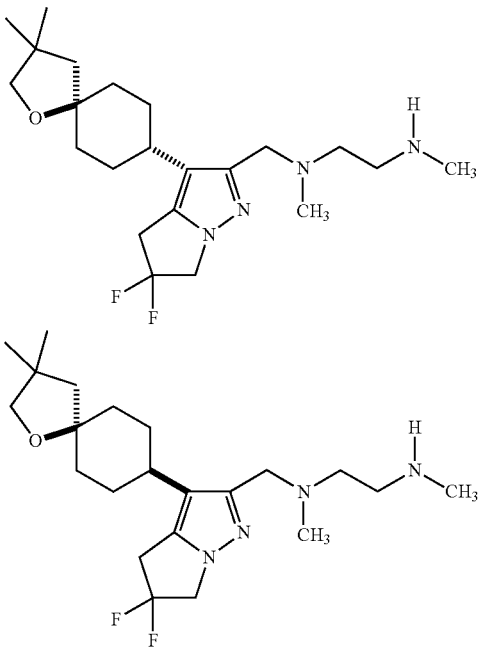

N¹-((3-((5r,8r)-3,3-dimethyl-1-oxaspiro[4.5]decan-8-yl)-5,5-difluoro-5,6-dihydro-4H-pyrrolo[1,2-b]pyrazol-2-yl)methyl)-N¹,N²-dimethylethane-1,2-diamine and N¹-((3-((5s,8s)-3,3-dimethyl-1-oxaspiro[4.5]decan-8-yl)-5,5-difluoro-5,6-dihydro-4H-pyrrolo[1,2-b]pyrazol-2-yl)methyl)-N¹,N²-dimethylethane-1,2-diamine

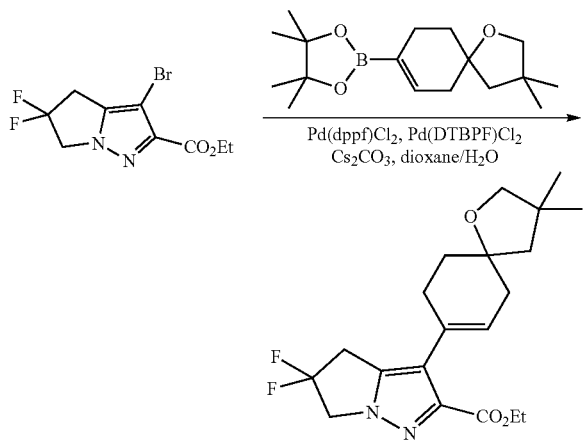

Ethyl-3-(3,3-dimethyl-1-oxaspiro[4.5]dec-7-en-8-yl)-5,5-difluoro-5,6-dihydro-4H-pyrrolo[1,2-b]pyrazole-2-carboxylate To a mixture of ethyl 3-bromo-5,5-difluoro-5,6-dihydro-4H-pyrrolo[1,2-b]pyrazole-2-carboxylate (Intermediate A, Step 7; 1.5 g, 5.08 mmol), Intermediate N (1.49 g, 5.08 mmol, 1 eq) and Cs$_2$CO$_3$ (4.97 g, 15.25 mmol, 3 eq) in dioxane (30 mL) and H$_2$O (6 mL) were added Pd(dppf)Cl$_2$ (372 mg, 508.34 mol, 0.1 eq) and ditert-butyl(cyclopentyl)phosphane-dichloropalladium-iron (331 mg, 508 μmol, 0.1 eq). The mixture was purged and degassed with N$_2$ for three times, heated to 90° C. and stirred for 16 hr. The reaction was then diluted with EtOAc (100 mL), dried (Na$_2$SO$_4$), filtered and concentrated under reduced pressure. The residue was purified by SiO$_2$ gel chromatography (PE:EtOAc=50:1 to 10:1) to give the title compound (1.35 g, 3.55 mmol, 70% yield) as a yellow solid. MS (ES$^+$) C$_{20}$H$_{26}$F$_2$N$_2$O$_3$ requires: 380, found: 381 [M+H]$^+$

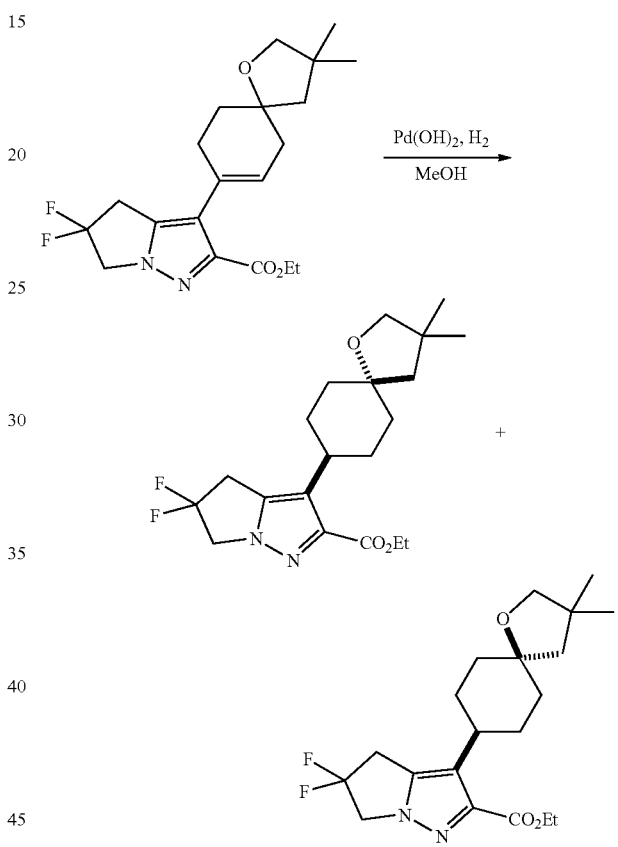

Ethyl-3-((5r,8r)-3,3-dimethyl-1-oxaspiro[4.5]decan-8-yl)-5,5-difluoro-5,6-dihydro-4H-pyrrolo[1,2-b]pyrazole-2-carboxylate (Compound 78-2a) and ethyl-3-((5s,8s)-3,3-dimethyl-1-oxaspiro[4.5]decan-8-yl)-5,5-difluoro-5,6-dihydro-4H-pyrrolo[1,2-b]pyrazole-2-carboxylate (Compound 78-2b). A Parr reaction vessel was charged with the product from the previous step (1.35 g, 3.55 mmol), Pd/C (200 mg, 10% weight), Pd(OH)$_2$/C (200 mg, 10% weight) and MeOH (20 mL). The suspension was degassed under vacuum and with N$_2$ three times, purged with H$_2$ and stirred under an atmosphere of H$_2$ (15 Psi) at 20° C. for 16 hr in a Parr shaker. The reaction mixture was then purged with N$_2$, filtered through a pad of Celite and concentrated under reduced pressure to give the title compound. The residue was purified by prep-HPLC (column: Phenomenex Synergi Max-RP 250*50 mm*10 um; mobile phase: [water(0.1% TFA)-ACN]; B %: 45ACN %-75ACN %, 31 min, 56% min) to afford two distinct stereoisomer products of undefined stereochemistry as white solids.

Compound 78-2a: 370 mg, 962 mol, 35% yield; $^1$H NMR (400 MHz, CDCl$_3$) δ 4.52 (t, J=12.8 Hz, 2H), 4.41 (q, J=7.2 Hz, 2H), 3.54-3.48 (m, 4H), 3.22-3.16 (m, 1H), 2.00-1.98 (m, 2H), 1.85-1.82 (m, 2H), 1.68-1.62 (m, 4H), 1.41 (t, J=7.2 Hz, 3H), 1.34-1.23 (m, 2H), 1.13 (s, 6H). MS (ES$^+$) C$_{20}$H$_{28}$F$_2$N$_2$O$_3$, requires: 382, found: 383 [M+H]$^+$.

Compound 78-2b: 550 mg, 1.42 mmol, 40% yield; $^1$H NMR (400 MHz, CDCl$_3$) δ 4.50 (t, J=12.8 Hz, 2H), 4.40 (q, J=7.2 Hz, 2H), 3.56 (t, J=13.6 Hz, 2H), 3.50 (s, 2H), 3.20-3.14 (m, 1H), 1.93-1.89 (m, 2H), 1.77-1.73 (m, 2H), 1.70-1.63 (m, 2H), 1.55 (s, 2H), 1.54-1.46 (m, 2H), 1.41 (t, J=7.2 Hz, 3H), 1.10 (s, 6H). MS (ES$^+$) C$_{20}$H$_{28}$F$_2$N$_2$O$_3$, requires: 382, found: 383 [M+H]$^+$.

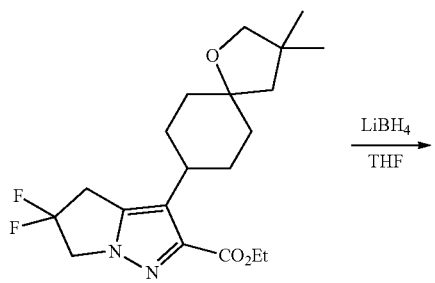

(3-(3,3-dimethyl-1-oxaspiro[4.5]decan-8-yl)-5,5-difluoro-5,6-dihydro-4H-pyrrolo[1,2-b]pyrazol-2-yl)methanol (Compound 78-3a) To a solution of Compound 78-2a (150 mg, 392.21 μmol) in THF (5 mL) at 20° C. was added LiBH$_4$ (17.09 mg, 784.43 mol, 2 eq). The resulting mixture was heated to 40° C. and stirred for 16 hr, then quenched by the addition of saturated aq. NH$_4$Cl solution (10 mL) and extracted with EtOAc (10 mL×3). The combined organic layers were dried (Na$_2$SO$_4$), filtered and concentrated under reduced pressure to give the title compound (140 mg, crude) as a white solid. MS (ES$^+$) C$_{18}$H$_{26}$F$_2$N$_2$O$_2$ requires: 340, found: 341 [M+H]$^+$

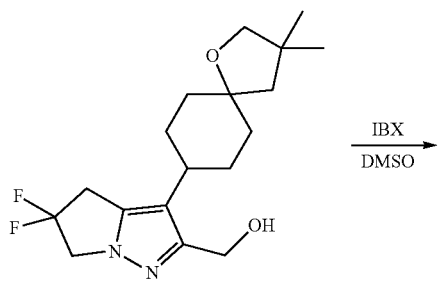

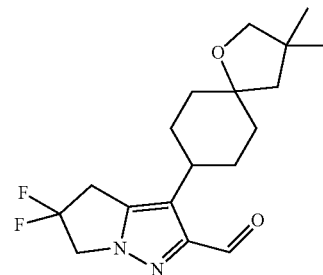

3-(3,3-Dimethyl-1-oxaspiro[4.5]decan-8-yl)-5,5-difluoro-5,6-dihydro-4H-pyrrolo[1,2-b]pyrazole-2-carbaldehyde (Compound 78-4a). To a solution of Compound 78-3a (140 mg, 411.27 μmol) in DMSO (5 mL) at 20° C. was added IBX (230.33 mg, 822.54 mol, 2 eq). The resulting mixture was stirred for 1 h, then partitioned between water (15 mL) and EtOAc (10 mL). The organic layer was washed with brine (10 mL), dried (Na$_2$SO$_4$), filtered and concentrated under reduced pressure to give the title compound (140 mg) as a white solid. MS (ES$^+$) C$_{18}$H$_{24}$F$_2$N$_2$O$_2$ requires: 338, found: 339 [M+H]$^+$

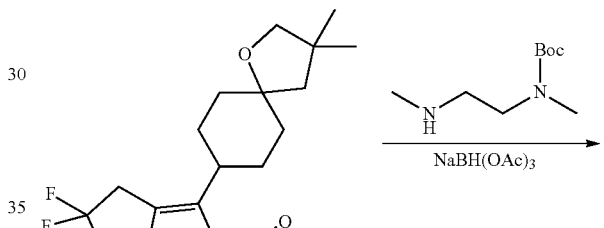

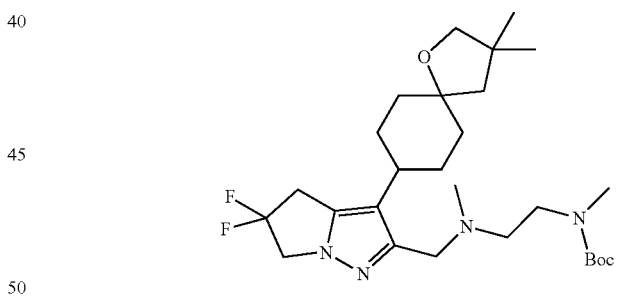

Tert-butyl-(2-(((3-(3,3-dimethyl-1-oxaspiro[4.5]decan-8-yl)-5,5-difluoro-5,6-dihydro-4H-pyrrolo[1,2-b]pyrazol-2-yl)methyl)(methyl)amino)ethyl)(methyl)carbamate (Compound 78-5a). A mixture of Compound 78-4a (140 mg, 413.72 μmol) and tert-butyl N-methyl-N-[2-(methylamino)ethyl]carbamate (77.89 mg, 413.72 mol, 1 eq) in DCE (5 mL) was stirred at 20° C. for 0.5 h. Then AcOH (2.48 mg, 41.37 μmol 0.1 eq) and NaBH(OAc)$_3$ (175.37 mg, 827.45 mol, 2 eq) were added and the resulting mixture was stirred at 20° C. for 11.5 hrs. The reaction was diluted with DCM (40 mL), washed with saturated aq. NaHCO$_3$ (10 mL) and brine (10 mL), dried (Na$_2$SO$_4$), filtered and concentrated under reduced pressure to give the title compound (200 mg, crude) as a yellow oil. MS (ES$^+$) C$_{27}$H$_{44}$F$_2$N$_4$O$_3$ requires: 510, found: 511 [M+H]$^+$

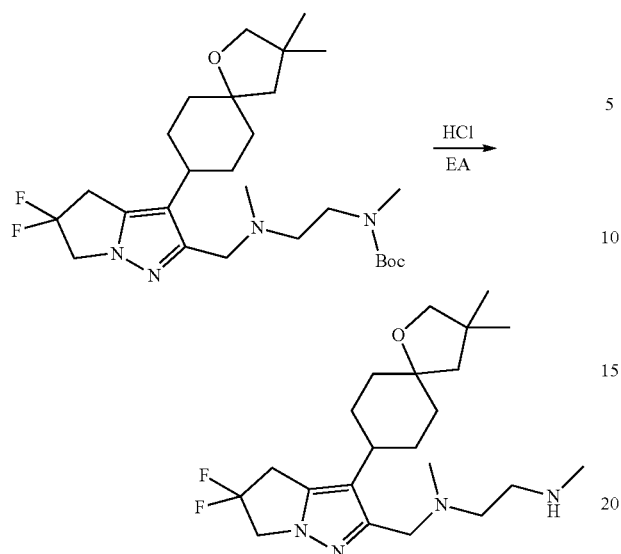

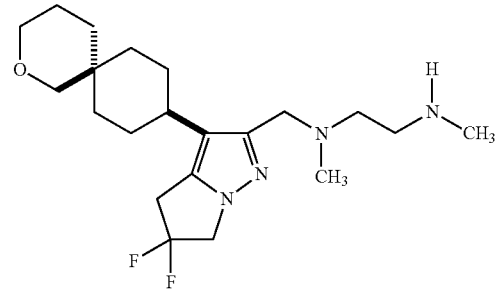

N[1]-((5,5-difluoro-3-((6r,9r)-2-oxaspiro[5.5]undecan-9-yl)-5,6-dihydro-4H-pyrrolo[1,2-b]pyrazol-2-yl)methyl)-N[1],N[2]-dimethylethane-1,2-diamine and N[1]-((5,5-difluoro-3-((6s,9s)-2-oxaspiro[5.5]undecan-9-yl)-5,6-dihydro-4H-pyrrolo[1,2-b]pyrazol-2-yl)methyl)-N[1],N[2]-dimethylethane-1,2-diamine Compound 78a. To a solution of Compound 78-5a (200 mg, 391.65 μmol) in EtOAc (2 mL) was added HCl (4 M in EtOAc, 2 mL, 20.43 eq) at 20° C. The mixture was stirred at 20° C. for 1 h, then concentrated under reduced pressure. The residue was purified by prep-HPLC (column: Phenomenex Synergi C18 150*25*10 um; mobile phase: [water (0.1% TFA)-ACN]; B %: 18%-42%, 10 min). The eluents were concentrated to remove the organic phase. The residual aqueous solution was lyophilized to afford the title compound (60 mg, 93.96 mol, 24% yield) as a white solid. $^1$H NMR (400 MHz, CD$_3$OD) δ 4.53 (t, J=12.8 Hz, 2H), 4.13 (s, 2H), 3.61-3.53 (m, 4H), 3.40-3.37 (m, 2H), 3.28-3.26 (m, 2H), 2.75-2.72 (m, 6H), 2.58-2.52 (m, 1H), 1.87-1.84 (m, 4H), 1.75 (s, 2H), 1.63-1.56 (m, 2H), 1.46-1.40 (m, 2H), 1.13 (s, 6H). MS (ES$^+$) C$_{22}$H$_{36}$F$_2$N$_4$O, requires: 410, found: 411 [M+H]$^+$.

In a similar manner, Compound 78b was obtained from Compound 78-2b using the same procedures described to obtain Compound 78a from Compound 78-2a.

Compound 78b: 90 mg, 140.94 mol, 36% yield; $^1$H NMR (400 MHz, CD$_3$OD) δ 4.53 (t, J=12.8 Hz, 2H), 4.33 (s, 2H), 3.62-3.48 (m, 8H), 2.89 (s, 3H), 2.77 (s, 3H), 2.56-2.50 (m, 1H), 1.93-1.90 (m, 2H), 1.74-1.50 (m, 8H), 1.13 (s, 6H). MS (ES$^+$) C$_{22}$H$_{36}$F$_2$N$_4$O, requires: 410, found: 411 [M+H]$^+$.

Example 79 a/b

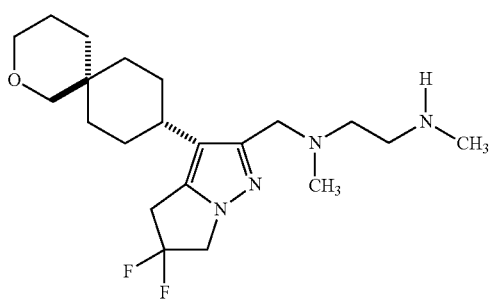

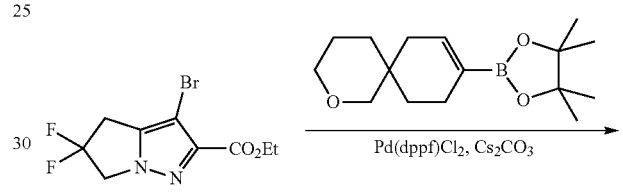

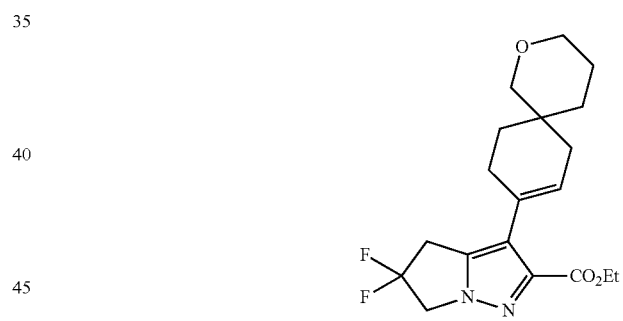

Ethyl 5,5-difluoro-3-(2-oxaspiro[5.5]undec-8-en-9-yl)-5,6-dihydro-4H-pyrrolo[1,2-b]pyrazole-2-carboxylate To a solution of ethyl 3-bromo-5,5-difluoro-5,6-dihydro-4H-pyrrolo[1,2-b]pyrazole-2-carboxylate (Intermediate A, Step 7; 1.5 g, 5.08 mmol, 1 eq) in dioxane (20 mL) and H$_2$O (4 mL) were added Intermediate O (1.94 g, 5.59 mmol, 1.1 eq), Pd(dppf)Cl$_2$ (370 mg, 0.506 mmol, 0.0995 eq) and Cs$_2$CO$_3$ (4.95 g, 15.19 mmol, 2.99 eq) under N$_2$. The mixture was stirred at 90° C. for 16 h under N$_2$, then filtered. The filtrate was dried (Na$_2$SO$_4$), filtered and concentrated under reduced pressure. The residue was purified by SiO$_2$ gel chromatography (PE to PE:EtOAc=10/1) to give the title compound (1.8 g, 4.27 mmol, 84% yield) as a yellow solid. MS (ES$^+$) C$_{19}$H$_{24}$F$_2$N$_2$O$_3$, requires: 366, found: 367 [M+H]$^+$.

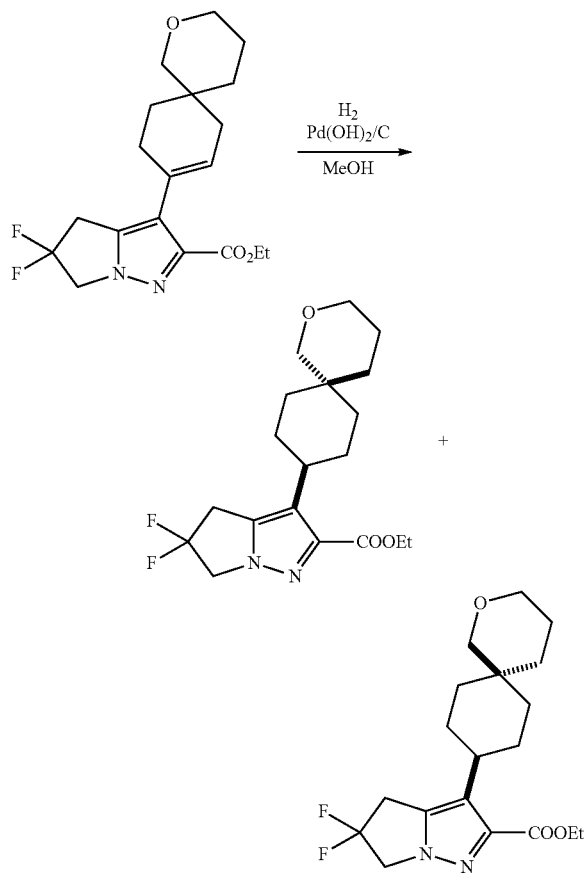

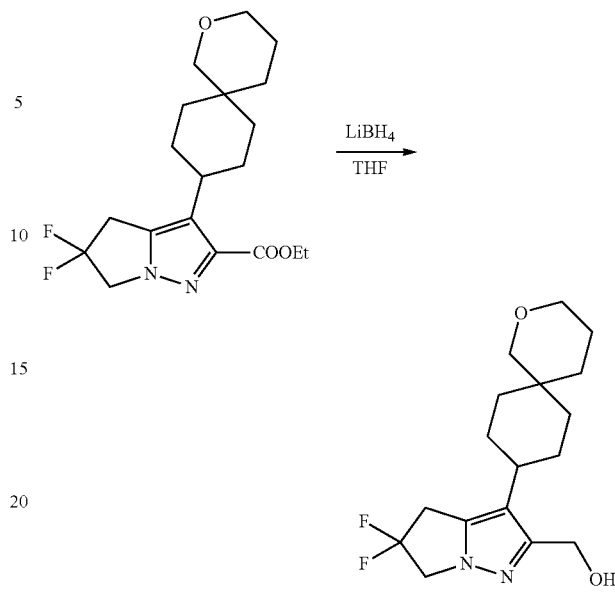

Ethyl 5,5-difluoro-3-((6r,9r)-2-oxaspiro[5.5]undecan-9-yl)-5,6-dihydro-4H-pyrrolo[1,2-b]pyrazole-2-carboxylate (Compound 79-2a) and ethyl 5,5-difluoro-3-((6s,9s)-2-oxaspiro[5.5]undecan-9-yl)-5,6-dihydro-4H-pyrrolo[1,2-b]pyrazole-2-carboxylate (Compound 79-2b). A Parr reaction vessel was charged with the product from the previous step (1.8 g, 4.27 mmol), Pd/C (300 mg, 10% weight), Pd(OH)$_2$/C (300 mg, 10% weight) and MeOH (20 mL). The suspension was degassed under vacuum and with N$_2$ three times, purged with H$_2$ and stirred under an atmosphere of H$_2$ (15 Psi) at 20° C. for 16 hr in a Parr shaker. The reaction mixture was then purged with N$_2$, filtered through a pad of Celite and concentrated under reduced pressure to give the title compound. The residue was purified by Prep-HPLC(column: Phenomenex Synergi Max-RP 250*50 mm*10 um; mobile phase: [water(0.1% TFA)-ACN]; B %: 42 ACN %-72 ACN %, 33 min, 39% min) to afford two distinct stereoisomer products of undefined stereochemistry as pale yellow oils.

Compound 79-2a: 600 mg, 1.53 mmol, 36% yield; $^1$H NMR (400 MHz, CDCl$_3$) δ 4.52 (t, J=12.8 Hz, 2H), 4.38 (q, J=7.2 Hz, 2H), 3.68-3.61 (m, 2H), 3.54 (t, J=13.6 Hz, 2H), 3.29 (s, 2H), 3.18-3.08 (m, 1H), 1.79-1.75 (m, 4H), 1.65-1.55 (m, 4H), 1.52-1.34 (m, 5H), 1.25-1.12 (m, 2H). MS (ES$^+$) C$_{19}$H$_{26}$F$_2$N$_2$O$_3$, requires: 368, found: 369 [M+H]$^+$.

Compound 79-2b: 770 mg, 2.05 mmol, 48% yield; $^1$H NMR (400 MHz, CDCl$_3$) δ 4.52 (t, J=12.4 Hz, 2H), 4.37 (q, J=7.2 Hz, 2H), 3.68-3.64 (m, 2H), 3.58-3.42 (m, 4H), 3.16-3.12 (m, 1H), 1.97-1.85 (m, 2H), 1.82-1.71 (m, 2H), 1.65-1.51 (m, 2H), 1.46-1.32 (m, 7H), 1.31-1.15 (m, 2H). MS (ES$^+$) C$_{19}$H$_{26}$F$_2$N$_2$O$_3$, requires: 368, found: 369 [M+H]$^+$.

(5,5-Difluoro-3-(2-oxaspiro[5.5]undecan-9-yl)-5,6-dihydro-4H-pyrrolo[1,2-b]pyrazol-2-yl)methanol (Compound 79-3a). To a solution of LiBH$_4$ (72.38 mg, 3.32 mmol, 2.04 eq) in THF (5 mL) at 20 C was added Compound 79-2a. The mixture was stirred at 40° C. for 5 h, then quenched at 0° C. by addition of H$_2$O (10 mL), diluted with EtOAc (30 mL) and extracted with EtOAc (30 mL×3). The combined organic layers were washed with brine (50 mL), dried (Na$_2$SO$_4$), filtered and concentrated under reduced pressure to give the title compound (520 mg, 1.50 mmol, 92% yield) as a light yellow solid. MS (ES$^+$) C$_{17}$H$_{24}$F$_2$N$_2$O$_2$, requires: 326, found: 327 [M+H]$^+$.

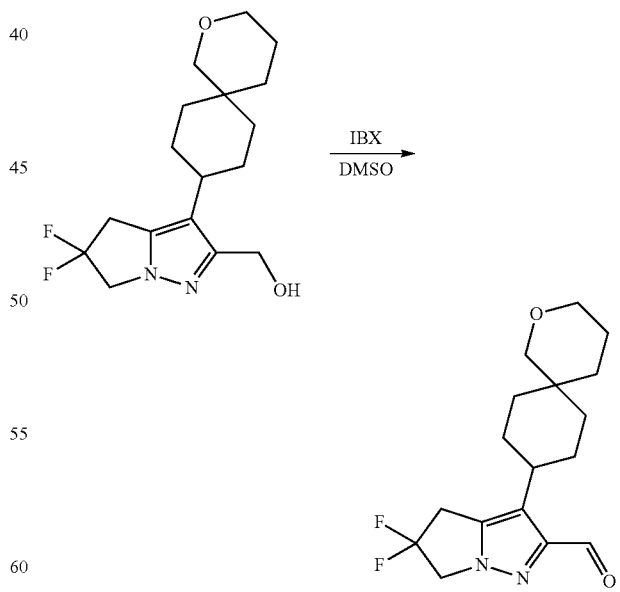

5,5-Difluoro-3-(2-oxaspiro[5.5]undecan-9-yl)-5,6-dihydro-4H-pyrrolo[1,2-b]pyrazole-2-carbaldehyde (Compound 79-4a). To a solution of Compound 79-3a (520 mg, 1.59 mmol) in DMSO (5 mL) was added IBX (900 mg, 3.21 mmol, 2.02 eq) at 25° C., and the mixture was stirred for 2 h. The reaction mixture was partitioned between brine (30 mL) and EtOAc (50 mL). The organic layer was dried (Na$_2$SO$_4$), filtered and concentrated under reduced pressure to give the title compound (510 mg, 1.54 mmol, 97% yield) was obtained as a light yellow solid. MS (ES$^+$) C$_{17}$H$_{22}$F$_2$N$_2$O$_2$, requires: 324, found: 325 [M+H]$^+$.

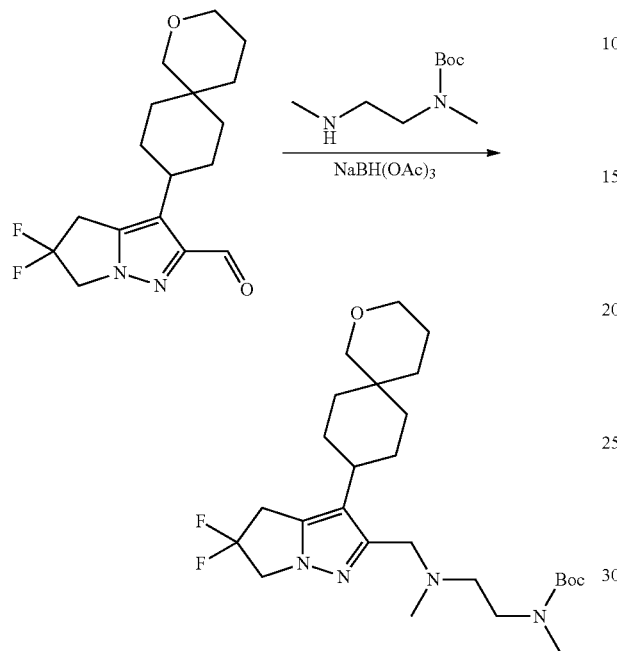

Tert-butyl (2-(((5,5-difluoro-3-(2-oxaspiro[5.5]undecan-9-yl)-5,6-dihydro-4H-pyrrolo[1,2-b]pyrazol-2-yl)methyl)(methyl)amino)ethyl)(methyl)carbamate (Compound 79-5a). To a solution of Compound 79-4a (510 mg, 1.57 mmol) in DCE (5 mL) at 25° C. was added tert-butyl N-methyl-N-[2-(methylamino)ethyl]carbamate (300 mg, 1.59 mmol, 1.01 eq). The mixture was stirred for 1 h, AcOH (52.50 mg, 0.874 mmol, 0.0556 eq) and NaBH(OAc)$_3$ (666.47 mg, 3.14 mmol, 2 eq) were added and the mixture was stirred at RT for 3 hr, then partitioned between saturated aq. NaHCO$_3$ (50 mL) and EtOAc (100 mL). The organic layer was washed with brine (50 mL), dried (Na$_2$SO$_4$), filtered and concentrated under reduced pressure to give the title compound (0.77 g, 1.38 mmol, 88% yield) as yellow oil. MS (ES$^+$) C$_{26}$H$_{42}$F$_2$N$_4$O$_3$, requires: 496, found: 497 [M+H]$^+$.

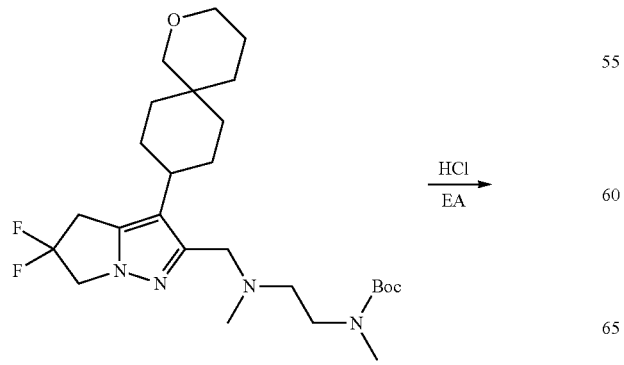

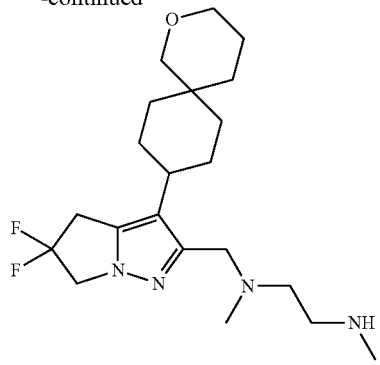

Compound 79a. To a solution of Compound 79-5a (0.77 g, 1.38 mmol, 1 eq) in MeOH (4 mL) was added HCl (4 M in MeOH, 4 mL) and the mixture was stirred at 25° C. for 2 hr, then concentrated under reduced pressure. The residue was purified by prep-HPLC (column: Phenomenex Synergi C18 150*25*10 um; mobile phase: [water(0.05% HCl)-ACN]; B %: 10%-30%, 10 min) and followed by lyophilization to give the title compound (311.8 mg, 0.657 mmol, 48% yield) as a white solid. $^1$H NMR (400 MHz, CD$_3$OD) δ 4.58 (t, J=12.8 Hz, 2H), 4.47 (s, 2H), 3.66-3.52 (m, 5H), 3.56-3.45 (m, 3H), 3.31-3.25 (m, 2H), 2.99 (s, 3H), 2.79 (s, 3H), 2.65-2.52 (m, 1H), 1.84-1.76 (m, 2H), 1.75-1.48 (m, 8H), 1.29-1.18 (m, 2H). MS (ES$^+$) C$_{21}$H$_{34}$F$_2$N$_4$O, requires: 396, found: 397 [M+H]$^+$.

In a similar manner, Compound 79b was obtained from Compound 79-2b using the same procedures described to obtain Compound 79a from Compound 79-2a.

Compound 79b: 330.3 mg, 0.682 mmol, 46% yield; $^1$H NMR (400 MHz, CD$_3$OD) δ 4.58 (t, J=12.8 Hz, 2H), 4.47 (s, 2H), 3.89-3.58 (m, 7H), 3.56-3.43 (m, 3H), 2.99 (s, 3H), 2.80 (s, 3H), 2.68-2.52 (m, 1H), 1.91-1.89 (m, 2H), 1.75-1.57 (m, 4H), 1.55-1.39 (m, 4H), 1.35-1.22 (m, 2H). MS (ES$^+$) C$_{21}$H$_{34}$F$_2$N$_4$O, requires: 396, found: 397 [M+H]$^+$.

Example 80 a/b

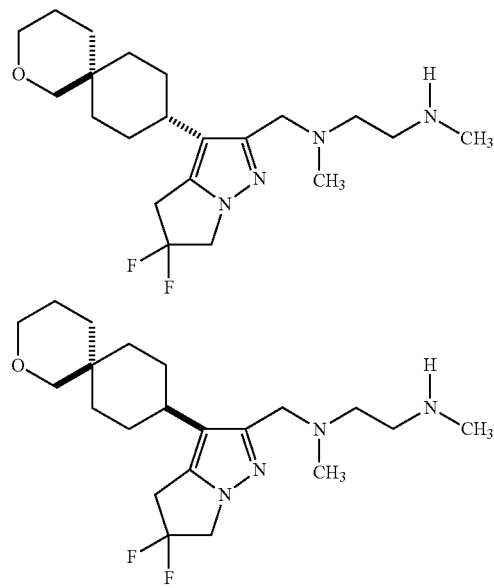

N$^1$-((5,5-difluoro-3-((6r,9r)-2-oxaspiro[5.5]undecan-9-yl)-5,6-dihydro-4H-pyrrolo[1,2-b]pyrazol-2-yl)methyl)-N$^1$,N$^2$-dimethylethane-1,2-diamine and N$^1$-((5,5-difluoro-3-((6s,9s)-2-oxaspiro[5.5]undecan-9-yl)-5,6-dihydro-4H-pyrrolo[1,2-b]pyrazol-2-yl)methyl)-N$^1$,N$^2$-dimethylethane-1,2-diamine The title compounds were obtained using the same procedures already described for Example 79a and 79b, using Intermediate P instead of Intermediate O.

Compound 80a: 35 mg; $^1$H NMR (400 MHz, CD$_3$OD) δ. 4.58 (t, J=12.8 Hz, 2H), 4.48 (s, 2H), 3.78-3.52 (m, 8H), 3.00 (s, 3H), 2.80 (s, 3H), 2.73-2.60 (m, 1H), 2.18-2.02 (m, 2H), 1.83-1.82 (m, 2H), 1.77-1.69 (m, 4H), 1.60-1.39 (m, 6H). MS (ES$^+$) C$_{21}$H$_{34}$F$_2$N$_4$O, requires: 396 found: 397 [M+H]$^+$.

Compound 80b: 100 mg; $^1$H NMR (400 MHz, CD$_3$OD) δ 4.58 (t, J=12.8 Hz, 2H), 4.48 (s, 2H), 3.83-3.48 (m, 8H), 3.00 (s, 3H), 2.80 (s, 3H), 2.67-2.66 (m, 1H), 2.12-2.08 (m, 2H), 1.73-1.51 (m, 8H), 1.50-1.31 (m, 4H). MS (ES$^+$) C$_{21}$H$_{34}$F$_2$N$_4$O, requires: 396 found: 397[M+H]$^+$.

Example 81

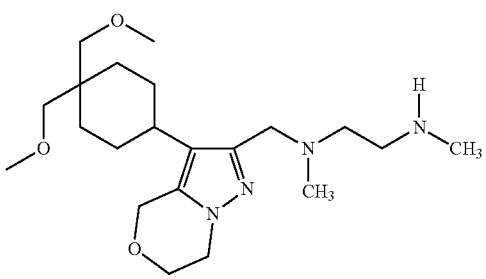

N$^1$-((3-(4,4-bis(methoxymethyl)cyclohexyl)-6,7-dihydro-4H-pyrazolo[5,1-c][1,4]oxazin-2-yl)methyl)-N$^1$,N$^2$-dimethylethane-1,2-diamine The title compound was obtained using the same procedures already described for Example 5, using Intermediate C and Intermediate H as starting materials.

Compound 81: 120 mg; $^1$H NMR (400 MHz, CD$_3$OD) δ 4.91 (s, 2H), 4.44 (s, 2H), 4.18-4.16 (m, 2H), 4.10-4.08 (m, 2H), 3.75-3.51 (m, 4H), 3.42 (s, 2H), 3.35 (s, 3H), 3.30-3.27 (m, 3H), 3.14 (s, 2H), 2.98 (s, 3H), 2.80 (s, 3H), 2.62-2.47 (m, 1H), 1.73-1.72 (m, 2H), 1.65-1.48 (m, 4H), 1.45-1.32 (m, 2H). MS (ES$^+$) C$_{21}$H$_{38}$N$_4$O$_3$, requires: 394 found: 395 [M+H]$^+$.

Example 82 a/b

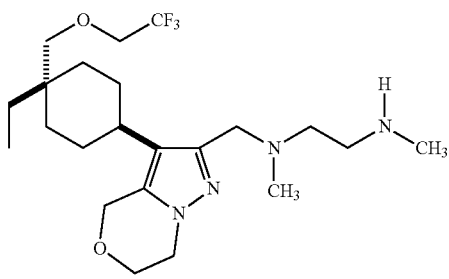

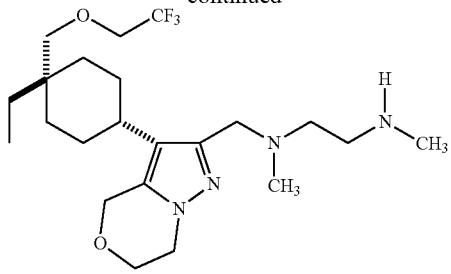

N$^1$-((3-((1r,4r)-4-ethyl-4-((2,2,2-trifluoroethoxy)methyl)cyclohexyl)-6,7-dihydro-4H-pyrazolo[5,1-c][1,4]oxazin-2-yl)methyl)-N$^1$,N$^2$-dimethylethane-1,2-diamine and N$^1$-((3-((1s,4s)-4-ethyl-4-((2,2,2-trifluoroethoxy)methyl)cyclohexyl)-6,7-dihydro-4H-pyrazolo[5,1-c][1,4]oxazin-2-yl)methyl)-N$^1$,N$^2$-dimethylethane-1,2-diamine The title compounds were obtained using the same procedures already described for Example 7a and 7b, using Intermediate C and Intermediate K as starting materials.

Compound 82a: 20 mg; $^1$H NMR (400 MHz, CD$_3$OD) δ. 4.92 (s, 2H), 4.43 (s, 2H), 4.21-4.14 (m, 2H), 4.13-4.06 (m, 2H), 3.89 (q, J=9.2 Hz, 2H), 3.70-3.48 (m, 4H), 3.34 (s, 2H), 2.96 (s, 3H), 2.80 (s, 3H), 2.59-2.46 (m, 1H), 1.69-1.50 (m, 8H), 1.49-1.36 (m, 2H), 0.86 (t, J=7.6 Hz, 3H). MS (ES$^+$) C$_{22}$H$_{37}$F$_3$N$_4$O$_2$, requires: 446 found: 447 [M+H]$^+$.

Compound 82b: 15 mg; $^1$H NMR (400 MHz, CD$_3$OD) δ 4.92 (s, 2H), 4.42 (s, 2H), 4.21-4.14 (m, 2H), 4.13-4.06 (m, 2H), 3.96 (q, J=9.2 Hz, 2H), 3.69-3.43 (m, 6H), 2.96 (s, 3H), 2.80 (s, 3H), 2.66-2.41 (m, 1H), 1.76 (d, J=13.6 Hz, 2H), 1.68-1.43 (m, 4H), 1.41-1.22 (m, 4H), 0.86 (t, J=7.6 Hz, 3H). MS (ES$^+$) C$_{22}$H$_{37}$F$_3$N$_4$O$_2$, requires: 446 found: 447 [M+H]$^+$.

Example 83 a/b

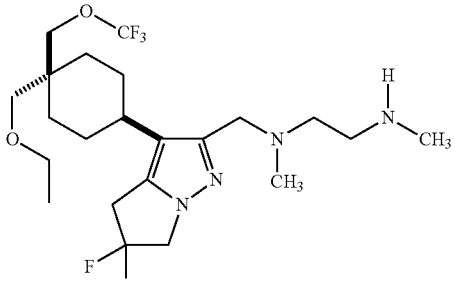

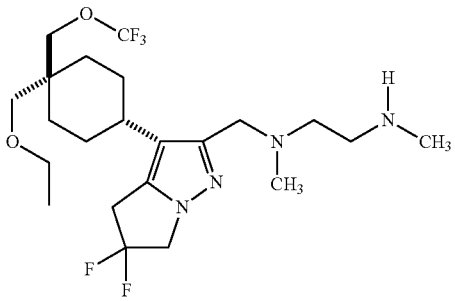

N¹-((3-((1r,4r)-4-(ethoxymethyl)-4-(3,3,3-trifluoro-propyl)cyclohexyl)-5,5-difluoro-5,6-dihydro-4H-pyrrolo[1,2-b]pyrazol-2-yl)methyl)-N¹,N²-dimethyl-ethane-1,2-diamine and N¹-((3-((1s,4s)-4-(ethoxymethyl)-4-(3,3,3-trifluoropropyl)cyclohexyl)-5,5-difluoro-5,6-dihydro-4H-pyrrolo[1,2-b]pyrazol-2-yl)methyl)-N¹,N²-dimethylethane-1,2-diamine The title compounds were obtained using the same procedures described elsewhere for Example 7a and 7b, using ethyl 3-bromo-5,5-difluoro-5,6-dihydro-4H-pyrrolo[1,2-b]pyrazole-2-carboxylate (Intermediate A, Step 7) and Intermediate L as starting materials.

Compound 83a: 32.6 mg; ¹H NMR (400 MHz, CD₃OD) δ 4.58 (t, J=12.8 Hz, 2H), 4.46 (s, 2H), 3.63-3.47 (m, 8H), 3.15 (s, 2H), 2.98 (s, 3H), 2.79 (s, 3H), 2.63-2.57 (m, 1H), 2.18-2.14 (m, 2H), 1.78-1.65 (m, 6H), 1.50-1.42 (m, 4H), 1.17 (t, J=7.2 Hz, 3H). MS (ES⁺) C₂₃H₃₇F₅N₄O, requires: 480, found: 481 [M+H]⁺.

Compound 83b: 10.3 mg; ¹H NMR (400 MHz, CD₃OD) δ 4.57 (t, J=12.8 Hz, 2H), 4.44 (s, 2H), 3.65-3.49 (m, 8H), 3.43 (s, 2H), 2.97 (s, 3H), 2.79 (s, 3H), 2.63-2.57 (m, 1H), 2.18-2.14 (m, 2H), 1.81-1.77 (m, 2H), 1.68-1.60 (m, 2H), 1.59-1.50 (m, 4H), 1.36-1.28 (m, 2H), 1.20 (t, J=6.8 Hz, 3H). MS (ES⁺) C₂₃H₃₇F₅N₄O, requires: 480, found: 481 [M+H]⁺.

Example 84

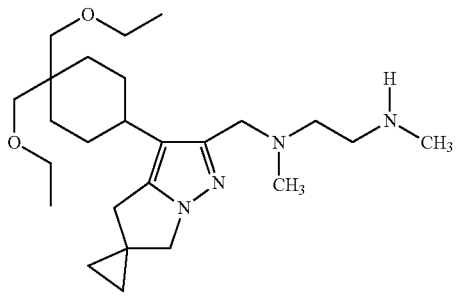 [SMILES: CCOCC1(COCC)CCC(c2c(CN(C)CCNC)nn3c2CC2(CC2)C3)CC1]

N¹-((3'-(4,4-bis(ethoxymethyl)cyclohexyl)-4'H,6'H-spiro[cyclopropane-1,5'-pyrrolo[1,2-b]pyrazol]-2'-yl)methyl)-N¹,N²-dimethylethane-1,2-diamine The title compound was obtained using the same procedures already described for Example 5, using Intermediate C-1 and Intermediate I as starting materials.

Compound 84: 57 mg; ¹H NMR (400 MHz, CD₃OD) δ 4.43 (s, 2H), 4.04 (s, 2H), 3.71-3.52 (m, 4H), 3.52-3.42 (m, 6H), 3.20 (s, 2H), 2.98-2.96 (m, 5H), 2.80 (s, 3H), 2.62-2.48 (m, 1H), 1.76-1.51 (m, 6H), 1.46-1.32 (m, 2H), 1.18-1.14 (m, 6H), 0.86 (d, J=6.4 Hz, 4H). MS (ES+) C₂₅H₄₄N₄O₂, requires: 432 found: 433 [M+H]⁺.

Example 85

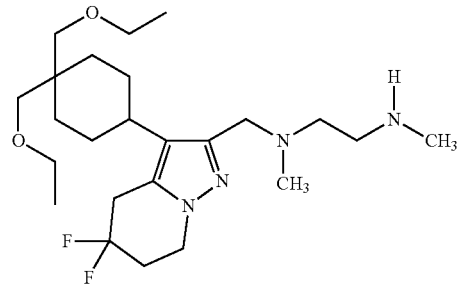 [SMILES: CCOCC1(COCC)CCC(c2c(CN(C)CCNC)nn3c2CC(F)(F)CC3)CC1]

N¹-((3-(4,4-bis(ethoxymethyl)cyclohexyl)-5,5-difluoro-4,5,6,7-tetrahydropyrazolo[1,5-a]pyridin-2-yl)methyl)-N¹,N²-dimethylethane-1,2-diamine The title compound was obtained using the same procedures already described for Example 5, using Intermediate C-3 and Intermediate I as starting materials.

Compound 85: 42.4 mg; ¹H NMR (400 MHz, CD₃OD) δ 4.45 (s, 2H), 4.34-4.32 (m, 2H), 3.77-3.36 (m, 12H), 3.20 (s, 2H), 2.99 (s, 3H), 2.80 (s, 3H), 2.56-2.53 (m, 3H), 1.77-1.60 (m, 6H), 1.40-1.30 (m, 2H), 1.22-1.14 (m, 6H). MS (ES⁺) C₂₄H₄₂F₂N₄O₂, requires: 456 found: 457 [M+H]⁺.

Example 86 a/b

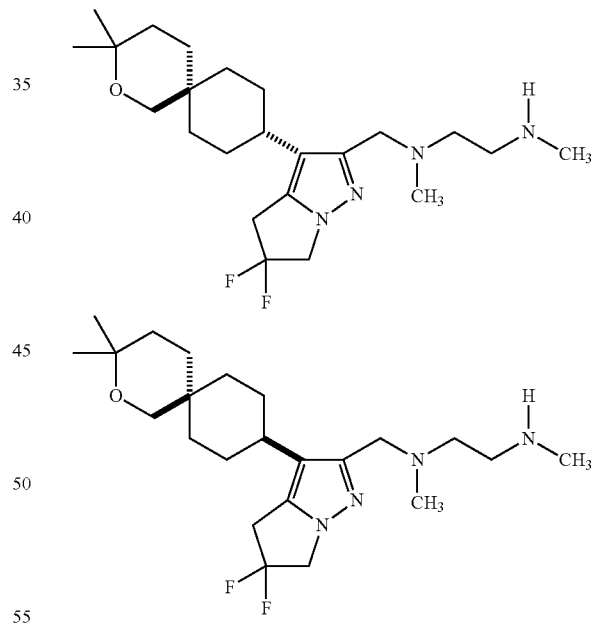

N¹-((3-((6r,9r)-3,3-dimethyl-2-oxaspiro[5.5]undecan-9-yl)-5,5-difluoro-5,6-dihydro-4H-pyrrolo-[1,2-b]pyrazol-2-yl)methyl)-N¹,N²-dimethylethane-1,2-diamine and N¹-((3-((6s,9s)-3,3-dimethyl-2-oxaspiro[5.5]undecan-9-yl)-5,5-difluoro-5,6-dihydro-4H-pyrrolo-[1,2-b]pyrazol-2-yl)methyl)-N¹,N²-dimethylethane-1,2-diamine The title compounds were obtained using the same procedures already described for Example 7a and 7b, using ethyl 3-bromo-5,5-difluoro-5,6-dihydro-4H-pyrrolo[1,2-b]pyrazole-2-carboxylate (Intermediate A, Step 7) and Intermediate Q as starting materials.

Compound 86a: 81.8 mg; $^1$H NMR (400 MHz, CD$_3$OD) δ. 4.84-4.83 (m, 2H), 4.59 (t, J=12.8 Hz, 2H), 4.48 (s, 2H), 3.86-3.47 (m, 6H), 3.00 (s, 3H), 2.80 (s, 3H), 2.67-2.52 (m, 1H), 1.81-1.80 (m, 2H), 1.76-1.65 (m, 4H), 1.61-1.48 (m, 4H), 1.25-1.22 (m, 8H). MS (ES+) C$_{23}$H$_{38}$F$_2$N$_4$O, requires: 424 found: 425 [M+H]$^+$.

Compound 86b: 79.5 mg; $^1$H NMR (400 MHz, CD$_3$OD) δ 4.59 (t, J=12.8 Hz, 2H), 4.48 (s, 2H), 3.83-3.51 (m, 8H), 3.00 (s, 3H), 2.80 (s, 3H), 2.70-2.60 (m, 1H), 1.91-1.87 (m, 2H), 1.69 (d, J=12.0 Hz, 2H), 1.59-1.38 (m, 6H), 1.23-1.20 (m, 2H), 1.21 (s, 6H). MS (ES+) C$_{23}$H$_{38}$F$_2$N$_4$O, requires: 424 found: 425 [M+H]$^+$.

Example 87 a/b

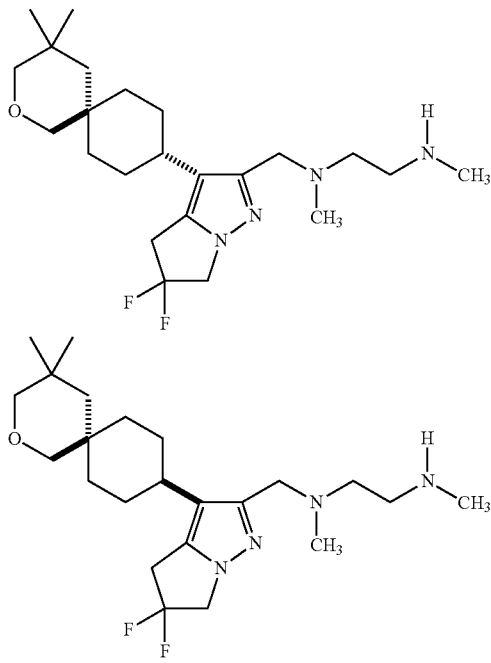

N$^1$-((3-((6r,9r)-4,4-dimethyl-2-oxaspiro[5.5]undecan-9-yl)-5,5-difluoro-5,6-dihydro-4H-pyrrolo-[1,2-b]pyrazol-2-yl)methyl)-N$^1$,N$^2$-dimethylethane-1,2-diamine and N$^1$-((3-((6s,9s)-4,4-dimethyl-2-oxaspiro[5.5]undecan-9-yl)-5,5-difluoro-5,6-dihydro-4H-pyrrolo-[1,2-b]pyrazol-2-yl)methyl)-N$^1$,N$^2$-dimethylethane-1,2-diamine The title compounds were obtained using the same procedures already described for Example 7a and 7b, using ethyl 3-bromo-5,5-difluoro-5,6-dihydro-4H-pyrrolo[1,2-b]pyrazole-2-carboxylate (Intermediate A, Step 7) and Intermediate R as starting materials.

Compound 87a: 196 mg; $^1$H NMR (400 MHz, CD$_3$OD) δ 4.59 (t, J=12.8 Hz, 2H), 4.47 (s, 2H), 3.65 (t, J=13.8 Hz, 3H), 3.56 (s, 2H), 3.31-3.28 (m, 5H), 2.99 (s, 3H), 2.80 (s, 3H), 2.67-2.50 (m, 1H), 1.83 (d, J=12.8 Hz, 2H), 1.74-1.56 (m, 4H), 1.56 (s, 2H), 1.29-1.23 (m, 2H), 1.01 (s, 6H). MS (ES+) C$_{23}$H$_{38}$F$_2$N$_4$O, requires: 424, found: 425 [M+H]$^+$.

Compound 87b: 136 mg; $^1$H NMR (400 MHz, CD$_3$OD) δ 4.57 (t, J=12.8 Hz, 2H), 4.46 (s, 2H), 3.65-3.55 (m, 7H), 3.31-3.30 (m, 3H), 2.99 (s, 3H), 2.80 (s, 3H), 2.61-2.53 (m, 1H), 1.92 (d, J=13.3 Hz, 2H), 1.67 (d, J=12.3 Hz, 2H), 1.52-1.43 (m, 2H), 1.41-1.30 (m, 2H), 1.28 (s, 2H), 0.97 (s, 6H). MS (ES+) C$_{23}$H$_{38}$F$_2$N$_4$O, requires: 424, found: 425 [M+H]$^+$.

Example 88 a/b

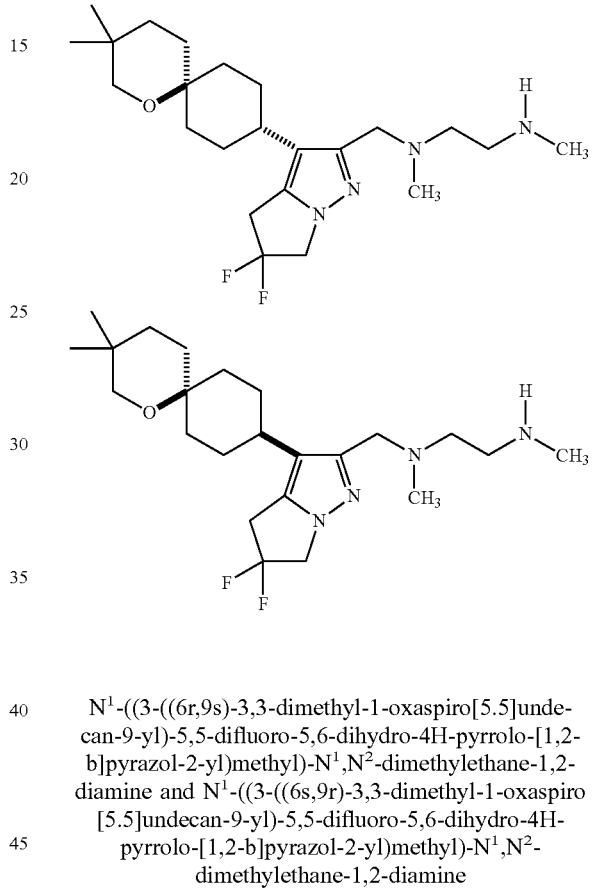

N$^1$-((3-((6r,9s)-3,3-dimethyl-1-oxaspiro[5.5]undecan-9-yl)-5,5-difluoro-5,6-dihydro-4H-pyrrolo-[1,2-b]pyrazol-2-yl)methyl)-N$^1$,N$^2$-dimethylethane-1,2-diamine and N$^1$-((3-((6s,9r)-3,3-dimethyl-1-oxaspiro[5.5]undecan-9-yl)-5,5-difluoro-5,6-dihydro-4H-pyrrolo-[1,2-b]pyrazol-2-yl)methyl)-N$^1$,N$^2$-dimethylethane-1,2-diamine The title compounds were obtained using the same procedures described elsewhere for Example 7a and 7b, using ethyl 3-bromo-5,5-difluoro-5,6-dihydro-4H-pyrrolo[1,2-b]pyrazole-2-carboxylate (Intermediate A, Step 7) and Intermediate T as starting materials.

Compound 88a: 9.9 mg; $^1$H NMR (400 MHz, CD$_3$OD) δ 4.57 (t, J=12.8 Hz, 2H), 4.44 (s, 2H), 3.64-3.54 (m, 6H), 3.33 (s, 2H), 2.97 (s, 3H), 2.79 (s, 3H), 2.66-2.64 (m, 1H), 2.10-2.08 (m, 2H), 1.83-1.79 (m, 2H), 1.75-1.72 (m, 2H), 1.50-1.44 (m, 6H), 0.93 (s, 6H). MS (ES$^+$) C$_{23}$H$_{38}$F$_2$N$_4$O, requires: 424, found: 425 [M+H]$^+$.

Compound 88b: 47.5 mg; $^1$H NMR (400 MHz, CD$_3$OD) δ 4.59 (t, J=12.8 Hz, 2H), 4.49 (s, 2H), 3.63-3.56 (m, 6H), 3.30 (s, 2H), 3.01 (s, 3H), 2.81 (s, 3H), 2.66-2.63 (m, 1H), 2.14-2.10 (m, 2H), 1.70-1.61 (m, 4H), 1.52-1.46 (m, 4H), 1.41-1.33 (m, 2H), 0.95 (s, 6H). MS (ES$^+$) C$_{23}$H$_{38}$F$_2$N$_4$O, requires: 424, found: 425 [M+H]$^+$.

Example 89 a/b

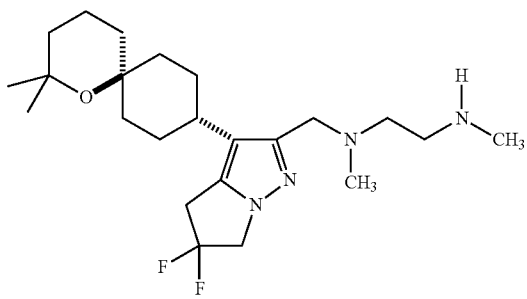

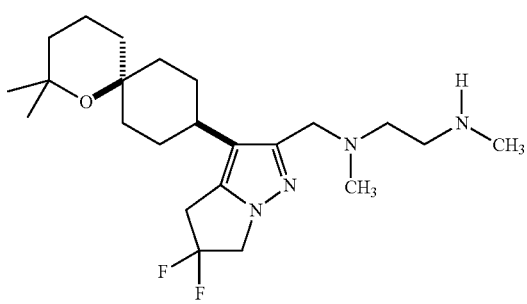

N¹-((3-(((6r,9s)-2,2-dimethyl-1-oxaspiro[5.5]undecan-9-yl)-5,5-difluoro-5,6-dihydro-4H-pyrrolo-[1,2-b]pyrazol-2-yl)methyl)-N¹,N²-dimethylethane-1,2-diamine and N¹-((3-((6s,9r)-2,2-dimethyl-1-oxaspiro[5.5]undecan-9-yl)-5,5-difluoro-5,6-dihydro-4H-pyrrolo-[1,2-b]pyrazol-2-yl)methyl)-N¹,N²-dimethylethane-1,2-diamine The title compounds were obtained using the same procedures already described for Example 7a and 7b, using ethyl 3-bromo-5,5-difluoro-5,6-dihydro-4H-pyrrolo[1,2-b]pyrazole-2-carboxylate (Intermediate A, Step 7) and Intermediate S as starting materials.

Compound 89a: 14.4 mg; $^1$H NMR (400 MHz, CD$_3$OD) δ 4.63-4.53 (m, 2H), 4.50-4.44 (m, 2H), 3.77-3.52 (m, 6H), 2.99 (s, 3H), 2.80 (s, 3H), 2.68-2.52 (m, 1H), 2.13-1.61 (m, 11H), 1.60-1.42 (m, 6H), 1.22 (s, 3H). MS (ES$^+$) C$_{23}$H$_{38}$F$_2$N$_4$O, requires: 424, found: 425 [M+H]$^+$.

Compound 89b: 270.2 mg; $^1$H NMR (400 MHz, CD$_3$OD) δ 4.59 (t, J=12.8 Hz, 2H), 4.47 (s, 2H), 3.62-3.55 (m, 6H), 2.99 (s, 3H), 2.80 (s, 3H), 2.64-2.60 (m, 1H), 2.00-1.79 (m, 4H), 1.75-1.65 (m, 2H), 1.63-1.54 (m, 2H), 1.51-1.34 (m, 6H), 1.26 (s, 6H). MS (ES+) C$_{23}$H$_{38}$F$_2$N$_4$O, requires: 424, found: 425 [M+H]$^+$.

Example 90

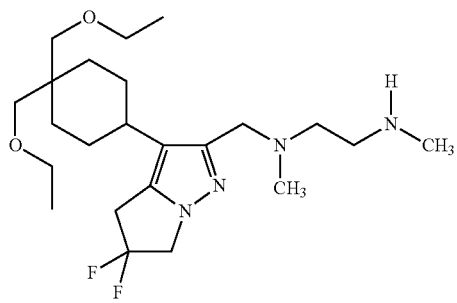 [SMILES: CCOCC1(COCC)CCC(c2c(CN(C)CCNC)nn3c2CC(F)(F)C3)CC1]

N¹-((3-(4,4-bis(ethoxymethyl)cyclohexyl)-5,5-difluoro-5,6-dihydro-4H-pyrrolo[1,2-b]pyrazol-2-yl)methyl)-N²-methylethane-1,2-diamine

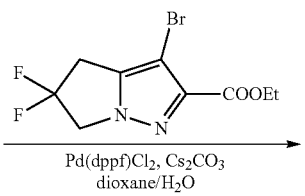

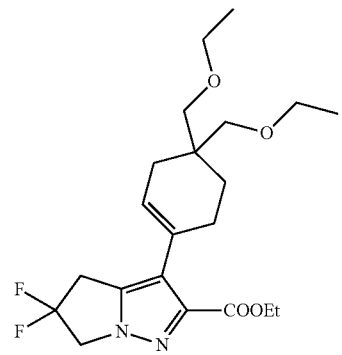

Ethyl 3-(4,4-bis(ethoxymethyl)cyclohex-1-en-1-yl)-5,5-difluoro-5,6-dihydro-4H-pyrrolo[1,2-b]pyrazole-2-carboxylate A mixture of Intermediate I (17.14 g, 52.87 mmol, 1.2 eq), 3-bromo-5,5-difluoro-5,6-dihydro-4H-pyrrolo[1,2-b]pyrazole-2-carboxylate (Intermediate A, Step 7; 13 g, 44.06 mmol, 1 eq), Cs$_2$CO$_3$ (43.06 g, 132.17 mmol, 3 eq) and Pd(dppf)Cl$_2$ (3.22 g, 4.41 mmol, 0.1 eq) in dioxane (200 mL) and H$_2$O (40 mL) was degassed and purged with N$_2$ for 3 times, and then stirred at 85° C. for 16 hr under N$_2$ atmosphere. The reaction mixture was then concentrated under reduced pressure, and the residue diluted with EtOAc (200 mL). The organic layer was washed with brine (200 mL), dried (Na$_2$SO$_4$), filtered and concentrated under reduced pressure. The residue was purified by SiO$_2$ gel chromatography (PE:EtOAc=10:1 to 6:1) to afford the title compound (31 g, 63.8 mmol, 72% yield) as a yellow solid. MS (ES$^+$) C$_{21}$H$_{30}$F$_2$N$_2$O$_4$, requires: 412, found: 413 [M+H]$^+$.

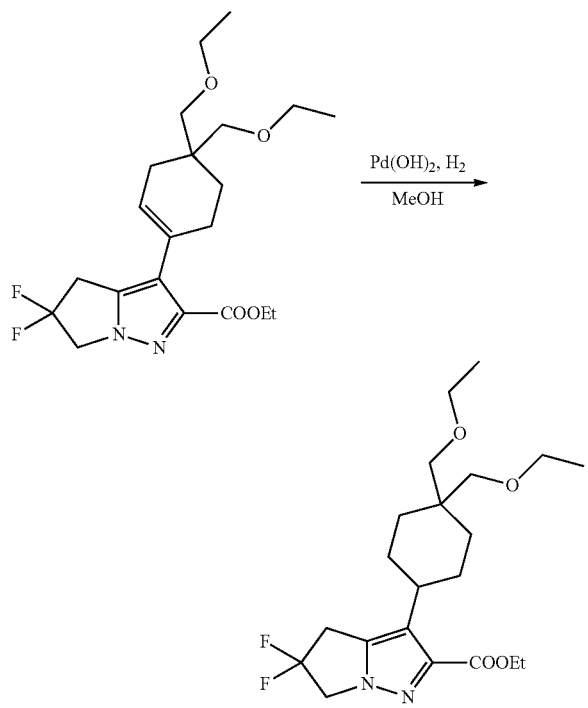

Ethyl 3-(4,4-bis(ethoxymethyl)cyclohexyl)-5,5-difluoro-5,6-dihydro-4H-pyrrolo[1,2-b]pyrazole-2-carboxylate A Parr reaction vessel was charged with the product from the previous step (31 g, 63.88 mmol), Pd(OH)$_2$/C (4 g, 10% weight) and MeOH (500 mL). The suspension was degassed under vacuum and with N$_2$ three times, purged with H$_2$ and stirred under an atmosphere of H$_2$ (15 Psi) at 25° C. for 16 hr in a Parr shaker. The reaction mixture was then purged with N$_2$, filtered through a pad of Celite and concentrated under reduced pressure to give the title compound (30 g, 64 mmol, 99.7% yield) as a yellow oil. MS (ES$^+$) C$_{21}$H$_{32}$F$_2$N$_2$O$_4$, requires: 414, found: 415 [M+H]$^+$.

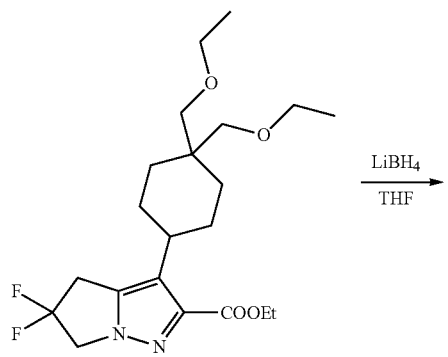

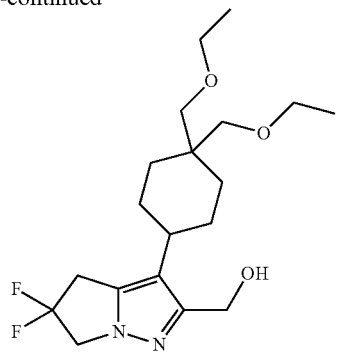

(3-(4,4-Bis(ethoxymethyl)cyclohexyl)-5,5-difluoro-5,6-dihydro-4H-pyrrolo[1,2-b]pyrazol-2-yl)methanol To a solution of the product from the previous step (30 g, 63.69 mmol) in THF (400 mL) was added LiBH$_4$ (2.77 g, 127.39 mmol, 2 eq). The mixture was stirred at 20° C. for 5 hr, then quenched at 0° C. by addition of saturated aq. NH$_4$Cl (300 mL), and extracted with EtOAc (300 mL×3). The combined organic layers were washed with brine (400 mL), dried (Na$_2$SO$_4$), filtered and concentrated under reduced pressure to give the title compound (26 g, 62.83 mmol, 99% yield) as a yellow oil. MS (ES$^+$) C$_{19}$H$_{30}$F$_2$N$_2$O$_3$, requires: 372, found: 373 [M+H]$^+$.

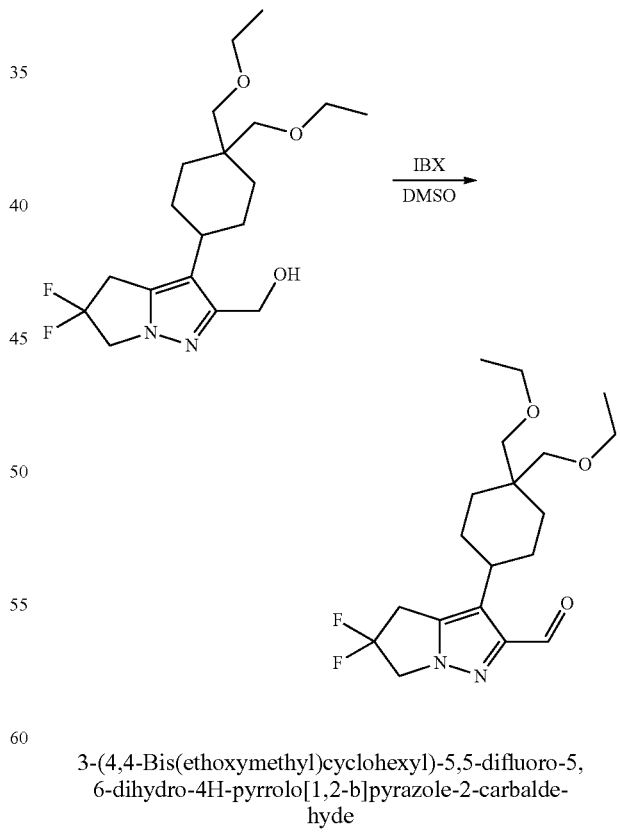

3-(4,4-Bis(ethoxymethyl)cyclohexyl)-5,5-difluoro-5,6-dihydro-4H-pyrrolo[1,2-b]pyrazole-2-carbaldehyde To a solution of the product from previous step (800 mg, 2.15 mmol) in DMSO (10 mL) was added IBX (1.80 g, 6.44 mmol, 3 eq). The mixture was stirred at 40° C. for 2 hr, then cooled to RT, quenched by addition of H₂O (25 mL), and then diluted with EtOAc (150 mL). The organic layer was washed with brine (100 mL), dried (Na₂SO₄), filtered and concentrated under reduced pressure. The residue was purified by SiO₂ gel chromatography (PE:EtOAc=20/1 to 7/1) to afford the title compound (720 mg, 1.94 mmol, 90% yield) as a colorless oil. MS (ES⁺) $C_{19}H_{28}F_2N_2O_3$, requires: 370, found: 371 [M+H]⁺.

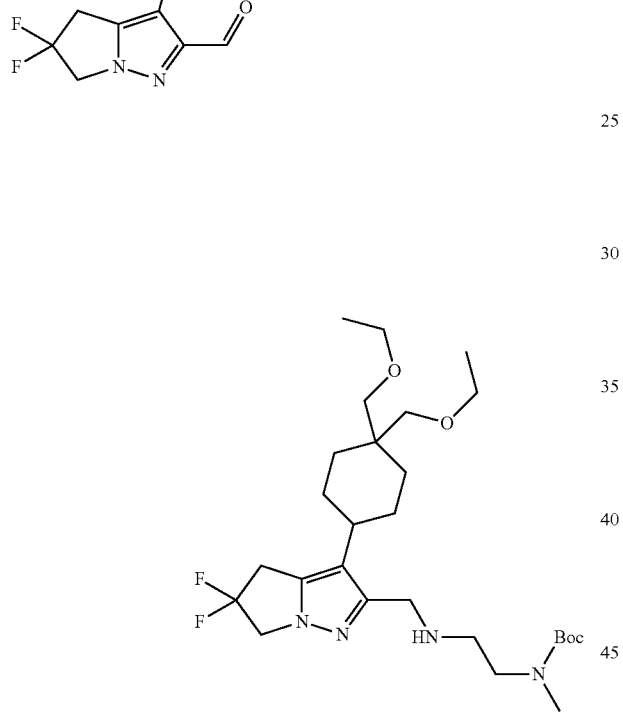

tert-Butyl (2-(((3-(4,4-bis(ethoxymethyl)cyclo-hexyl)-5,5-difluoro-5,6-dihydro-4H-pyrrolo[1,2-b] pyrazol-2-yl)methyl)amino)ethyl)(methyl)carbamate To a solution of the product from previous step (160 mg, 0.43 mmol) in DCE (2 mL) were added tert-butyl N-(2-aminoethyl)-N-methyl-carbamate (82.78 mg, 0.47 mmol, 0.085 mL, 1.1 eq), NaBH(OAc)₃ (274.63 mg, 1.30 mmol, 3 eq) and HOAc (1.30 mg, 0.022 mmol, 0.05 eq). The mixture was stirred at 30° C. for 16 hr, then quenched by addition saturated aq. NaHCO₃ (20 mL) and extracted with DCM (30 mL). The organic layer was washed with brine (30 mL), dried (Na₂SO₄), filtered and concentrated under reduced pressure to give the title compound (220 mg, crude) as a yellow oil. MS (ES⁺) $C_{27}H_{46}F_2N_4O_4$, requires: 528, found: 529 [M+H]⁺.

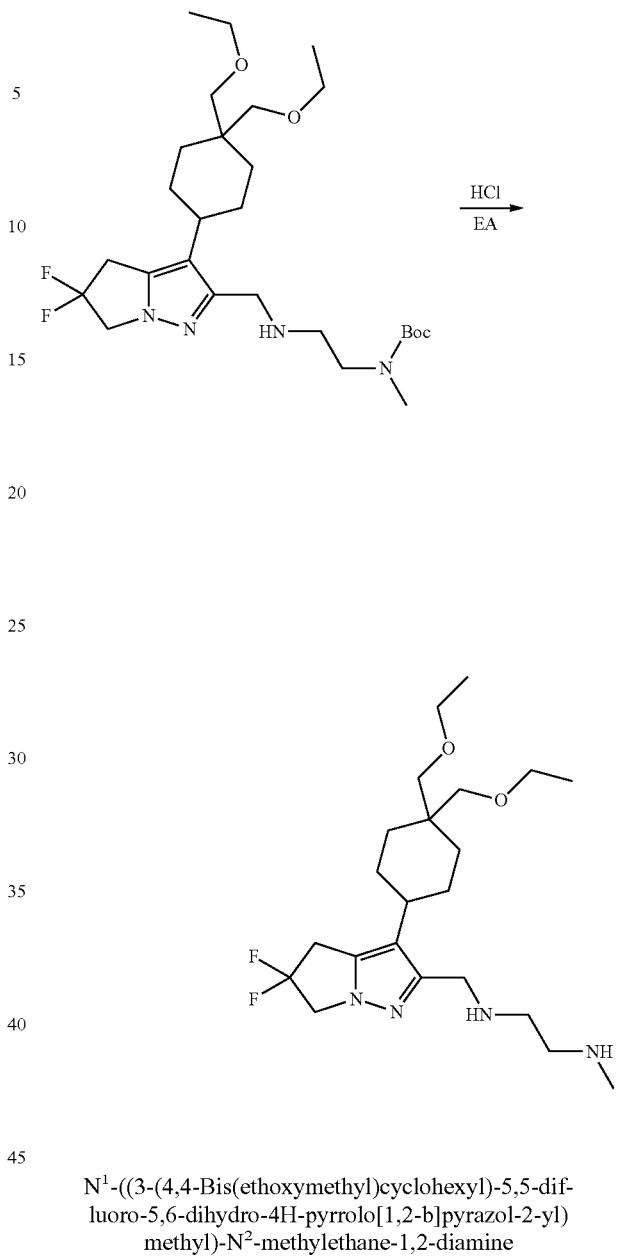

N¹-((3-(4,4-Bis(ethoxymethyl)cyclohexyl)-5,5-difluoro-5,6-dihydro-4H-pyrrolo[1,2-b]pyrazol-2-yl) methyl)-N²-methylethane-1,2-diamine To a solution of the product from the previous step (220 mg, 0.42 mmol) in EtOAc (1 mL) was added HCl (4 M in EtOAc, 1.04 mL, 10 eq). The mixture was stirred at 20° C. for 1 hr, then concentrated under reduced pressure. The residue was purified by prep-HPLC (column: Phenomenex Synergi C18 150*30 mm*4 um; mobile phase: [water (0.05% HCl)-ACN]; B %: 19%-39%, 11 min) and followed by lyophilization to afford the title compound (52 mg, 0.10 mmol, 25% yield) as a white solid.

¹H NMR (400 MHz, D₂O) δ 4.52 (t, J=12.8 Hz, 2H), 4.29 (s, 2H), 3.66-3.50 (m, 8H), 3.50-3.38 (m, 4H), 3.26 (s, 2H), 2.75 (s, 3H), 2.46 (t, J=12.2 Hz, 1H), 1.63-1.60 (m, 4H), 1.52-1.39 (m, 2H), 1.33-1.22 (m, 2H), 1.15 (q, J=7.2 Hz, 6H).

MS (ES⁺) $C_{22}H_{38}F_2N_4O_2$, requires: 428, found: 429 [M+H]⁺.

Example 91

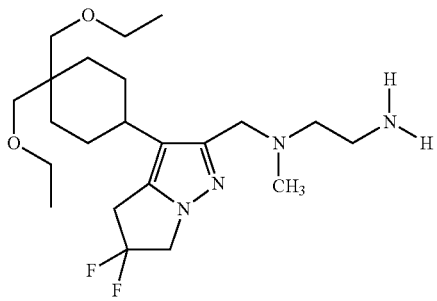 [SMILES: CCOCC1(COCC)CCC(c2c(CN(C)CCN)nn3c2CC(F)(F)C3)CC1]

N¹-((3-(4,4-bis(ethoxymethyl)cyclohexyl)-5,5-difluoro-5,6-dihydro-4H-pyrrolo[1,2-b]pyrazol-2-yl)methyl)-N¹-methylethane-1,2-diamine The title compound was obtained using the same procedures already described for Example 90, using tert-butyl N-[2-(methylamino)ethyl]carbamate in the reductive amination step.

Compound 91. White solid; 250 mg, 0.50 mmol, 48% yield; ¹H NMR (400 MHz, D$_2$O) δ 4.55 (t, J=12.8 Hz, 2H), 4.40 (s, 2H), 3.70-3.41 (m, 12H), 3.26 (s, 2H), 2.87 (s, 3H), 2.45 (t, J=12.4 Hz, 1H), 1.62-1.60 (m, 4H), 1.54-1.37 (m, 2H), 1.34-1.22 (m, 2H), 1.19-1.09 (m, 6H). MS (ES$^+$) C$_{22}$H$_{38}$F$_2$N$_4$O$_2$, requires: 428, found: 429 [M+H]$^+$.

Example 92

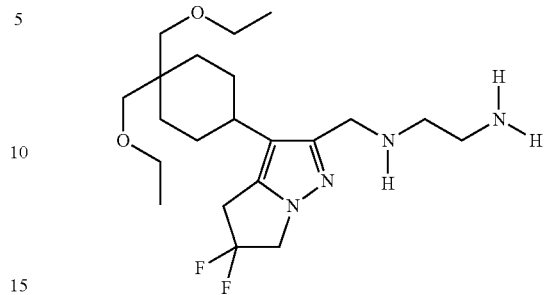

N¹-((3-(4,4-bis(ethoxymethyl)cyclohexyl)-5,5-difluoro-5,6-dihydro-4H-pyrrolo[1,2-b]pyrazol-2-yl)methyl)ethane-1,2-diamine The title compound was obtained using the same procedures already described for Example 90, using tert-butyl N-(2-aminoethyl)carbamate in the reductive amination step.

Compound 92. White solid; 40.5 mg, 0.083 mmol, 19% yield; ¹H NMR (400 MHz, D$_2$O) δ 4.52 (t, J=12.8 Hz, 2H), 4.28 (d, J=3.2 Hz, 2H), 3.67-3.49 (m, 8H), 3.47-3.33 (m, 4H), 3.26 (s, 2H), 2.46 (t, J=12.2 Hz, 1H), 1.64-1.61 (m, 4H), 1.52-1.39 (m, 2H), 1.33-1.22 (m, 2H), 1.15 (q, J=7.2 Hz, 6H). MS (ES$^+$) C$_{21}$H$_{36}$F$_2$N$_4$O$_2$, requires: 414, found: 415 [M+H]$^+$.

The following Example compounds were prepared using the methods disclosed above. Diastereomeric mixtures were separated into diastereomerically pure compounds. The stereochemistry has been assigned using spectroscopic methods; for all compounds, each of a pair of diastereomers can be assigned based on a physical property, for example, retention time.

TABLE 3

Example compounds 93a/b to 107a/b

| Ex | Structure | IUPAC Name | MWt/ [M + H] | Ex. Method |
|---|---|---|---|---|
| 93a | 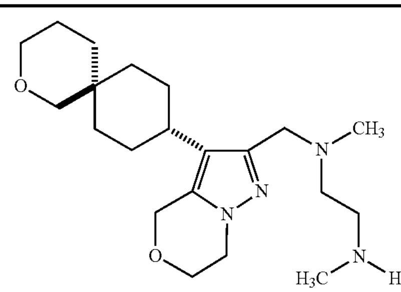 | N¹-((3-((6r,9r)-2-oxaspiro-[5.5]undecan-9-yl)-6,7-dihydro-4H-pyrazolo[5,1-c]-[1,4]oxazin-2-yl)methyl)-N¹,N²-dimethylethane-1,2-diamine | 376/ 377 | 79a/b |
| 93b | 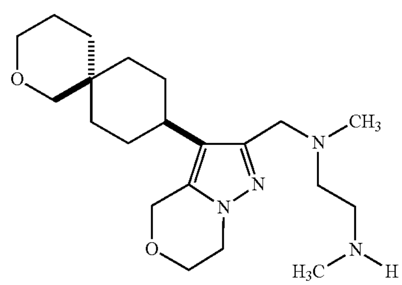 [SMILES: CNCCN(C)Cc1nn2c(c1[C@H]1CC[C@]3(CCCOC3)CC1)COCC2] | N¹-((3-((6s,9s)-2-oxaspiro-[5.5]undecan-9-yl)-6,7-dihydro-4H-pyrazolo[5,1-c]-[1,4]oxazin-2-yl)methyl)-N¹,N²-dimethylethane-1,2-diamine | 376/ 377 | 79a/b |

TABLE 3-continued

Example compounds 93a/b to 107a/b

| Ex | Structure | IUPAC Name | MWt/ [M + H] | Ex. Method |
|---|---|---|---|---|
| 94a | 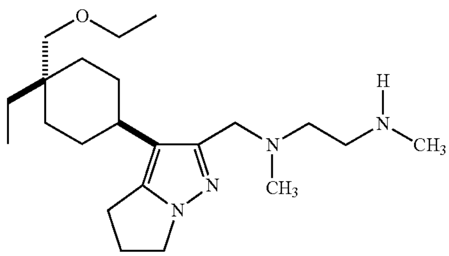 | N[1]-((3-((1r,4r)-4-(ethoxy-methyl)-4-ethylcyclohexyl)-5,6-dihydro-4H-pyrrolo[1,2-b]pyrazol-2-yl)methyl)-N[1],N[2]-dimethylethane-1,2-diamine | 376/ 377 | 5a/b |
| 94b | 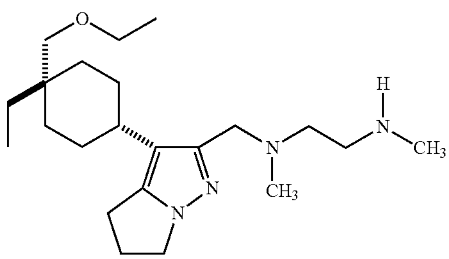 | N[1]-((3-((1r,4r)-4-(ethoxy-methyl)-4-ethylcyclohexyl)-5,6-dihydro-4H-pyrrolo[1,2-b]pyrazol-2-yl)methyl)-N[1],N[2]-dimethylethane-1,2-diamine | 376/ 377 | 5a/b |
| 95a | 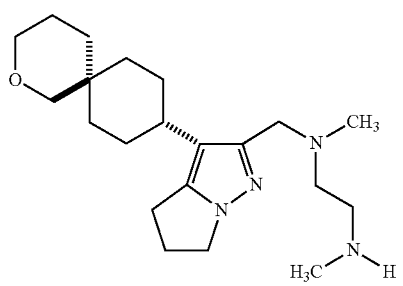 [SMILES: CNCCN(C)Cc1nn2c(c1[C@H]1CC[C@@]3(CCCOC3)CC1)CCC2] | N[1]-((3-((6r,9r)-2-oxaspiro-[5.5]undecan-9-yl)-5,6-dihydro-4H-pyrrolo[1,2-b]pyrazol-2-yl)methyl)-N[1],N[2]-dimethylethane-1,2-diamine | 360/ 361 | 79a/b |
| 95b | 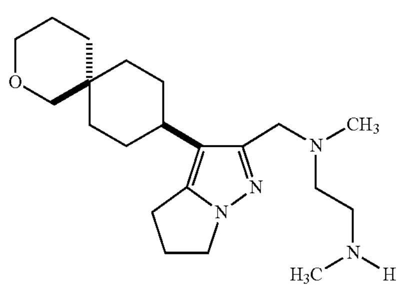 [SMILES: CNCCN(C)Cc1nn2c(c1[C@H]1CC[C@]3(CCCOC3)CC1)CCC2] | N[1]-((3-((6s,9s)-2-oxaspiro-[5.5]undecan-9-yl)-5,6-dihydro-4H-pyrrolo[1,2-b]-pyrazol-2-yl)methyl)-N[1],N[2]-dimethylethane-1,2-diamine | 360/ 361 | 79a/b |
| 96a | 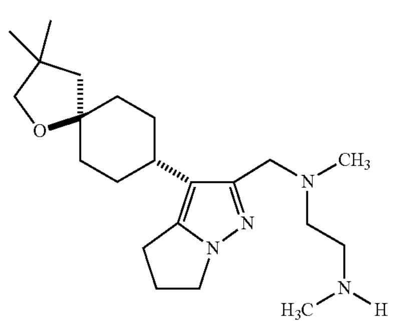 | N[1]-((3-((5r,8r)-3,3-dimethyl-1-oxaspiro[4.5]decan-8-yl)-5,6-dihydro-4H-pyrrolo[1,2-b]pyrazol-2-yl)methyl)-N[1],N[2]-dimethylethane-1,2-diamine | 374/ 375 | 78a/b |

TABLE 3-continued

Example compounds 93a/b to 107a/b

| Ex | Structure | IUPAC Name | MWt/ [M + H] | Ex. Method |
|---|---|---|---|---|
| 96b | 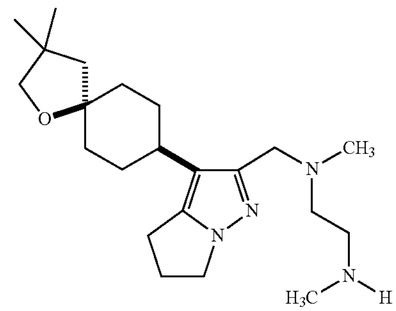 | N¹-((3-((5s,8s)-3,3-dimethyl-1-oxaspiro[4.5]decan-8-yl)-5,6-dihydro-4H-pyrrolo[1,2-b]pyrazol-2-yl)methyl)-N¹,N²-dimethylethane-1,2-diamine | 374/ 375 | 78a/b |
| 97a | 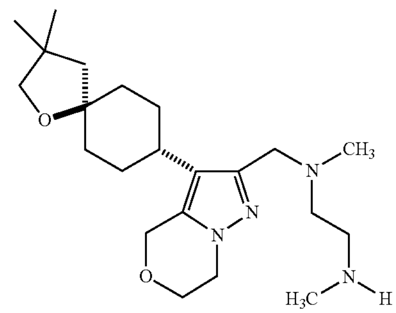 | N¹-((3-((5r,8r)-3,3-dimethyl-1-oxaspiro[4.5]decan-8-yl)-6,7-dihydro-4H-pyrazolo[5,1-c][1,4]oxazin-2-yl)methyl)-N¹,N²-dimethylethane-1,2-diamine | 390/ 391 | 78a/b |
| 97b | 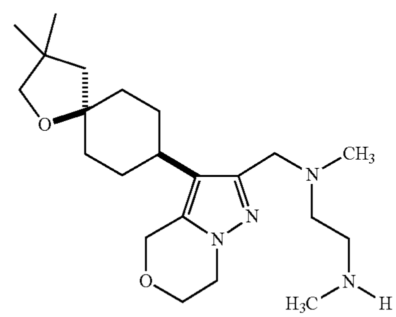 | N¹-((3-((5s,8s)-3,3-dimethyl-1-oxaspiro[4.5]decan-8-yl)-6,7-dihydro-4H-pyrazolo[5,1-c][1,4]oxazin-2-yl)methyl)-N¹,N²-dimethylethane-1,2-diamine | 390/ 391 | 78a/b |
| 98a | 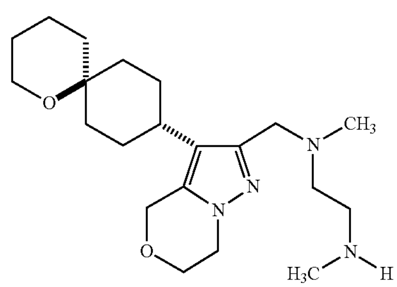 | N¹-((3-((6r,9s)-1-oxaspiro-[5.5]undecan-9-yl)-6,7-dihydro-4H-pyrazo[5,1-c]-[1,4]oxazin-2-yl)methyl)-N¹,N²-dimethylethane-1,2-diamine | 376/ 377 | 80a/b |
| 98b | 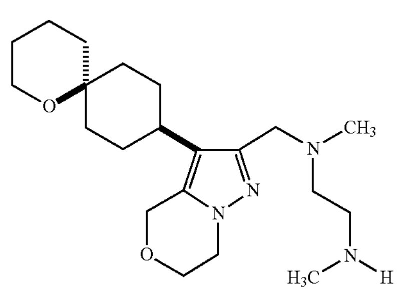 | N¹-((3-((6r,9r)-1-oxaspiro-[5.5]undecan-9-yl)-6,7-dihydro-4H-pyrazo[5,1-c]-[1,4]oxazin-2-yl)methyl)-N¹,N²-dimethylethane-1,2-diamine | 376/ 377 | 80a/b |

| Ex | Structure | IUPAC Name | MWt/ [M + H] | Ex. Method |
|---|---|---|---|---|
| 99 | 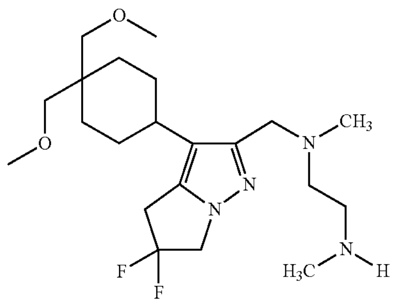 [SMILES: CNCCN(C)Cc1nn2c(c1C1CCC(COC)(COC)CC1)CC(F)(F)C2] | N¹-((3-(4,4-bis(methoxymethyl)cyclohexyl)-5,5-difluoro-5,6-dihydro-4H-pyrrolo[1,2-b]pyrazol-2-yl)methyl)-N¹,N²-dimethylethane-1,2-diamine | 414/ 415 | 81 |
| 100a | 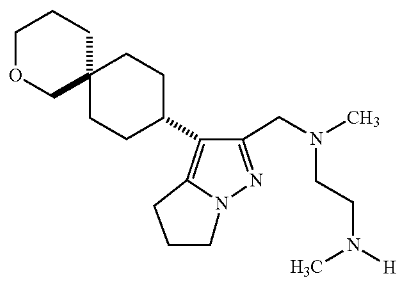 | N¹-((3-((6r,9r)-2-oxaspiro-[5.5]undecan-9-yl)-5,6-dihydro-4H-pyrrolo[1,2-b]pyrazol-2-yl)methyl)-N¹,N²-dimethylethane-1,2-diamine | 360/ 361 | 80a/b |
| 100b | 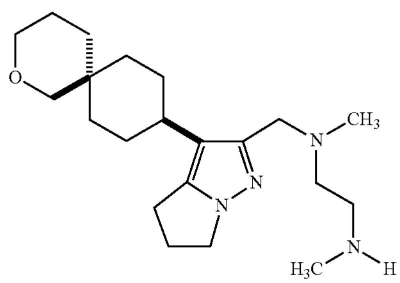 | N¹-((3-((6s,9s)-2-oxaspiro-[5.5]undecan-9-yl)-5,6-dihydro-4H-pyrrolo[1,2-b]-pyrazol-2-yl)methyl)-N¹,N²-dimethylethane-1,2-diamine | 360/ 361 | 80a/b |
| 101a | 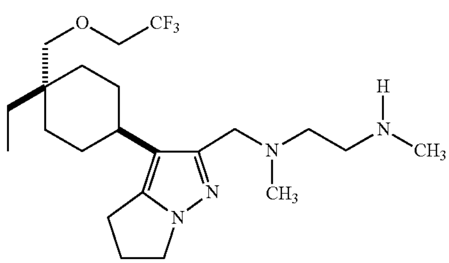 [SMILES: CC[C@]1(COCC(F)(F)F)CC[C@H](c2c(CN(C)CCNC)nn3c2CCC3)CC1] | N¹-((3-((1r,4r)-4-ethyl-4-((2,2,2-trifluoroethoxy)-methyl)cyclohexyl)-5,6-dihydro-4H-pyrrolo[1,2-b]-pyrazol-2-yl)methyl)-N¹,N²-dimethylethane-1,2-diamine | 430/ 431 | 82a/b |
| 101b | 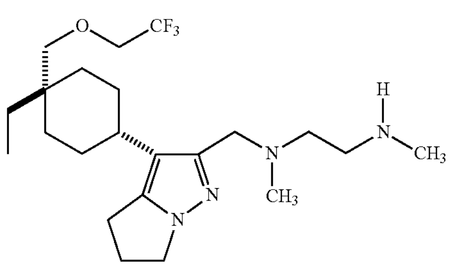 [SMILES: CC[C@]1(COCC(F)(F)F)CC[C@@H](c2c(CN(C)CCNC)nn3c2CCC3)CC1] | N¹-((3-((1s,4s)-4-ethyl-4-((2,2,2-trifluoroethoxy)-methyl)cyclohexyl)-5,6-dihydro-4H-pyrrolo[1,2-b]-pyrazol-2-yl)methyl)-N¹,N²-dimethylethane-1,2-diamine | 430/ 431 | 82a/b |

TABLE 3-continued

Example compounds 93a/b to 107a/b

| Ex | Structure | IUPAC Name | MWt/ [M + H] | Ex. Method |
|---|---|---|---|---|
| 102 | 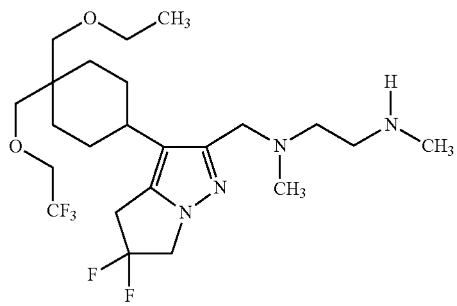 [SMILES: CCOCC1(COCC(F)(F)F)CCC(c2c(CN(C)CCNC)nn3c2CC(F)(F)C3)CC1] | $N^1$-((3-(4,4-bis((2,2,2-trifluoroethoxy)methyl)-cyclohexyl)-5,5-difluoro-5,6-dihydro-4H-pyrrolo[1,2-b]-pyrazol-2-yl)methyl)-$N^1$,$N^2$-dimethylethane-1,2-diamine | 550/ 551 | 81 |
| 103a | 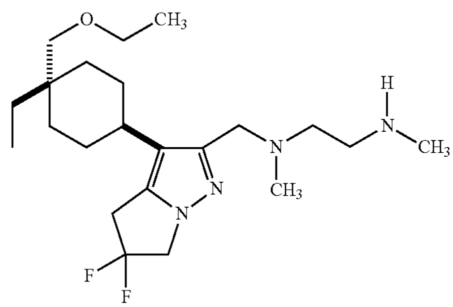 [SMILES: CCOC[C@]1(CC)CC[C@@H](c2c(CN(C)CCNC)nn3c2CC(F)(F)C3)CC1] | $N^1$-((3-((1r,4r)-4-ethyl-4-((2,2,2-trifluoroethoxy)-methyl)cyclohexyl)-5,5-difluoro-5,6-dihydro-4H-pyrrolo[1,2-b]pyrazol-2-yl)-methyl)-$N^1$,$N^2$-dimethyl-ethane-1,2-diamine | 466/ 467 | 82a/b |
| 103b | 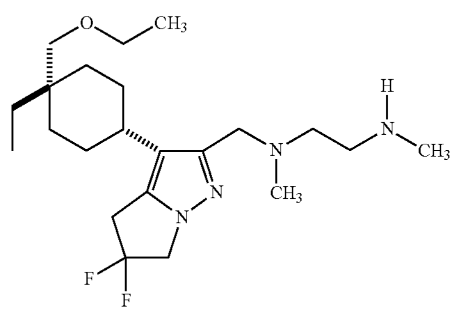 [SMILES: CCOC[C@]1(CC)CC[C@H](c2c(CN(C)CCNC)nn3c2CC(F)(F)C3)CC1] | $N^1$-((3-((1s,4s)-4-ethyl-4-((2,2,2-trifluoroethoxy)-methyl)cyclohexyl)-5,5-difluoro-5,6-dihydro-4H-pyrrolo[1,2-b[pyrazol-2-yl)-methyl)-$N^1$,$N^2$-dimethyl-ethane-1,2-diamine | 466/ 467 | 82a/b |
| 104a | 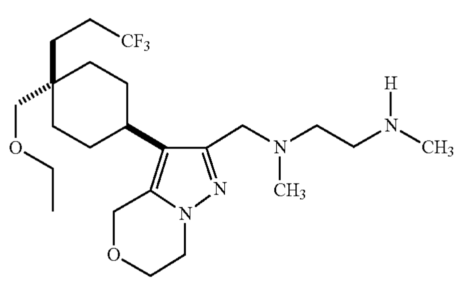 [SMILES: CCOC[C@]1(CCC(F)(F)F)CC[C@@H](c2c(CN(C)CCNC)nn3c2COCC3)CC1] | $N^1$-((3-((1r,4r)-4-(ethoxy-methyl)-4-(3,3,3-trifluoro-propyl)cyclohexyl)-6,7-dihydro-4H-pyrazolo[5,1-c]-[1,4]oxazin-2-yl)methyl)-$N^1$,$N^2$-dimethylethane-1,2-diamine | 460/ 461 | 83a/b |
| 104b | 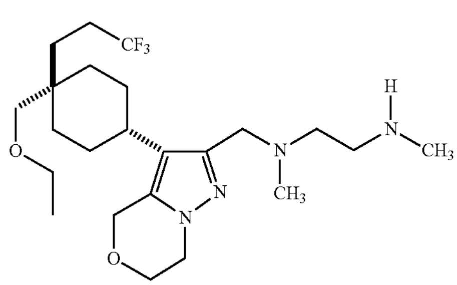 [SMILES: CCOC[C@]1(CCC(F)(F)F)CC[C@H](c2c(CN(C)CCNC)nn3c2COCC3)CC1] | $N^1$-((3-((1s,4s)-4-(ethoxy-methyl)-4-(3,3,3-trifluoro-propyl)cyclohexyl)-6,7-dihydro-4H-pyrazolo[5,1-c]-[1,4]oxazin-2-yl)methyl)-$N^1$,$N^2$-dimethylethane-1,2-diamine | 460/ 461 | 83a/b |

TABLE 3-continued

Example compounds 93a/b to 107a/b

| Ex | Structure | IUPAC Name | MWt/ [M + H] | Ex. Method |
|---|---|---|---|---|
| 105 | 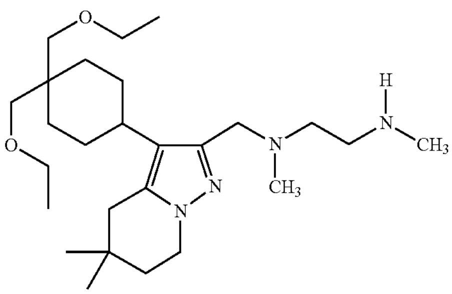 [SMILES: CCOCC1(COCC)CCC(c2c(CN(C)CCNC)nn3c2CC(C)(C)CC3)CC1] | $N^1$-((3-(4,4-bis(ethoxymethyl)cyclohexyl)-5,5-dimethyl-4,5,6,7-tetrahydropyrazolo[1,5-a]pyridin-2-yl)methyl)-$N^1$,$N^2$-dimethylethane-1,2-diamine | 434/ 435 | 84 |
| 106 | 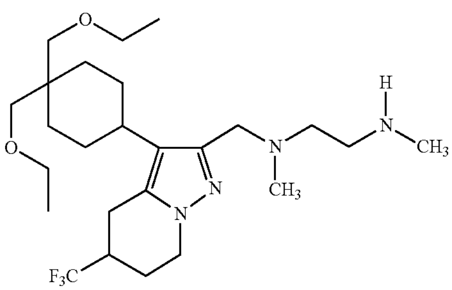 [SMILES: CCOCC1(COCC)CCC(c2c(CN(C)CCNC)nn3c2CC(C(F)(F)F)CC3)CC1] | $N^1$-((3-(4,4-bis(ethoxymethyl)cyclohexyl)-5-(trifluoromethyl)-4,5,6,7-tetrahydropyrazolo[1,5-c]pyridin-2-yl)methyl)-$N^1$,$N^2$-dimethylethane-1,2-diamine | 488/ 489 | 84 |
| 107a | 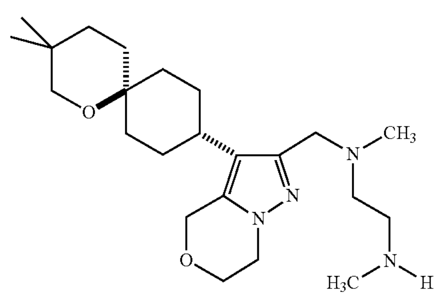 | $N^1$-((3-((6r,9s)-3,3-dimethyl-1-oxaspiro[5.5]undecan-9-yl)-6,7-dihydro-4H-pyrazolo[5,1-c][1,4]oxazin-2-yl)methyl)-$N^1$,$N^2$-dimethylethane-1,2-diamine | 404/ 405 | 86a/b |
| 107b | 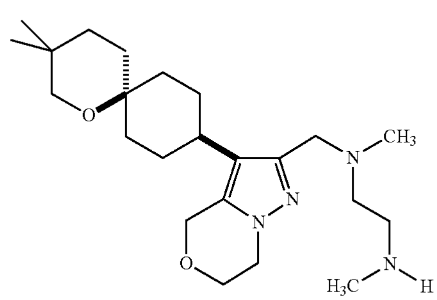 | $N^1$-((3-((6s,9r)-3,3-dimethyl-1-oxaspiro[5.5]undecan-9-yl)-6,7-dihydro-4H-pyrazolo[5,1-c][1,4]oxazin-2-yl)methyl)-$N^1$,$N^2$-dimethylethane-1,2-diamine | 404/ 405 | 86a/b |

The following compounds can generally be made using the methods described above. It is expected that these compounds when made will have activity similar to those that have been made in the examples above.

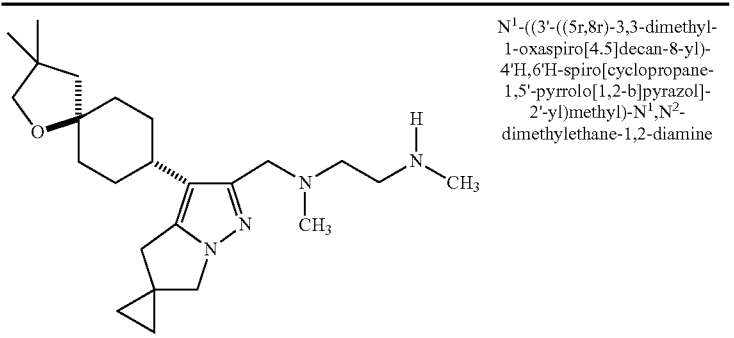

N¹-((3'-((5r,8r)-3,3-dimethyl-1-oxaspiro[4.5]decan-8-yl)-4'H,6'H-spiro[cyclopropane-1,5'-pyrrolo[1,2-b]pyrazol]-2'-yl)methyl)-N¹,N²-dimethylethane-1,2-diamine

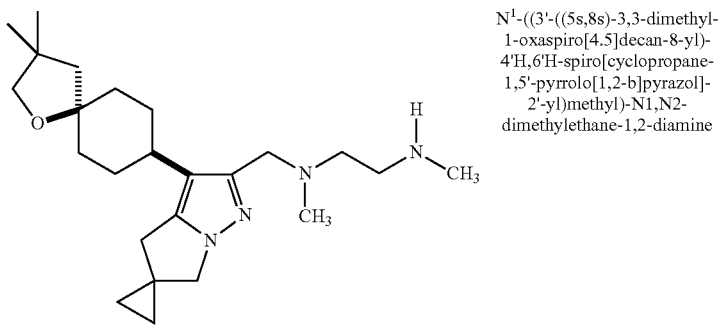

N¹-((3'-((5s,8s)-3,3-dimethyl-1-oxaspiro[4.5]decan-8-yl)-4'H,6'H-spiro[cyclopropane-1,5'-pyrrolo[1,2-b]pyrazol]-2'-yl)methyl)-N1,N2-dimethylethane-1,2-diamine

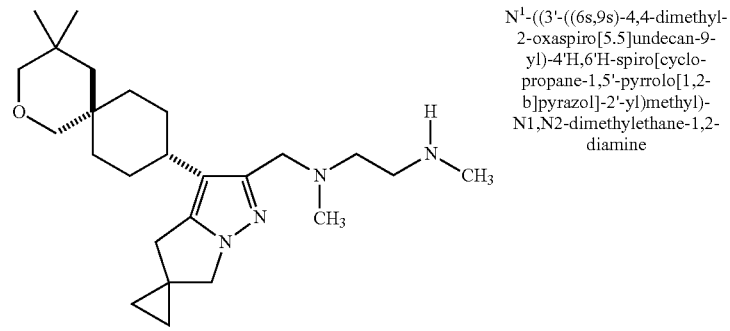

N¹-((3'-((6s,9s)-4,4-dimethyl-2-oxaspiro[5.5]undecan-9-yl)-4'H,6'H-spiro[cyclopropane-1,5'-pyrrolo[1,2-b]pyrazol]-2'-yl)methyl)-N1,N2-dimethylethane-1,2-diamine

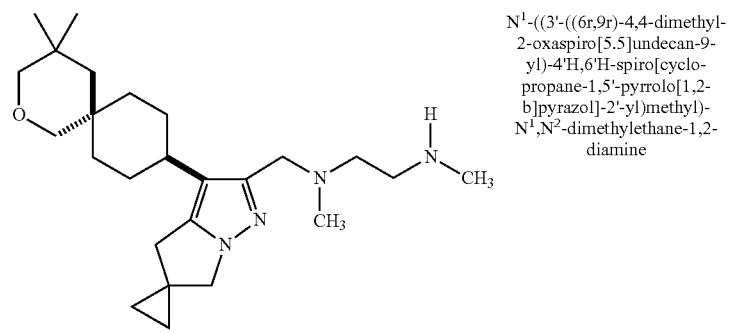

N¹-((3'-((6r,9r)-4,4-dimethyl-2-oxaspiro[5.5]undecan-9-yl)-4'H,6'H-spiro[cyclopropane-1,5'-pyrrolo[1,2-b]pyrazol]-2'-yl)methyl)-N¹,N²-dimethylethane-1,2-diamine -continued

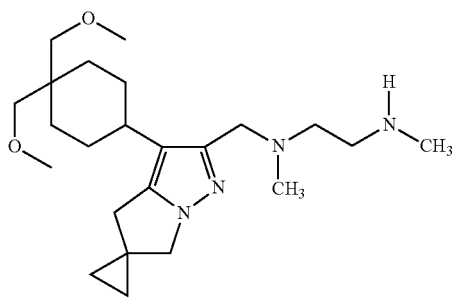 [SMILES: CNCCN(C)Cc1nn2c(c1C1CCC(COC)(COC)CC1)CC1(CC1)C2]

N1-((3'-(4,4-bis(methoxymethyl)cyclohexyl)-4'H,6'H-spiro[cyclopropane-1,5'-pyrrolo[1,2-b]pyrazol]-2'-yl)methyl)-$N^1,N^2$-dimethyl-ethane-1,2-diamine

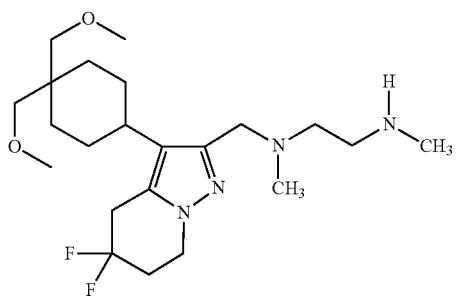 [SMILES: CNCCN(C)Cc1nn2c(c1C1CCC(COC)(COC)CC1)CC(F)(F)CC2]

$N^1$-((3-(4,4-bis-(methoxymethyl)cyclohexyl)-5,5-difluoro-4,5,6,7-tetrahydropyrazolo[1,5-a]pyridin-2-yl)methyl)-$N^1,N^2$-dimethylethane-1,2-diamine

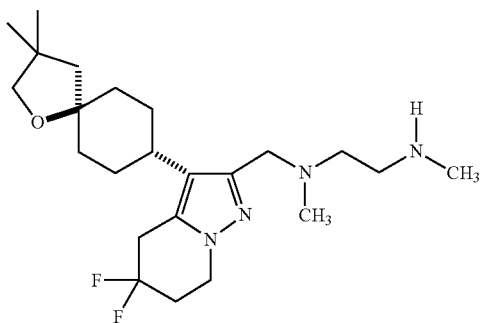

$N^1$-((3-((5r,8r)-3,3-dimethyl-1-oxaspiro[4.5]decan-8-yl)-5,5-difluoro-4,5,6,7-tetrahydropyrazolo[1,5-a]pyridin-2-yl)methyl)-$N^1,N^2$-dimethylethane-1,2-diamine

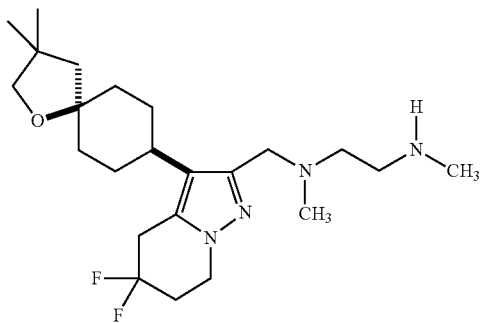

N1-((3-((5s,8s)-3,3-dimethyl-1-oxaspiro[4.5]decan-8-yl)-5,5-difluoro-4,5,6,7-tetrahydropyrazolo[1,5-a]pyridin-2-yl)methyl)-$N^1,N^2$-dimethylethane-1,2-diamine

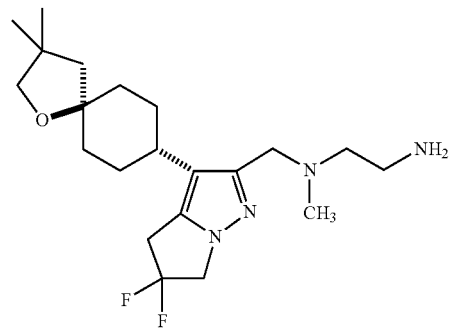

$N^1$-((3-((5r,8r)-3,3-dimethyl-1-oxaspiro[4.5]decan-8-yl)-5,5-difluoro-5,6-dihydro-4H-pyrrolo[1,2-b]pyrazol-2-yl)methyl)-$N^1$-methylethane-1,2-diamine

| | |
|---|---|
| 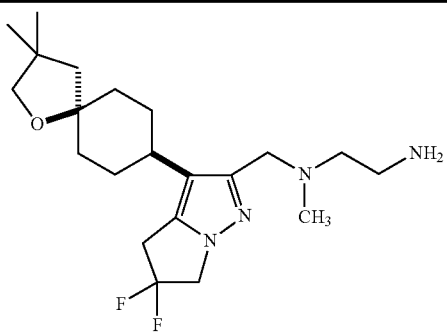 | N[1]-((3-((5s,8s)-3,3-dimethyl-1-oxaspiro[4.5]decan-8-yl)-5,5-difluoro-5,6-dihydro-4H-pyrrolo[1,2-b]pyrazol-2-yl)-methyl)-N[1]-methylethane-1,2-diamine |
| 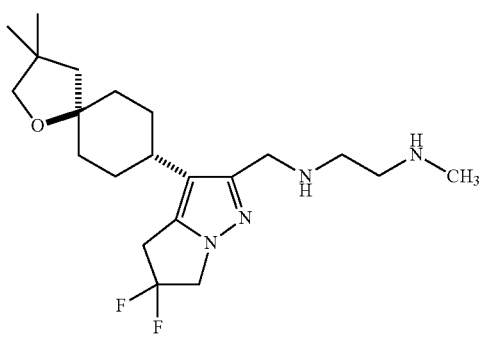 | N[1]-((3-((5r,8r)-3,3-dimethyl-1-oxaspiro[4.5]decan-8-yl)-5,5-difluoro-5,6-dihydro-4H-pyrrolo[1,2-b]pyrazol-2-yl)methyl)-N[2]-methylethane-1,2-diamine |
| 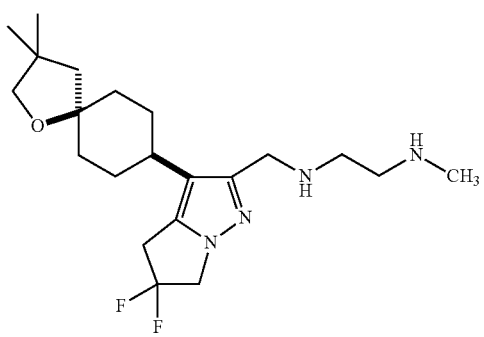 | N[1]-((3-((5s,8s)-3,3-dimethyl-1-oxaspiro[4.5]decan-8-yl)-5,5-difluoro-5,6-dihydro-4H-pyrrolo[1,2-b]pyrazol-2-yl)-methyl)-N[2]-methylethane-1,2-diamine |
| 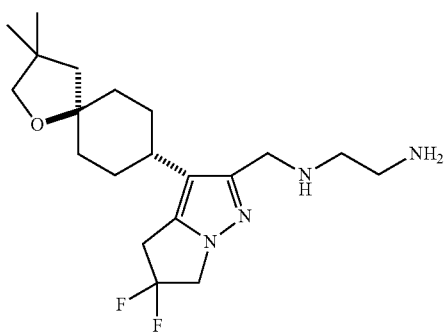 | N[1]-((3-((5r,8r)-3,3-dimethyl-1-oxaspiro[4.5[decan-8-yl)-5,5-difluoro-5,6-dihydro-4H-pyrrolo[1,2-b]pyrazol-2-yl)-methyl)ethane-1,2-diamine |

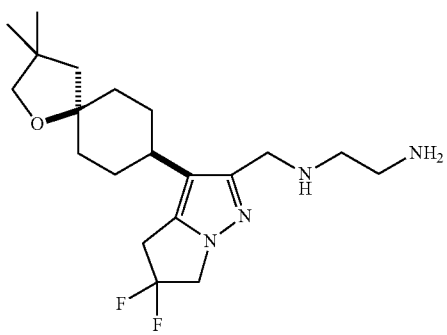

N1-((3-((5s,8s)-3,3-dimethyl-1-oxaspiro[4.5]decan-8-yl)-5,5-difluoro-5,6-dihydro-4H-pyrrolo[1,2-b]pyrazol-2-yl)methyl)ethane-1,2-diamine

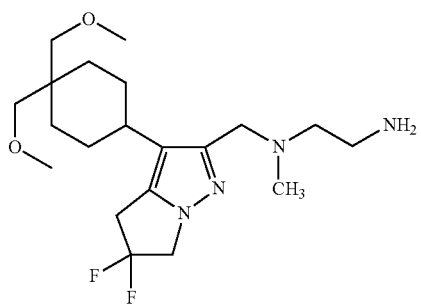 [SMILES: COCC1(COC)CCC(c2c(CN(C)CCN)nn3c2CC(F)(F)C3)CC1]

N1-((3-(4,4-bis(methoxymethyl)cyclohexyl)-5,5-difluoro-5,6-dihydro-4H-pyrrolo[1,2-b]pyrazol-2-yl)methyl)-$N^1$-methylethane-1,2-diamine

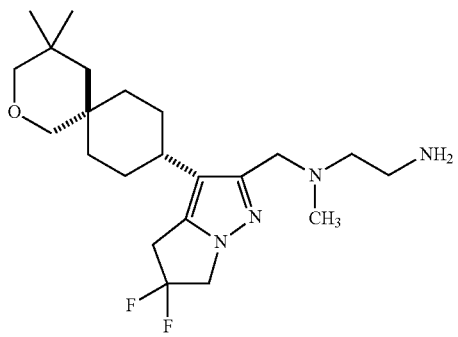

$N^1$-((3-((6s,9s)-4,4-dimethyl-2-oxaspiro[5.5]undecan-9-yl)-5,5-difluoro-5,6-dihydro-4H-pyrrolo[1,2-b]pyrazol-2-yl)methyl)-$N^1$-methylethane-1,2-diamine

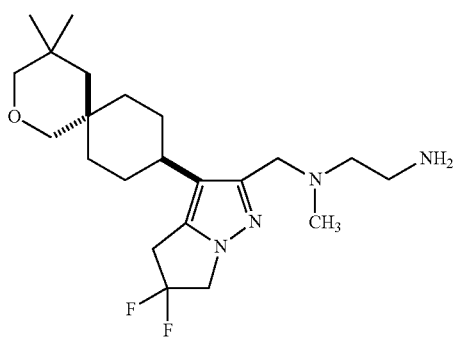

$N^1$-((3-((6r,9r)-4,4-dimethyl-2-oxaspiro[5.5]undecan-9-yl)-5,5-difluoro-5,6-dihydro-4H-pyrrolo[1,2-b]pyrazol-2-yl)methyl)-$N^1$-methylethane-1,2-diamine

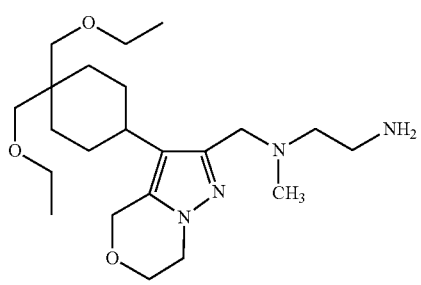 [SMILES: CCOCC1(COCC)CCC(c2c(CN(C)CCN)nn3c2COCC3)CC1]

$N^1$-((3-(4,4-bis(ethoxymethyl)cyclohexyl)-6,7-dihydro-4H-pyrazolo[5,1-c]-[1,4]oxazin-2-yl)methyl)-$N^1$-methylethane-1,2-diamine -continued

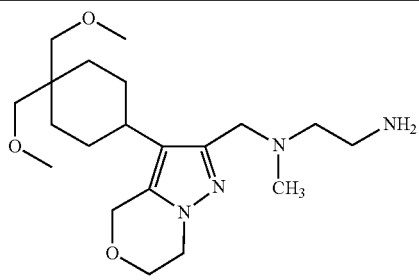

N$^1$-((3-(4,4-bis(methoxymethyl)cyclohexyl)-6,7-dihydro-4H-pyrazolo[5,1-c]-[1,4]oxazin-2-yl)methyl)-N$^1$-methylethane-1,2-diamine

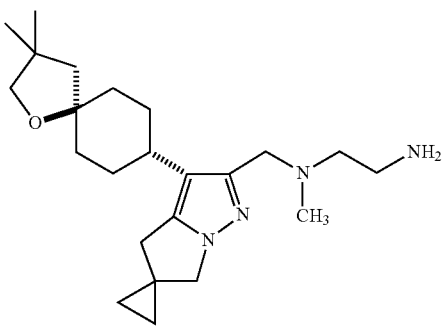

N$^1$-((3'-((5r,8r)-3,3-dimethyl-1-oxaspiro[4.5]decan-8-yl)-4'H,6'H-spiro[cyclopropane-1,5'-pyrrolo[1,2-b]pyrazol]-2'-yl)methyl)-N$^1$-methyl-ethane-1,2-diamine

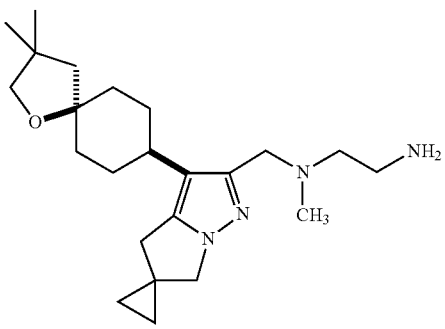

N$^1$-((3'-((5s,8s)-3,3-dimethyl-1-oxaspiro[4.5]decan-8-yl)-4'H,6'H-spiro[cyclopropane-1,5'-pyrrolo[1,2-b]pyrazol]-2'-yl)methyl)-N$^1$-methyl-ethane-1,2-diamine

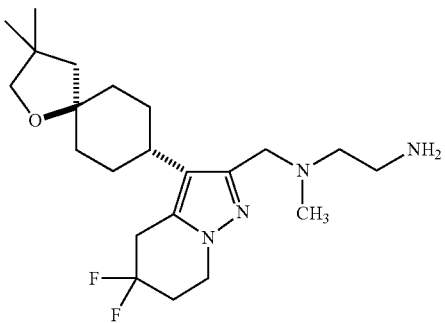

N$^1$-((3-((5r,8r)-3,3-dimethyl-1-oxaspiro[4.5]decan-8-yl)-5,5-difluoro-4,5,6,7-tetrahydropyrazolo[1,5-a]pyridin-2-yl)methyl)-N$^1$-methyl-ethane-1,2-diamine

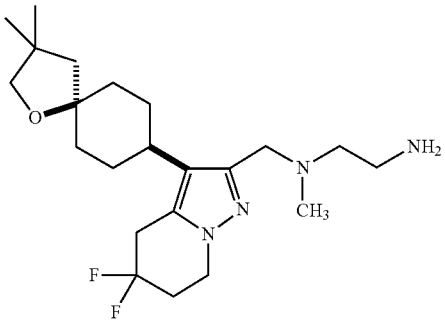

N$^1$-((3-((5s,8s)-3,3-dimethyl-1-oxaspiro[4.5]decan-8-yl)-5,5-difluoro-4,5,6,7-tetrahydropyrazolo[1,5-a]pyridin-2-yl)methyl)-N$^1$-methyl-ethane-1,2-diamine

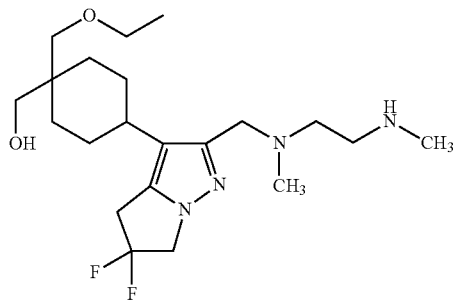 [SMILES: CCOCC1(CO)CCC(c2c(CN(C)CCNC)nn3c2CC(F)(F)C3)CC1]

(4-(5,5-difluoro-2-((methyl-(2-(methylamino)ethyl)-amino)methyl)-5,6-dihydro-4H-pyrrolo[1,2-b]pyrazol-3-yl)-1-(ethoxymethyl)-cyclohexyl)methanol

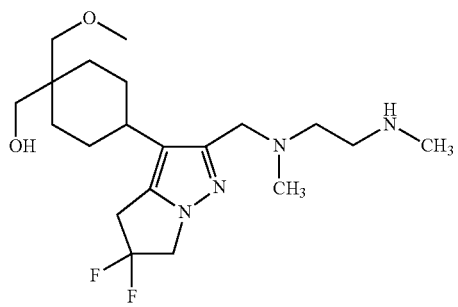 [SMILES: CNCCN(C)Cc1nn2c(c1C1CCC(CO)(COC)CC1)CC(F)(F)C2]

(4-(5,5-difluoro-2-((methyl-(2-(methylamino)ethyl)-amino)methyl)-5,6-dihydro-4H-pyrrolo[1,2-b]pyrazol-3-yl)-1-(methoxymethyl)-cyclohexyl)methanol

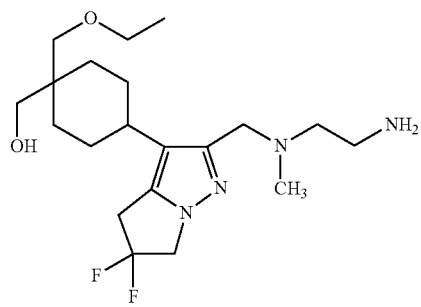 [SMILES: CCOCC1(CO)CCC(c2c(CN(C)CCN)nn3c2CC(F)(F)C3)CC1]

(4-(2-(((2-aminoethyl)-(methyl)amino)methyl)-5,5-difluoro-5,6-dihydro-4H-pyrrolo[1,2-b]pyrazol-3-yl)-1-(ethoxymethyl)-cyclohexyl)methanol

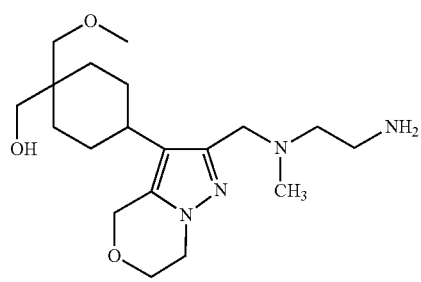 [SMILES: COCC1(CO)CCC(c2c(CN(C)CCN)nn3c2COCC3)CC1]

(4-(2-(((2-aminoethyl)-(methyl)amino)methyl)-6,7-dihydro-4H-pyrazolo[5,1-c]-[1,4]oxazin-3-yl)-1-(methoxymethyl)-cyclohexyl)methanol

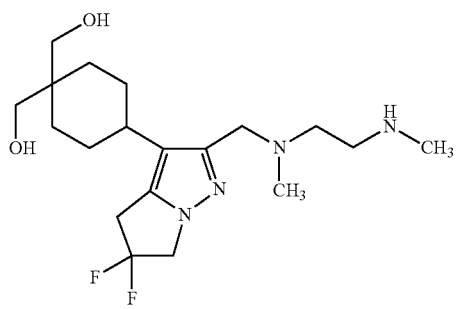 [SMILES: CNCCN(C)Cc1nn2c(c1C1CCC(CO)(CO)CC1)CC(F)(F)C2]

(4-(5,5-difluoro-2-((methyl-(2-(methylamino)ethyl)-amino)methyl)-5,6-dihydro-4H-pyrrolo[1,2-b]pyrazol-3-yl)cyclohexane-1,1-diyl)-dimethanol

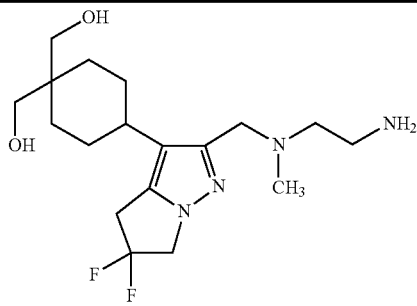
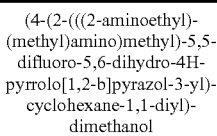

(4-(2-(((2-aminoethyl)-(methyl)amino)methyl)-5,5-difluoro-5,6-dihydro-4H-pyrrolo[1,2-b]pyrazol-3-yl)-cyclohexane-1,1-diyl)-dimethanol Certain compounds disclosed herein exist as diastereomers. This disclosure contemplates the use of individual purified diastereomers as well as mixtures. The mixtures can contain an essentially equal fractions of each possible diastereomer, or the mixtures can contain nonequal fractions of diastereomers, either as afforded directly from the reaction that creates the stereocenter, or from a later purification or separation step. Both mixtures of diastereomers and purified diastereomers can be assayed for biological activity. The absolute stereochemistry of certain individual diastereomers can be assigned based on spectroscopic and crystallographic techniques known in the art. Certain individual diastereomers can be assigned based on physical properties, for example, retention time on a chromatographic column.

BIOLOGICAL ACTIVITY ASSAY

PRMT1 Enzymatic Assay

In order to measure PRMT1 enzymatic activity the LANCE TR-FRET assay from PerkinElmer was used to follow the methylation of histone H4 at Arg3 using S-adenosyl-L-methionine (SAM) as the methyl group donor.

This enzymatic assay was performed in a 384 well, white, low volume plate (PerkinElmer, Catalog 6008289) with assay buffer consisting of 50 mM Hepes (pH 8) (Teknova, Catalog #H1090), 1 mM TCEP (Sigma, Catalog #C4706), and 0.003% Tween-20 (Thermo, Catalog #85114). Stock solutions of the test compounds were prepared in 100% DMSO (Sigma, Catalog #D2650) and serially diluted 1:3 using 100% DMSO. Compounds were additionally diluted 1:40 in assay buffer, and 2 uL/well were transferred to the assay plate. 4 uL/well (final concentration 1.5 nM) of PRMT1 protein (SignalChem, Catalog #P365-380G) diluted in assay buffer was added to the assay plate followed by a 15 min preincubation at room temperature. 4 uL/well of SAM (Sigma, Catalog #A7007) and biotinylated histone H4 (1-21) (AnaSpec, Catalog #62555) (final concentrations 1 µM and 25 nM, respectively) diluted in assay buffer were then added to the assay plate followed by a 1 hour reaction time. Final concentrations of PRMT1, SAM, and histone H4 (1-21) refer to a 10 µL volume.

Detection of methylated histone H4 (H4R3me) was achieved by combining LANCE Ultra Europium-anti-H4R3me antibody (PerkinElmer, Catalog #TRF04-14), LANCE Ultra ULight-anti-streptavidin antibody (PerkinElmer, Catalog #TRF0102), and sinefungin (Sigma, Catalog #S8559) (final concentrations 2 nM, 50 nM, and 100 µM respectively) in 1x LANCE detection buffer (PerkinElmer, Catalog #CR97-100) and adding 10 µL/well of the detection solution to the assay plate. Detection reagents were allowed to react for 1 hour at room temperature. Final concentrations in the detection solution refer to a 20 µL volume. The europium fluorescence signal and the ULight TR-FRET signal were measured using a BioTek Synergy Neo plate reader: excitation at 330 nm, emission at 620 nm and 665 nm respectively, and the ratio of the two signals (665 nm/620 nm) was used for curve fitting. $IC_{50}$ values were calculated using a four-parameter logistic curve fit using Genedata Screener software.

PRMT1 RKO Cellular Target Engagement Assay

RKO cells were routinely maintained in EMEM media (ATCC, Catalog #30-2003) supplemented with 10% fetal bovine serum (Sigma, Catalog #F2442) using a humidified incubator (37° C., 5% $CO_2$, and ambient $O_2$).

In preparation for the In-Cell Western assay, cells were harvested and resuspended in EMEM media supplemented with 10% fetal bovine serum. Cells were seeded onto a 384 well, black, clear bottom, Poly-D-Lysine coated tissue culture plate (Greiner, Catalog #781946) at a density of 1,000 cells/well in a volume of 40 µL. The culture plate was incubated for 24 hr at 37° C. with 5% $CO_2$ and ambient $O_2$. Stock solutions of the test compounds were prepared in 100% DMSO (Sigma, Catalog #D2650) and serially diluted 1:3 using 100% DMSO. Compounds were additionally diluted 1:40 in culture medium, and 10 µL/well was transferred to the tissue culture plate. Following the compound addition the microplate was incubated at 37° C. for 48 hr.

The media was removed, the plate was washed with 1x PBS (Fisher Bioreagents, Catalog #BP399-20), and cells were fixed for 10 min using 30 µL/well of 4% paraformaldehyde (Electron Microscopy Sciences, Catalog #15710). The paraformaldehyde was removed, the plate was again washed with 1x PBS, and cells were permeabilized for 15 min using 30 µL/well of 1x PBS containing 0.5% Triton-X 100 (Sigma, Catalog #1001748095). The permeabilization buffer was removed, the plate was washed with 1x PBST (Boston BioProducts, Catalog #IBB-171X), and 50 µL/well of blocking buffer (LI-COR, Catalog #927-40000) was added followed by a 1 hour incubation at room temperature. The blocking buffer was removed, and 20 µL/well of anti-asymmetric di-methyl arginine antibody (Cell Signaling, Catalog #13522S) diluted 1:1000 in LI-COR blocking buffer was added to the plate and incubated overnight, in the dark at 4° C.

The primary antibody was then removed, and the plate was washed three times with 1x PB ST. 20 µL/well of CellTag (LI-COR, Catalog #926-41090) and IRDye 800CW goat anti-rabbit IgG antibody (LI-COR, Catalog #926-32211), each diluted 1:500 in LI-COR blocking buffer supplemented with 0.1% Tween-20 (Thermo Scientific, Catalog #85114), were added to the plate. The plate was then incubated in the dark, at room temperature for 1 hour followed by three washes with 1× PBST and one wash with H₂O. The IRDye secondary antibody signal (800 channel) and the CellTag signal (700 channel) were measured using a Licor Odyssey Imager, and the 800 channel signal was then normalized to the 700 channel signal. $IC_{50}$ values were calculated using a four-parameter logistic curve fit using Genedata Screener software.

PRMT1, 4 and 6 RapidFire Mass Spectrometry Selectivity Assays

Protein arginine methyltransferases (PRMTs) catalyze the transfer of the methyl group from the cofactor S-5'-adenosyl-L-methionine (SAM) to arginine residues of a variety of histone and nonhistone proteins. The production of 5-(5'-Adenosyl)-L-homocysteine (SAH) was measured using Agilent's RapidFire 365-Agilent QQQ 6460 to assess selectivity between PRMT1, 4 and 6. Reactions were performed in a 384-well plate (Greiner, catalog #MPG-784201) with assay buffer consisting of 50 mM TRIS pH 8.0 (Invitrogen, catalog #15568-025), 1 mM TCEP (Sigma #C4706-2G), and 0.0015% Tween-20 (Thermo Scientific, catalog #85114).

Full-length human PRMT1 (1-361) was expressed in E. coli and purified. The PRMT1 assay was performed by dispensing 6 µL/well (final concentration of 2 nM) of PRMT1 protein diluted in assay buffer to the plate. Stock solutions of the test compounds were prepared in 100% DMSO (Sigma, Catalog #D2650) and serially diluted 1:3 using 100% DMSO. Compounds were additionally diluted 1:50 in assay buffer, and 6 µL/well were transferred to the assay plate. Plates were allowed to incubate for 15 min at room temperature. 12 µL/well of SAM (Cayman Chemical, Catalog #13956) and biotinylated histone H4 (1-21) (AnaSpec, catalog #62555) (final concentrations of 1 µM and 50 nM, respectively) diluted in assay buffer were added to the plate followed by a 20 min reaction time. A final reaction volume of 20 µL was quenched with the addition of 43 µL of 0.6% (w/v) trifluoroacetic acid solution (Sigma, catalog #302031).

Full-length human GST-PRMT4 (SignalChem, catalog #P365-380DG) was expressed by baculovirus in Sf9 insect cells. The PRMT4 assay was performed by dispensing 6 µL/well (final concentration of 0.5 nM) of PRMT4 protein diluted in assay buffer to the plate. Stock solutions of the test compounds were prepared in 100% DMSO (Sigma, Catalog #D2650) and serially diluted 1:3 using 100% DMSO. Compounds were additionally diluted 1:50 in assay buffer, and 6 µL/well were transferred to the assay plate. Plates were allowed to incubate for 15 min at room temperature. 12 µL/well of SAM (Cayman Chemical, Catalog #13956) and Histone H3.3 (Reaction Biology, catalog #HMT-11-134) (final concentrations of 0.5 µM and 15 nM, respectively) diluted in assay buffer, were added to the plate followed by a 60 min reaction time. A final reaction volume of 20 µL was quenched with the addition of 43 µL of 0.6% (w/v) trifluoroacetic acid solution (Sigma, catalog #302031).

Full-length human PRMT6 (1-375) was expressed in E. coli and purified. The PRMT6 assay was performed by dispensing 6 uL/well (final concentration of 10 nM) of PRMT6 protein diluted in assay buffer to the plate. Stock solutions of the test compounds were prepared in 100% DMSO (Sigma, Catalog #D2650) and serially diluted 1:3 using 100% DMSO. Compounds were additionally diluted 1:50 in assay buffer, and 6 µL/well were transferred to the assay plate. Plates were allowed to incubate for 15 min at room temperature. 12 µL/well of SAM (Cayman Chemical, Catalog #13956) and Histone H4 (36-50) K44 Me1 (Rockland, catalog, #000-001-K44) (final concentrations of 3 µM and 250 nM, respectively) diluted in assay buffer, were added to the plate followed by a 30 min reaction time. A final reaction volume of 20 µL was quenched with the addition of 43 µL of 0.6% (w/v) trifluoroacetic acid solution (Sigma, catalog #302031).

PRMT1, 4 and 6 assay plates were transferred to the RapidFire 365 autosampler coupled to an Agilent QQQ 6460 mass spectrometer. RapidFire buffer A contained H₂O and buffer B was 80% acetonitrile/H₂O. The samples were loaded onto a C18 type C (Agilent, catalog #G9203-80105) cartridge with load/wash time=3000 ms, elute time=4000 ms and re-equilibrate time=500 ms. The flow rates for pumps 1, 2 and 3 are as follows: 1.5 mL/min, 1.25 mL/min and 1.25 mL/min, respectively. SAH peaks were integrated using RapidFire peak software and $IC_{50}$ values were calculated using a four-parameter logistic curve fit using Genedata Screener software.

TABLE 4

| PRMT-1 Enzymatic Assay $IC_{50}$ values | |
|---|---|
| Ex. no. | PRMT-1 $IC_{50}$, nM |
| 1a | 93 |
| 1b | 58 |
| 2 | 88 |
| 3a | 58 |
| 3b | 125 |
| 4 | 163 |
| 5 | N.D. |
| 5a | 48 |
| 5b | 33 |
| 6a | 63 |
| 6b | 67 |
| 7a | N.D. |
| 7b | N.D. |
| 8a | 50 |
| 8b | 52 |
| 9a | 49 |
| 9b | 55 |
| 10 | 62 |
| 11 | 44 |
| 12 | 151 |
| 13 | 37 |
| 14 | 173 |
| 15 | 128 |
| 16 | 42 |
| 17 | 76 |
| 18 | 64 |
| 19 | 156 |
| 20 | 59 |
| 21 | 53 |
| 22 | 44 |
| 23 | 125 |
| 24 | 203 |
| 25 | 54 |
| 26 | 64 |
| 27 | 48 |
| 28 | 65 |
| 29 | 87 |
| 30 | 71 |
| 31 | 117 |
| 32 | 43 |
| 33 | 95 |
| 34 | 84 |
| 35 | 172 |
| 36 | 156 |
| 37 | 75 |
| 38 | 168 |
| 39 | 80 |
| 40 | 166 |
| 41 | 98 |
| 42 | 114 |
| 43 | 47 |
| 44 | 99 |
| 45 | 70 |
| 46 | 89 |
| 47 | 87 |

TABLE 4-continued

PRMT-1 Enzymatic Assay IC$_{50}$ values

| Ex. no. | PRMT-1 IC$_{50}$, nM |
|---|---|
| 48 | 176 |
| 49 | 39 |
| 50 | 444 |
| 51 | 29 |
| 52 | 256 |
| 53 | 317 |
| 54 | 398 |
| 55 | 134 |
| 56 | 95 |
| 57 | 555 |
| 58 | 128 |
| 59 | 362 |
| 60 | 148 |
| 61 | 126 |
| 62a | 70 |
| 62b | 70 |
| 63a | 45 |
| 63b | 217 |
| 64a | 69 |
| 64b | 111 |
| 65a | 34 |
| 65b | 40 |
| 66a | 68 |
| 66b | 70 |
| 67a | 66 |
| 67b | 590 |
| 68a | 62 |
| 68b | 434 |
| 69a | 174 |
| 69b | 101 |
| 70a | 47 |
| 70b | 51 |
| 71a | 69 |
| 71b | 537 |
| 72a | 243 |
| 72b | 163 |
| 73a | 74 |
| 73b | 65 |
| 74a | 74 |
| 74b | 51 |
| 75a | 147 |
| 75b | 53 |
| 76a | 79 |
| 76b | 50 |
| 77a | 127 |
| 77b | 457 |
| 78a | 75 |
| 78b | 46 |
| 79a | 42 |
| 79b | 36 |
| 80a | 59 |
| 80b | 24 |
| 81 | 62 |
| 82a | 70 |
| 82b | 34 |
| 83a | 83 |
| 83b | 78 |
| 84 | 71 |
| 85 | 99 |
| 86a | 41 |
| 86b | 30 |
| 87a | 40 |
| 87b | 24 |
| 88a | 98 |
| 88b | 48 |
| 89a | 71 |
| 89b | 29 |
| 90 | 68 |
| 91 | 22 |
| 92 | 73 |
| 93a | 57 |
| 93b | 52 |
| 94a | 43 |
| 94b | 27 |
| 95a | 30 |
| 95b | 27 |
| 96a | 46 |
| 96b | 34 |
| 97a | 66 |
| 97b | 52 |
| 98a | 71 |
| 98b | 47 |
| 99 | 42 |
| 100a | 52 |
| 100b | 22 |
| 101a | 52 |
| 101b | 29 |
| 102 | 128 |
| 103a | 63 |
| 103b | 37 |
| 104a | 76 |
| 104b | 91 |
| 105 | 105 |
| 106 | 173 |
| 107a | 46 |
| 107b | 55 |

TABLE 5

PRMT-1 Target Engagement IC$_{50}$ values

| Ex. no. | RKO Cellular IC$_{50}$ (nM) |
|---|---|
| 1a | 374 |
| 1b | 348 |
| 2 | 364 |
| 3a | 370 |
| 3b | 856 |
| 4 | 367 |
| 5 | N.D. |
| 5a | 212 |
| 5b | 444 |
| 6a | 2854 |
| 6b | 370 |
| 7a | N.D. |
| 7b | N.D. |
| 8a | 794 |
| 8b | 258 |
| 9a | 362 |
| 9b | 288 |
| 10 | 3344 |
| 11 | 14013 |
| 12 | 3963 |
| 13 | 766 |
| 14 | 26030 |
| 15 | 6586 |
| 16 | 1238 |
| 17 | 2093 |
| 18 | 5814 |
| 19 | 954 |
| 20 | 361 |
| 21 | 13604 |
| 22 | 3536 |
| 23 | 233 |
| 24 | 357 |
| 25 | 16608 |
| 26 | 50000 |
| 27 | 1309 |
| 28 | 1574 |
| 29 | 438 |
| 30 | 1076 |
| 31 | 1090 |
| 32 | 9231 |
| 33 | 7404 |
| 34 | 448 |
| 35 | 504 |
| 36 | 1674 |
| 37 | 1644 |
| 38 | 846 |

TABLE 5-continued

PRMT-1 Target Engagement IC$_{50}$ values

| Ex. no. | RKO Cellular IC$_{50}$ (nM) |
|---|---|
| 39 | 1613 |
| 40 | 10929 |
| 41 | 2754 |
| 42 | 2140 |
| 43 | 2116 |
| 44 | 1382 |
| 45 | 1270 |
| 46 | 563 |
| 47 | 6314 |
| 48 | 10000 |
| 49 | 1716 |
| 50 | 50000 |
| 51 | 2691 |
| 52 | 37056 |
| 53 | 50000 |
| 54 | 50000 |
| 55 | 17538 |
| 56 | 353 |
| 57 | 3286 |
| 58 | 9158 |
| 59 | 2674 |
| 60 | 233 |
| 61 | 1495 |
| 62a | 32008 |
| 62b | 29494 |
| 63a | 617 |
| 63b | 43456 |
| 64a | 772 |
| 64b | 564 |
| 65a | 678 |
| 65b | 351 |
| 66a | 459 |
| 66b | 263 |
| 67a | 590 |
| 67b | 5227 |
| 68a | 9428 |
| 68b | 10000 |
| 69a | 1758 |
| 69b | 370 |
| 70a | 2656 |
| 70b | 1718 |
| 71a | 304 |
| 71b | 7416 |
| 72a | 3460 |
| 72b | 2354 |
| 73a | 232 |
| 73b | 556 |
| 74a | 223 |
| 74b | 372 |
| 75a | 6326 |
| 75b | 948 |
| 76a | 1635 |
| 76b | 356 |
| 77a | 3927 |
| 77b | 10000 |
| 78a | 705 |
| 78b | 370 |
| 79a | 214 |
| 79b | 203 |
| 80a | 3828 |
| 80b | 335 |
| 81 | 504 |
| 82a | 2382 |
| 82b | 1075 |
| 83a | 153 |
| 83b | 341 |
| 84 | 177 |
| 85 | 296 |
| 86a | 769 |
| 86b | 1258 |
| 87a | 83 |
| 87b | 5868 |
| 88a | 2900 |
| 88b | 348 |
| 89a | 4574 |
| 89b | 423 |
| 93a | 251 |
| 93b | 198 |
| 94a | 254 |
| 94b | 585 |
| 95a | 395 |
| 95b | 250 |
| 96a | 1073 |
| 96b | 369 |
| 97a | 1436 |
| 97b | 364 |
| 98a | 5271 |
| 98b | 360 |
| 99 | 461 |
| 100a | 4452 |
| 100b | 1883 |
| 101a | 2550 |
| 101b | 1663 |
| 102 | 370 |
| 103a | 3204 |
| 103b | 1232 |
| 104a | 180 |
| 104b | 385 |
| 105 | 1176 |
| 106 | 428 |
| 107a | 555 |
| 107b | 1884 |

TABLE 6

Rapid fire PRMT-1/-4/-6 Enzyme IC50 values

| Example n | PRMT-1 IC$_{50}$ (nM) | PRMT-4 IC$_{50}$ (nM) | PRMT-6 IC$_{50}$ (nM) |
|---|---|---|---|
| 2 | 331 | 79 | 314 |
| 11 | 93 | 654 | 99 |
| 21 | 84 | 1124 | 141 |
| 49 | 106 | 114 | 74 |
| 51 | 53 | 337 | 79 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment of a cancer chosen from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor, comprising the administration of a therapeutically effective amount of a compound of structural Formula I

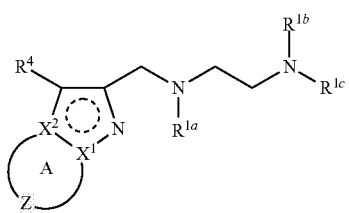
(I)

or a salt thereof, wherein:
A is a monocyclic heterocycloalkyl ring comprising 5 to 7 ring members including:
$X^1$ and $X^2$,
Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and
all other ring members Y, which are chosen from —$CH_2$—, —$CHR_2$—, and —$C(R^2)_2$—;
$R^{1a}$, $R^{1b}$, and $R^{1c}$ are independently chosen from H and $CH_3$;
either $X^1$ is C and $X^2$ is N, or $X^1$ is N and $X^2$ is C;
each $R^2$ and $R^3$ is independently chosen from cyano, halo, hydroxy, $C_{1-6}$alkyl, $C_{1-6}$haloalkyl, $C_{1-6}$hydroxyalkyl, $(C_{1-6}$alkoxy$)C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5a}C(O)OR^{5b}$, $NR^{5c}C(O)NR^{5a}R^{5b}$, and $NR^{5a}SO_2R^{5b}$, or
any two $R^2$ or $R^3$, when directly attached to the same atom, forms a 3-7 membered cycloalkyl or heterocycloalkyl ring;
$R^4$ is chosen from cycloalkyl, heterocycloalkyl, aryl and heteroaryl, any of which is optionally substituted with 1, 2, 3, or 4 $R^6$ groups;
each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl, or
$R^{5a}$ and $R^{5b}$, when directly attached to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl;
each $R^6$ is independently chosen from $C_{1-6}$alkyl, cyano$C_{1-6}$ alkyl, halo$C_{1-6}$alkyl, hydroxy$C_{1-6}$alkyl, $(C_{1-6}$alkoxy$)C_{1-6}$alkyl, $(haloC_{1-6}$alkoxy$)C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, $(C_{3-6}$alkoxy$)C_{3-6}$cycloalkyl, $(C_{3-6}$cycloalkyl$)C_{1-6}$alkyl, (heterocycloalkyl)$C_{1-6}$alkyl, (aryl)$C_{1-6}$alkyl, (heteroaryl)$C_{1-6}$alkyl, $((C_{1-6}$alkyl)aryl)$C_{1-6}$alkyl, $((C_{1-6}$ (alkyl)heteroaryl)$C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;
each $R^7$ is independently chosen from $C_{1-6}$alkyl, halo$C_{1-6}$ alkyl, aryl, heteroaryl, $C_{3-6}$cycloalkyl, heterocycloalkyl, (aryl)$C_{1-6}$alkyl, (heteroaryl)$C_{1-6}$alkyl, (cycloalkyl)$C_{1-6}$ alkyl, and (heterocycloalkyl)$C_{1-6}$alkyl, any of which is optionally substituted with 1 or 2 $R^8$ groups; and
each $R^8$ is independently chosen from $C_{1-6}$alkyl, halo$C_{1-6}$ alkyl, $C_{3-6}$cycloalkyl, and halo$C_{3-6}$cycloalkyl;
to a patient in need thereof.

2. The method as recited in claim 1, further comprising the administration of a non-chemical method of cancer treatment.

3. The method as recited in claim 2, wherein said non-chemical method of cancer treatment is chosen from surgery, radiation therapy, thermoablation, focused ultrasound therapy, and cryotherapy.

4. The method as recited in claim 1, wherein the compound of structural Formula I is of structural Formula II:

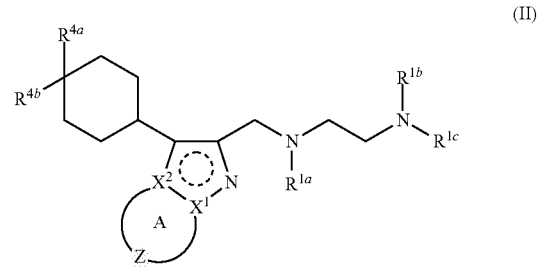
(II)

or a salt thereof, wherein:
A is a monocyclic heterocycloalkyl ring comprising 5 to 7 ring members including:
$X^1$ and $X^2$,
Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and all other ring members Y, which are chosen from —$CH_2$—, —$CHR^2$—, and —$C(R^2)_2$—;
$R^{1a}$, $R^{1b}$, and $R^{1c}$ are independently chosen from H and $CH_3$;
either $X_1$ is C and $X_2$ is N, or $X_1$ is N and $X_2$ is C;
each $R^2$ and $R^3$ is independently chosen from cyano, halo, hydroxy, $C_{1-6}$alkyl, $C_{1-6}$haloalkyl, $C_{1-6}$hydroxyalkyl, $(C_{1-6}$alkoxy$)C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5a}C(O)OR^{5b}$, $NR^{5c}C(O)NR^{5a}R^{5b}$, and $NR^{5a}SO_2R^{5b}$, or any two $R^2$ or $R^3$, when directly attached to the same atom, forms a 3-7 membered cycloalkyl or heterocycloalkyl ring;

$R^{4a}$ and $R^{4b}$, together with the atom to which they are attached, form a cycloalkyl or heterocycloalkyl ring, which is optionally substituted with 1, 2, or 3 $R^6$ groups;

each $R^{5a}$ and $R^{5b}$ is independently chosen from H, $C_{1-6}$alkyl, cyano$C_{1-6}$alkyl, halo$C_{1-6}$ alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$ alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl;

each $R^6$ is independently chosen from $C_{1-6}$alkyl, cyano$C_{1-6}$ alkyl, halo$C_{1-6}$alkyl, hydroxy$C_{1-6}$alkyl, $(C_{1-6}$alkoxy$)C_{1-6}$alkyl, (halo$C_{1-6}$alkoxy$)C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, $(C_{3-6}$alkoxy$)C_{3-6}$cycloalkyl, $(C_{3-6}$cycloalkyl$)C_{1-6}$alkyl, $(C_{3-6}$heterocycloalkyl$)C_{1-6}$alkyl, (aryl$)C_{1-6}$alkyl, (heteroaryl$)C_{1-6}$alkyl, $((C_{1-6}$alkyl)aryl$)C_{1-6}$alkyl, $((C_{1-6}$ alkyl)heteroaryl$)C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

each $R^7$ is independently chosen from $C_{1-6}$alkyl, halo$C_{1-6}$ alkyl, aryl, heteroaryl, $C_{3-6}$ cycloalkyl, $C_{3-6}$heterocycloalkyl, (aryl$)C_{1-6}$alkyl, (heteroaryl$)C_{1-6}$alkyl, (cycloalkyl$)C_{1-6}$alkyl, and (heterocycloalkyl$)C_{1-6}$alkyl, any of which is optionally substituted with 1 or 2 $R^8$ groups; and each $R^8$ is independently chosen from $C_{1-6}$alkyl, halo$C_{1-6}$ alkyl, $C_{3-6}$cycloalkyl, and halo$C_{3-6}$cycloalkyl.

5. The method as recited in claim 4, wherein:

A comprises 5 or 6 ring members; and each $R^6$ is independently chosen from $C_{1-6}$alkyl, halo$C_{1-6}$ alkyl, $(C_{1-6}$alkoxy$)C_{1-6}$alkyl, (halo$C_{1-6}$alkoxy$)C_{1-6}$alkyl, $(C_{3-6}$cycloalkyl$)C_{1-6}$alkyl, $(C_{3-6}$heterocycloalkyl$)C_{1-6}$alkyl, (aryl$)C_{1-6}$alkyl, (heteroaryl$)C_{1-6}$alkyl, $((C_{1-6}$alkyl)aryl$)C_{1-6}$alkyl, and $((C_{1-6}$ alkyl)heteroaryl$)C_{1-6}$alkyl.

6. The method as recited in claim 5, wherein:

$R^{4a}$ and $R^{4b}$, together with the atom to which they are attached, form a ring chosen from oxetane, tetrahydrofuran, oxane, azetidine, pyrrolidine, and piperidine, any of which is optionally substituted with 1 or 2 $R^6$ groups.

7. The method as recited in claim 6, wherein the compound of structural Formula II is chosen from:

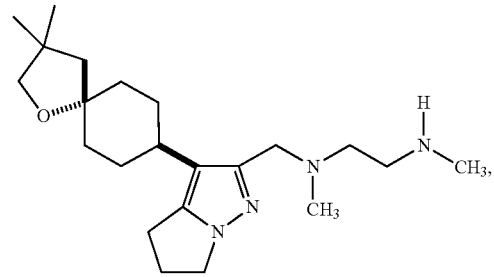

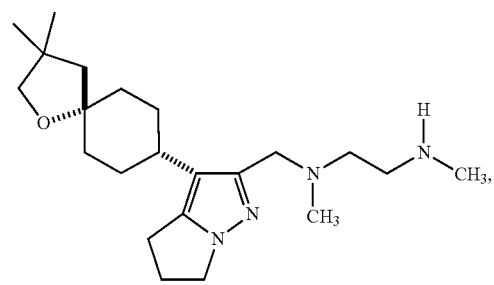

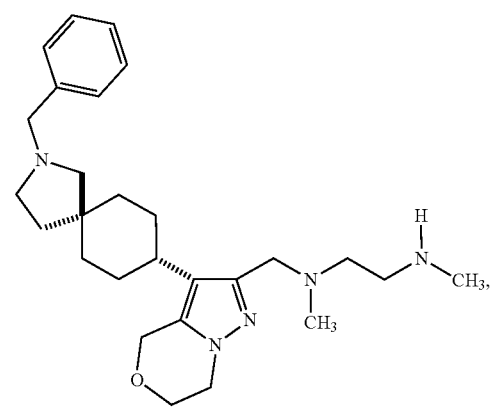

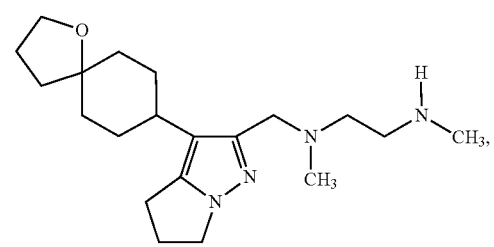

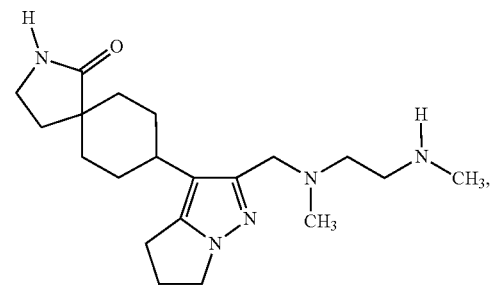

289
-continued
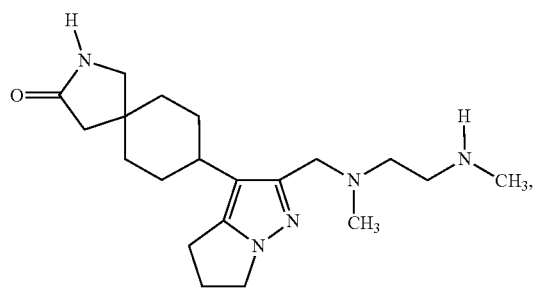
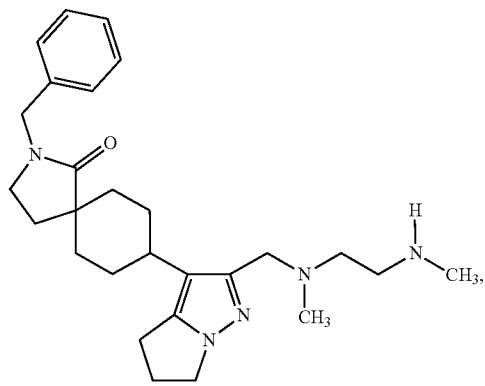
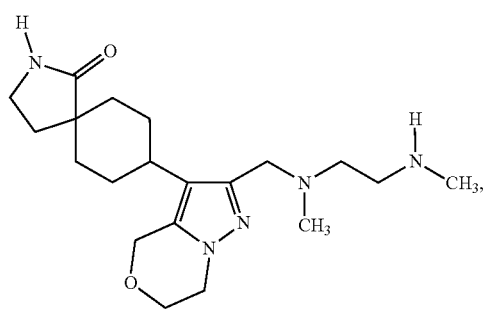
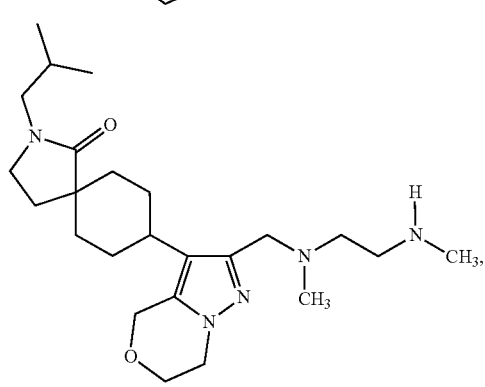
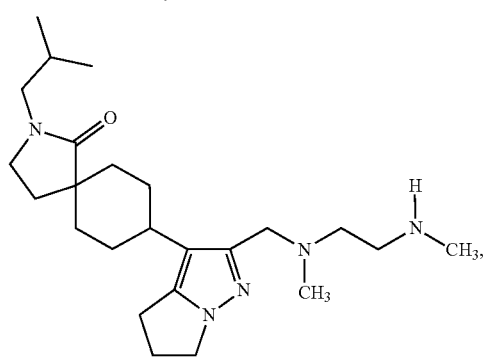
290
-continued
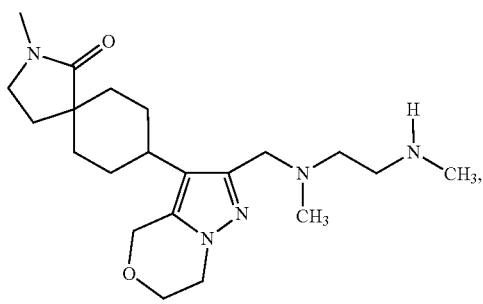
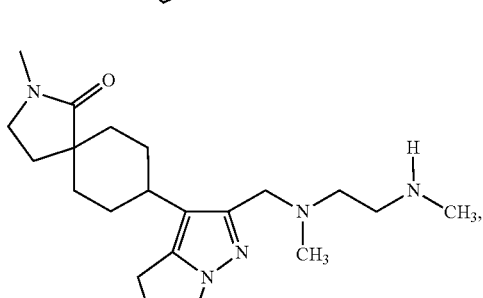
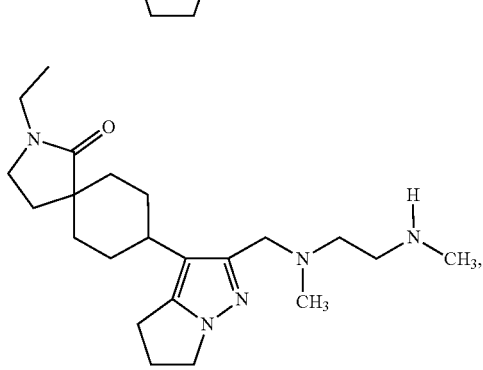
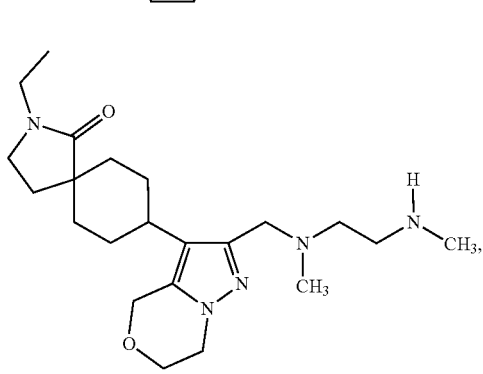
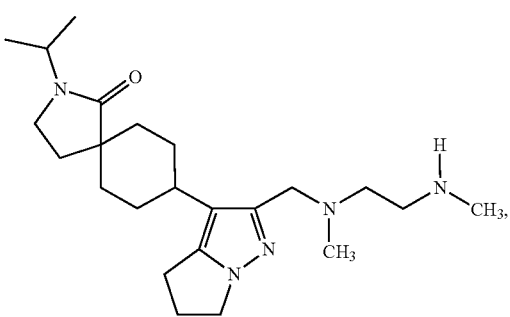

291
-continued
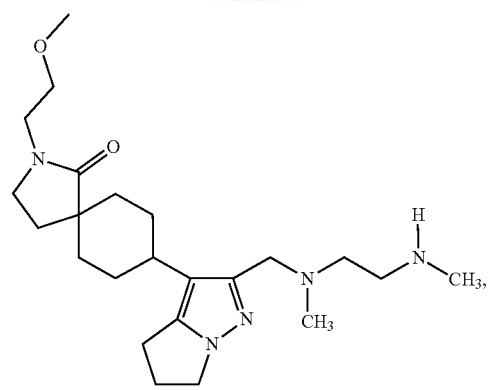
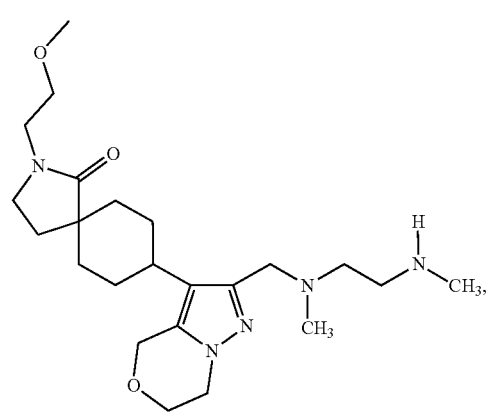
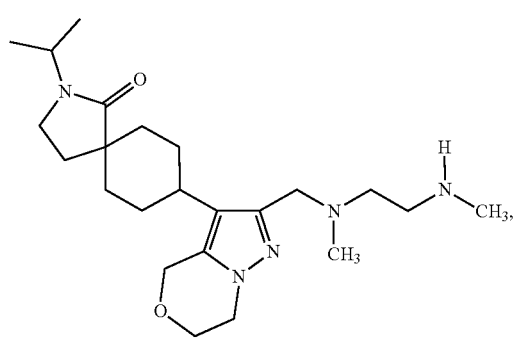
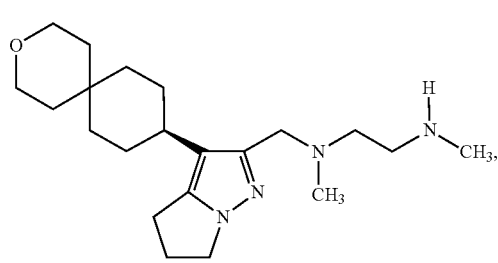
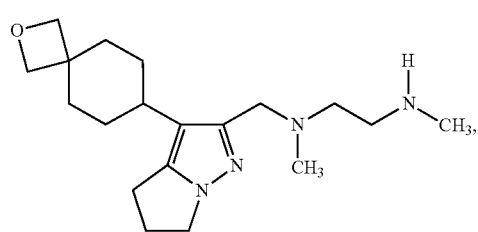
292
-continued
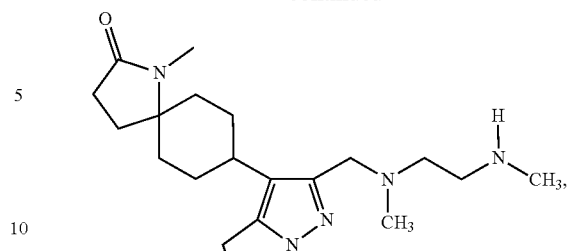
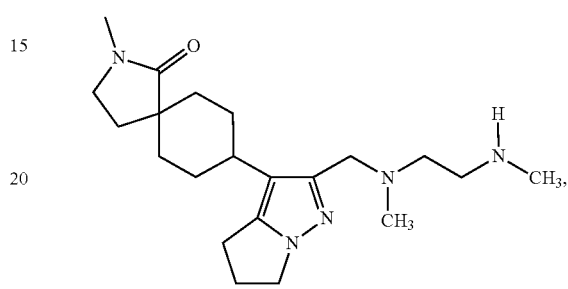
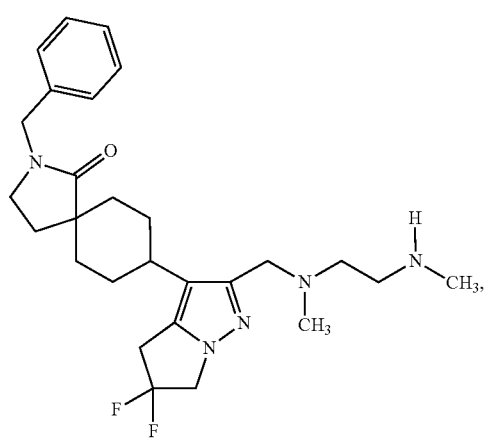
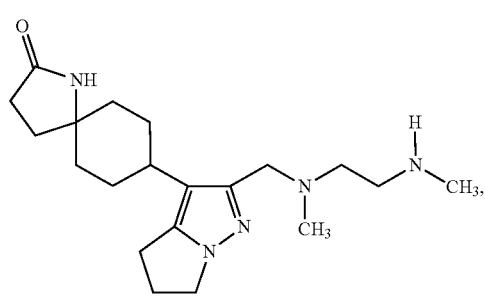
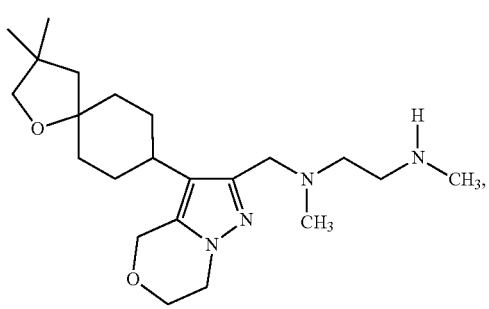

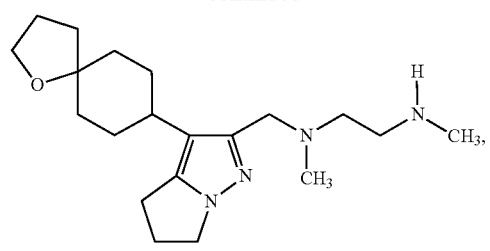
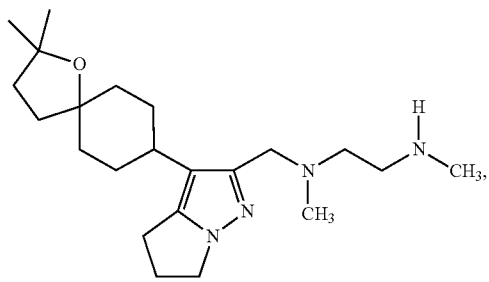
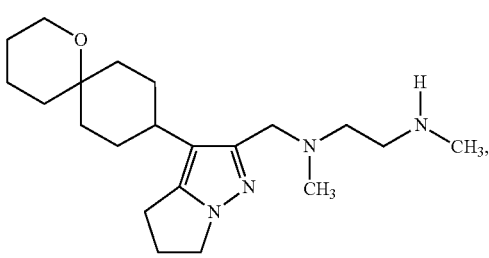
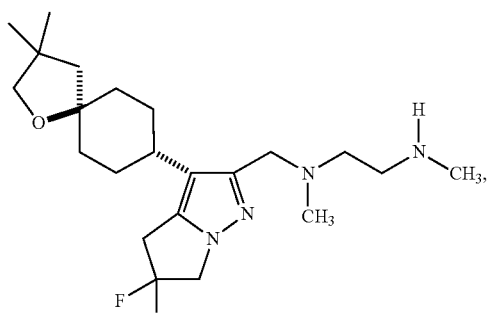
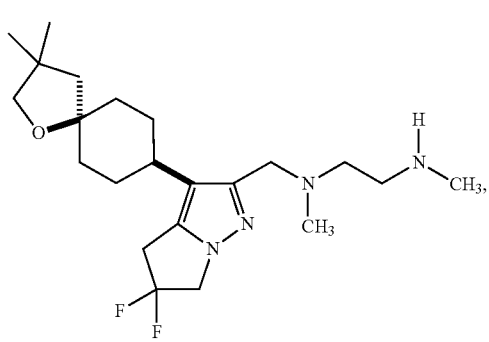
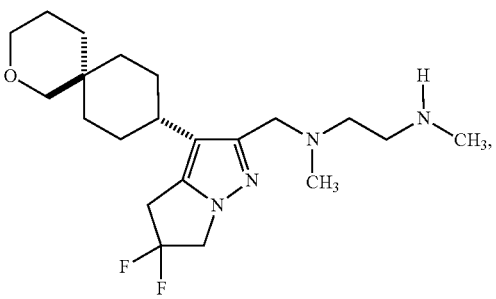

295
-continued
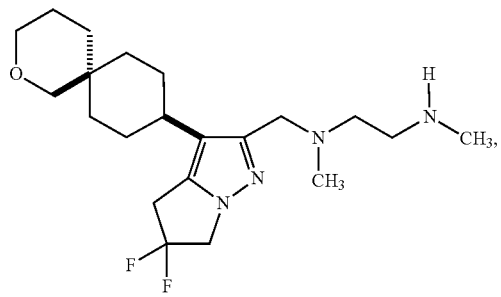
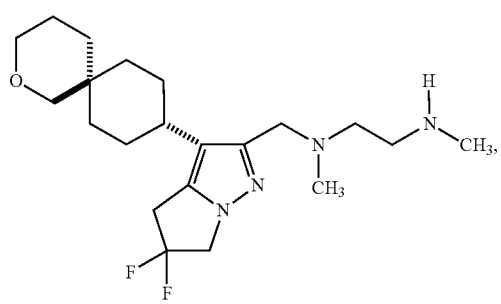
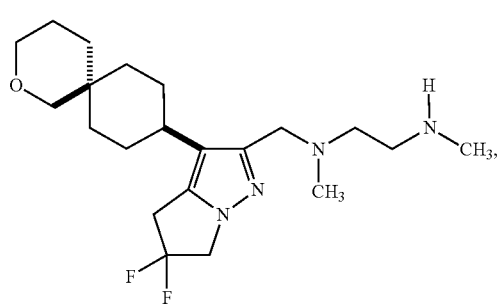
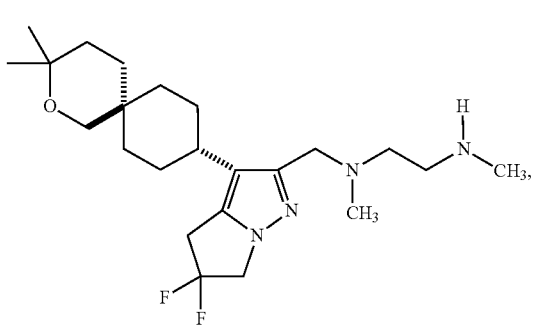
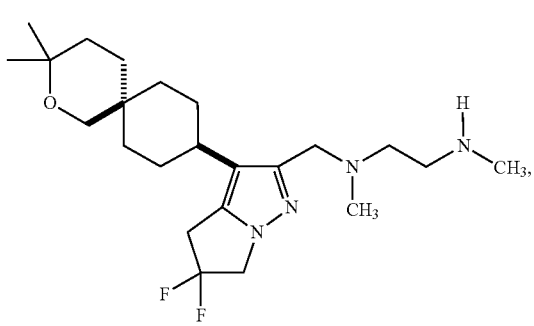
296
-continued
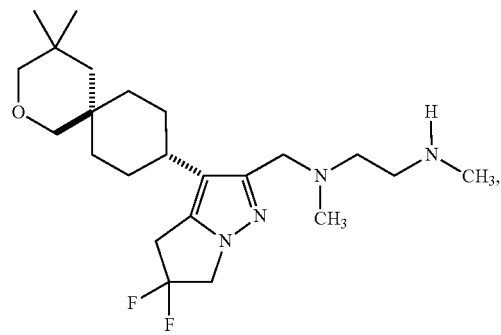
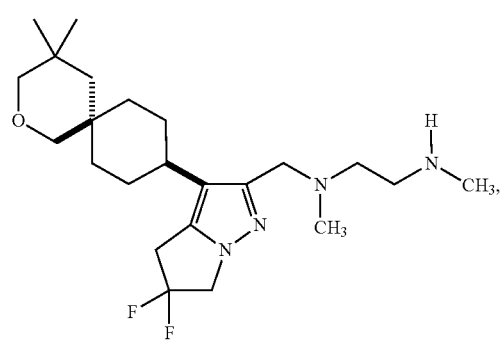
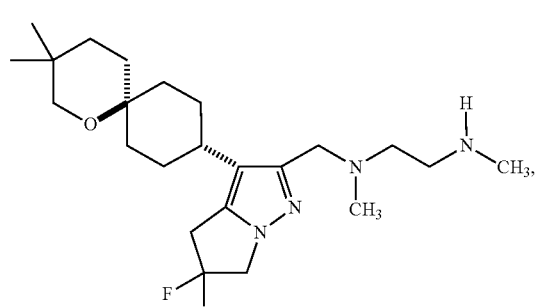
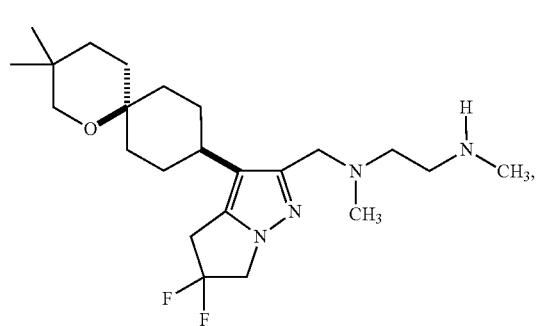
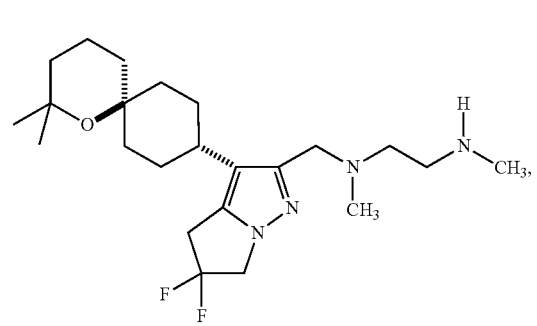

297
-continued
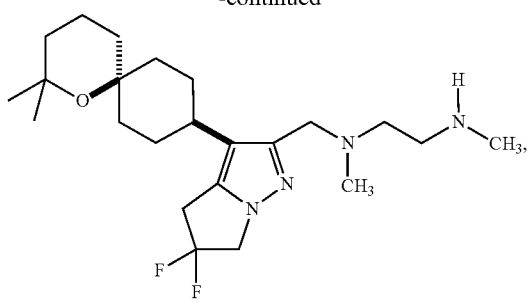
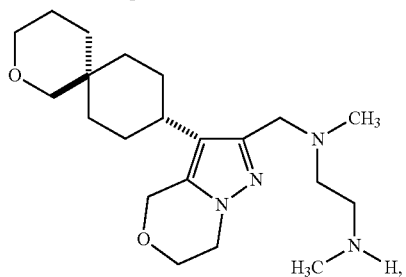
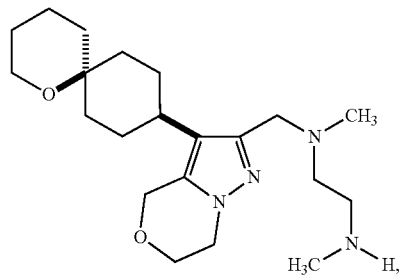
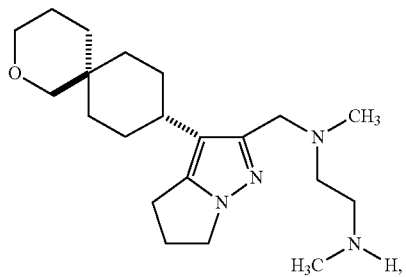
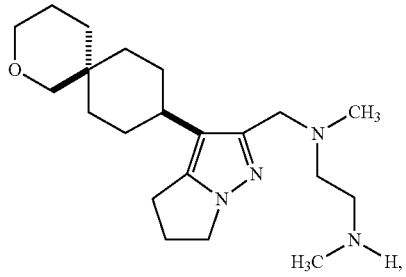
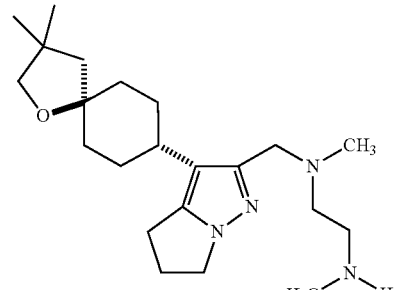
298
-continued
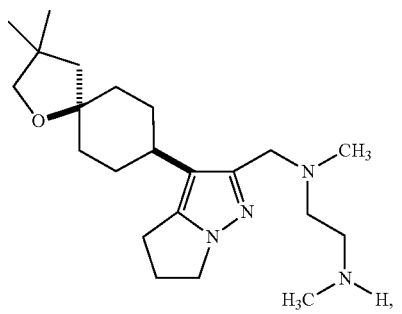
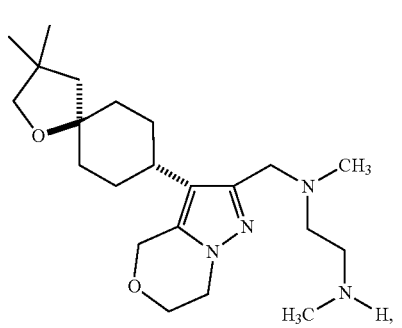
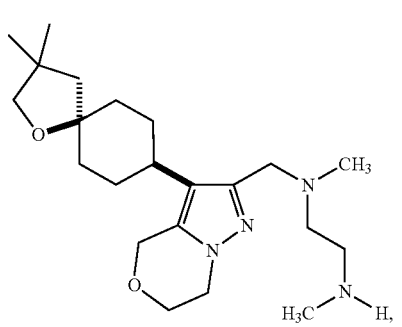
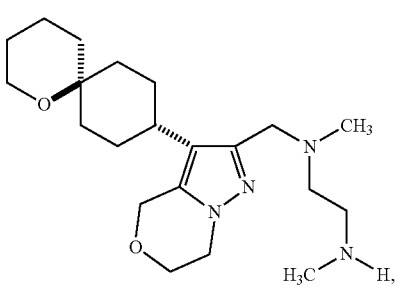
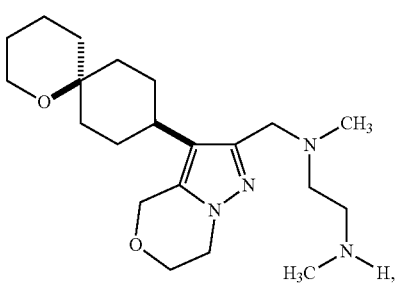

-continued

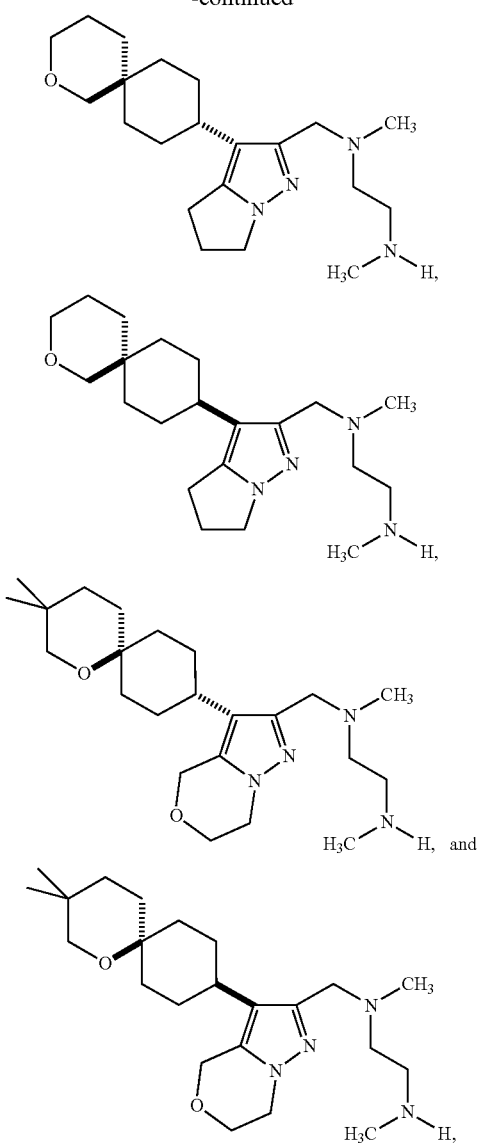

or a salt thereof.

8. The method as recited in claim 1, wherein the compound of structural Formula I is of structural Formula III

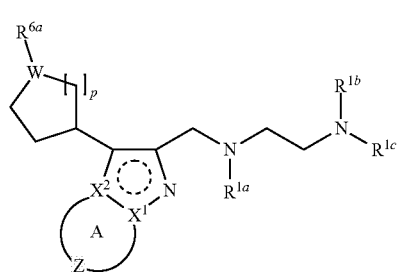

(III)

or a salt thereof, wherein:

A is a monocyclic heterocycloalkyl ring comprising 5 to 7 ring members including:

$X^1$ and $X^2$,

Z, which is chosen from —$CH_2$—, —$CHR^3$—, —$C(R^3)_2$—, —$N(R^{5a})$—, $N(COR^{5a})$—, $N(CONR^{5a}R^{5b})$—, $N(SO_2R^{5a})$—, —O—, and —$SO_2$—, and all other ring members Y, which are chosen from —$CH_2$—, —$CHR^2$—, and —$C(R^2)_2$—;

$R^{1a}$, $R^{1b}$, and $R^{1c}$ are independently chosen from H and $CH_3$;

either $X^1$ is C and $X^2$ is N, or $X^1$ is N and $X^2$ is C;

W is chosen from $C(R^{6b})$ and N;

each $R^2$ and $R^3$ is independently chosen from cyano, halo, hydroxy, $C_{1-6}$alkyl, $C_{1-6}$haloalkyl, $C_{1-6}$hydroxyalkyl, $(C_{1-6}$alkoxy$)C_{1-6}$alkyl; $OR^{5a}$, $C(O)R^{5a}$, $C(O)OR^{5a}$, $C(O)NR^{5a}R^{5b}$, $SO_2R^{5a}$; $SO_2NR^{5a}R^{5b}$, $NR^{5a}R^{5b}$, $NR^{5a}C(O)R^{5b}$, $NR^{5a}C(O)OR^{5b}$, $NR^{5c}C(O)NR^{5a}R^{5b}$, and $NR^{5a}SO_2R^{5b}$, or any two $R^2$ or $R^3$, when directly attached to the same atom, forms a 3-7 membered cycloalkyl or heterocycloalkyl ring;

each $R^{5a}$ and $R^{5b}$ is independently chosen from H, $C_{1-6}$alkyl, cyano$C_{1-6}$alkyl, halo$C_{1-6}$alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl, or $R^{5a}$ and $R^{5b}$, when attached directly to the same atom, forms a 3-7 membered cycloalkyl or heterocycloalkyl ring;

$R^{5c}$ is chosen from H, $C_{1-6}$alkyl, cyano$C_{1-6}$alkyl, halo$C_{1-6}$alkyl, hydroxy$C_{1-6}$alkyl, $(C_{1-6}$alkoxy$)C_{1-6}$alkyl; $C_{3-6}$cycloalkyl, cyano$C_{3-6}$cycloalkyl, halo$C_{3-6}$cycloalkyl, hydroxy$C_{3-6}$cycloalkyl, and $(C_{3-6}$alkoxy$)C_{3-6}$cycloalkyl;

$R^{6a}$ and $R^{6b}$ are independently chosen from H, $C_{1-6}$alkyl, cyano$C_{1-6}$alkyl, halo$C_{1-6}$alkyl, hydroxy$C_{1-6}$alkyl, $(C_{1-6}$alkoxy$)C_{1-6}$alkyl, (halo$C_{1-6}$alkoxy$)C_{1-6}$alkyl, $C_{3-6}$cycloalkyl, cyano$C_{3-6}$cycloalkyl, halo$C_{3-6}$cycloalkyl, hydroxy$C_{3-6}$cycloalkyl, $(C_{3-6}$alkoxy$)C_{3-6}$cycloalkyl, $(C_{3-6}$cycloalkyl$)C_{1-6}$alkyl, $(C_{3-6}$heterocycloalkyl$)C_{1-6}$alkyl, (aryl)$C_{1-6}$alkyl, (heteroaryl)$C_{1-6}$alkyl, $((C_{1-6}$alkyl$)$aryl$)C_{1-6}$alkyl, $((C_{1-6}$alkyl$)$heteroaryl$)C_{1-6}$alkyl, $OR^7$, $CH_2OR^7$, $CH_2CH_2OR^7$, $COR^7$, COOH, $COOR^7$, $CONH_2$, $CONHR^7$, $CON(R^7)_2$, $NHCOR^7$, $NR^7COR^7$, $NHCONH_2$, $NHCONHR^7$, $NHCON(R^7)_2$, $NR^7CONH_2$, $NR^7CONHR^7$, $NR^7CON(R^7)_2$, $SO_2R^7$, $SO_2NHR^7$, $SO_2N(R^7)_2$, $NHSO_2R^7$, $NR^7SO_2R^7$, carboxy, cyano, halo, hydroxy, and oxo;

each $R^7$ is independently chosen from $C_{1-6}$alkyl, halo$C_{1-6}$alkyl, aryl, heteroaryl, $C_{3-6}$cycloalkyl, $C_{3-6}$heterocycloalkyl, (aryl)$C_{1-6}$alkyl, (heteroaryl)$C_{1-6}$alkyl, (cycloalkyl)$C_{1-6}$alkyl, and (heterocycloalkyl)$C_{1-6}$alkyl, any of which is optionally substituted with 1 or 2 $R^8$ groups;

each $R^8$ is independently chosen from $C_{1-6}$alkyl, halo$C_{1-6}$alkyl, $C_{3-6}$cycloalkyl, and halo$C_{3-6}$cycloalkyl; and p is chosen from 1 and 2.

9. The method as recited in claim 8, wherein:

A comprises 5 or 6 ring members; and $R^{6a}$ and $R^{6b}$ are independently chosen from H, $C_{1-6}$alkyl, $(C_{1-6}$alkoxy$)C_{1-6}$alkyl, (halo$C_{1-6}$alkoxy$)C_{1-6}$alkyl, $C_{3-6}$cycloalkyl, $(C_{3-6}$alkoxy$)C_{3-6}$cycloalkyl, $OR^7$, $COR^7$, COOH, $COOR^7$, $CONH_2$, $CONHR^7$, $CON(R^7)_2$, $HCOR^7$, $NHCONHR^7$, $NHCON(R^7)_2$, $SO_2R^7$, $SO_2NHR^7$, $SO_2N(R^7)_2$, $NHSO_2R^7$, cyano, halo, hydroxy, and oxo.

10. The method as recited in claim 9, wherein:

Z is chosen from —$CH_2$—, —$CF_2$—, —$C(R^3)_2$—, —$N(R^{5a})$—, $N(COR^{5a})$—, and —O—; and each Y is —$CH_2$—.

11. The method of claim 10, wherein:

$R^{6a}$ and $R^{6b}$ are independently chosen from H, $C_{1-6}$alkyl, $(C_{1-6}$alkoxy$)C_{1-6}$alkyl, (fluoro$C_{1-6}$alkoxy$)C_{1-6}$alkyl, $C_{3-6}$cycloalkyl, $(C_{3-6}$alkoxy$)C_{3-6}$cycloalkyl, $OR^7$, $COR^7$, COOH, and $COOR^7$; and each $R^7$ is independently chosen from $C_{1-6}$alkyl and fluoro$C_{1-6}$alkyl.

12. The method of claim 11, wherein:

$R^{6a}$ and $R^{6b}$ are independently chosen from $C_{1-6}$alkyl, $(C_{1-6}$alkoxy$)C_{1-6}$alkyl, (fluoro$C_{1-6}$alkoxy$)C_{1-6}$alkyl, $C_{3-6}$cycloalkyl, $(C_{3-6}$alkoxy$)C_{3-6}$cycloalkyl, and $OR^7$;

W is $C(R^{6b})$;

p is 2; and at least one of $R^{6a}$ and $R^{6b}$ is chosen from $C_{1-6}$alkyl, $(C_{1-6}$alkoxy$)C_{1-6}$alkyl, and (fluoro$C_{1-6}$alkoxy$)C_{1-6}$alkyl.

13. The method as recited in claim 12, wherein the compound of structural Formula II is chosen from:

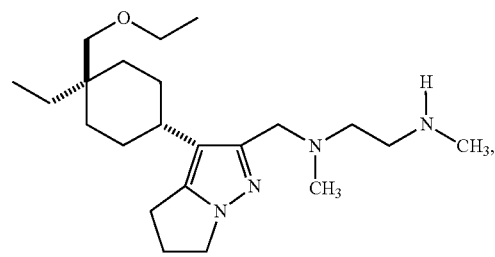

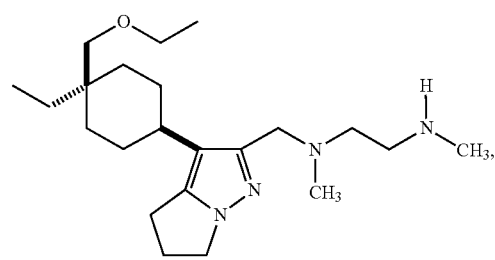

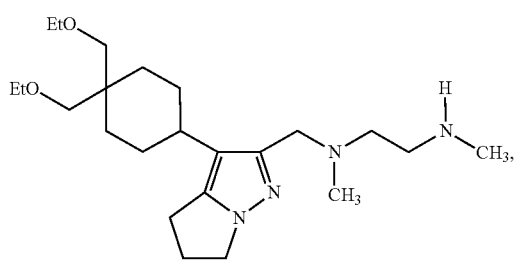

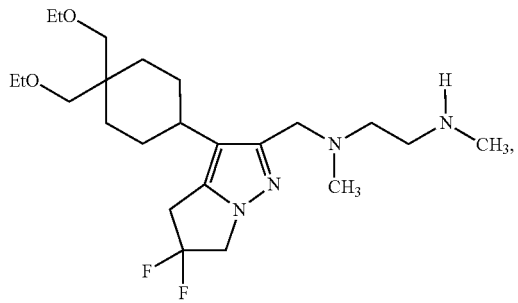

-continued

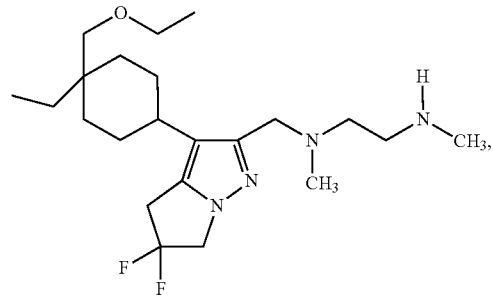

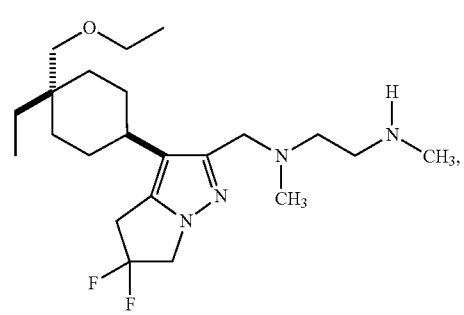

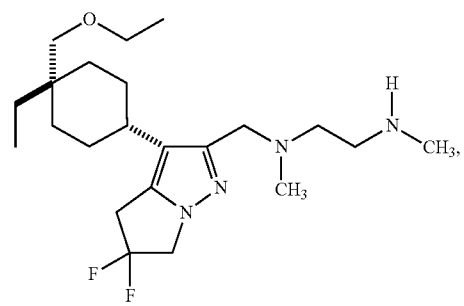

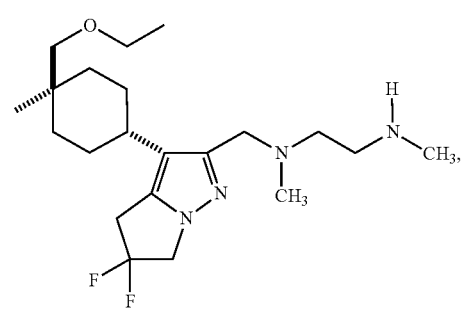

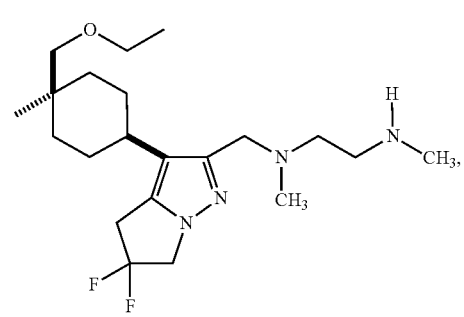

303
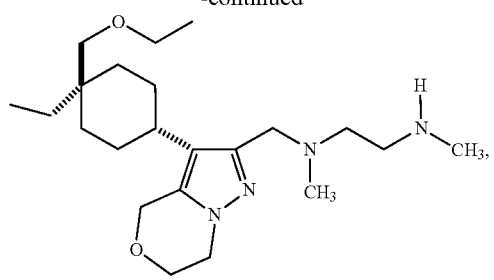
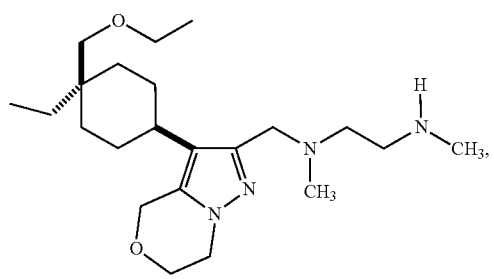
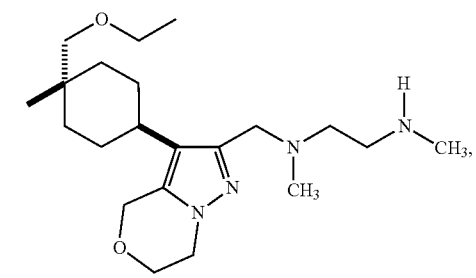
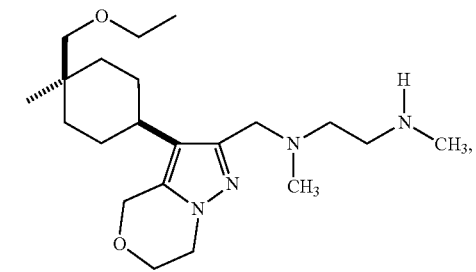
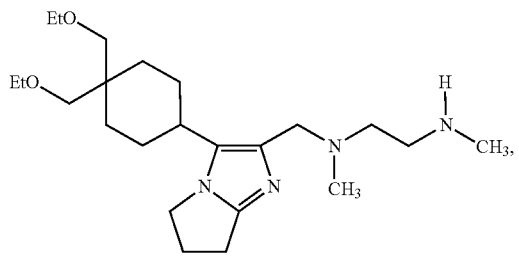
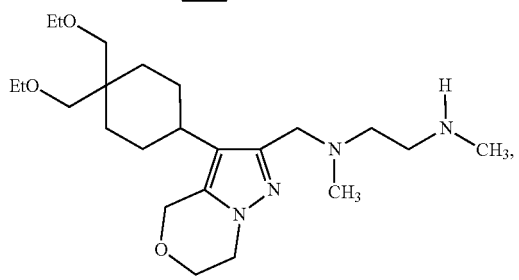
304
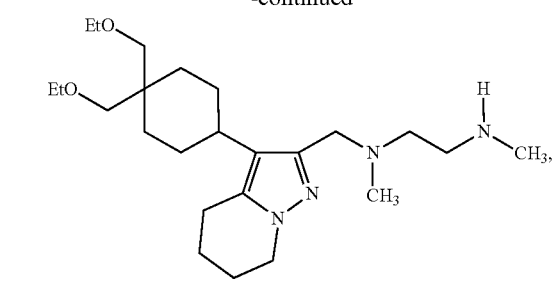
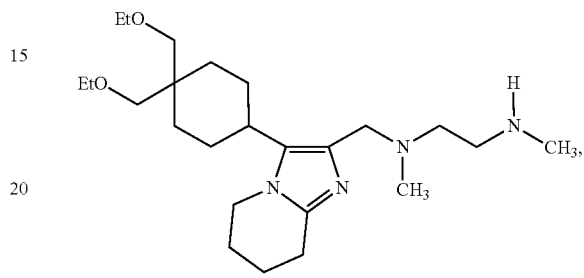
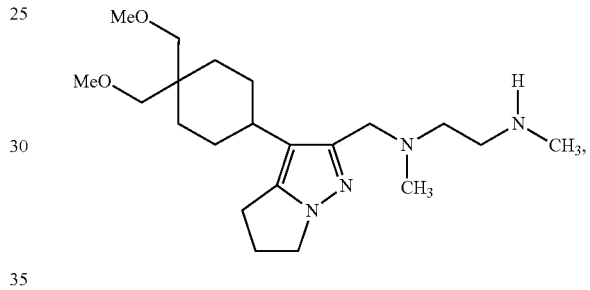
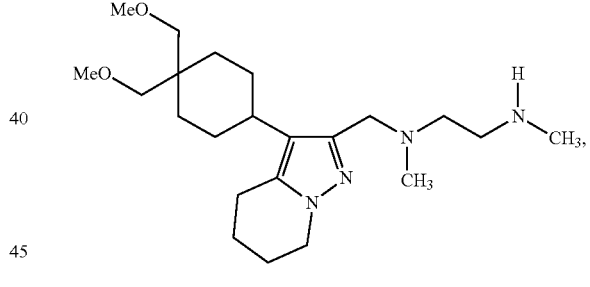
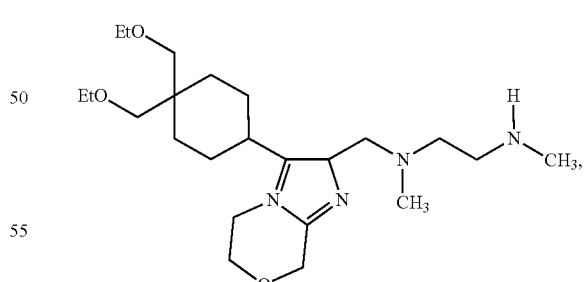
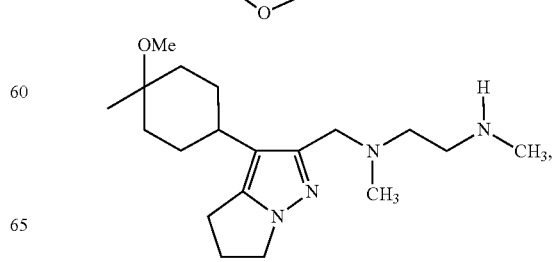

305
-continued
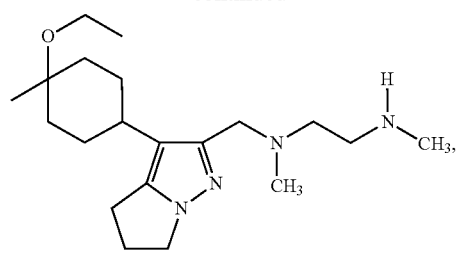
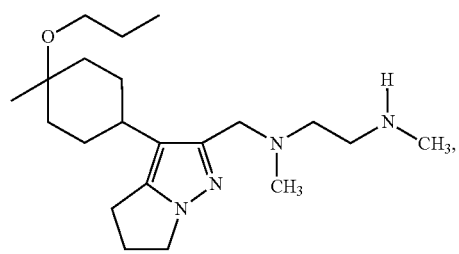
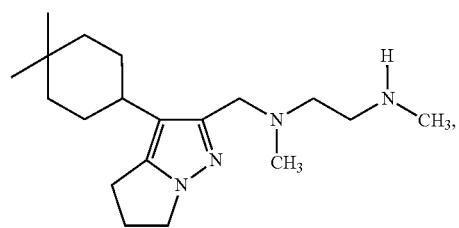
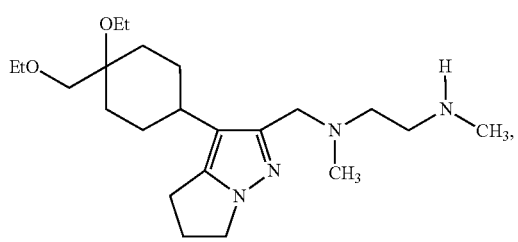
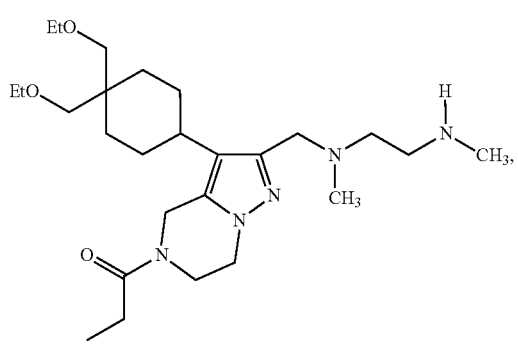
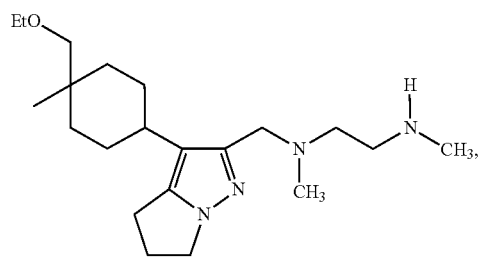
306
-continued
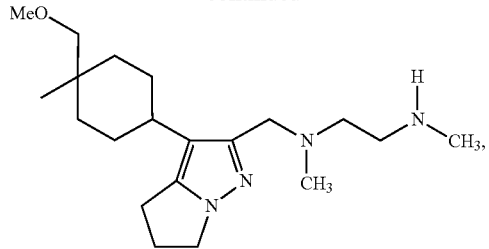
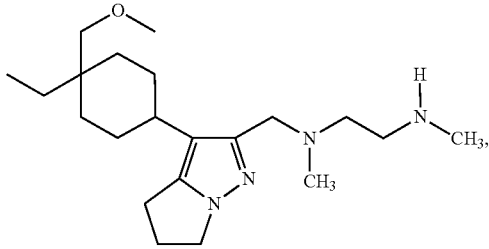
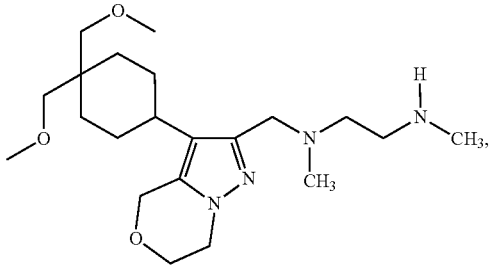
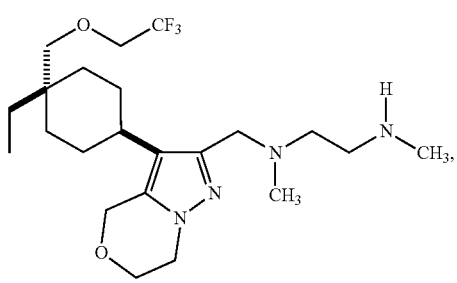
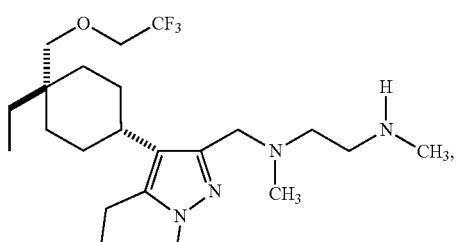
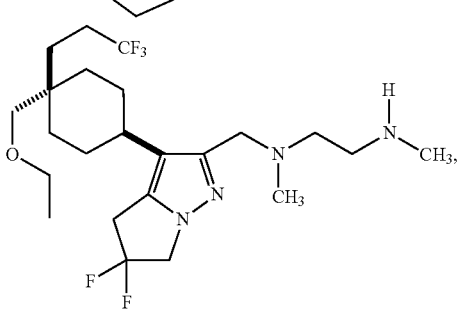

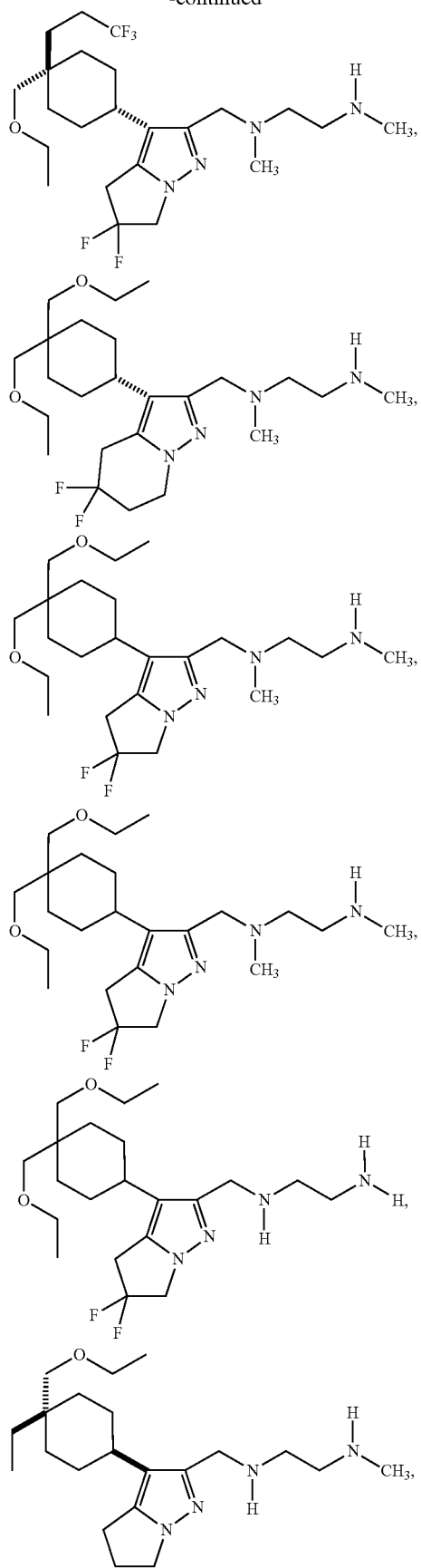
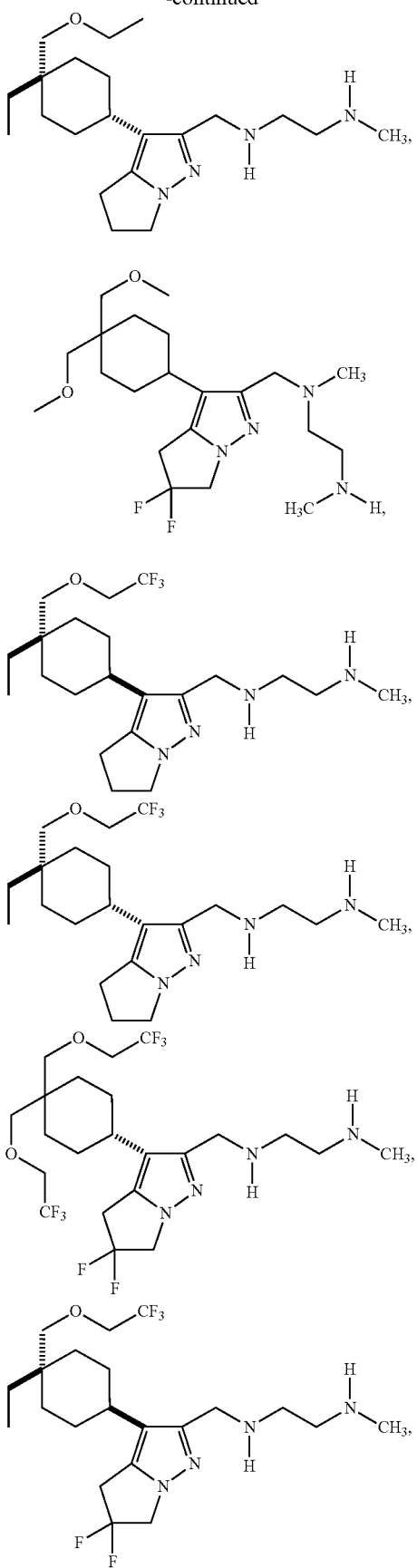

309
-continued
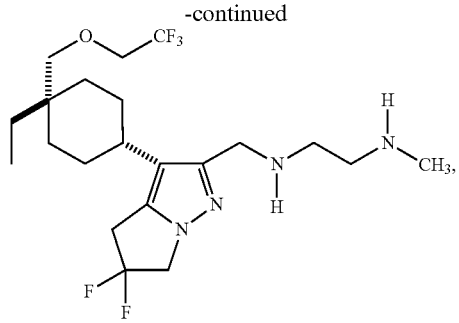
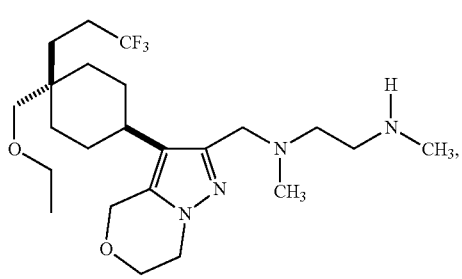
310
-continued
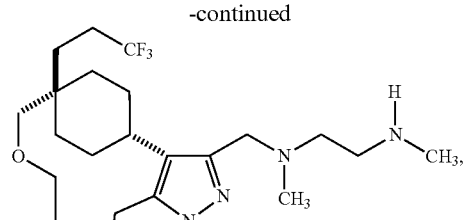
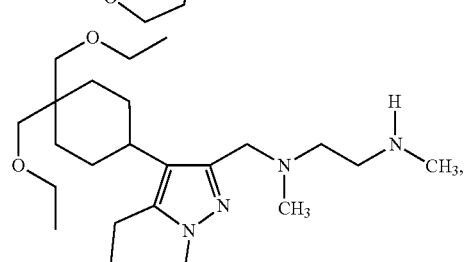
or a salt thereof.
* * * * *